(12) United States Patent
Falkner et al.

(10) Patent No.: US 10,189,889 B2
(45) Date of Patent: Jan. 29, 2019

(54) VIRAL VECTORS ENCODING RECOMBINANT FVIII VARIANTS WITH INCREASED EXPRESSION FOR GENE THERAPY OF HEMOPHILIA A

(71) Applicants: Baxalta Incorporated, Bannockburn, IL (US); Baxalta GmbH, Zug (CH)

(72) Inventors: Falko-Günter Falkner, Orth/Donau (AT); Franziska Horling, Gaenserndorf (AT); Johannes Lengler, Vienna (AT); Hanspeter Rottensteiner, Vienna (AT); Friedrich Scheiflinger, Vienna (AT)

(73) Assignees: Baxalta Incorporated, Bannockburn, IL (US); Baxalta GmbH, Zug (CH)

( * ) Notice: Subject to any disclaimer, the term of this patent is extended or adjusted under 35 U.S.C. 154(b) by 0 days.

(21) Appl. No.: 15/349,940

(22) Filed: Nov. 11, 2016

(65) Prior Publication Data

US 2017/0226188 A1     Aug. 10, 2017

Related U.S. Application Data

(60) Provisional application No. 62/255,323, filed on Nov. 13, 2015.

(51) Int. Cl.
  C07K 14/755   (2006.01)
  C12N 7/00     (2006.01)
  C12N 15/86    (2006.01)
  A61K 38/00    (2006.01)

(52) U.S. Cl.
  CPC ............. *C07K 14/755* (2013.01); *C12N 7/00* (2013.01); *C12N 15/86* (2013.01); *A61K 38/00* (2013.01); *C12N 2750/14143* (2013.01); *C12N 2840/007* (2013.01)

(58) Field of Classification Search
  None
  See application file for complete search history.

(56) References Cited

U.S. PATENT DOCUMENTS

| | | |
|---|---|---|
| 4,797,368 A | 1/1989 | Carter et al. |
| 4,868,112 A | 9/1989 | Toole, Jr. |
| 5,112,950 A | 5/1992 | Meulien et al. |
| 5,139,941 A | 8/1992 | Muzyczka et al. |
| 5,171,844 A | 12/1992 | Van Ooyen et al. |
| 5,543,502 A | 8/1996 | Nordfang et al. |
| 5,595,886 A | 1/1997 | Chapman et al. |
| 5,610,278 A | 3/1997 | Nordfang et al. |
| 5,789,203 A | 4/1998 | Chapman et al. |
| 5,935,935 A | 8/1999 | Connelly et al. |
| 5,972,885 A | 10/1999 | Spira et al. |
| 5,994,136 A | 11/1999 | Naldini et al. |
| 6,013,516 A | 1/2000 | Verma et al. |
| 6,048,720 A | 4/2000 | Dalborg et al. |
| 6,060,447 A | 5/2000 | Chapman et al. |
| 6,114,148 A | 9/2000 | Seed et al. |
| 6,200,560 B1 | 3/2001 | Couto et al. |
| 6,228,620 B1 | 5/2001 | Chapman et al. |
| 6,316,226 B1 | 11/2001 | Van Ooyen et al. |
| 6,346,513 B1 | 2/2002 | Van Ooyen et al. |
| 6,458,563 B1 | 10/2002 | Lollar |
| 6,649,375 B2 | 11/2003 | Connelly et al. |
| 6,924,365 B1 | 8/2005 | Miller et al. |
| 7,041,635 B2 | 5/2006 | Kim et al. |
| 7,635,763 B2 | 12/2009 | Lollar |
| 7,943,374 B2 | 5/2011 | Hildinger |
| 7,973,374 B2 | 7/2011 | Jeong |
| 8,188,246 B2 | 5/2012 | Lollar |
| 8,519,111 B2 | 8/2013 | Lollar |
| 8,986,991 B2 | 3/2015 | Denning et al. |
| 9,393,323 B2 | 7/2016 | Nathwani et al. |
| 9,447,168 B2 | 9/2016 | Nathwani et al. |
| 9,504,762 B2 | 11/2016 | Colosi et al. |
| 2013/0017997 A1 | 1/2013 | Schellenberger et al. |
| 2013/0024960 A1 | 1/2013 | Nathwani et al. |
| 2015/0071883 A1 | 3/2015 | Colosi et al. |
| 2015/0158930 A1 | 6/2015 | Nathwani et al. |
| 2015/0283267 A1 | 10/2015 | Vandendriessche et al. |
| 2015/0361158 A1 | 12/2015 | Tan et al. |
| 2017/0233455 A1 | 8/2017 | Falkner et al. |

FOREIGN PATENT DOCUMENTS

| | | |
|---|---|---|
| WO | WO 2003/052051 A2 | 6/2003 |
| WO | WO 2013/123503 A1 | 8/2013 |
| WO | WO 2013/151666 A2 | 10/2013 |
| WO | WO 2013/186563 A2 | 12/2013 |
| WO | WO 2014/064277 A1 | 5/2014 |
| WO | WO 2014/127215 A1 | 8/2014 |
| WO | WO 2016/025764 A2 | 2/2016 |
| WO | WO 2016/146757 A1 | 9/2016 |

OTHER PUBLICATIONS

Asokan et al. "The AAV Vector Toolkit: Poised at the Clinical Crossroads" Molecular Therapy, vol. 20, No. 4, pp. 699-708 (2012).
Bancel. S. et al., EBII Accession No. GSN:BAW43417.
Blomer et al. "Highly Efficient and Sustained Gene Transfer in Adult Neurons with a Lentivirus Vector" Journal of Virology, vol. 71, No. 9, pp. 6641-6649 (1997).
Cao et al. "ASGCT abstract #460; details of mutations disclosed in oral presentation" (2014).
Cotten et al. "High-efficiency receptor-mediated delivery of small and large (48 kilobase gene constructs using the endosome-disruption activity of defective or chemically inactivated adenovirus particles" Proc. Natl. Acad. Sci. USA, vol. 89, pp. 6094-6098 (1992).

(Continued)

*Primary Examiner* — James D Schultz
(74) *Attorney, Agent, or Firm* — Morgan, Lewis & Bockius LLP

(57) ABSTRACT

The present disclosure provides, among other aspects, codon-altered polynucleotides encoding Factor VIII variants for expression in mammalian cells. In some embodiments, the disclosure also provides mammalian gene therapy vectors and methods for treating hemophilia A.

10 Claims, 46 Drawing Sheets
Specification includes a Sequence Listing.

(56) References Cited

OTHER PUBLICATIONS

Curiel "High-efficiency gene transfer employing adenovirus-polylysine-DNA complexes." Natural Immunity, vol. 13, pp. 141-164 (1994).
Daya and Berns "Gene Therapy Using Adeno-Associated Virus Vectors" Clinical Microbiology Reviews, vol. 21, No. 4, pp. 583-593 (2008).
Donath et al. "Characterization of des-(741-1668)-factor VIII, a single-chain factor VIII variant with a fusion site susceptible to proteolysis by thrombin and factor Xa" Biochem Journal, vol. 312, pp. 49-55 (1995).
Fath et al. "Multiparameter RNA and Codon Optimization: A Standardized Tool to Assess and Enhance Autologous Mammalian Gene Expression" PLoS ONE, vol. 6, Issue 3, pp. 1-14 (2011).
Gardinier-Garden et al. "CpG Islands in vertebrate genomes" Journal of Molecular Biology, vol. 196, Issue 2, pp. 261-282 (1987).
Gray et al. "Optimizing Promoters for Recombinant Adeno-Associated Virus-Mediated Gene Expression in the Peripheral and Central Nervous System Using Self-Complementary Vectors" Human Gene Therapy, vol. 22, pp. 1143-1153 (2011).
Grieger et al. "Production of Recombinant Adeno-associated Virus Vectors Using Suspension HEK293 Cells and Continuous Harvest of Vector From the Culture Media for GMP FIX and FLT1 Clinical Vector" Molecular Therapy, vol. 24, No. 2, pp. 287-297 (2015).
Grote et al. "JCat: a novel tool to adapt codon usage of a target gene to its potential expression host" Nucleic Acid Research, vol. 33, pp. W526-W531 (2005).
Gupta, R. et al., "NetNGlyc 1.0 Server," located at: http://www.cbs.dtu.dk/services/NetNGlyc/, 2004, last accessed, May 30, 2018.
Haas et al. "Codon usage limitation in the expression of HIV-1 envelope glycoprotein" Current Biology, vol. 6, No. 3, pp. 315-324 (1996).
International Search Report for International Application No. PCT/US2016/061684, dated Feb. 15, 2017, 16 pages.
International Search Report for International Application No. PCT/US2016/061688, dated Feb. 6, 2017, 16 pages.
Kelleher and Vos, "Long-term episomal gene delivery in human lymphoid cells using human and avian adenoviral-assisted transfection" Biotechniques, vol. 17, pp. 1110-1117 (1994).
Kriegler "Gene Transfer and Expression, A Laboratory Manual" (1990).
Krinner et al. "CpG domains downstream of TSSs promote high levels of gene expression" Nucleic Acid Research, vol. 42, No. 6, pp. 3551-3564 (2014).
Kudla et al. "High Guanine and Cytosine Content Increases mRNA Levels in Mammalian Cells" PLoS Biology, vol. 4, Issue 6, pp. 0933-0942 (2006).
Mann et al. "Construction of a retrovirus packaging mutant and its use to produce helper-free defective retrovirus" Cell, vol. 33, Issue 1, pp. 153-159 (1983).
Manno et al. "Successful transduction of liver in hemophilia by AAV-Factor IX and limitations imposed by the host immune response." Nature Medicine, vol. 12 pp. 342-347 (2006).
McIntosh et al. "Therapeutic levels of FVIII following a single peripheral vein administration of rAAV vector encoding a novel human factor VIII variant" Blood Journal, vol. 121, No. 17, pp. 3335-3344 (2013).
Miao et al. "Bioengineering of coagulation factor VIII for improved secretion" Blood Journal, vol. 103, No. 9, pp. 3412-3419 (2004).
Mirsafian et al. "A Comparative Analysis of Synonymous Codon Usage Bias Pattern in Human Albumin Superfamily" Scientific World Journal, vol. 2014, Article 639682, pp. 1-7 (2014).
Murray, E.J., "Gene Transfer and Expression Protocols" Methods in Molecular Biology, vol. 7, Humana Press, Inc. (1991).
Muzyczka "Use of adeno-associated virus as a general transduction vector for mammalian cells." Current Topics Microbiology and Immunology, vol. 158, pp. 97-129 (1992).
Naldini et al. "In Vivo Gene Delivery and Stable Transduction of Nondividing Cells by a Lentiviral Vector" Science, vol. 272, Issue 5259, pp. 263-267 (1996).
Nicolas and Rubenstein, "Retroviral vectors," In: Vectors. A survey of molecular cloning vectors and their uses, Rodriguez and Denhardt (eds.), Stoneham: Butterworth, pp. 494-513 (1988).
Oh et al. "Purification of Recombinant Human B-Domain-Deleted Factor VIII Using Anti-Factor VIII Monoclonal Antibody Selected by the Surface Plasmon Resonance Biosensor" Biotechnol. Prog., vol. 17, pp. 1119-1127 (2001).
Radcliff et al. "Analysis of factor VIII mediated suppression of lentiviral vector titres" Gene Therapy, vol. 15, pp. 289-297 (2008).
Sandberg et al. "Structural and functional characteristics of the B-domain-deleted recombinant factor VIII, r-VIII SQ", Journal of Thrombosis and Haemostasis, vol. 85, pp. 93-100 (2001).
Selvaraj et al. "Bioengineering of coagulation factor VIII for efficient expression through elimination of a dispensable disulfide loop" Journal of Thrombosis and Haemostasis, vol. 10, pp. 107-115 (2012).
Swaaroop et al. "Mutagenesis of a Potential Immunoglobulin-binding Protein-binding Site Enhances Secretion of Coagulation Factor VIII" Journal of Biological Chemistry, vol. 272, No. 39, pp. 24121-24124 (1997).
Tats et al. "Preferred and avoided codon pairs in three domains of life" BMC Genomics, vol. 9, Issue 463, pp. 1-15 (2008).
Temin, H.M. "Retrovirus Vectors for Gene Transfer: Efficient Integration into and Expression of Exogenous DNA in Vertebrate Cell Genomes" In: Kucherlapati R. (eds) Gene Transfer (1986).
Thim et al., "Purification and characterization of a new recombinant factor VIII (N8)" Haemophilia, vol. 16, Issue 2, pp. 349-359 (2010).
Toschi et al. OBI-1, porcine recombinant Factor VIII for the potential treatment of patients with congenital hemophilia A and alloantibodies against human Factor VIII, Current Opinion in Molecular Therapy, vol. 12, No. 5, pp. 617-625 (2010).
Varfaj et al. "Residues Surrounding Arg336 and Arg562 Contribute to the Disparate Rates of Proteolysis of Factor VIIIa Catalyzed by Activated Protein C" Journal of Biological Chemistry, vol. 282, No. 28, pp. 20264-20272 (2007).
Wakabayashi et al. "A Glu113Ala mutation within a factor VIII Ca2+ binding site enhances cofactor interactions in factor Xase" Biochemistry, vol. 44, pp. 10298-10304 (2005).
Wakabayashi et al. "Ca(2+) binding to both the heavy and light chains of factor VIII is required for cofactor activity" Biochemistry, vol. 41, pp. 8485-8492 (2002).
Wakabayashi et al. "Combining mutations of charged residues at the A2 domain interface enhances factor VIII stability over single point mutations" Journal of Thrombosis and Haemostasis, vol. 7, pp. 438-444 (2009).
Wakabayashi et al. "Enhancing factor VIII and VIIIa stability by combining mutations at the A2 domain interface and A1-C2 domain interface" Journal of Thrombosis and Haemostasis., vol. 10, pp. 492-495 (2012).
Wakabayashi et al. "Generation of enhanced stability factor VIII variants by replacement of charged residues at the A2 domain interface" Blood, vol. 12, No. 7, pp. 2761-2769 (2008).
Wakabayashi et al. "Increasing Hydrophobicity or Disulfide Bridging at the Factor VIII A1 and C2 Domain Interface Enhances Procofactor Stability" Journal of Biological Chemistry, vol. 286, No. 29 pp. 25748-25755 (2011).
Wakabayashi et al. "Residues 110-126 in the A1 Domain of Factor VIII Contain a Ca2+ Binding Site Required for Cofactor Activity" Journal of Biochemistry, vol. 279, No. 13, pp. 12677-12684 (2004).
Ward et al. "Codon optimization of human factor VIII cDNAs leads to high-level expression" Blood Journal, vol. 117, No. 3, pp. 798-807 (2011).
Zollner et al. "Non-clinical pharmacokinetics and pharmacodynamics of rVIII-SingleChain, a novel recombinant single-chain factor VIII", Thrombosis Research, vol. 134, pp. 125-131 (2014).
Zufferey et al. "Multiply attenuated lentiviral vector achieves efficient gene delivery in vivo" Nature Biotechnology, vol. 15, pp. 871-875 (1997).

CS04-FL-NA atgcagattgagctgagcacctgcttcttcctgtgcctgctgaggttctgcttctctgccaccagga
gatactacctgggggctgtggagctttcttgggactacatgcagtctgacctgggggagctgcctgt
ggatgccaggttcccacccagagtgcccaaatccttcccattcaacacctctgtggtctacaagaag
accctctttgtggagttcactgaccacctgttcaacattgccaaacccaggccacoctggatgggac
tcctgggaccaccattcaggctgaggtgtatgacactgtggtcatcaccctcaagaacatggcctc
ccaccctgtgagcctgcatgctgtgggggtcagctactggaaggcctctgaggggctgagtatgat
gaccagacctcccagagggagaaggaggatgacaaagtgttccctgggggcagccacacctatgtgt
ggcaggtcctcaaggagaatggccccatggcctctgacccactctgcctgacctactcctaccttc
tcatgtggacctggtcaaggacctcaactctggactgattggggccctgctggtgtgcaggagggc
tccctggccaaagagaagacccagaccctgcacaagttcattctcctgtttgctgtctttgatgagg
gcaagagctggcactctgaaaccaagaactccctgatgcaggacagggatgctgcctctgccaggc
ctggcccaagatgcacactgtgaatggctatgtgaacaggagcctgcctggactcattggctgccac
aggaaatctgtctactggcatgtgattggcatggggacaacccctgaggtgcactccattttcctgg
agggccacaccttcctggtcaggaaccacagacaggccagcctggagatcagcccatcaccttcct
cactgcccagaccctgctgatggacctcggacagttcctgctgttctgccacatcagctcccaccag
catgatggcatggaggcctatgtcaaggtggacagctgccctgaggagccacagctcaggatgaaga
acaatgaggagctgaggactatgatgatgacctgactgactctgagatggatgtggtccgctttga
tgatgacaacagcccatccttcattcagatcaggtctgtggccaagaaacaccccaagacctgggtg
cactacattgctgctgaggaggaggactgggactatgcccactggtcctggcccctgatgacagga
gctacaagagccagtacctcaacaatggcccacagaggattggacgcaagtacaagaaagtcaggtt
catggcctacactgatgaaaccttcaagaccagggaggccattcagcatgagtctggcatcctgggc
ccactcctgtatggggaggtgggggacaccctgctcatcatcttcaagaaccaggcctccaggccct
acaacatctacccacatggcatcactgatgtcaggcccctgtacagccgcaggctgccaaaggggt
gaaacacctcaaggacttccccattctgcctggggagatcttcaagtacaagtggactgtcactgtg
gaggatggaccaaccaaatctgacccccaggtgcctcaccagatactactccagctttgtgaacatgg
agagggacctggcctctggcctgattggcccactgctcatctgctacaaggagtctgtggaccagag
gggaaaccagatcatgtctgacaagaggaatgtgattctgttctctgtctttgatgagaacaggagc
tggtacctgactgagaacattcagcgcttcctgcccaaccctgctggggtgcagctggaggaccctg
agttccaggccagcaacatcatgcactccatcaatggctatgtgtttgacagcctccagctttctgt
ctgcctgcatgaggtggcctactggtacattctttctattgggcccagactgacttcctttctgtc
ttcttctctggctacaccttcaaacacaagatggtgtatgaggacaccctgacoctcttcccattct
ctggggagactgtgttcatgagcatggagaaccctggcctgtggattctgggatgccacaactctga
cttccgcaacaggggcatgactgccctgctcaaagtctcctcctgtgacaagaacactggggactac
tatgaggacagctatgaggacatctctgcctacctgctcagcaagaacaatgccattgagcccagga
gcttcagccagaatccacctgtcctgaaacgccaccagagggagatcaccaggaccaccctccagtc
tgaccaggaggagattgactatgatgacaccatttctgtggagatgaagaagaggactttgacatc
tatgacgaggacgagaaccagagcccaaggagcttccagaagaagaccaggcactacttcattgctg
ctgtggagcgcctgtgggactatggcatgagctccagccccatgtcctcaggaacagggccagtc
tggctctgtgccacagttcaagaaagtggtcttccaagagttcactgatggcagcttcacccagccc
ctgtacagaggggagctgaatgagcacctgggactcctgggccatacatcagggctgaggtggagg
acaacatcatggtgaccttccgcaaccaggcctccaggccctacagcttctacagctccctcatcag
ctatgagGaggaccagaggcaggggctgagccacgcaagaactttgtgaaaccaatgaaaccaag
acctacttctggaaagtccagcaccacatggccccaccaaggatgagtttgactgcaaggcctggg (Continued)

Figure 2A

```
cctacttctctgatgtggacctggagaaggatgtgcactctggcctgattggcccactcctggtctg
ccacaccaacaccctgaaccctgcccatggaaggcaagtgactgtgcaggagtttgccctcttcttc
accatctttgatgaaaccaagagctggtacttcactgagaacatggagcgcaactgcagggcccat
gcaacattcagatggaggaccccaccttcaaagagaactaccgcttccatgccatcaatggctacat
catggacaccctgcctgggcttgtcatggcccaggaccagaggatcaggtggtacctgctttctatg
ggctccaatgagaacattcactccatccacttctctgggcatgtcttcactgtgcgcaagaaggagg
agtacaagatggccctgtacaacctctaccctggggtctttgagactgtggagatgctgccctccaa
agctggcatctggagggtggagtgcctcattggggagcacctgcatgctggcatgagcaccctgttc
ctggtctacagcaacaagtgccagaccccctgggaatggcctctggccacatcagggacttccaga
tcactgcctctggccagtatggccagtgggcccccaagctggccaggctccactactctggatccat
caatgcctggagcaccaaggagccattcagctggatcaaagtggacctgctggcccccatgatcatc
catggcatcaagaccaggggggccaggcagaagttctccagcctgtacatcagccagttcatcatca
tgtacagcctggatggcaagaaatggcagacctacagaggcaactccactggaacactcatggtctt
ctttggcaatgtggacagctctggcatcaagcacaacatcttcaaccccccaatcatcgccagatac
atcaggctgcaccccacccactacagcatccgcagcaccctcaggatggagctgatgggctgtgacc
tgaactcctgcagcatgcccctgggcatggagagcaaggccatttctgatgcccagatcactgcctc
cagctacttcaccaacatgtttgccacctggagcccaagcaaggccaggctgcacctccagggaagg
agcaatgcctggaggccccaggtcaacaacccaaaggagtggctgcaggtggacttccagaagacca
tgaaggtcactggggtgaccacccagggggtcaagagcctgctcaccagcatgtatgtgaaggagtt
cctgatcagctccagccaggatggccaccagtggaccctcttcttccagaatggcaaggtcaaggtg
ttccagggcaaccaggacagcttcacCcctgtggtgaacagcctggaccccccctcctgaccagat
acctgaggattcaccccagagctgggtccaccagattgccctgaggatggaggtcctgggatgtga
ggcccaggacctgtactga (SEQ ID NO:1)
```

CS04-FL-AA

MQIELSTCFFLCLLRFCFSATRRYYLGAVELSWDYMQSDLGELPVDAR'FPPRVPKSFPFNTSVVYK
KTLFVEFTDHLFNIAKPRPPWMGLLGPTIQAEVYDTVVITLKNMASHPVSLHAVGVSYWKASEGAEY
DDQTSQREKEDDKVFPGGSHTYVWQVLKENGPMASDPLCLTYSYLSHVDLVKDLNSGLIGALLVCRE
GSLAKEKTQTLHKFILLFAVFDEGKSWHSETKNSLMQDRDAASARAWPKMHTVNGYVNRSLPGLIGC
HRKSVYWHVIGMGTTPEVHSIFLEGHTFLVRNHRQASLEISPITFLTAQTLLMDLGQFLLFCHISSH
QHDGMEAYVKVDSCPEEPQLRMKNNEEAEDYDDDLTDSEMDVVRFDDDNSPSFIQIRSVAKKHPKTW
VHYIAAEEEDWDYAPLVLAPDDRSYKSQYLNNGPQRIGRKYKKVRFMAYTDETFKTREAIQHESGIL
GPLLYGEVGDTLLIIFKNQASRPYNIYPHGITDVRPLYSRRLPKGVKHLKDFPILPGEIFKYKWTVT
VEDGPTKSDPRCLTRYYSSFVNMERDLASGLIGPLLICYKESVDQRGNQIMSDKRNVILFSVFDENR
SWYLTENIQRFLPNPAGVQLEDPEFQASNIMHSINGYVFDSLQLSVCLHEVAYWYILSIGAQTDFLS
VFFSGYTFKHKMVYEDTLTLFPFSGETVFMSMENPGLWILGCHNSDFRNRGMTALLKVSSCDKNTGD
YYEDSYEDISAYLLSKNNAIEPRSFSQNPPVLKRHQREITRTTLQSDQEEIDYDDTISVEMKKEDFD
IYDEDENQSPRSFQKKTRHYFIAAVERLWDYGMSSSPHVLRNRAQSGSVPQFKKVVFQEFTDGSFTQ
PLYRGELNEHLGLLGPYIRAEVEDNIMVTFRNQASRPYSFYSSLISYEEDQRQGAEPRKNFVKPNET
KTYFWKVQHHMAPTKDEFDCKAWAYFSDVDLEKDVHSGLIGPLLVCHTNTLNPAHGRQVTVQEFALF
FTIFDETKSWYFTENMERNCRAPCNIQMEDPTFKENYRFHAINGYIMDTLPGLVMAQDQRIRWYLLS
MGSNENIHSIHFSGHVFTVRKKEEYKMALYNLYPGVFETVEMLPSKAGIWRVECLIGEHLHAGMSTL
FLVYSNKCQTPLGMASGHIRDFQITASGQYGQWAPKLARLHYSGSINAWSTKEPFSWIKVDLLAPMI
IHGIKTQGARQKFSSLYISQFIIMYSLDGKKWQTYRGNSTGTLMVFFGNVDSSGIKHNIFNPPIIAR
YIRLHPTHYSIRSTLRMELMGCDLNSCSMPLGMESKAISDAQITASSYFTNMFATWSPSKARLHLQG
RSNAWRPQVNNPKEWLQVDFQKTMKVTGVTTQGVKSLLTSMYVKEFLISSSQDGHQWTLFFQNGKVK
VFQGNQDSFTPVVNSLDPPLLTRYLRIHPQSWVHQIALRMEVLGCEAQDLY     (SEQ ID NO:2)

```
                                                                gcc
accaggagat actacctggg ggctgtggag ctttcttggg actacatgca gtctgacctg
ggggagctgc ctgtggatgc caggttccca cccagagtgc ccaaatcctt cccattcaac
acctctgtgg tctacaagaa gaccctcttt gtggagttca ctgaccacct gttcaacatt
gccaaaccca ggccaccctg gatgggactc ctgggaccca ccattcaggc tgaggtgtat
gacactgtgg tcatcaccct caagaacatg gcctccacc ctgtgagcct gcatgctgtg
ggggtcagct actggaaggc ctctgagggg gctgagtatg atgaccagac ctcccagagg
gagaaggagg atgacaaagt gttccctggg ggcagccaca cctatgtgtg gcaggtcctc
aaggagaatg gccccatggc ctctgaccca ctctgcctga cctactccta cctttctcat
gtggacctgg tcaaggacct caactctgga ctgattgggg ccctgctggt gtgcagggag
ggctccctgg ccaaagagaa gacccagacc ctgcacaagt tcattctcct gtttgctgtc
tttgatgagg gcaagagctg gcactctgaa accaagaact ccctgatgca ggacagggat
gctgcctctg ccagggcctg gcccaagatg cacactgtga atggctatgt gaacaggagc
ctgcctggac tcattggctg ccacaggaaa tctgtctact ggcatgtgat tggcatgggg
acaaccctg aggtgcactc cattttcctg gagggccaca ccttctggt caggaaccac
agacaggcca gctggagat cagccccatc accttcctca ctgcccagac cctgctgatg
gacctcggac agttcctgct gttctgccac atcagctccc accagcatga tggcatggag
gcctatgtca aggtggacag ctgccctgag gagccacagc tcaggatgaa gaacaatgag
gaggctgagg actatgatga tgacctgact gactctgaga tggatgtggt ccgctttgat
gatgacaaca gcccatcctt cattcagatc aggtctgtgg ccaagaaaca cccaagacc
tgggtgcact acattgctgc tgaggaggag gactgggact atgcccact ggtcctggcc
cctgatgaca ggagctacaa gagccagtac ctcaacaatg gccacagag gattggacgc
aagtacaaga agtcaggtt catggcctac actgatgaaa ccttcaagac cagggaggcc
attcagcatg agtctggcat cctgggccca ctcctgtatg gggaggtggg ggacaccctg
ctcatcatct tcaagaacca ggcctccagg ccctacaaca tctacccaca tggcatcact
gatgtcaggc cctgtacag ccgcaggctg ccaaaggggg tgaaacacct caaggacttc
cccattctgc ctggggagat cttcaagtac aagtggactg tcactgtgga ggatggacca
accaaatctg accccaggtg cctcaccaga tactactcca gctttgtgaa catggagagg
gacctggcct ctggcctgat tgcccactg ctcatctgct acaaggagtc tgtggaccag
agggaaacc agatcatgtc tgacaagagg aatgtgattc tgttctctgt ctttgatgag
aacaggagct ggtacctgac tgagaacatt cagcgcttcc tgccaaccc tgctggggtg
cagctggagg acctgagtt ccaggccagc aacatcatgc actccatcaa tggctatgtg
tttgacagcc tccagctttc tgtctgcctg catgaggtgg cctactggta cattcttct
attggggccc agactgactt cctttctgtc ttcttctctg gctacacctt caaacacaag
atggtgtatg aggacaccct gaccctcttc ccattctctg gggagactgt gttcatgagc
atggagaacc ctggcctgtg gattctggga tgccacaact ctgacttccg caacagggc
atgactgccc tgctcaaagt ctcctcctgt gacaagaaca ctggggacta ctatgaggac
agctatgagg acatctctgc ctacctgctc agcaagaaca atgccattga gcccagg
(SEQ ID NO:3)
```

```
                                                     g agatcaccag gaccaccctc
cagtctgacc aggaggagat tgactatgat gacaccattt ctgtggagat gaagaaagag
gactttgaca tctatgacga ggacgagaac cagagcccaa ggagcttcca gaagaagacc
aggcactact tcattgctgc tgtggagcgc ctgtgggact atggcatgag ctccagcccc
catgtcctca ggaacagggc ccagtctggc tctgtgccac agttcaagaa agtggtcttc
caagagttca ctgatgcag cttcacccag cccctgtaca gagggagct gaatgagcac
ctgggactcc tgggcccata catcagggct gaggtggagg acaacatcat ggtgaccttc
cgcaaccagg cctccaggcc ctacagcttc tacagctccc tcatcagcta tgaggaggac
cagaggcagg gggctgagcc acgcaagaac tttgtgaaac ccaatgaaac caagacctac
ttctggaaag tccagcacca catggcccc accaaggatg agtttgactg caaggcctgg
gcctacttct ctgatgtgga cctggagaag gatgtgcact ctggcctgat tggcccactc
ctggtctgcc acaccaacac cctgaaccct gccatggaa ggcaagtgac tgtgcaggag
tttgccctct tcttcaccat ctttgatgaa accaagagct ggtacttcac tgagaacatg
gagcgcaact gcagggcccc atgcaacatt cagatggagg accccacctt caaagagaac
taccgcttcc atgccatcaa tggctacatc atggacaccc tgcctgggct tgtcatggcc
caggaccaga ggatcaggtg gtacctgctt tctatgggct ccaatgagaa cattcactcc
atccacttct ctgggcatgt cttcactgtg cgcaagaagg aggagtacaa gatggccctg
tacaacctct accctggggt ctttgagact gtggagatgc tgccctccaa agctggcatc
tggagggtgg agtgcctcat tggggagcac ctgcatgctg catgagcac cctgttcctg
gtctacagca acaagtgcca gaccccctg ggaatggcct ctggccacat cagggacttc
cagatcactg cctctggcca gtatggccag tgggcccca agctggccag gtccactac
tctggatcca tcaatgcctg gagcaccaag gagccattca gctggatcaa agtggacctg
ctggccccca tgatcatcca tggcatcaag acccagggg ccaggcagaa gttctccagc
ctgtacatca gccagttcat catcatgtac agcctggatg caagaaatg cagacctac
agaggcaact ccactggaac actcatggtc ttctttggca atgtggacag ctctggcatc
aagcacaaca tcttcaaccc ccaatcatc gccagataca tcaggctgca cccacccac
tacagcatcc gcagcaccct caggatggag ctgatgggct gtgacctgaa ctcctgcagc
atgccctgg gcatggagag caaggcatt tctgatgccc agatcactgc ctccagctac
ttcaccaaca tgtttgccac ctggagccca agcaaggcca ggctgcacct ccagggaagg
agcaatgcct ggaggcccca ggtcaacaac ccaaaggagt ggctgcaggt ggacttccag
aagaccatga aggtcactgg ggtgaccacc caggggtca agagcctgct caccagcatg
tatgtgaagg agttcctgat cagctccagc caggatggcc accagtggac cctcttcttc
cagaatggca aggtcaaggt gttccagggc aaccaggaca gcttcacccc tgtggtgaac
agcctggacc ccccctct gaccagatac ctgaggattc accccagag ctgggtccac
cagattgccc tgaggatgga ggtcctggga tgtgaggccc aggacctgta c
(SEQ ID NO:4)
```

Figure 5

```
BDL001   agc ttctctcaga atccacctgt cctgaagaga caccagaga  (SEQ ID NO:5)
BDL004   agc ttcagccaga atccacctgt cctgaaacgc caccagagg  (SEQ ID NO:6)
BDL023   agc ttcagccaga acccccccgt gctgaagagg caccagagg  (SEQ ID NO:7)
```

```
   1  tcgcgcgttt cggtgatgac ggtgaaaacc tctgacacat gcagctcccg gagacggtca
  61  cagcttgtct gtaagcggat gccgggagca gacaagcccg tcagggcgcg tcagcgggtg
 121  ttggcgggtg tcggggctgg cttaactatg cggcatcaga gcagattgta ctgagagtgc
 181  accatatgcg gtgtgaaata ccgcacagat gcgtaaggag aaaataccgc atcaggcgcc
 241  attgccatt  caggctgcgc aactgttggg aagggcgatc ggtgcgggcc tcttcgctat
 301  tacgccagct ggcgaaaggg ggatgtgctg caaggcgatt aagttgggta acgccaggt
 361  tttcccagtc acgacgttgt aaaacgacgg ccagtgaatt cctcgagatt taaatgacgt
 421  tggccactcc ctctctgcgc gctcgctcgc tcactgaggc cgggcgacca aaggtcgccc
 481  gacgcccggg ctttgcccgg gcggcctcag tgagcgagcg agcgcgcaga gagggagtgg
 541  ccaactccat cactagggt  tcctgagttt aaacttcgtc gacgattcga gcttggcctg
 601  caggtcgagg gcactgggag gatgttgagt aagatggaaa actactgatg acccttgcag
 661  agacagagta ttaggacatg tttaacagg  gccgggcga  tcagcaggta gtctagagg
 721  atcccgtct  gtctgcacat ttcgtagagc gagtgttccg atactctaat ctccctaggc
 781  aaggttcata tttgtgtagg ttacttattc tcctttttgtt gactaagtca ataatcagaa
 841  tcagcaggtt ggagtcagc  ttggcaggga tcagcagcct gggttggaag gaggggtat
 901  aaaagcccct tcaccaggag aagccgtcac acagactagg cgcgccacg  ccaccatgca
 961  gattgagctg agcacctgct tcttcctgtg cctgctgagg ttctgcttct ctgccaccag
1021  gagatactac ctgggggctg tggagctttc ttgggactac atgcagtctg acctggggga
1081  gctgctgtg  gatgccaggt tccacccag  agtgcccaaa tccttcccat tcaacaccctc
1141  tgtggtctac aagaagaccc tctttgtgga gttcactgac cacctgttca acattgccaa
1201  accaggcca  cctggatgg  gactcctggg accaccatt  caggctgagg tgtatgacac
1261  tgtggtcatc ccctcaaga  acatggcctc ccacctgtg  agcctgcatg ctgtgggggt
1321  cagctactgg aaggcctctg aggggctga  gtatgatgac cagacctccc agagggagaa
1381  ggaggatgac aaagtgttcc ctggggcag  ccacacctat gtgtggcagg tcctcaagga
1441  gaatggcccc atggctctg  accactctg  cctgacctac tctacctttt ctcatgtgga
1501  cctggtcaag gacctcaact ctggactgat tggggccctg ctggtgtgca gggagggctc
1561  cctggccaaa gagaagaccc agacctgca  caagttcatt ctcctgtttg ctgtctttga
1621  tgagggcaag agctggcact ctgaaaccaa gaactccctg atgcaggaca gggatgctgc
1681  ctctgccagg gcctggccca agatgcacac tgtgaatggc tatgtgaaca ggagcctgcc
1741  tggactcatt ggctgccaca ggaaatctgt ctactggcat gtgattggca tggggacaac
1801  ccctgaggtg cactccattt cctggaggg  ccacaccttc ctggtcagga accacagaca
1861  ggccagcctg gagatcagcc ccatcacctt cctcactgcc agacctgc  tgatggacct
1921  cggacagttc ctgctgttct gccacatcag ctcccaccag catgatggca tggaggccta
1981  tgtcaaggtg gacagctgcc ctgaggagcc acagctcagg atgaagaaca atgaggaggc
2041  tgaggactat gatgatgacc tgactgactc tgagatggat gtggtccgct tgatgatga
2101  caacagccca tccttcatc  agatcaggtc tgtggccaag aaacaccca  agacctggt
2161  gcactacatt gctgctgagg aggaggactg gactatgcc  ccactggtcc tggccctga
2221  tgacaggagc tacaagagcc agtacctcaa caatggccca cagaggattg gacgcaagta
2281  caagaaagtc aggttcatgg cctacactga tgaaaccttc aagaccaggg aggccattca
2341  gcatgagtct ggcatcctgg gccactctg  tatggggag  gtggggaca  ccctgctcat
2401  catcttcaag aaccaggcct ccaggcccta caacatctac ccacatggca tcactgatgt
2461  caggccctg  tacagccgca ggctgccaaa ggggtgaaa  cacctcaagg acttccccat
```

Figure 7A

```
2521 tctgcctggg gagatcttca agtacaagtg gactgtcact gtggaggatg gaccaaccaa
2581 atctgacccc aggtgcctca ccagatacta ctccagcttt gtgaacatgg agagggacct
2641 ggcctctggc ctgattggcc cactgctcat ctgctacaag gagtctgtgg accagagggg
2701 aaaccagatc atgtctgaca agaggaatgt gattctgttc tctgtctttg atgagaacag
2761 gagctggtac ctgactgaga acattcagcg cttcctgccc aaccctgctg gggtgcagct
2821 ggaggaccct gagttccagg ccagcaacat catgcactcc atcaatggct atgtgtttga
2881 cagcctccag ctttctgtct gcctgcatga ggtggcctac tggtacattc tttctattgg
2941 ggcccagact gacttccttt ctgtcttctt ctctggctac accttcaaac acaagatggt
3001 gtatgaggac accctgaccc tcttcccatt ctctggggag actgtgttca tgagcatgga
3061 gaaccctggc ctgtggattc tgggatgcca caactctgac ttccgcaaca ggggcatgac
3121 tgccctgctc aaagtctcct cctgtgacaa gaacactggg gactactatg aggacagcta
3181 tgaggacatc tctgcctacc tgctcagcaa gaacaatgcc attgagccca ggagcttcag
3241 ccagaatcca cctgtcctga aacgccacca gagggagatc accaggacca ccctccagtc
3301 tgaccaggag gagattgact atgatgacac catttctgtg gagatgaaga aagaggactt
3361 tgacatctat gacgaggacg agaaccagag cccaaggagc ttccagaaga gaccaggca
3421 ctacttcatt gctgctgtgg agcgcctgtg ggactatggc atgagctcca gccccatgt
3481 cctcaggaac agggcccagt ctggctctgt gccacagttc aagaaagtgg tcttccaaga
3541 gttcactgat ggcagcttca cccagcccct gtacagaggg gagctgaatg agcacctggg
3601 actcctgggc ccatacatca gggctgaggt ggaggacaac atcatggtga ccttccgcaa
3661 ccaggcctcc aggccctaca gcttctacag ctccctcatc agctatgagg aggaccagag
3721 gcaggggct gagccacgca agaactttgt gaaacccaat gaaaccaaga cctacttctg
3781 gaaagtccag caccacatgg cccccaccaa ggatgagttt gactgcaagg cctggccta
3841 cttctctgat gtggacctgg agaaggatgt gcactctggc ctgattggcc cactcctggt
3901 ctgccacacc aacacctga accctgccca tggaaggcaa gtgactgtgc aggagtttgc
3961 cctcttcttc accatctttg atgaaaccaa gagctggtac ttcactgaga acatggagcg
4021 caactgcagg gccccatgca acattcagat ggaggacccc accttcaaag agaactaccg
4081 cttccatgcc atcaatggct acatcatgga caccctgcct gggcttgtca tggcccagga
4141 ccagaggatc aggtggtacc tgcttctat gggctccaat gagaacattc actccatcca
4201 cttctctggg catgtcttca ctgtgcgcaa gaaggaggag tacaagatgg ccctgtacaa
4261 cctctaccct ggggtctttg agactgtgga gatgctgccc tccaaagctg gcatctggag
4321 ggtggagtgc ctcattgggg agcacctgca tgctggcatg agcacctgt tcctggtcta
4381 cagcaacaag tgccagaccc cctgggaat ggcctctggc acatcaggg acttccagat
4441 cactgcctct ggccagtatg ccagtgggc cccaagctg gccaggctcc actactctgg
4501 atccatcaat gctggagca ccaaggagcc attcagctgg atcaaagtgg acctgctggc
4561 ccccatgatc atccatggca tcaagaccca gggggccagg cagaagttct ccagcctgta
4621 catcagccag ttcatcatca tgtacagcct ggatggcaag aaatggcaga ctacagagg
4681 caactccact ggaacactca tggtcttctt tggcaatgtg gacagctctg catcaagca
4741 caacatcttc aacccccaa tcatcgccag atacatcagg ctgcacccca ccactacag
4801 catccgcagc ccctcagga tggagctgat gggctgtgac ctgaactcct gcagcatgcc
4861 cctgggcatg gagagcaagg ccatttctga tgcccagatc actgcctcca gctacttcac
4921 caacatgttt gccacctgga gcccaagcaa ggccaggctg cacctccagg aaggagcaa
4981 tgcctggagg cccaggtca acaacccaaa ggagtggctg caggtggact tccagaagac
```

Figure 7B

```
5041 catgaaggtc actggggtga ccacccaggg ggtcaagagc ctgctcacca gcatgtatgt
5101 gaaggagttc ctgatcagct ccagccagga tggccaccag tggaccctct tcttccagaa
5161 tggcaaggtc aaggtgttcc agggcaacca ggacagcttc accctgtgg tgaacagcct
5221 ggaccccccc ctcctgacca gatacctgag gattcacccc cagagctggg tccaccagat
5281 tgccctgagg atggaggtcc tgggatgtga ggcccaggac ctgtactgat gacgagcggc
5341 cgctcttagt agcagtatcg ataataaaag atctttattt tcattagatc tgtgtgttgg
5401 ttttttgtgt gttaattaag ctcgcgaagg aaccctagt gatggagttg gccactccct
5461 ctctgcgcgc tcgctcgctc actgaggccg ggcgaccaaa ggtcgcccga cgcccgggct
5521 ttgccgggc ggcctcagtg agcgagcgag cgcgcagaga gggagtggcc aagacgattt
5581 aaatgacaag cttggcgtaa tcatggtcat agctgtttcc tgtgtgaaat tgttatccgc
5641 tcacaattcc acacaacata cgagccggaa gcataaagtg taaagcctgg ggtgcctaat
5701 gagtgagcta actcacatta attgcgttgc gctcactgcc cgctttccag tcgggaaacc
5761 tgtcgtgcca gctgcattaa tgaatcggcc aacgcgcggg gagaggcggt ttgcgtattg
5821 ggcgctcttc cgcttcctcg ctcactgact cgctgcgctc ggtcgttcgg ctgcggcgag
5881 cggtatcagc tcactcaaag gcggtaatac ggttatccac agaatcaggg gataacgcag
5941 gaaagaacat gtgagcaaaa ggccagcaaa aggccaggaa ccgtaaaaag gccgcgttgc
6001 tggcgttttt ccataggctc cgcccccctg acgagcatca caaaaatcga cgctcaagtc
6061 agaggtggcg aaacccgaca ggactataaa gataccaggc gtttccccct ggaagctccc
6121 tcgtgcgctc tcctgttccg accctgccgc ttaccggata cctgtccgcc tttctccctt
6181 cggaagcgt ggcgctttct catagctcac gctgtaggta tctcagttcg gtgtaggtcg
6241 ttcgctccaa gctgggctgt gtgcacgaac cccccgttca gcccgaccgc tgcgccttat
6301 ccggtaacta tcgtcttgag tccaacccgg taagacacga cttatcgcca ctggcagcag
6361 ccactggtaa caggattagc agagcgaggt atgtaggcgg tgctacagag ttcttgaagt
6421 ggtggcctaa ctacggctac actagaagaa cagtatttgg tatctgcgct ctgctgaagc
6481 cagttacctt cggaaaaaga gttggtagct cttgatccgg caaacaaacc accgctggta
6541 gcggtggttt ttttgttgc aagcagcaga ttacgcgcag aaaaaaagga tctcaagaag
6601 atcctttgat cttttctacg ggtctgacg ctcagtggaa cgaaaactca cgttaaggga
6661 ttttggtcat gagattatca aaaaggatct tcacctagat ccttttaaat taaaaatgaa
6721 gttttaaatc aatctaaagt atatatgagt aaacttggtc tgacagttac caatgcttaa
6781 tcagtgaggc acctatctca gcgatctgtc tatttcgttc atccatagtt gcctgactcc
6841 ccgtcgtgta gataactacg atacgggagg gcttaccatc tggccccagt gctgcaatga
6901 taccgcgaga cccacgctca ccggctccag atttatcagc aataaaccag ccagccggaa
6961 gggccgagcg cagaagtggt cctgcaactt tatccgcctc catccagtct attaattgtt
7021 gccgggaagc tagagtaagt agttcgccag ttaatagttt gcgcaacgtt gttgccattg
7081 ctacaggcat cgtggtgtca cgctcgtcgt ttggtatggc ttcattcagc tccggttccc
7141 aacgatcaag gcgagttaca tgatccccca tgttgtgcaa aaaagcggtt agctccttcg
7201 gtcctccgat cgttgtcaga agtaagttgg ccgcagtgtt atcactcatg gttatggcag
7261 cactgcataa ttctcttact gtcatgccat ccgtaagatg cttttctgtg actggtgagt
7321 actcaaccaa gtcattctga gaatagtgta tgcggcgacc gagttgctct tgcccggcgt
7381 caatacggga taataccgcg ccacatagca gaactttaaa agtgctcatc attggaaaac
7441 gttcttcggg gcgaaaactc tcaaggatct taccgctgtt gagatccagt tcgatgtaac
7501 ccactcgtgc acccaactga tcttcagcat cttttacttt caccagcgtt tctgggtgag
7561 caaaaacagg aaggcaaaat gccgcaaaaa agggaataag ggcgacacgg aaatgttgaa
7621 tactcatact cttcctttt caatattatt gaagcattta tcagggttat tgtctcatga
7681 gcggatacat atttgaatgt atttagaaaa ataaacaaat aggggttccg cgcacatttc
7741 cccgaaaagt gccacctgac gtctaagaaa ccattattat catgacatta acctataaaa
7801 ataggcgtat cacgaggccc tttcgtc    (SEQ ID NO:8)
```

```
ATGCAGATTGAGCTGAGCACCTGCTTCTTCCTGTGCCTGCTGAGGTTCTGCTTCTCTGCCACCAGGAGATAC
TACCTGGGGGCTGTGGAGCTTTCTTGGGACTACATGCAGTCTGACCTGGGGAGCTGCCTGTGGATGCCAGG
TTCCCACCCAGAGTGCCCAAATCCTTCCCATTCAACACCTCTGTGGTCTACAAGAAGACCCTCTTTGTGGAG
TTCACTGACCACCTGTTCAACATTGCCAAACCCAGGCCACCCTGGATGGGACTCCTGGGACCCACCATTCAG
GCTGAGGTGTATGACACTGTGGTCATCACCCTCAAGAACATGGCCTCCCACCCTGTGAGCCTGCATGCTGTG
GGGGTCAGCTACTGGAAGGCCTCTGAGGGGGCTGAGTATGATGACCAGACCTCCCAGAGGGAGAAGGAGGAT
GACAAAGTGTTCCCTGGGGGCAGCCACACCTATGTGTGGCAGGTCCTCAAGGAGAATGGCCCCATGGCCTCT
GACCCACTCTGCCTGACCTACTCCTACCTTTCTCATGTGGACCTGGTCAAGGACCTCAACTCTGGACTGATT
GGGGCCCTGCTGGTGTGCAGGGAGGGCTCCCTGGCCAAAGAGAAGACCCAGACCCTGCACAAGTTCATTCTC
CTGTTTGCTGTCTTTGATGAGGGCAAGAGCTGGCACTCTGAAACCAAGAACTCCCTGATGCAGGACAGGGAT
GCTGCCTCTGCCAGGGCCTGGCCCAAGATGCACACTGTGAATGGCTATGTGAACAGGAGCCTGCCTGGACTC
ATTGGCTGCCACAGGAAATCTGTCTACTGGCATGTGATTGGCATGGGGACAACCCCTGAGGTGCACTCCATT
TTCCTGGAGGGCCACACCTTCCTGGTCAGGAACCACAGACAGGCCAGCCTGGAGATCAGCCCCATCACCTTC
CTCACTGCCCAGACCCTGCTGATGGACCTCGGACAGTTCCTGCTGTTCTGCCACATCAGCTCCCACCAGCAT
GATGGCATGGAGGCCTATGTCAAGGTGGACAGCTGCCCTGAGGAGCCACAGCTCAGGATGAAGAACAATGAG
GAGGCTGAGGACTATGATGATGACCTGACTGACTCTGAGATGGATGTGGTCCGCTTTGATGATGACAACAGC
CCATCCTTCATTCAGATCAGGTCTGTGGCCAAGAAACACCCCAAGACCTGGGTGCACTACATTGCTGCTGAG
GAGGAGGACTGGGACTATGCCCCACTGGTCCTGGCCCCTGATGACAGGAGCTACAAGAGCCAGTACCTCAAC
AATGGCCCACAGAGGATTGGACGCAAGTACAAGAAAGTCAGGTTCATGGCCTACACTGATGAAACCTTCAAG
ACCAGGGAGGCCATTCAGCATGAGTCTGGCATCCTGGGCCCACTCCTGTATGGGGAGGTGGGGGACACCCTG
CTCATCATCTTCAAGAACCAGGCCTCCAGGCCCTACAACATCTACCCACATGGCATCACTGATGTCAGGCCC
CTGTACAGCCGCAGGCTGCCAAAGGGGGTGAAACACCTCAAGGACTTCCCCATTCTGCCTGGGGAGATCTTC
AAGTACAAGTGGACTGTCACTGTGGAGGATGGACCAACCAAATCTGACCCCAGGTGCCTCACCAGATACTAC
TCCAGCTTTGTGAACATGGAGAGGGACCTGGCCTCTGGCCTGATTGGCCCACTGCTCATCTGCTACAAGGAG
TCTGTGGACCAGAGGGGAAACCAGATCATGTCTGACAAGAGGAATGTGATTCTGTTCTCTGTCTTTGATGAG
AACAGGAGCTGGTACCTGACTGAGAACATTCAGCGCTTCCTGCCCAACCCTGCTGGGGTGCAGCTGGAGGAC
CCTGAGTTCCAGGCCAGCAACATCATGCACTCCATCAATGGCTATGTGTTTGACAGCCTCCAGCTTTCTGTC
TGCCTGCATGAGGTGGCCTACTGGTACATTCTTTCTATTGGGGCCCAGACTGACTTCCTTTCTGTCTTCTTC
TCTGGCTACACCTTCAAACACAAGATGGTGTATGAGGACACCCTGACCCTCTTCCCATTCTCTGGGGAGACT
GTGTTCATGAGCATGGAGAACCCTGGCCTGTGGATTCTGGGATGCCACAACTCTGACTTCCGCAACAGGGGC
ATGACTGCCCTGCTCAAAGTCTCCTCCTGTGACAAGAACACTGGGGACTACTATGAGGACAGCTATGAGGAC
ATCTCTGCCTACCTGCTCAGCAAGAACAATGCCATTGAGCCCAGGGAGATCACCAGGACCACCCTCCAGTCT
GACCAGGAGGAGATTGACTATGATGACACCATTTCTGTGGAGATGAAGAAAGAGGACTTTGACATCTATGAC
GAGGACGAGAACCAGAGCCCAAGGAGCTTCCAGAAGAAGACCAGGCACTACTTCATTGCTGCTGTGGAGCGC
CTGTGGGACTATGGCATGAGCTCCAGCCCCATGTCCTCAGGAACAGGGCCCAGTCTGGCTCTGTGCCACAG
TTCAAGAAAGTGGTCTTCCAAGAGTTCACTGATGGCAGCTTCACCCAGCCCCTGTACAGAGGGGAGCTGAAT
GAGCACCTGGGACTCCTGGGCCCATACATCAGGGCTGAGGTGGAGGACAACATCATGGTGACCTTCCGCAAC
CAGGCCTCCAGGCCCTACAGCTTCTACAGCTCCCTCATCAGCTATGAGGAGGACCAGAGGCAGGGGCTGAG
CCACGCAAGAACTTTGTGAAACCCAATGAAACCAAGACCTACTTCTGGAAAGTCCAGCACCACATGGCCCCC
```

```
ACCAAGGATGAGTTTGACTGCAAGGCCTGGGCCTACTTCTCTGATGTGGACCTGGAGAAGGATGTGCACTCT
GGCCTGATTGGCCCACTCCTGGTCTGCCACACCAACACCCTGAACCCTGCCCATGGAAGGCAAGTGACTGTG
CAGGAGTTTGCCCTCTTCTTCACCATCTTTGATGAAACCAAGAGCTGGTACTTCACTGAGAACATGGAGCGC
AACTGCAGGGCCCCATGCAACATTCAGATGGAGGACCCCACCTTCAAAGAGAACTACCGCTTCCATGCCATC
AATGGCTACATCATGGACACCCTGCCTGGGCTTGTCATGGCCCAGGACCAGAGGATCAGGTGGTACCTGCTT
TCTATGGGCTCCAATGAGAACATTCACTCCATCCACTTCTCTGGGCATGTCTTCACTGTGCGCAAGAAGGAG
GAGTACAAGATGGCCCTGTACAACCTCTACCCTGGGGTCTTTGAGACTGTGGAGATGCTGCCCTCCAAAGCT
GGCATCTGGAGGGTGGAGTGCCTCATTGGGGAGCACCTGCATGCTGGCATGAGCACCCTGTTCCTGGTCTAC
AGCAACAAGTGCCAGACCCCCTGGGAATGGCCTCTGGCCACATCAGGGACTTCCAGATCACTGCCTCTGGC
CAGTATGGCCAGTGGGCCCCCAAGCTGGCCAGGCTCCACTACTCTGGATCCATCAATGCCTGGAGCACCAAG
GAGCCATTCAGCTGGATCAAAGTGGACCTGCTGGCCCCCATGATCATCCATGGCATCAAGACCCAGGGGGCC
AGGCAGAAGTTCTCCAGCCTGTACATCAGCCAGTTCATCATCATGTACAGCCTGGATGGCAAGAAATGGCAG
ACCTACAGAGGCAACTCCACTGGAACACTCATGGTCTTCTTTGGCAATGTGGACAGCTCTGGCATCAAGCAC
AACATCTTCAACCCCCCAATCATCGCCAGATACATCAGGCTGCACCCCACCCACTACAGCATCCGCAGCACC
CTCAGGATGGAGCTGATGGGCTGTGACCTGAACTCCTGCAGCATGCCCCTGGGCATGGAGAGCAAGGCCATT
TCTGATGCCCAGATCACTGCCTCCAGCTACTTCACCAACATGTTTGCCACCTGGAGCCCAAGCAAGGCCAGG
CTGCACCTCCAGGGAAGGAGCAATGCCTGGAGGCCCCAGGTCAACAACCCAAAGGAGTGGCTGCAGGTGGAC
TTCCAGAAGACCATGAAGGTCACTGGGGTGACCACCCAGGGGGTCAAGAGCCTGCTCACCAGCATGTATGTG
AAGGAGTTCCTGATCAGCTCCAGCCAGGATGGCCACCAGTGGACCCTCTTCTTCCAGAATGGCAAGGTCAAG
GTGTTCCAGGGCAACCAGGACAGCTTCACCCCTGTGGTGAACAGCCTGGACCCCCCCTCCTGACCAGATAC
CTGAGGATTCACCCCAGAGCTGGGTCCACCAGATTGCCCTGAGGATGGAGGTCCTGGGATGTGAGGCCCAG
GACCTGTACTGA     (SEQ ID NO:9)
```

MQIELSTCFFLCLLRFCFSATRRYYLGAVELSWDYMQSDLGELPVDARFPPRVPKSFPFNTSVVYKK
TLFVEFTDHLFNIAKPRPPWMGLLGPTIQAEVYDTVVITLKNMASHPVSLHAVGVSYWKASEGAEYD
DQTSQREKEDDKVFPGGSHTYVWQVLKENGPMASDPLCLTYSLSHVDLVKDLNSGLIGALLVCREG
SLAKEKTQTLHKFILLFAVFDEGKSWHSETKNSLMQDRDAASARAWPKMHTVNGYVNRSLPGLIGCH
RKSVYWHVIGMGTTPEVHSIFLEGHTFLVRNHRQASLEISPITFLTAQTLLMDLGQFLLFCHISSHQ
HDGMEAYVKVDSCPEEPQLRMKNNEEAEDYDDDLTDSEMDVVRFDDDNSPSFIQIRSVAKKHPKTWV
HYIAAEEEDWDYAPLVLAPDDRSYKSQYLNNGPQRIGRKYKKVRFMAYTDETFKTREAIQHESGILG
PLLYGEVGDTLLIIFKNQASRPYNIYPHGITDVRPLYSRRLPKGVKHLKDFPILPGEIFKYKWTVTV
EDGPTKSDPRCLTRYYSSFVNMERDLASGLIGPLLICYKESVDQRGNQIMSDKRNVILFSVFDENRS
WYLTENIQRFLPNPAGVQLEDPEFQASNIMHSINGYVFDSLQLSVCLHEVAYWYILSIGAQTDFLSV
FFSGYTFKHKMVYEDTLTLFPFSGETVFMSMENPGLWILGCHNSDFRNRGMTALLKVSSCDKNTGDY
YEDSYEDISAYLLSKNNAIEPREITRTTLQSDQEEIDYDDTISVEMKKEDFDIYDEDENQSPRSFQK
KTRHYFIAAVERLWDYGMSSSPHVLRNRAQSGSVPQFKKVVFQEFTDGSFTQPLYRGELNEHLGLLG
PYIRAEVEDNIMVTFRNQASRPYSFYSSLISYEEDQRQGAEPRKNFVKPNETKTYFWKVQHHMAPTK
DEFDCKAWAYFSDVDLEKDVHSGLIGPLLVCHTNTLNPAHGRQVTQEFALFFTIFDETKSWYFTEN
MERNCRAPCNIQMEDPTFKENYRFHAINGYIMDTLPGLVMAQDQRIRWYLLSMGSNENIHSIHFSGH
VFTVRKKEEYKMALYNLYPGVFETVEMLPSKAGIWRVECLIGEHLHAGMSTLFLVYSNKCQTPLGMA
SGHIRDFQITASGQYGQWAPKLARLHYSGSINAWSTKEPFSWIKVDLLAPMIIHGIKTQGARQKFSS
LYISQFIIMYSLDGKKWQTYRGNSTGTLMVFFGNVDSSGIKHNIFNPPIIARYIRLHPTHYSIRSTL
RMELMGCDLNSCSMPLGMESKAISDAQITASSYFTNMFATWSPSKARLHLQGRSNAWRPQVNNPKEW
LQVDFQKTMKVTGVTTQGVKSLLTSMYVKEFLISSSQDGHQWTLFFQNGKVKVFQGNQDSFTPVVNS
LDPPLLTRYLRIHPQSWVHQIALRMEVLGCEAQDLY    (SEQ ID NO:10)

ATGCAGATTGAGCTGAGCACCTGCTTCTTCCTGTGCCTGCTGAGGTTCTGCTTCTCTGCCACCAGG
AGATACTACCTGGGGGCTGTGGAGCTTTCTTGGGACTACATGCAGTCTGACCTGGGGGAGCTGCCT
GTGGATGCCAGGTTCCCACCCAGAGTGCCCAAATCCTTCCCATTCAACACCTCTGTGGTCTACAAG
AAGACCCTCTTTGTGGAGTTCACTGACCACCTGTTCAACATTGCCAAACCCAGGCCACCCTGGATG
GGACTCCTGGGACCCACCATTCAGGCTGAGGTGTATGACACTGTGGTCATCACCCTCAAGAACATG
GCCTCCCACCCTGTGAGCCTGCATGCTGTGGGGGTCAGCTACTGGAAGGCCTCTGAGGGGCTGAG
TATGATGACCAGACCTCCCAGAGGGAGAAGGAGGATGACAAAGTGTTCCCTGGGGGCAGCCACACC
TATGTGTGGCAGGTCCTCAAGGAGAATGGCCCCATGGCCTCTGACCCACTCTGCCTGACCTACTCC
TACCTTTCTCATGTGGACCTGGTCAAGGACCTCAACTCTGGACTGATTGGGGCCCTGCTGGTGTGC
AGGGAGGGCTCCCTGGCCAAAGAGAAGACCCAGACCCTGCACAAGTTCATTCTCCTGTTTGCTGTC
TTTGATGAGGGCAAGAGCTGGCACTCTGAAACCAAGAACTCCCTGATGCAGGACAGGGATGCTGCC
TCTGCCAGGGCCTGGCCCAAGATGCACACTGTGAATGGCTATGTGAACAGGAGCCTGCCTGGACTC
ATTGGCTGCCACAGGAAATCTGTCTACTGGCATGTGATTGGCATGGGGACAACCCCTGAGGTGCAC
TCCATTTTCCTGGAGGGCCACACCTTCCTGGTCAGGAACCACAGACAGGCCAGCCTGGAGATCAGC
CCCATCACCTTCCTCACTGCCCAGACCCTGCTGATGGACCTCGGACAGTTCCTGCTGTTCTGCCAC
ATCAGCTCCCACCAGCATGATGGCATGGAGGCCTATGTCAAGGTGGACAGCTGCCCTGAGGAGCCA
CAGCTCAGGATGAAGAACAATGAGGAGGCTGAGGACTATGATGATGACCTGACTGACTCTGAGATG
GATGTGGTCCGCTTTGATGATGACAACAGCCCATCCTTCATTCAGATCAGGTCTGTGGCCAAGAAA
CACCCCAAGACCTGGGTGCACTACATTGCTGCTGAGGAGGAGGACTGGGACTATGCCCCACTGGTC
CTGGCCCCTGATGACAGGAGCTACAAGAGCCAGTACCTCAACAATGGCCCACAGAGGATTGGACGC
AAGTACAAGAAAGTCAGGTTCATGGCCTACACTGATGAAACCTTCAAGACCAGGGAGGCCATTCAG
CATGAGTCTGGCATCCTGGGCCCACTCCTGTATGGGGAGGTGGGGGACACCCTGCTCATCATCTTC
AAGAACCAGGCCTCCAGGCCCTACAACATCTACCCACATGGCATCACTGATGTCAGGCCCCTGTAC
AGCCGCAGGCTGCCAAAGGGGGTGAAACACCTCAAGGACTTCCCCATTCTGCCTGGGGAGATCTTC
AAGTACAAGTGGACTGTCACTGTGGAGGATGGACCAACCAAATCTGACCCCAGGTGCCTCACCAGA
TACTACTCCAGCTTTGTGAACATGGAGAGGGACCTGGCCTCTGGCCTGATTGGCCCACTGCTCATC
TGCTACAAGGAGTCTGTGGACCAGAGGGGAAACCAGATCATGTCTGACAAGAGGAATGTGATTCTG
TTCTCTGTCTTTGATGAGAACAGGAGCTGGTACCTGACTGAGAACATTCAGCGCTTCCTGCCCAAC
CCTGCTGGGGTGCAGCTGGAGGACCCTGAGTTCCAGGCCAGCAACATCATGCACTCCATCAATGGC
TATGTGTTTGACAGCCTCCAGCTTTCTGTCTGCCTGCATGAGGTGGCCTACTGGTACATTCTTTCT
ATTGGGGCCCAGACTGACTTCCTTTCTGTCTTCTTCTCTGGCTACACCTTCAAACACAAGATGGTG
TATGAGGACACCCTGACCCTCTTCCCATTCTCTGGGGAGACTGTGTTCATGAGCATGGAGAACCCT
GGCCTGTGGATTCTGGGATGCCACAACTCTGACTTCCGCAACAGGGGCATGACTGCCCTGCTCAAA
GTCTCCTCCTGTGACAAGAACACTGGGGACTACTATGAGGACAGCTATGAGGACATCTCTGCCTAC
CTGCTCAGCAAGAACAATGCCATTGAGCCCAGGAGCTTCAGCCAGAATTCCAGACACCCCAGCACC
AGGGAGATCACCAGGACCACCCTCCAGTCTGACCAGGAGGAGATTGACTATGATGACACCATTTCT
GTGGAGATGAAGAAAGAGGACTTTGACATCTATGACGAGGACGAGAACCAGAGCCCAAGGAGCTTC (Continued)

Figure 10A

```
CAGAAGAAGACCAGGCACTACTTCATTGCTGCTGTGGAGCGCCTGTGGGACTATGGCATGAGCTCC
AGCCCCCATGTCCTCAGGAACAGGGCCCAGTCTGGCTCTGTGCCACAGTTCAAGAAAGTGGTCTTC
CAAGAGTTCACTGATGGCAGCTTCACCCAGCCCCTGTACAGAGGGGAGCTGAATGAGCACCTGGGA
CTCCTGGGCCCATACATCAGGGCTGAGGTGGAGGACAACATCATGGTGACCTTCCGCAACCAGGCC
TCCAGGCCCTACAGCTTCTACAGCTCCCTCATCAGCTATGAGGAGGACCAGAGGCAGGGGGCTGAG
CCACGCAAGAACTTTGTGAAACCCAATGAAACCAAGACCTACTTCTGGAAAGTCCAGCACCACATG
GCCCCCACCAAGGATGAGTTTGACTGCAAGGCCTGGGCCTACTTCTCTGATGTGGACCTGGAGAAG
GATGTGCACTCTGGCCTGATTGGCCCACTCCTGGTCTGCCACACCAACACCCTGAACCCTGCCCAT
GGAAGGCAAGTGACTGTGCAGGAGTTTGCCCTCTTCTTCACCATCTTTGATGAAACCAAGAGCTGG
TACTTCACTGAGAACATGGAGCGCAACTGCAGGGCCCCATGCAACATTCAGATGGAGGACCCCACC
TTCAAAGAGAACTACCGCTTCCATGCCATCAATGGCTACATCATGGACACCCTGCCTGGGCTTGTC
ATGGCCCAGGACCAGAGGATCAGGTGGTACCTGCTTTCTATGGGCTCCAATGAGAACATTCACTCC
ATCCACTTCTCTGGGCATGTCTTCACTGTGCGCAAGAAGGAGGAGTACAAGATGGCCCTGTACAAC
CTCTACCCTGGGGTCTTTGAGACTGTGGAGATGCTGCCCTCCAAAGCTGGCATCTGGAGGGTGGAG
TGCCTCATTGGGGAGCACCTGCATGCTGGCATGAGCACCCTGTTCCTGGTCTACAGCAACAAGTGC
CAGACCCCCCTGGGAATGGCCTCTGGCCACATCAGGGACTTCCAGATCACTGCCTCTGGCCAGTAT
GGCCAGTGGGCCCCCAAGCTGGCCAGGCTCCACTACTCTGGATCCATCAATGCCTGGAGCACCAAG
GAGCCATTCAGCTGGATCAAAGTGGACCTGCTGGCCCCATGATCATCCATGGCATCAAGACCCAG
GGGGCCAGGCAGAAGTTCTCCAGCCTGTACATCAGCCAGTTCATCATCATGTACAGCCTGGATGGC
AAGAAATGGCAGACCTACAGAGGCAACTCCACTGGAACACTCATGGTCTTCTTTGGCAATGTGGAC
AGCTCTGGCATCAAGCACAACATCTTCAACCCCCCAATCATCGCCAGATACATCAGGCTGCACCCC
ACCCACTACAGCATCCGCAGCACCCTCAGGATGGAGCTGATGGGCTGTGACCTGAACTCCTGCAGC
ATGCCCCTGGGCATGGAGAGCAAGGCCATTTCTGATGCCCAGATCACTGCCTCCAGCTACTTCACC
AACATGTTTGCCACCTGGAGCCCAAGCAAGGCCAGGCTGCACCTCCAGGGAAGGAGCAATGCCTGG
AGGCCCCAGGTCAACAACCCAAAGGAGTGGCTGCAGGTGGACTTCCAGAAGACCATGAAGGTCACT
GGGGTGACCACCCAGGGGGTCAAGAGCCTGCTCACCAGCATGTATGTGAAGGAGTTCCTGATCAGC
TCCAGCCAGGATGGCCACCAGTGGACCCTCTTCTTCCAGAATGGCAAGGTCAAGGTGTTCCAGGGC
AACCAGGACAGCTTCACCCCTGTGGTGAACAGCCTGGACCCCCCCTCCTGACCAGATACCTGAGG
ATTCACCCCAGAGCTGGGTCCACCAGATTGCCCTGAGGATGGAGGTCCTGGGATGTGAGGCCCAG
GACCTGTACTGA  (SEQ ID NO:11)
```

MQIELSTCFFLCLLRFCFSATRRYYLGAVELSWDYMQSDLGELPVDARFPPRVPKSFPFNTSVVYKK
TLFVEFTDRLFNIAKPRFPWMGLLGPTIQAEVYDTVVITLKNMASHPVSLHAVGVSYWKASEGAEYD
DQTSQREKEDDKVFPGGSHTYVWQVLKENGPMASDPLCLTYSYLSHVDLVKDLNSGLIGALLVCREG
SLAKEKTQTLHKFILLFAVFDEGKSWHSETKNSLMQDRDAASARAWPKMHTVNGYVNRSLPGLIGCH
RKSVYWHVIGMGTTPEVHSIFLEGHTFLVRNHRQASLEISPITFLTAQTLLMDLGQFLLFCHISSHQ
HDGMEAYVKVDSCPEEPQLRMKNNEEAEDYDDDLTDSEMDVVRFDDDNSPSFIQIRSVAKKHPKTWV
HYIAAEEEDWDYAPLVLAPDDRSYKSQYLNNGPQRIGRKYKKVRFMAYTDETFKTREAIQHESGILG
PLLYGEVGDTLLIIFKNQASRPYNIYPHGITDVRPLYSRRLPKGVKHLKDFPILPGEIFKYKWTVTV
EDGPTKSDPRCLTRYYSSFVNMERDLASGLIGPLLICYKESVDQRGNQIMSDKRNVILFSVFDENRS
WYLTENIQRFLPNPAGVQLEDPEFQASNIMHSINGYVFDSLQLSVCLHEVAYWYILSIGAQTDFLSV
FFSGYTFKHKMVYEDTLTLFPFSGETVFMSMENPGLWILGCHNSDFRNRGMTALLKVSSCDKNTGDY
YEDSYEDISAYLLSKNNAIEPRSFSQNSRHPSTREITRTTLQSDQEEIDYDDTISVEMKKEDFDIYD
EDENQSPRSFQKKTRHYFIAAVERLWDYGMSSSPHVLRNRAQSGSVPQFKKVVFQEFTDGSFTQPLY
RGELNEHLGLLGPYIRAEVEDNIMVTFRNQASRPYSFYSSLISYEEDQRQGAEPRKNFVKPNETKTY
FWKVQHHMAPTKDEFDCKAWAYFSDVDLEKDVHSGLIGPLLVCHTNTLNPAHGRQVTQEFALFFTI
FDETKSWYFTENMERNCRAPCNIQMEDPTFKENYRFHAINGYIMDTLPGLVMAQDQRIRWYLLSMGS
NENIHSIHFSGHVFTVRKKEEYKMALYNLYPGVFETVEMLPSKAGIWRVECLIGEHLHAGMSTLFLV
YSNKCQTPLGMASGHIRDFQITASGQYGQWAPKLARLHYSGSINAWSTKEPFSWIKVDLLAPMIIHG
IKTQGARQK

CS01-FL-NA

```
ATGCAGATTGAGCTGTCCACCTGCTTCTTTCTGTGCCTGCTGAGATTCTGCTTCTCTGCCACCAGG
AGATACTACCTGGGGGCTGTGGAACTTTCTTGGGACTACATGCAGTCTGACCTGGGAGAGCTGCCT
GTGGATGCCAGGTTCCCACCCAGAGTGCCCAAGTCCTTCCCATTCAACACCTCTGTGGTCTACAAG
AAGACACTCTTTGTGGAATTCACTGACCACCTGTTCAACATTGCAAAACCCAGACCACCCTGGATG
GGACTCCTGGGACCCACCATTCAGGCTGAGGTGTATGACACTGTGGTCATCACCCTCAAGAACATG
GCATCCCACCCTGTGTCTCTGCATGCTGTGGGAGTCTCATACTGGAAAGCCTCTGAAGGGGCTGAG
TATGATGACCAGACATCCCAGAGAGAGAAAGAGGATGACAAGGTGTTCCCTGGGGGATCTCACACC
TATGTGTGGCAAGTCCTCAAGGAGAATGGACCCATGGCATCTGACCCACTCTGCCTGACATACTCC
TACCTTTCTCATGTGGACCTGGTCAAGGACCTCAACTCTGGACTGATTGGGGCACTGCTGGTGTGC
AGGGAAGGATCCCTGGCCAAGGAGAAAACCCAGACACTGCACAAGTTCATTCTCCTGTTTGCTGTC
TTTGATGAGGGCAAGTCTTGGCACTCTGAAACAAAGAACTCCCTGATGCAAGACAGGGATGCTGCC
TCTGCCAGGGCATGGCCCAAGATGCACACTGTGAATGGCTATGTGAACAGATCACTGCCTGGACTC
ATTGGCTGCCACAGGAAATCTGTCTACTGGCATGTGATTGGCATGGGGACAACCCCTGAAGTGCAC
TCCATTTTCCTGGAGGGACACACCTTCCTGGTCAGGAACCACAGACAAGCCTCTCTGGAGATCTCT
CCCATCACCTTCCTCACTGCACAGACACTGCTGATGGACCTTGGACAGTTCCTGCTGTTCTGCCAC
ATCTCTTCCCACCAGCATGATGGCATGGAAGCCTATGTCAAGGTGGACTCATGCCCTGAGGAACCA
CAGCTCAGGATGAAGAACAATGAGGAGGCTGAGGACTATGATGATGACCTGACTGACTCTGAGATG
GATGTGGTCAGATTTGATGATGACAACTCTCCATCCTTCATTCAGATCAGGTCTGTGGCAAAGAAA
CACCCCAAGACATGGGTGCACTACATTGCTGCTGAGGAAGAGGACTGGGACTATGCACCACTGGTC
CTGGCCCCTGATGACAGGAGCTACAAGTCTCAGTACCTCAACAATGGCCCACAAAGAATTGGAAGA
AAGTACAAGAAAGTCAGATTCATGGCCTACACTGATGAAACCTTCAAGACAAGAGAAGCCATTCAG
CATGAGTCTGGCATTCTGGGACCACTCCTGTATGGGGAAGTGGGAGACACCCTGCTCATCATCTTC
AAGAACCAGGCCTCCAGGCCCTACAACATCTACCCACATGGCATCACTGATGTCAGGCCCCTGTAC
AGCAGGAGACTGCCAAAAGGGGTGAAACACCTCAAGGACTTCCCCATTCTGCCTGGAGAGATCTTC
AAGTACAAGTGGACTGTCACTGTGGAGGATGGACCAACAAAGTCTGACCCCAGGTGCCTCACCAGA
TACTACTCCTCTTTTGTGAACATGGAGAGAGACCTGGCATCTGGACTGATTGGACCACTGCTCATC
TGCTACAAGGAGTCTGTGGACCAGAGAGGCAACCAGATCATGTCTGACAAGAGAAATGTGATTCTG
TTCTCTGTCTTTGATGAGAACAGATCATGGTACCTGACTGAGAACATTCAGAGATTCCTGCCCAAC
CCTGCTGGGGTGCAACTGGAAGACCCTGAGTTCCAGGCAAGCAACATCATGCACTCCATCAATGGC
TATGTGTTTGACTCTCTCCAGCTTTCTGTCTGCCTGCATGAGGTGGCCTACTGGTACATTCTTTCT
ATTGGGGCACAAACTGACTTCCTTTCTGTCTTCTTCTCTGGATACACCTTCAAGCACAAGATGGTG
TATGAGGACACCCTGACACTCTTCCCATTCTCTGGGGAAACTGTGTTCATGAGCATGGAGAACCCT
GGACTGTGGATTCTGGGATGCCACAACTCTGACTTCAGAAACAGGGGAATGACTGCACTGCTCAAA
GTCTCCTCCTGTGACAAGAACACTGGGGACTACTATGAGGACTCTTATGAGGACATCTCTGCCTAC
CTGCTCAGCAAGAACAATGCCATTGAGCCCAGAAGCTTCTCTCAGAATCCACCTGTCCTGAAGAGA
CACCAGAGAGAGATCACCAGGACAACCCTCCAGTCTGACCAGGAAGAGATTGACTATGATGACACC
ATTTCTGTGGAGATGAAGAAGGAGGACTTTGACATCTATGATGAGGACGAGAACCAGTCTCCAAGA
TCATTCCAGAAGAAGACAAGACACTACTTCATTGCTGCTGTGGAAAGACTGTGGGACTATGGCATG
TCTTCCTCTCCCCATGTCCTCAGGAACAGGGCACAGTCTGGCTCTGTGCCACAGTTCAAGAAAGTG
GTCTTCCAGGAGTTCACTGATGGCTCATTCACCCAGCCCCTGTACAGAGGGGAACTGAATGAGCAC
```

```
CTGGGACTCCTGGGACCATACATCAGGGCTGAGGTGGAAGACAACATCATGGTGACATTCAGAAAC
CAGGCCTCCAGGCCCTACAGCTTCTACTCTTCCCTCATCAGCTATGAGGAAGACCAGAGACAAGGG
GCTGAGCCAAGAAAGAACTTTGTGAAACCCAATGAAACCAAGACCTACTTCTGGAAAGTCCAGCAC
CACATGGCACCCACCAAGGATGAGTTTGACTGCAAGGCCTGGGCATACTTCTCTGATGTGGACCTG
GAGAAAGATGTGCACTCTGGCCTGATTGGCCCACTCCTGGTCTGCCACACCAACACCCTGAACCCT
GCACATGGAAGGCAAGTGACTGTGCAGGAGTTTGCCCTCTTCTTCACCATCTTTGATGAAACCAAG
TCATGGTACTTCACTGAGAACATGGAGAGAAACTGCAGAGCACCATGCAACATTCAGATGGAAGAC
CCCACCTTCAAGGAGAACTACAGGTTCCATGCCATCAATGGCTACATCATGGACACCCTGCCTGGG
CTTGTCATGGCACAGGACCAGAGAATCAGATGGTACCTGCTTTCTATGGGATCCAATGAGAACATT
CACTCCATCCACTTCTCTGGGCATGTCTTCACTGTGAGAAAGAAGGAGGAATACAAGATGGCCCTG
TACAACCTCTACCCTGGGGTCTTTGAGACTGTGGAGATGCTGCCCTCCAAAGCTGGCATCTGGAGG
GTGGAATGCCTCATTGGGGAGCACCTGCATGCTGGCATGTCAACCCTGTTCCTGGTCTACAGCAAC
AAGTGCCAGACACCCCTGGGAATGGCCTCTGGCCACATCAGGGACTTCCAGATCACTGCCTCTGGC
CAGTATGGCCAGTGGGCACCCAAACTGGCCAGGCTCCACTACTCTGGCTCCATCAATGCATGGTCA
ACCAAGGAGCCATTCTCTTGGATCAAGGTGGACCTGCTGGCACCCATGATCATTCATGGCATCAAG
ACACAGGGGGCAAGACAGAAATTCTCCTCTCTGTACATCTCACAGTTCATCATCATGTACTCTCTG
GATGGCAAGAAGTGGCAGACATACAGAGGCAACTCCACTGGCACCCTCATGGTCTTCTTTGGCAAT
GTGGACAGCTCTGGCATCAAGCACAACATCTTCAACCCTCCCATCATTGCCAGATACATCAGGCTG
CACCCCACCCACTACTCAATCAGATCAACCCTCAGGATGGAACTGATGGGATGTGACCTGAACTCC
TGCTCAATGCCCCTGGGAATGGAGAGCAAGGCCATTTCTGATGCCCAGATCACTGCATCCTCTTAC
TTCACCAACATGTTTGCCACCTGGTCACCATCAAAAGCCAGGCTGCACCTCCAGGGAAGAAGCAAT
GCCTGGAGACCCCAGGTCAACAACCCAAAGGAATGGCTGCAAGTGGACTTCCAGAAGACAATGAAA
GTCACTGGGGTGACAACCCAGGGGGTCAAGTCTCTGCTCACCTCAATGTATGTGAAGGAGTTCCTG
ATCTCTTCCTCACAGGATGGCCACCAGTGGACACTCTTCTTCCAGAATGGCAAAGTCAAGGTGTTC
CAGGGCAACCAGGACTCTTTCACACCTGTGGTGAACTCACTGGACCCCCCCTCCTGACAAGATAC
CTGAGAATTCACCCCAGTCTTGGGTCCACCAGATTGCCCTGAGAATGGAAGTCCTGGGATGTGAG
GCACAAGACCTGTACTGA     (SEQ ID NO:13)
```

ATGCAGATCGAACTGAGCACTTGCTTCTTCCTGTGTCTCCTGCGCTTTTGCTTCTCCGCCACAAGG
AGATACTATCTCGGTGCCGTGGAGCTCAGCTGGGACTACATGCAGAGCGACTTGGGTGAACTGCCT
GTGGACGCCAGGTTTCCACCCCGCGTGCCCAAGAGTTTCCCGTTCAACACCAGTGTCGTGTACAAG
AAAACCCTCTTCGTGGAATTCACCGACCACCTGTTCAACATCGCCAAACCGCGCCCTCCCTGGATG
GGGCTGCTCGGCCCGACGATCCAGGCTGAGGTCTATGACACGGTGGTGATTACCCTCAAGAACATG
GCTAGCCACCCGGTGAGCCTGCACGCCGTGGGCGTGTCCTATTGGAAAGCGTCCGAGGGTGCGGAG
TACGATGACCAGACTTCACAGCGGGAGAAGGAAGACGACAAAGTGTTCCCCGGGGGTTCCACACC
TATGTCTGGCAGGTCCTGAAGGAGAATGGTCCTATGGCCTCCGACCCATTGTGCCTCACCTACTCT
TACCTAAGCCATGTGGATCTCGTCAAGGACCTGAACTCGGGGCTGATCGGCGCCCTGCTCGTGTGC
CGGGAGGGCTCACTGGCCAAGGAGAAGACCCAAACTCTGCACAAGTTCATCCTGCTGTTCGCGGTA
TTCGACGAGGGGAAGTCCTGGCACTCCGAGACCAAGAACAGCCTGATGCAGGACCGCGACGCAGCC
TCGGCCCGTGCGTGGCCAAAGATGCACACCGTGAACGGCTACGTTAACAGGAGCCTACCCGGCCTG
ATCGGCTGCCACCGCAAATCGGTCTACTGGCATGTGATCGGAATGGGCACAACGCCCGAGGTCCAC
AGTATCTTCCTCGAGGGCCACACTTTCCTGGTCCGGAATCACCGCCAGGCCAGCCTGGAGATCAGC
CCCATAACCTTTCTGACGGCGCAGACCTTACTCATGGATCTCGGCCAGTTCCTCCTGTTCTGCCAC
ATTCGTCCCACCAGCACGATGGGATGGAAGCATATGTGAAAGTGGACTCCTGCCCCGAGGAACCC
CAGCTTAGGATGAAGAACAATGAGGAGGCCGAGGACTACGACGATGACCTTACCGATTCAGAAATG
GACGTAGTACGCTTTGACGACGACAACTCTCCATCCTTCATACAGATTCGCTCCGTCGCCAAGAAG
CACCCTAAGACTTGGGTGCACTACATCGCGGCCGAGGAGGAGGACTGGGATTATGCTCCCCTGGTG
CTGGCCCCGACGACCGCAGCTACAAGAGCCAGTACCTGAATAACGGGCCCCAGCGCATCGGCCGG
AAGTACAAGAAAGTGCGGTTCATGGCTTACACGGACGAGACCTTCAAGACCCGGGAGGCTATCCAG
CATGAGAGCGGCATCTTGGGGCCCCTCCTGTACGGCGAAGTTGGAGACACACTGCTGATCATCTTC
AAGAACCAGGCGAGCAGGCCCTACAACATCTACCCCCACGGCATTACCGATGTCCGGCCGTTGTAC
AGCCGACGGCTGCCCAAGGGCGTGAAGCACCTGAAGGACTTTCCGATCCTGCCGGGCGAGATCTTC
AAGTACAAGTGGACTGTGACCGTGGAGGATGGGCCGACCAAGAGCGATCCGCGCTGCCTGACCCGT
TACTACTCCAGCTTTGTCAATATGGAGCGCGACCTCGCTAGCGGCTTGATTGGCCCTCTGCTGATC
TGCTACAAGGAGTCCGTGGACCAGAGGGGGAATCAGATCATGAGTGACAAGAGGAACGTGATCCTG
TTCTCCGTGTTCGACGAAAACCGCAGCTGGTATCTCACCGAGAATATCCAGCGCTTCCTGCCCAAC
CCGGCCGGTGTGCAGCTGGAGGACCCCGAGTTTCAGGCAGCAACATCATGCATTCTATCAACGGA
TATGTGTTTGATTCCCTGCAGCTCTCAGTGTGTCTGCACGAGGTCGCCTACTGGTATATCCTCAGC
ATTGGGGCACAGACCGACTTCCTGAGCGTGTTCTTCTCCGGGTATACCTTCAAGCACAAGATGGTG
TACGAGGATACCCTGACCCTGTTCCCCTTTAGCGGCGAAACCGTGTTTATGTCTATGGAGAACCCC
GGGCTCTGGATCCTTGGCTGCCATAACTCCGACTTCCGCAACCGCGGAATGACCGCGCTCCTGAAA
GTGTCGAGTTGTGACAAGAACACCGGCGACTATTACGAGGACAGTTACGAGGACATCTCTGCGTAC
CTCCTTAGCAAGAATAACGCCATCGAGCCAAGATCCTTCAGCCAGAACCCCCCAGTGCTGAAGAGG
CATCAGCGGGAGATCACCCGCACGACCCTGCAGTCGGATCAGGAGGAGATTGATTACGACGACACG
ATCAGTGTGGAGATGAAGAAGGAGGACTTCGACATCTACGACGAAGATGAAAACCAGTCCCCTCGG
TCCTTCCAAAAGAAGACCCGGCACTACTTCATCGCCGCTGTGGAACGCCTGTGGGACTATGGAATG (Continued)

Figure 13A

```
TCTTCTAGCCCTCACGTTTTGAGGAACCGCGCCCAGTCGGGCAGCGTGCCCCAGTTCAAGAAAGTG
GTGTTCCAGGAGTTCACCGACGGCTCCTTCACCCAGCCACTTTACCGGGGCGAGCTCAATGAACAT
CTGGGCCTGCTGGGACCCTACATCAGGGCTGAGGTGGAGGACAACATCATGGTGACATTCCGGAAT
CAGGCCAGCAGACCATACAGTTTCTACAGTTCACTCATCTCCTACGAGGAGGACCAGCGCCAGGGG
GCTGAACCCCGTAAGAACTTCGTGAAGCCAAACGAAACAAAGACCTACTTCTGGAAGGTCCAGCAC
CACATGGCACCTACCAAGGACGAGTTCGATTGCAAGGCCTGGGCCTACTTCTCCGACGTGGACCTG
GAGAAAGATGTGCACAGCGGCCTGATTGGCCCTCTGCTGGTGTGTCACACGAACACACTCAACCCT
GCACACGGGCGGCAGGTCACTGTGCAGGAATTCGCCCTGTTCTTTACCATCTTTGATGAGACGAAG
TCCTGGTATTTCACCGAAAACATGGAGAGGAACTGCCGCGCACCCTGCAACATCCAGATGGAAGAT
CCGACATTCAAGGAGAACTACCGGTTCCATGCCATCAATGGCTACATCATGGACACCCTGCCTGGC
CTCGTGATGGCCCAAGACCAGCGTATCCGCTGGTATCTGCTGTCGATGGGCTCCAACGAGAACATC
CATAGTATCCACTTCAGCGGGCATGTCTTCACGGTGAGGAAAAAGGAGGAGTACAAGATGGCACTG
TACAACCTCTATCCCGGCGTGTTCGAGACCGTGGAGATGCTGCCCTCCAAGGCCGGCATCTGGAGA
GTGGAATGCCTGATCGGCGAGCACCTCCACGCTGGGATGTCCACGCTGTTCCTCGTTTACAGCAAT
AAGTGCCAGACCCCTCTGGGCATGGCGAGCGGCCACATCCGCGACTTCCAGATTACAGCCAGCGGC
CAGTACGGTCAGTGGGCTCCAAAGCTGGCCCGTCTGCACTACTCCGGATCCATCAACGCCTGGTCC
ACCAAGGAACCGTTCTCCTGGATCAAAGTAGACCTGCTAGCCCCATGATCATTCACGGCATCAAG
ACACAAGGCGCCCGACAGAAGTTCTCGAGCCTCTATATCTCCCAGTTCATCATCATGTATAGCCTG
GACGGAAAGAAGTGGCAGACTTACCGCGGAAACTCGACAGGGACCCTGATGGTATTCTTCGGTAAC
GTGGACAGCTCCGGAATCAAGCACAACATCTTCAACCCACCCATTATCGCCCGCTACATCCGCCTG
CACCCCACTCACTATAGCATTAGGTCCACCCTGCGAATGGAGCTCATGGGCTGTGACCTGAACAGC
TGTAGCATGCCCCTCGGCATGGAGTCTAAGGCGATCTCCGACGCACAGATAACGGCATCATCCTAC
TTTACCAACATGTTCGCTACCTGGTCCCCCTCCAAGGCCCGACTCCACCTGCAAGGGAGATCCAAC
GCCTGGCGGCCACAGGTCAACAATCCCAAGGAGTGGCTGCAAGTGGACTTTCAGAAAACTATGAAA
GTCACCGGAGTGACCACACAGGGAGTGAAGTCTCTGCTGACCAGCATGTACGTGAAGGAGTTCCTC
ATCTCCAGTTCGCAGGATGGCCACCAGTGGACGTTGTTCTTCCAAAACGGTAAAGTCAAAGTCTTC
CAAGGGAACCAGGACAGCTTTACACCCGTCGTGAACTCCCTGGACCCCCCGCTTCTCACTAGATAC
CTCCGCATCCACCCTCAGAGCTGGGTGCACCAGATTGCCCTGCGCATGGAGGTTCTGGGGTGTGAA
GCCCAGGACCTGTACTAA (SEQ ID NO:14)
```

```
ATGCAGATTGAGCTCTCCACCTGCTTCTTTCTCTGCCTTCTTCGCTTCTGCTTTTCTGCCACACGC
AGGTACTATTTGGGAGCAGTGGAACTGAGCTGGGATTACATGCAGAGTGACCTTGGTGAACTTCCT
GTGGACGCTCGTTTTCCACCTAGAGTTCCCAAGTCCTTCCCCTTCAACACCTCAGTGGTCTACAAG
AAAACGCTGTTTGTGGAGTTCACTGACCACCTCTTCAACATTGCCAAACCAAGACCCCCTTGGATG
GGATTGCTGGGACCCACAATACAAGCAGAAGTCTACGACACGGTGGTGATTACCCTGAAGAACATG
GCGTCACACCCTGTTTCACTTCACGCTGTTGGGGTCAGTTATTGGAAAGCCTCAGAGGGTGCGGAA
TACGATGATCAAACCAGCCAGAGGGAGAAGGAAGATGACAAGGTCTTTCCTGGGGGTAGCCATACC
TATGTTTGGCAGGTGCTGAAAGAGAATGGGCCTATGGCCTCTGATCCCTTGTGCCTCACATACTCT
TACCTGAGTCACGTCGACCTGGTGAAAGACCTGAATAGCGGTCTGATTGGTGCACTGCTTGTTTGT
AGAGAGGGGAGTTTGGCCAAGGAGAAAACTCAGACTCTCCACAAGTTTATCCTCCTGTTTGCTGTG
TTCGACGAGGGCAAGTCTTGGCACTCTGAAACAAAGAACTCCCTGATGCAGGACAGAGATGCTGCA
TCTGCAAGGGCTTGGCCAAAAATGCACACAGTGAACGGCTATGTGAATCGATCACTGCCAGGACTG
ATAGGCTGTCATCGCAAGTCAGTGTATTGGCACGTTATCGGGATGGGAACAACTCCAGAAGTGCAC
AGCATCTTCCTTGAGGGCCACACTTTCCTGGTTCGGAATCATAGACAGGCCAGCCTTGAGATCAGC
CCAATCACCTTTCTGACTGCCCAAACCTTGCTGATGGATCTGGGACAGTTCCTCCTGTTTTGTCAC
ATCTCCTCCACCAACATGACGGGATGGAGGCTTATGTGAAGGTCGATAGCTGTCCGGAGGAACCA
CAACTGAGGATGAAGAACAACGAAGAGGCAGAGGACTATGACGACGATCTGACTGACAGTGAAATG
GACGTGGTTCGGTTCGACGATGACAATTCTCCTTCATTTATCCAGATCCGTTCCGTGGCCAAGAAG
CACCCCAAGACTTGGGTTCATTACATCGCTGCTGAGGAGGAGGATTGGGACTACGCGCCCTTGGTG
TTGGCCCCAGACGATCGCTCATACAAGAGCCAGTACCTTAACAATGGTCCACAAAGGATCGGCCGG
AAGTACAAGAAGGTTAGATTTATGGCTTATACCGACGAGACTTTTAAAACTAGGGAAGCAATTCAG
CATGAAAGTGGCATTCTTGGACCCCTGCTGTATGGCGAGGTTGGCGACACCCTGCTGATTATCTTT
AAGAACCAGGCAAGCCGGCCCTACAACATCTACCCGCACGGCATAACCGATGTACGACCCCTGTAC
AGTCGCAGACTTCCTAAAGGGGTGAAACACCTGAAGGACTTCCCAATTCTGCCCGGGGAGATCTTC
AAGTATAAATGGACCGTGACGGTTGAGGATGGTCCCACAAAGTCCGATCCGAGATGCCTTACCCGA
TATTATTCCAGCTTCGTGAACATGGAAAGGGACCTGGCCAGCGGGCTGATTGGCCCACTGCTGATT
TGTTACAAGGAGTCTGTCGATCAAAGAGGAAACCAAATAATGAGCGACAAACGTAACGTCATCCTG
TTCAGCGTCTTTGATGAGAATAGAAGCTGGTACCTCACAGAAAATATTCAGCGGTTTCTGCCTAAC
CCCGCAGGCGTCCAGCTGGAAGATCCCGAGTTCCAAGCCTCAAACATCATGCATAGCATCAACGGA
TACGTATTCGATAGCCTGCAGCTGTCCGTCTGTCTCCATGAAGTGGCATATTGGTACATCCTGAGT
ATCGGGGCGCAGACCGACTTCCTGAGCGTGTTCTTTTCTGGATACACGTTCAAACACAAAATGGTC
TATGAAGATACCCTGACTCTGTTTCCATTCTCAGGAGAGACAGTCTTTATGAGTATGGAAAATCCT
GGACTGTGGATCCTGGGCTGTCACAATTCTGATTTCGGAACAGAGGCATGACAGCCCTGCTTAAA
GTGAGCTCATGCGACAAGAACACCGGTGATTACTACGAAGATAGCTATGAGGACATCAGTGCGTAT
TTGCTCTCCAAGAACAACGCTATCGAGCCACGGTCTTTCAGTCAGAATCCTCCCGTTCTGAAGCGG
CATCAGCGCGAAATAACACGCACAACCCTTCAGTCAGACCAAGAGGAAATCGACTACGATGATACT
ATCTCTGTGGAGATGAAGAAGGAGGATTTCGACATTTACGACGAGGACGAGAATCAGTCCCCAAGG
AGCTTTCAGAAGAAAACAAGACACTATTTCATTGCCGCCGTGGAGCGACTGTGGGACTACGGCATG
```

```
TCTAGCTCTCCGCATGTACTTAGAAATAGGGCACAAAGCGGATCCGTGCCTCAGTTTAAGAAAGTT
GTCTTTCAGGAGTTTACAGATGGCTCCTTCACCCAGCCCTTGTATCGCGGGGAACTCAATGAACAC
CTGGGCCTCCTGGGTCCTTATATTAGGGCCGAAGTCGAGGACAATATCATGGTGACCTTTAGGAAC
CAGGCATCTAGACCTTACTCTTTCTACTCCTCCCTGATATCCTATGAGGAGGACCAGCGGCAAGGC
GCTGAGCCTCGGAAGAACTTTGTGAAGCCAAATGAAACCAAAACATACTTTTGGAAAGTTCAGCAC
CACATGGCTCCCACGAAGGACGAATTTGACTGTAAAGCCTGGGCCTACTTCTCAGATGTAGATCTC
GAGAAAGACGTGCACTCAGGGCTCATTGGTCCCCTCCTGGTCTGTCATACTAATACCCTCAATCCA
GCACACGGACGTCAGGTAACCGTCCAGGAATTTGCCCTGTTCTTTACCATTTTCGATGAGACTAAA
TCCTGGTACTTTACCGAAAACATGGAGAGGAATTGCAGAGCCCCATGCAACATCCAGATGGAGGAC
CCTACCTTCAAAGAGAACTATCGCTTCCATGCCATTAACGGTTACATTATGGATACTCTCCCAGGA
CTTGTGATGGCACAGGATCAGCGGATAAGATGGTATCTGTTGAGCATGGGCTCCAACGAGAATATT
CACAGCATCCATTTCTCCGGTCACGTGTTTACAGTGAGAAAGAAAGAAGAGTACAAGATGGCTCTG
TATAATCTCTATCCAGGCGTATTCGAAACGGTGGAGATGTTGCCTAGCAAGGCCGGCATTTGGCGA
GTAGAATGCCTTATCGGGGAACATCTGCATGCCGGAATGAGCACGCTCTTCCTGGTGTATAGTAAC
AAGTGCCAGACTCCGCTGGGCATGGCATCTGGCCATATACGGGACTTTCAGATTACGGCTAGCGGG
CAGTATGGGCAGTGGGCACCCAAACTTGCGCGACTGCACTATTCAGGCTCTATCAATGCATGGTCC
ACCAAGGAACCCTTCTCTTGGATTAAGGTGGACCTTTTGGCGCCCATGATAATCCATGGGATCAAA
ACCCAGGGCGCTCGTCAGAAATTCTCATCACTCTACATCTCTCAGTTCATAATAATGTATTCACTG
GATGGGAAGAAATGGCAGACTTACAGAGGAAACAGCACCGGGACGCTGATGGTGTTCTTTGGCAAC
GTGGACAGCAGCGGCATCAAACACAACATCTTCAATCCTCCCATTATTGCCCGTTATATTAGACTG
CATCCCACTCACTACTCTATACGCAGCACACTTAGGATGGAGCTCATGGGATGCGACCTGAACAGT
TGTAGTATGCCCTTGGGGATGGAGTCCAAAGCTATAAGCGACGCACAAATTACAGCTAGCTCTTAC
TTTACGAATATGTTCGCCACGTGGAGCCCAAGCAAAGCCCGGCTGCATTTGCAGGGTCGGAGTAAT
GCTTGGCGCCCACAGGTGAATAACCCTAAGGAATGGTTGCAAGTAGATTTCCAGAAAACTATGAAG
GTAACCGGCGTCACTACACAGGGAGTCAAGTCCCTCTTGACCTCTATGTACGTCAAGGAGTTCCTG
ATTAGCAGCAGTCAGGATGGGCACCAATGGACACTGTTCTTCCAGAATGGGAAAGTTAAAGTATTT
CAGGGTAACCAGGACTCCTTTACACCTGTGGTGAATAGCCTCGACCCACCCCTGCTGACACGATAC
CTCCGCATCCACCCTCAGTCTTGGGTGCATCAAATTGCCCTGCGAATGGAGGTGTTGGGATGCGAA
GCTCAGGACCTCTACTGA (SEQ ID NO:15)
```

ATGCAGATCGAACTCTCTACTTGCTTCTTCCTGTGCCTTCTGAGGTTCTGCTTCTCTGCCACTCGC
CGATATTACCTCGGGGCCGTGGAGTTGAGTTGGGACTACATGCAATCAGATCTGGGCGAACTCCCT
GTGGATGCCCGATTCCCACCGCGCGTGCCCAAGTCTTTCCCATTTAATACTTCTGTGGTGTACAAG
AAGACATTGTTTGTGGAGTTTACCGATCACCTGTTCAACATCGCCAAACCGCGGCCCCATGGATG
GGTCTGCTTGGGCCCACCATTCAAGCGGAGGTCTATGATACAGTGGTGATAACGCTTAAGAACATG
GCGAGCCACCCAGTGTCTCTGCATGCCGTTGGTGTATCATATTGGAAGGCCAGCGAAGGAGCGGAG
TACGATGACCAGACCTCTCAGAGAGAGAAGGAAGACGATAAGGTTTTTCCTGGCGGAAGTCATACA
TATGTATGGCAGGTCCTGAAAGAGAATGGGCCGATGGCTTCTGACCCCTTTGTCTTACCTATAGT
TATCTGAGCCACGTGGACCTGGTCAAGGACCTCAACAGTGGTCTGATTGGGGCTCTGCTTGTTTGT
AGAGAGGGTAGCTTGGCTAAGGAGAAAACCCAAACACTCCATAAGTTCATTTTGCTGTTCGCGGTG
TTCGACGAGGGAAAGAGTTGGCACAGCGAAACAAAGAATTCACTGATGCAAGACAGGGACGCCGCT
TCCGCAAGGGCTTGGCCTAAGATGCATACGGTGAATGGGTATGTGAACCGGAGCCTCCCGGGGCTG
ATCGGGTGCCATCGCAAGTCTGTTACTGGCACGTCATTGGAATGGGACAACGCCAGAGGTACAT
AGTATATTTCTTGAAGGCCACACGTTCCTCGTACGGAACCACCGACAGGCTTCCCTGGAGATAAGC
CCCATTACCTTTCTGACCGCTCAGACTCTGCTGATGGACCTTGGCCAGTTTCTCCTGTTCTGCCAT
ATTAGCAGCCACCAGCACGACGGTATGGAAGCATACGTGAAAGTCGATAGCTGTCCTGAGGAGCCT
CAGCTCAGAATGAAGAACAACGAGGAGGCCGAAGACTATGACGATGACCTTACAGATTCCGAGATG
GACGTGGTGCGCTTTGACGACGATAACAGTCCTAGTTTCATTCAAATCAGATCCGTAGCCAAAAAG
CATCCAAAGACATGGGTGCATTACATTGCAGCCGAAGAGGAGGATTGGGATTATGCGCCCCTTGTT
CTGGCTCCAGATGACAGGAGCTATAAGTCCCAGTACTTGAACAACGGGCCACAGCGAATCGGTAGA
AAATATAAGAAGGTAAGATTCATGGCCTACACTGACGAAACATTTAAAACCAGGGAAGCTATCCAA
CACGAATCTGGAATTCTCGGCCCTCTGCTCTACGGTGAGGTGGGGACACCTTGCTGATCATTTTC
AAAAATCAGGCATCCAGGCCTTACAACATATACCCCATGGCATCACCGATGTCCGCCCGCTGTAT
TCCAGAAGACTCCCCAAGGGAGTGAAACATCTGAAAGATTTTCCCATCCTGCCGGGCAGATCTTT
AAATACAAATGGACTGTGACTGTAGAGGACGGGCCTACAAAATCAGACCCACGGTGCCTGACAAGG
TATTACAGTAGCTTCGTCAACATGGAACGCGACCTCGCCAGCGGACTCATTGGCCCACTGTTGATC
TGTTACAAAGAGTCAGTGGATCAGAGGGGAAATCAGATCATGAGCGATAAGAGAAACGTTATCCTG
TTTAGTGTCTTCGACGAGAACCGGTCTTGGTACCTTACTGAGAACATCCAGAGGTTCCTGCCGAAT
CCGGCTGGCGTTCAGCTCGAGGACCCAGAGTTCCAGGCCAGTAATATAATGCACTCAATCAACGGT
TATGTGTTCGATAGCCTGCAGCTGAGCGTCTGCCTCCACGAGGTAGCCTATTGGTACATATTGTCC
ATCGGGGCTCAGACCGATTTTCTGTCCGTGTTCTTTAGCGGGTATACCTTTAAACATAAAATGGTC
TATGAAGACACCCTGACCCTGTTCCCATTCTCCGGTGAGACTGTGTTCATGTCCATGGGAGAACCCA
GGGCTGTGGATCCTGGGGTGTCACAATAGTGACTTTAGGAATCGGGGAATGACGGCACTGCTGAAG
GTGAGTTCTTGCGATAAAAATACAGGAGATTACTATGAGGATAGTTACGAGGATATCAGTGCCTAT
CTGCTTTCAAAAAACAACGCAATTGAGCCCCGGTCTTTCTCACAAAACCCCCGGTGCTGAAGCGC
CACCAGCGCGAAATTACCCGGACAACCTTGCAGTCCGACCAGGAGGAAATCGATTATGACGATACT
ATCAGTGTAGAAATGAAAAGGAGGATTTTGATATTTACGACGAAGACGAGAACCAGTCTCCGCGA (Continued)

Figure 15A

```
AGTTTTCAGAAGAAAACGCGACACTACTTTATAGCTGCCGTGGAACGACTCTGGGATTATGGCATG
TCCTCCAGCCCTCATGTCCTTAGGAATCGAGCGCAGAGTGGCTCTGTGCCTCAGTTCAAAAAGGTT
GTGTTCCAGGAATTCACCGACGGCTCATTTACCCAGCCGCTGTACAGAGGCGAACTCAACGAACAC
CTTGGGCTGCTTGGGCCATATATTCGAGCAGAGGTGGAAGATAATATCATGGTAACCTTTAGAAAC
CAGGCGTCAAGACCCTATTCCTTCTACAGTTCTCTGATCAGCTACGAGGAGGACCAAAGACAGGGA
GCTGAACCCAGGAAGAACTTTGTGAAACCTAATGAGACCAAGACCTACTTCTGGAAGGTCCAGCAC
CATATGGCCCCAACTAAAGATGAATTCGATTGCAAGGCCTGGGCTTATTTCAGCGACGTGGATCTC
GAAAAGGATGTGCACAGCGGGTTGATCGGACCGCTTTTGGTGTGCCACACAAATACCCTCAATCCT
GCCCACGGGCGGCAGGTCACAGTTCAAGAGTTTGCACTCTTCTTTACAATATTTGACGAGACAAAG
TCATGGTATTTTACAGAGAATATGGAGAGAAATTGTCGCGCACCTTGCAACATTCAGATGGAGGAC
CCCACATTTAAGGAGAATTACAGATTTCATGCTATCAATGGGTACATTATGGATACTCTGCCTGGT
CTGGTCATGGCCCAGGATCAGCGCATAAGGTGGTACTTGCTGAGCATGGGATCTAATGAGAATATA
CACAGCATTCACTTCAGTGGCCACGTTTTTACTGTTAGAAAGAAGGAGGAGTACAAAATGGCGCTC
TACAACCTTTACCCGGGTGTGTTTGAGACAGTGGAGATGCTGCCAAGCAAGGCAGGCATCTGGAGG
GTTGAGTGTCTTATTGGGGAGCATCTGCATGCTGGAATGTCCACCCTCTTTCTTGTGTACAGCAAT
AAGTGCCAGACACCGCTTGGCATGGCCAGCGGCCACATTAGGGACTTTCAGATAACTGCCAGTGGA
CAGTACGGCCAGTGGGCTCCCAAGCTTGCAAGACTCCACTACTCCGGAAGCATAAACGCATGGAGC
ACCAAGGAACCCTTCTCTTGGATTAAGGTGGACCTGCTGGCGCCAATGATCATTCACGGCATAAAA
ACCCAAGGGGCACGACAGAAATTTTCATCTTTGTATATTAGTCAGTTTATCATCATGTACAGCTTG
GATGGAAAGAAGTGGCAGACGTACAGGGGCAATTCTACAGGAACACTTATGGTGTTTTTTGGGAAT
GTCGATTCCAGCGGGATCAAACATAACATCTTCAATCCTCCTATTATCGCCCGATATATCCGCCTG
CACCCTACGCATTACTCCATCAGGTCCACATTGAGAATGGAACTGATGGGGTGCGACCTGAATAGT
TGTAGTATGCCACTGGGCATGGAGTCTAAAGCCATCAGCGATGCACAGATCACTGCCAGCTCTTAC
TTCACCAACATGTTTGCAACTTGGTCCCCCTCTAAAGCTCGCCTGCATCTGCAGGGACGCTCAAAT
GCATGGCGACCACAGGTGAACAATCCAAAAGAGTGGCTCCAGGTCGACTTTCAGAAGACAATGAAG
GTAACAGGAGTGACAACCCAGGGTGTAAAAAGCCTCCTTACGAGTATGTACGTTAAGGAGTTTCTG
ATTTCTAGCTCCCAGGACGGACACCAGTGGACTCTGTTCTTCCAGAACGGCAAAGTGAAGGTATTT
CAGGGAAACCAGGATTCTTTTACCCCGGTAGTGAATAGCCTGGATCCACCGTTGCTGACCCGCTAT
CTGAGAATTCATCCACAATCCTGGGTGCATCAGATTGCCCTCCGGATGGAAGTGCTCGGCTGTGAA
GCTCAGGATCTGTATTAG (SEQ ID NO:16)
```

ATGCAAATAGAGCTCTCCACCTGCTTCTTTCTGTGCCTTTTGCGATTCTGCTTTAGTGCCACCAGA
AGATACTACCTGGGTGCAGTGGAACTGTCATGGGACTATATGCAAAGTGATCTCGGTGAGCTGCCT
GTGGACGCAAGATTTCCTCCTAGAGTGCCAAAATCTTTTCCATTCAACACCTCAGTCGTGTACAAA
AAGACTCTGTTTGTAGAATTCACGGATCACCTTTTCAACATCGCTAAGCCAAGGCCACCCTGGATG
GGTCTGCTAGGTCCTACCATCCAGGCTGAGGTTTATGATACAGTGGTCATTACACTTAAGAACATG
GCTTCCCATCCTGTCAGTCTTCATGCTGTTGGTGTATCCTACTGGAAAGCTTCTGAGGGAGCTGAA
TATGATGATCAGACCAGTCAAAGGGAGAAAGAAGATGATAAAGTCTTCCCTGGTGGAAGCCATACA
TATGTCTGGCAGGTCCTGAAAGAGAATGGTCCAATGGCCTCTGACCCACTGTGCCTTACCTACTCA
TATCTTTCTCATGTGGACCTGGTAAAAGACTTGAATTCAGGCCTCATTGGAGCCCTACTAGTATGT
AGAGAAGGGAGTCTGGCCAAGGAAAAGACACAGACCTTGCACAAATTTATACTACTTTTTGCTGTA
TTTGATGAAGGGAAAAGTTGGCACTCAGAAACAAAGAACTCCTTGATGCAGGATAGGGATGCTGCA
TCTGCTCGGGCCTGGCCTAAAATGCACACAGTCAATGGTTATGTAAACAGGTCTCTGCCAGGTCTG
ATTGGATGCCACAGGAAATCAGTCTATTGGCATGTGATTGGAATGGGCACCACTCCTGAAGTGCAC
TCAATATTCCTCGAAGGTCACACATTTCTTGTGAGGAACCATCGCCAGGCGTCCTTGGAAATCTCG
CCAATAACTTTCCTTACTGCTCAAACACTCTTGATGGACCTTGGACAGTTTCTACTGTTTGTCAT
ATCTCTTCCCACCAACATGATGGCATGGAAGCTTATGTCAAAGTAGACAGCTGTCCAGAGGAACCC
CAACTACGAATGAAAAATAATGAAGAAGCGGAAGACTATGATGATGATCTTACTGATTCTGAAATG
GATGTGGTCAGGTTTGATGATGACAACTCTCCTTCCTTTATCCAAATTCGCTCAGTTGCCAAGAAG
CATCCTAAAACTTGGGTACATTACATTGCTGCTGAAGAGGAGGACTGGGACTATGCTCCCTTAGTC
CTCGCCCCGATGACAGAAGTTATAAAAGTCAATATTTGAACAATGGCCCTCAGCGGATTGGTAGG
AAGTACAAAAAAGTCCGATTTATGGCATACACAGATGAAACCTTTAAGACTCGTGAAGCTATTCAG
CATGAATCAGGAATCTTGGGACCTTTACTTTATGGGGAAGTTGGAGACACACTGTTGATTATATTT
AAGAATCAAGCAAGCAGACCATATAACATCTACCCTCACGGAATCACTGATGTCCGTCCTTTGTAT
TCAAGGAGATTACCAAAAGGTGTAAAACATTTGAAGGATTTTCCAATTCTGCCAGGAGAAATATTC
AAATATAAATGGACAGTGACTGTAGAAGATGGGCCAACTAAATCAGATCCTCGGTGCCTGACCCGC
TATTACTCTAGTTTCGTTAATATGGAGAGAGATCTAGCTTCAGGACTCATTGGCCCTCTCCTCATC
TGCTACAAAGAATCTGTAGATCAAAGAGGAAACCAGATAATGTCAGACAAGAGGAATGTCATCCTG
TTTTCTGTATTTGATGAGAACCGAAGCTGGTACCTCACAGAGAATATACAACGCTTTCTCCCCAAT
CCAGCTGGAGTGCAGCTTGAGGATCCAGAGTTCCAAGCCTCCAACATCATGCACAGCATCAATGGC
TATGTTTTTGATAGTTTGCAGTTGTCAGTTTGTTTGCATGAGGTGGCATACTGGTACATTCTAAGC
ATTGGAGCACAGACTGACTTCCTTTCTGTCTTCTTCTCTGGATATACCTTCAAACACAAAATGGTC
TATGAAGACACACTCACCCTATTCCCATTCTCAGGAGAAACTGTCTTCATGTCGATGGAAAACCCA
GGTCTATGGATTCTGGGGTGCCACAACTCAGACTTTCGGAACAGAGGCATGACCGCCTTACTGAAG
GTTTCTAGTTGTGACAAGAACACTGGTGATTATTACGAGGACAGTTATGAAGATATTTCAGCATAC
TTGCTGAGTAAAAACAATGCCATTGAACCAAGAAGCTTCTCCCAGAATCCACCAGTCTTGAAACGC
CATCAACGGGAAATAACTCGTACTACTCTTCAGTCAGATCAAGAGGAAATTGACTATGATGATACC
ATATCAGTTGAAATGAAGAAGGAAGATTTTGACATTTATGATGAGGATGAAAATCAGAGCCCCCGC
AGCTTTCAAAAGAAAACACGACACTATTTTATTGCTGCAGTGGAGAGGCTCTGGGATTATGGGATG (Continued)

Figure 16A

```
AGTAGCTCCCCACATGTTCTAAGAAACAGGGCTCAGAGTGGCAGTGTCCCTCAGTTCAAGAAAGTT
GTTTTCCAGGAATTTACTGATGGCTCCTTTACTCAGCCCTTATACCGTGGAGAACTAAATGAACAT
TTGGGACTCCTGGGGCCATATATAAGAGCAGAAGTTGAAGATAATATCATGGTAACTTTCAGAAAT
CAGGCCTCTCGTCCCTATTCCTTCTATTCTAGCCTTATTTCTTATGAGGAAGATCAGAGGCAAGGA
GCAGAACCTAGAAAAAACTTTGTCAAGCCTAATGAAACCAAAACTTACTTTTGGAAAGTGCAACAT
CATATGGCACCCACTAAAGATGAGTTTGACTGCAAAGCCTGGGCTTATTTCTCTGATGTTGACCTG
GAAAAAGATGTGCACTCAGGCCTGATTGGACCCCTTCTGGTCTGCCACACTAACACACTGAACCCT
GCTCATGGGAGACAAGTGACAGTACAGGAATTTGCTCTGTTTTTCACCATCTTTGATGAGACCAAA
AGCTGGTACTTCACTGAAAATATGGAAAGAAACTGCAGGGCTCCCTGCAATATCCAGATGGAAGAT
CCCACTTTTAAAGAGAATTATCGCTTCCATGCAATCAATGGCTACATAATGGATACACTACCTGGC
TTAGTAATGGCTCAGGATCAAAGGATTCGATGGTATCTGCTCAGCATGGGCAGCAATGAAAACATC
CATTCTATTCATTTCAGTGGACATGTGTTCACTGTACGAAAAAAAGAGGAGTATAAAATGGCACTG
TACAATCTCTATCCAGGTGTTTTTGAGACAGTGGAAATGTTACCATCCAAAGCTGGAATTTGGCGG
GTGGAATGCCTTATTGGCGAGCATCTACATGCTGGGATGAGCACACTTTTTCTGGTGTACAGCAAT
AAGTGTCAGACTCCCCTGGGAATGGCTTCTGGACACATTAGAGATTTTCAGATTACAGCTTCAGGA
CAATATGGACAGTGGGCCCCAAAGCTGGCCAGACTTCATTATTCCGGATCAATCAATGCCTGGAGC
ACCAAGGAGCCCTTTTCTTGGATCAAGGTGGATCTGTTGGCACCAATGATTATTCACGGCATCAAG
ACCCAGGGTGCCCGTCAGAAGTTCTCCAGCCTCTACATCTCTCAGTTTATCATCATGTATAGTCTT
GATGGGAAGAAGTGGCAGACTTATCGAGGAAATTCCACTGGAACCTTAATGGTCTTCTTTGGCAAT
GTGGATTCATCTGGGATAAAACACAATATTTTTAACCCTCCAATTATTGCTCGATACATCCGTTTG
CACCCAACTCATTATAGCATTCGCAGCACTCTTCGCATGGAGTTGATGGGCTGTGATTTAAATAGT
TGCAGCATGCCATTGGGAATGGAGAGTAAAGCAATATCAGATGCACAGATTACTGCTTCATCCTAC
TTTACCAATATGTTTGCCACCTGGTCTCCTTCAAAAGCTCGACTTCACCTCCAAGGGAGGAGTAAT
GCCTGGAGACCTCAGGTGAATAATCCAAAAGAGTGGCTGCAAGTGGACTTCCAGAAGACAATGAAA
GTCACAGGAGTAACTACTCAGGGAGTAAAATCTCTGCTTACCAGCATGTATGTGAAGGAGTTCCTC
ATCTCCAGCAGTCAAGATGGCCATCAGTGGACTCTCTTTTTCAGAATGGCAAAGTAAAGGTTTTT
CAGGGAAATCAAGACTCCTTCACACCTGTGGTGAACTCTCTAGACCCACCGTTACTGACTCGCTAC
CTTCGAATTCACCCCCAGAGTTGGGTGCACCAGATTGCCCTGAGGATGGAGGTTCTGGGCTGCGAG
GCACAGGACCTCTACTGA (SEQ ID NO:17)
```

```
ATGCAGATCGAGCTGTCCACATGCTTTTTTCTGTGCCTGCTGCGGTTCTGCTTCAGCGCCACCCGG
CGGTACTACCTGGGCGCCGTGGAGCTGTCCTGGGACTACATGCAGAGCGACCTGGGCGAGCTGCCC
GTGGACGCCCGGTTCCCCCCCAGAGTGCCCAAGAGCTTCCCCTTCAACACCAGCGTGGTGTACAAG
AAAACCCTGTTCGTGGAGTTCACCGACCACCTGTTCAACATCGCCAAGCCCAGGCCCCCCTGGATG
GGCCTGCTGGGCCCCACCATCCAGGCCGAGGTGTACGACACCGTGGTGATCACCCTGAAGAACATG
GCCAGCCACCCCGTGAGCCTGCACGCCGTGGGCGTGAGCTACTGGAAGGCCTCCGAGGGCGCCGAG
TACGACGACCAGACCAGCCAGCGGGAGAAAGAGGACGACAAAGTCTTTCCTGGCGGCAGCCACACC
TACGTGTGGCAGGTCCTGAAAGAAAACGGCCCCATGGCCTCCGACCCCCTGTGCCTGACCTACAGC
TACCTGAGCCACGTGGACCTGGTGAAGGACCTGAACAGCGGGCTGATTGGGGCCCTGCTGGTCTGC
CGGGAGGGCAGCCTGGCCAAAGAGAAAACCCAGACCCTGCACAAGTTCATCCTGCTGTTCGCCGTG
TTCGACGAGGGCAAGAGCTGGCACAGCGAGACCAAGAACAGCCTGATGCAGGACCGGGACGCCGCC
TCTGCCAGAGCCTGGCCCAAGATGCACACCGTGAACGGCTACGTGAACAGAAGCCTGCCCGGCCTG
ATTGGCTGCCACCGGAAGAGCGTGTACTGGCACGTGATCGGCATGGGCACCACACCCGAGGTGCAC
AGCATCTTTCTGGAAGGGCACACCTTTCTGGTGCGGAACCACCGGCAGGCCAGCCTGGAAATCAGC
CCTATCACCTTCCTGACCGCCCAGACACTGCTGATGGACCTGGGCCAGTTCCTGCTGTTTTGCCAC
ATCAGCTCTCACCAGCACGACGGCATGGAAGCCTACGTGAAGGTGGACTCCTGCCCCGAGGAACCC
CAGCTGCGGATGAAGAACAACGAGGAAGCCGAGGACTACGACGACGACCTGACCGACAGCGAGATG
GACGTGGTGCGGTTCGACGACGACAACAGCCCCAGCTTCATCCAGATCAGAAGCGTGGCCAAGAAG
CACCCCAAGACCTGGGTGCACTACATCGCCGCCGAGGAAGAGGACTGGGACTACGCCCCCCTGGTG
CTGGCCCCCGACGACAGAAGCTACAAGAGCCAGTACCTGAACAATGGCCCCAGCGGATCGGCCGG
AAGTACAAGAAAGTGCGGTTCATGGCCTACACCGACGAGACCTTCAAGACCCGGGAGGCCATCCAG
CACGAGAGCGGCATCCTGGGCCCCCTGCTGTACGGCGAAGTGGGCGACACACTGCTGATCATCTTC
AAGAACCAGGCCAGCCGGCCCTACAACATCTACCCCCACGGCATCACCGACGTGCGGCCCCTGTAC
AGCAGGCGGCTGCCCAAGGGCGTGAAGCACCTGAAGGACTTCCCCATCCTGCCCGGCGAGATCTTC
AAGTACAAGTGGACCGTGACCGTGGAGGACGGCCCCACCAAGAGCGACCCCAGATGCCTGACCCGG
TACTACAGCAGCTTCGTGAACATGGAACGGGACCTGGCCTCCGGGCTGATCGGACCTCTGCTGATC
TGCTACAAAGAAAGCGTGGACCAGCGGGGCAACCAGATCATGAGCGACAAGCGGAACGTGATCCTG
TTCAGCGTGTTCGATGAGAACCGGTCCTGGTATCTGACCGAGAACATCCAGCGGTTTCTGCCCAAC
CCTGCCGGGGTGCAGCTGGAAGATCCCGAGTTCCAGGCCAGCAACATCATGCACTCCATCAATGGC
TACGTGTTCGACAGCCTGCAGCTGTCCGTGTGTCTGCACGAGGTGGCCTACTGGTACATCCTGAGC
ATCGGCGCCCAGACCGACTTCCTGAGCGTGTTCTTCAGCGGCTACACCTTCAAGCACAAGATGGTG
TACGAGGACACCCTGACCCTGTTCCCTTTCAGCGGCGAGACCGTGTTCATGAGCATGGAAAACCCC
GGCCTGTGGATCCTGGGCTGCCACAACAGCGACTTCCGGAACCGGGGCATGACCGCCCTGCTGAAG
GTGTCCAGCTGCGACAAGAACACCGGCGACTACTACGAGGACAGCTACGAGGATATCAGCGCCTAC
CTGCTGTCCAAGAACAACGCCATCGAGCCCAGAAGCTTCAGCCAGAACCCCCTGTGCTGAAGCGG
CACCAGAGAGAGATCACCCGGACCACCCTGCAGTCCGACCAGGAAGAGATCGATTACGACGACACC
```

```
ATCAGCGTGGAGATGAAAAAGAAGATTTCGACATCTACGACGAGGACGAGAACCAGAGCCCCCGG
TCCTTCCAGAAGAAAACCCGGCACTACTTTATCGCCGCCGTGGAGCGGCTGTGGGACTACGGCATG
AGCAGCAGCCCCCACGTGCTGCGGAACCGGGCCCAGAGCGGCAGCGTGCCCCAGTTCAAGAAAGTG
GTGTTCCAGGAATTCACCGACGGCAGCTTCACCCAGCCCCTGTACCGGGGCGAGCTGAACGAGCAC
CTGGGGCTGCTGGGGCCCTACATCAGGGCCGAAGTGGAGGACAACATCATGGTGACCTTCCGGAAT
CAGGCCAGCAGACCCTACTCCTTCTACAGCAGCCTGATCAGCTACGAAGAGGACCAGCGGCAGGGC
GCTGAACCCCGGAAGAACTTCGTGAAGCCCAATGAGACCAAGACCTACTTCTGGAAAGTGCAGCAC
CACATGGCCCCCACCAAGGACGAGTTCGACTGCAAGGCCTGGGCCTACTTCAGCGACGTGGATCTG
GAAAAGGACGTGCACTCTGGACTGATTGGCCCTCTGCTGGTGTGCCACACCAACACCCTGAACCCC
GCCCACGGCCGGCAGGTGACCGTGCAGGAATTCGCCCTGTTCTTCACCATCTTCGACGAGACCAAG
TCCTGGTACTTCACCGAGAATATGGAACGGAACTGCAGAGCCCCCTGCAACATCCAGATGGAAGAT
CCTACCTTCAAAGAGAACTACCGGTTCCACGCCATCAACGGCTACATCATGGACACCCTGCCTGGC
CTGGTGATGGCCCAGGACCAGAGGATCCGGTGGTATCTGCTGTCCATGGGCAGCAACGAGAATATC
CACAGCATCCACTTCAGCGGCCACGTGTTCACCGTGAGGAAGAAAGAAGAGTACAAGATGGCCCTG
TACAACCTGTACCCCGGCGTGTTCGAGACCGTGGAGATGCTGCCCAGCAAGGCCGGCATCTGGCGG
GTGGAGTGTCTGATCGGCGAGCACCTGCATGCCGGGATGAGCACCCTGTTTCTGGTGTACAGCAAC
AAGTGCCAGACCCCCCTGGGCATGGCCAGCGGCCACATCCGGGACTTCCAGATCACCGCCTCCGGC
CAGTACGGCCAGTGGGCCCCCAAGCTGGCCCGGCTGCACTACAGCGGCAGCATCAACGCCTGGTCC
ACCAAAGAGCCCTTCAGCTGGATCAAGGTGGACCTGCTGGCCCCTATGATCATCCACGGCATTAAG
ACCCAGGGCGCCAGGCAGAAGTTCAGCAGCCTGTACATCAGCCAGTTCATCATCATGTACAGCCTG
GACGGCAAGAAGTGGCAGACCTACCGGGGCAACAGCACCGGCACCCTGATGGTGTTCTTCGGCAAC
GTGGACAGCAGCGGCATCAAGCACAACATCTTCAACCCCCCCATCATCGCCCGGTACATCCGGCTG
CACCCCACCCACTACAGCATCAGATCCACCCTGCGGATGGAACTGATGGGCTGCGACCTGAACTCC
TGCAGCATGCCTCTGGGCATGGAAAGCAAGGCCATCAGCGACGCCCAGATCACAGCCAGCAGCTAC
TTCACCAACATGTTCGCCACCTGGTCCCCCTCCAAGGCCAGGCTGCACCTGCAGGGCCGGTCCAAC
GCCTGGCGGCCTCAGGTGAACAACCCCAAAGAATGGCTGCAGGTGGACTTTCAGAAAACCATGAAG
GTGACCGGCGTGACCACCCAGGGCGTGAAAAGCCTGCTGACCAGCATGTACGTGAAAGAGTTTCTG
ATCAGCAGCAGCCAGGACGGCCACCAGTGGACCCTGTTCTTTCAGAACGGCAAGGTGAAAGTGTTC
CAGGGCAACCAGGACTCCTTCACCCCCGTGGTGAACTCCCTGGACCCCCCCCTGCTGACCCGCTAC
CTGCGGATCCACCCCCAGTCTTGGGTGCACCAGATCGCCCTGAGGATGGAAGTGCTGGGATGTGAG
GCCCAGGATCTGTACTGA (SEQ ID NO:18)
```

Figure 17B

FVIII-FL-AA

```
mqielstcff lcllrfcfsa trryylgave lswdymqsdl gelpvdarfp prvpksfpfn
tsvvykktlf veftdhlfni akprppwmgl lgptiqaevy dtvvitlknm ashpvslhav
gvsywkaseg aeyddqtsqr ekeddkvfpg gshtyvwqvl kengpmasdp lcltysylsh
vdlvkdlnsg ligallvcre gslakektqt lhkfillfav fdegkswhse tknslmqdrd
aasarawpkm htvngyvnrs lpgligchrk svywhvigmg ttpevhsifl eghtflvrnh
rqasleispi tfltaqtllm dlgqfllfch isshqhdgme ayvkvdscpe epqlrmknne
eaedydddlt dsemdvvrfd ddnspsfiqi rsvakkhpkt wvhyiaaeee dwdyaplvla
pddrsyksqy lnngpqrigr kykkvrfmay tdetfktrea iqhesgilgp llygevgdtl
liifknqasr pyniyphgit dvrplysrrl pkgvkhlkdf pilpgeifky kwtvtvedgp
tksdprcltr yyssfvnmer dlasgligpl licykesvdq rgnqimsdkr nvilfsvfde
nrswylteni qrflpnpagv qledpefqas nimhsingyv fdslqlsvcl hevaywyils
igaqtdflsv ffsgytfkhk mvyedtltlf pfsgetvfms menpglwilg chnsdfrnrg
mtallkvssc dkntgdyyed syedisayll sknnaieprs fsqnsrhpst rqkqfnatti
pendiektdp wfahrtpmpk iqnvsssdll mllrqsptph glslsdlqea kyetfsddps
pgaidsnnsl semthfrpql hhsgdmvftp esglqlrlne klgttaatel kkldfkvsst
snnlistips dnlaagtdnt sslgppsmpv hydsqldttl fgkkssplte sggplslsee
nndskllesg lmnsqesswg knvsstesgr lfkgkrahgp alltkdnalf kvsisllktn
ktsnnsatnr kthidgpsll ienspsvwqn ilesdtefkk vtplihdrml mdknatalrl
nhmsnkttss knmemvqgkk egpippdaqn pdmsffkmlf lpesarwiqr thgknslnsg
qgpspkqlvs lgpeksvegq nflseknkvv vgkgeftkdv glkemvfpss rnlfltnldn
lbennthnqe kkiqeeiekk etliqenvvl pqihtvtgtk nfmknlflls trqnvegsyd
gayapvlqdf rslndstnrt kkhtafskk geeenleglg nqtkqiveky acttrispnt
sqqnfvtqrs kralkqfrlp leetelekri ivddtstqws knmkhltpst ltqidyneke
kgaitqspls dcltrshsip qanrsplpia kvssfpsirp iyltrvlfqd nsshlpaasy
rkkdsgvqes shflqgakkn nlslailtle mtgdqrevgs lgtsatnsvt ykkventvlp
kpdlpktsgk vellpkvhiy qkdlfptets ngspghldlv egsllqgteg aikwneanrp
gkvpflrvat essaktpskl ldplawdnhy gtqipkeewk sqekspekta fkkkdtilsl
nacesnhaia ainegqnkpe ievtwakqgr terlcsqnpp vlkrhqreit rttlqsdqee
idyddtisve mkkedfdiyd edenqsprsf qkktrhyfia averlwdygm sssphvlrnr
aqsgsvpqfk kvvfqeftdg sftqplyrge lnehlqllgp yiraevedni mvtfrnqasr
pysfysslis yeedqrqgae prknfvkpne tktyfwkvqh hmaptkdefd ckawayfsdv
dlekdvhsgl igpllvchtn tlnpahgrqv tvqefalfft ifdetkswyf tenmerncra
pcniqmedpt fkenyrfhai ngyimdtlpg lvmaqdqrir wyllsmgsne nihsihfsgh
vftvrkkeey kmalynlypg vfetvemlps kagiwrveol igehlhagms tlflvysnkc
qtplqmasgh irdfqitasg qygqwapkla rlhysqsina wstkepfswi kvdllapmii
hgiktqgarq kfsslyisqf iimysldgkk wqtyrqnstg tlmvffqnvd ssqikhnifn
ppiiaryirl hpthysirst lrmelmgcdl nscsmplgme skaisdaqit assyftnmfa
twspskarlh lqgrsnawrp qvnnpkewlq vdfqktmkvt qvttqgvksl ltsmyvkefl
isssqdghqw tlffqngkvk vfqgnqdsft pvvnsldppl ltrylrihpq swvhqialrm
evlgceaqdl y (SEQ ID NO:19)
```

```
atgcagattgagctgagcacctgcttcttcctgtgcctgctgaggttctgcttctctgccaccagg
agatactacctgggcgccgtggagctgagctgggactacatgcagtctgacctgggcgagctgcct
gtggacgccaggttccccccccagagtgcccaagagcttccccttcaacacctcagtggtgtacaag
aagacoctgttcgtggagttcaccgaccacctgttcaacatcgccaagcccaggccccctggatg
ggcctgctgggcccaccatccaggccgaggtgtacgacaccgtggtgatcaccctgaagaacatg
gccagccacccgtgagcctgcacgccgtgggcgtgagctactggaaggcctctgagggcgccgag
tatgacgaccagaccagccagagggagaaggaggacgacaaggtgttccccggcggcagccacacc
tacgtgtggcaggtgctgaaggagaacggccccatggccagcgaccccctgtgcctgacctacagc
tacctgagccacgtggacctggtgaaggacctgaactctggcctgatcggcgccctgctggtgtgc
agggagggcagcctggccaaggagaagacccagaccctgcacaagttcatcctgctgttcgccgtg
ttcgatgagggcaagagctggcacagcgagaccaagaacagcctgatgcaggacagggatgccgcc
tctgccagggcctggcccaagatgcacaccgtgaacggctacgtgaacaggagcctgcccggcctg
atcggctgccacaggaagtctgtgtactggcacgtgatcggcatgggcaccaccccgaggtgcac
agcatcttcctggagggccacaccttcctggtgaggaaccacaggcaggccagcctggagatcagc
cccatcaccttcctgaccgcccagaccctgctgatggacctgggccagttcctgctgttctgccac
atcagcagccaccagcacgacggcatggaggcctacgtgaaggtggacagctgccccgaggagccc
cagctgaggatgaagaacaacgaggaggccgaggactatgatgatgacctgaccgactctgagatg
gacgtggtgaggtttgatgatgacaacagccccagcttcatccagatcaggtctgtggccaagaag
cacccccaagacctgggtgcactacatcgccgccgaggaggaggactgggactacgcccccctggtg
ctggcccccgacgacaggagctacaagagccagtacctgaacaacggccccagaggatcggcagg
aagtacaagaaggtcagattcatggcctacaccgacgagaccttcaagaccagggaggccatccag
cacgagtctggcatcctgggccccctgctgtacggcgaggtgggcgacaccctgctgatcatcttc
aagaaccaggccagcaggccctacaacatctaccccacggcatcaccgatgtgaggcccctgtac
agcaggaggctgcccaagggcgtgaagcacctgaaggacttccccatcctgcccggcgagatcttc
aagtacaagtggaccgtgaccgtggaggatggccccaccaagtctgacccaggtgcctgaccagg
tactacagcagcttcgtgaacatggagagggacctggcctctggcctgatcggcccctgctgatc
tgctacaaggagagcgtggaccagaggggcaaccagatcatgtctgacaagaggaacgtgatcctg
ttctctgtgttcgatgagaacaggagctggtatctgaccgagaacatccagaggttcctgcccaac
cccgccggcgtgcagctggaggaccccgagttccaggccagcaacatcatgcacagcatcaacggc
tacgtgttcgacagcctgcagctgtctgtgtgcctgcacgaggtggcctactggtacatcctgagc
atcggcgcccagaccgacttcctgtctgtgttcttctctggctacaccttcaagcacaagatggtg
tacgaggacaccctgaccctgttccccttcagcggcgagaccgtgttcatgagcatggagaacccc
ggcctgtggatcctggctgccacaacagcgacttcaggaacagggggcatgaccgccctgctgaaa
gtcagcagctgcgacaagaacaccggcgactactacgaggacagctacgaggacatcagcgcctac
ctgctgagcaagaacaacgccatcgagcccaggagcttcagccagaaccccccgtgctgaagagg
caccagagggagatcaccaggaccaccctgcagagcgaccaggaggagatcgactatgatgacacc
```

```
atcagcgtggagatgaagaaggaggacttcgacatctacgacgaggacgagaaccagagccccagg
agcttccagaagaagaccaggcactacttcatcgccgcgtggagaggctgtgggactatggcatg
agcagcagcccccacgtgctgaggaacagggcccagagcggcagcgtgccccagttcaagaaggtg
gtgttccaggagttcaccgacggcagcttcaccagcccctgtacagaggcgagctgaacgagcac
ctgggcctgctggcccctacatcagggccgaggtggaggacaacatcatggtgaccttcaggaac
caggccagcaggccctacagcttctacagcagcctgatcagctacgaggaggaccagaggcaggc
gccgagccaggaagaacttcgtgaagcccaacgagaccaagacctacttctggaaggtgcagcac
cacatggcccccaccaaggacgagttcgactgcaaggcctgggcctacttctctgatgtggacctg
gagaaggacgtgcacagcggcctgatcggcccctgctggtgtgccacaccaacaccctgaacccc
gccacggcaggcaggtgaccgtgcaggagttcgccctgttcttcaccatcttcgacgagaccaag
agctggtacttcaccgagaacatggagaggaactgcagggccccctgcaacatccagatggaggac
cccaccttcaaggagaactacaggttccacgccatcaacggctacatcatggacaccctgccggc
ctggtgatggcccaggaccagaggatcaggtggtatctgctgagcatgggcagcaacgagaacatc
cacagcatccacttcagcggccacgtgttcaccgtgaggaagaaggaggagtacaagatggccctg
tacaacctgtaccccggcgtgttcgagaccgtggagatgctgcccagcaaggccggcatctggagg
gtggagtgcctgatcggcgagcacctgcacgccggcatgagcaccctgttcctggtgtacagcaac
aagtgccagacccccctgggcatggccagcggccacatcagggacttccagatcaccgcctctggc
cagtacggccagtgggcccccaagctggccaggctgcactacagcggcagcatcaacgcctggagc
accaaggagcccttcagctggatcaaggtggacctgctggccccatgatcatccacggcatcaag
acccagggcgccaggcagaagttcagcagcctgtacatcagccagttcatcatcatgtacagcctg
gacggcaagaagtggcagacctacaggggcaacagcaccggcaccctgatggtgttcttcggcaac
gtggacagcagcggcatcaagcacaacatcttcaacccccccatcatcgccaggtacatcaggctg
caccccacccactacagcatcaggagcaccctgcggatggaactgatgggctgcgacctgaacagc
tgcagcatgcccctgggcatggagagcaaggccatctctgacgcccagatcaccgccagcagctac
ttcaccaacatgttcgccacctggagccccagcaaggccaggctgcacctgcagggcaggagcaac
gcctggaggccccaggtgaacaaccccaaggagtggctgcaggtggacttccagaagaccatgaag
gtgaccggcgtgaccaccagggcgtgaagagcctgctgaccagcatgtacgtgaaggagttcctg
atcagcagcagccaggacggccaccagtggaccctgttcttccagaacggcaaagtgaaggtgttc
cagggcaaccaggacagcttcacCcccgtggtgaacagcctggaccccccctgctgaccaggtat
ctgaggatccaccccagagctgggtgcaccagatcgccctgagaatggaagtgctgggatgcgag
gcccaggacctgtactga (SEQ ID NO:20)
```

```
MQIELSTCFFLCLLRFCFSATRRYYLGAVELSWDYMQSDLGELPVDAR'FPPRVPKSFPFNTSVVYK
KTLFVEFTDHLFNIAKPRPPWMGLLGPTIQAEVYDTVVITLKNMASHPVSLHAVGVSYWKASEGAEY
DDQTSQREKEDDKVFPGGSHTYVWQVLKENGPMASDPLCLTYSYLSHVDLVKDLNSGLIGALLVCRE
GSLAKEKTQTLHKFILLFAVFDEGKSWHSETKNSLMQDRDAASARAWPKMHTVNGYVNRSLPGLIGC
HRKSVYWHVIGMGTTPEVHSIFLEGHTFLVRNHRQASLEISPITFLTAQTLLMDLGQFLLFCHISSH
QHDGMEAYVKVDSCPEEPQLRMKNNEEAEDYDDDLTDSEMDVVRFDDDNSPSFIQIRSVAKKHPKTW
VHYIAAEEEDWDYAPLVLAPDDRSYKSQYLNNGPQRIGRKYKKVRFMAYTDETFKTREAIQHESGIL
GPLLYGEVGDTLLIIFKNQASRPYNIYPHGITDVRPLYSRRLPKGVKHLKDFPILPGEIFKYKWTVT
VEDGPTKSDPRCLTRYYSSFVNMERDLASGLIGPLLICYKESVDQRGNQIMSDKRNVILFSVFDENR
SWYLTENIQRFLPNPAGVQLEDPEFQASNIMHSINGYVFDSLQLSVCLHEVAYWYILSIGAQTDFLS
VFFSGYTFKHKMVYEDTLTLFPFSGETVFMSMENPGLWILGCHNSDFRNRGMTALLKVSSCDKNTGD
YYEDSYEDISAYLLSKNNAIEPRSFSQNPPVLKRHQREITRTTLQSDQEEIDYDDTISVEMKKEDFD
IYDEDENQSPRSFQKKTRHYFIAAVERLWDYGMSSSPHVLRNRAQSGSVPQFKKVVFQEFTDGSFTQ
PLYRGELNEHLGLLGPYIRAEVEDNIMVTFRNQASRPYSFYSSLISYEEDQRQGAEPRKNFVKPNET
KTYFWKVQHHMAPTKDEFDCKAWAYFSDVDLEKDVHSGLIGPLLVCHTNTLNPAHGRQVTVQEFALF
FTIFDETKSWYFTENMERNCRAPCNIQMEDPTFKENYRFHAINGYIMDTLPGLVMAQDQRIRWYLLS
MGSNENIHSIHFSGHVFTVRKKEEYKMALYNLYPGVFETVEMLPSKAGIWRVECLIGEHLHAGMSTL
FLVYSNKCQTPLGMASGHIRDFQITASGQYGQWAPKLARLHYSGSINAWSTKEPFSWIKVDLLAPMI
IHGIKTQGARQKFSSLYISQFIIMYSLDGKKWQTYRGNSTGTLMVFFGNVDSSGIKHNIFNPPIIAR
YIRLHPTHYSIRSTLRMELMGCDLNSCSMPLGMESKAISDAQITASSYFTNMFATWSPSKARLHLQG
RSNAWRPQVNNPKEWLQVDFQKTMKVTGVTTQGVKSLLTSMYVKEFLISSSQDGHQWTLFFQNGKVK
VFQGNQDSFTPVVNSLDPPLLTRYLRIHPQSWVHQIALRMEVLGCEAQDLY    (SEQ ID NO:21)
```

```
                                                                gcc
accaggagat actacctggg cgccgtggag ctgagctggg actacatgca gtctgacctg
ggcgagctgc ctgtggacgc caggttcccc cccagagtgc ccaagagctt ccccttcaac
acctcagtgg tgtacaagaa gaccctgttc gtggagttca ccgaccacct gttcaacatc
gccaagccca ggccccctg gatgggcctg ctgggcccca ccatccaggc cgaggtgtac
gacaccgtgg tgatcaccct gaagaacatg gccagccacc ccgtgagcct gcacgccgtg
ggcgtgagct actggaaggc ctctgagggc gccgagtatg acgaccagac cagccagagg
gagaaggagg acgacaaggt gttccccggc ggcagccaca cctacgtgtg gcaggtgctg
aaggagaacg gccccatggc cagcgacccc ctgtgcctga cctacagcta cctgagccac
gtggacctgg tgaaggacct gaactctggc ctgatcggcg ccctgctggt gtgcagggag
ggcagcctgg ccaaggagaa gacccagacc ctgcacaagt tcatcctgct gttcgccgtg
ttcgatgagg gcaagagctg gcacagcgag accaagaaca gctgatgca ggacagggat
gccgcctct ccagggcctg gcccaagatg cacaccgtga acggctacgt gaacaggagc
ctgcccggcc tgatcggctg ccacaggaag tctgtgtact ggcacgtgat cggcatgggc
accacccccg aggtgcacag catcttcctg gagggccaca cctcctggt gaggaaccac
aggcaggcca gcctggagat cagccccatc accttcctga ccgcccagac cctgctgatg
gacctgggcc agttcctgct gttctgccac atcagcagcc accagcacga cggcatggag
gcctacgtga aggtggacag ctgccccgag gagcccagc tgaggatgaa gaacaacgag
gaggccgagg actatgatga tgacctgacc gactctgaga tggacgtggt gaggtttgat
gatgacaaca gcccagctt catccagatc aggtctgtgg ccaagaagca cccaagacc
tgggtgcact acatcgccgc cgaggaggag gactgggact acgcccct ggtgctggcc
cccgacgaca ggagctacaa gagccagtac ctgaacaacg gccccagag gatcggcagg
aagtacaaga aggtcagatt catggcctac accgacgaga ccttcaagac cagggaggcc
atccagcacg agtctggcat cctgggcccc ctgctgtacg gcgaggtggg cgacaccctg
ctgatcatct tcaagaacca ggccagcagg ccctacaaca tctaccccca cggcatcacc
gatgtgaggc ccctgtacag caggagctg cccaagggcg tgaagcacct gaaggacttc
cccatcctgc ccggcgagat cttcaagtac aagtggaccg tgaccgtgga ggatggcccc
accaagtctg accccaggtg cctgaccagg tactacagca gcttcgtgaa catggagagg
gacctggcct ctggcctgat cggcccctg ctgatctgct acaaggagag cgtggaccag
aggggcaacc agatcatgtc tgacaagagg aacgtgatcc tgttctctgt gttcgatgag
aacaggagct ggtatctgac cgagaacatc cagaggttcc tgcccaaccc cgccggcgtg
cagctggagg accccgagtt ccaggccagc aacatcatgc acagcatcaa cggctacgtg
ttcgacagcc tgcagctgtc tgtgtgcctg cacgaggtgg cctactggta catcctgagc
atcggcgccc agaccgactt cctgtctgtg ttcttctctg gctacacctt caagcacaag
atggtgtacg aggacacct gaccctgttc cccttcagcg gcgagaccgt gttcatgagc
atggagaacc ccggcctgtg gatcctgggc tgccacaaca gcgacttcag gaacaggggc
atgaccgccc tgctgaaagt cagcagctgc gacaagaaca ccggcgacta ctacgaggac
agctacgagg acatcagcgc ctacctgctg agcaagaaca acgccatcga gcccagg
(SEQ ID NO:22)
```

```
                                        g agatcaccag gaccaccctg
cagagcgacc aggaggagat cgactatgat gacaccatca gcgtggagat gaagaaggag
gacttcgaca tctacgacga ggacgagaac cagagcccca ggagcttcca gaagaagacc
aggcactact tcatcgccgc cgtggagagg ctgtgggact atggcatgag cagcagcccc
cacgtgctga gaacagggc ccagagcggc agcgtgcccc agttcaagaa ggtggtgttc
caggagttca ccgacggcag cttcacccag cccctgtaca gaggcgagct gaacgagcac
ctgggcctgc tgggcccta catcagggcc gaggtggagg acaacatcat ggtgaccttc
aggaaccagg ccagcaggcc ctacagcttc tacagcagcc tgatcagcta cgaggaggac
cagaggcagg gcgccgagcc caggaagaac ttcgtgaagc ccaacgagac caagacctac
ttctgaagg tgcagcacca catggccccc accaaggacg agttcgactg caaggcctgg
gcctacttct ctgatgtgga cctggagaag gacgtgcaca gcggcctgat cggcccctg
ctggtgtgcc acaccaacac cctgaacccc gcccacggca ggcaggtgac cgtgcaggag
ttcgccctgt tcttcaccat cttcgacgag accaagagct ggtacttcac cgagaacatg
gagaggaact gcagggcccc ctgcaacatc cagatggagg accccacctt caaggagaac
tacaggttcc acgccatcaa cggctacatc atggacaccc tgcccggcct ggtgatggcc
caggaccaga ggatcaggtg gtatctgctg agcatgggca gcaacgagaa catccacagc
atccacttca gcggccacgt gttcaccgtg aggaagaagg aggagtacaa gatggccctg
tacaacctgt accccggcgt gttcgagacc gtggagatgc tgcccagcaa ggccggcatc
tggagggtgg agtgcctgat cggcgagcac ctgcacgccc gcatgagcac cctgttcctg
gtgtacagca acaagtgcca gaccccctg ggcatggcca gcggccacat cagggacttc
cagatcaccg cctctggcca gtacggccag tgggcccca agctggccag gctgcactac
agcggcagca tcaacgcctg gagcaccaag gagcccttca gctggatcaa ggtggacctg
ctggccccca tgatcatcca cggcatcaag acccagggcg ccaggcagaa gttcagcagc
ctgtacatca gccagttcat catcatgtac agcctggacg gcaagaagtg gcagacctac
aggggcaaca gcaccggcac cctgatggtg ttcttcggca acgtggacag cagcggcatc
aagcacaaca tcttcaaccc cccatcatc gccaggtaca tcaggctgca ccccacccac
tacagcatca ggagcaccct gcggatggaa ctgatgggct gcgacctgaa cagctgcagc
atgcccctgg gcatggagag caaggccatc tctgacgccc agatcaccgc cagcagctac
ttcaccaaca tgttcgccac ctggagcccc agcaaggcca ggctgcacct gcagggcagg
agcaacgcct ggaggcccca ggtgaacaac cccaaggagt ggctgcaggt ggacttccag
aagaccatga aggtgaccgg cgtgaccacc agggcgtga gagcctgct gaccagcatg
tacgtgaagg agttcctgat cagcagcagc caggacggcc accagtggac cctgttcttc
cagaacggca aagtgaaggt gttccaggc aaccaggaca gcttcacccc cgtggtgaac
agcctggacc cccctgct gaccaggtat ctgaggatcc accccagag ctgggtgcac
cagatcgccc tgagaatgga agtgctggga tgcgaggccc aggacctgta c
(SEQ ID NO:23)
```

```
                                                            gcc
accaggagat actacctggg ggctgtggaa cttttcttggg actacatgca gtctgacctg
ggagagctgc ctgtggatgc caggttccca cccagagtgc ccaagtcctt cccattcaac
acctctgtgg tctacaagaa gacactcttt gtggaattca ctgaccacct gttcaacatt
gcaaaaccca gaccaccctg gatgggactc ctgggaccca ccattcaggc tgaggtgtat
gacactgtgg tcatcaccct caagaacatg gcatcccacc ctgtgtctct gcatgctgtg
ggagtctcat actggaaagc ctctgaaggg gctgagtatg atgaccagac atcccagaga
gagaaagagg atgacaaggt gttccctggg ggatctcaca cctatgtgtg gcaagtcctc
aaggagaatg gacccatggc atctgaccca ctctgcctga catactccta cctttctcat
gtggacctgg tcaaggacct caactctgga ctgattgggg cactgctggt gtgcaggaa
ggatccctgg ccaaggagaa aacccagaca ctgcacaagt tcattctcct gtttgctgtc
tttgatgagg gcaagtcttg gcactctgaa acaaagaact ccctgatgca agacaggat
gctgcctctg ccagggcatg gcccaagatg cacactgtga atggctatgt gaacagatca
ctgcctggac tcattggctg ccacaggaaa tctgtctact ggcatgtgat tggcatgggg
acaacccctg aagtgcactc cattttcctg gagggacaca ccttcctggt caggaaccac
agacaagcct ctctggagat ctctcccatc accttcctca ctgcacagac actgctgatg
gaccttggac agttcctgct gttctgccac atctcttccc accagcatga tggcatggaa
gcctatgtca aggtggactc atgccctgag gaaccacagc tcaggatgaa gaacaatgag
gaggctgagg actatgatga tgacctgact gactctgaga tggatgtggt cagatttgat
gatgacaact ctccatcctt cattcagatc aggtctgtgg caaagaaaca ccccaagaca
tgggtgcact acattgctgc tgaggaagag gactgggact atgcaccact ggtcctggcc
cctgatgaca ggagctacaa gtctcagtac ctcaacaatg gccacaaag aattggaaga
aagtacaaga aagtcagatt catggcctac actgatgaaa ccttcaagac aagagaagcc
attcagcatg agtctggcat tctgggacca ctcctgtatg gggaagtggg agacaccctg
ctcatcatct tcaagaacca ggcctccagg cctacaaca tctacccaca tggcatcact
gatgtcaggc cctgtacag caggagactg ccaaaagggg tgaaacacct caaggacttc
cccattctgc ctggagagat cttcaagtac aagtggactg tcactgtgga ggatggacca
acaaagtctg accccaggtg cctcaccaga tactactcct cttttgtgaa catggagaga
gacctggcat ctggactgat tggaccactg ctcatctgct acaaggagtc tgtggaccag
agaggcaacc agatcatgtc tgacaagaga aatgtgattc tgttctctgt cttttgatgag
aacagatcat ggtacctgac tgagaacatt cagagattcc tgcccaaccc tgctggggtg
caactggaag accctgagtt ccaggcaagc aacatcatgc actccatcaa tggctatgtg
tttgactctc tccagctttc tgtctgcctg catgaggtgg cctactggta cattctttct
attggggcac aaactgactt cctttctgtc ttcttctctg gatacacctt caagcacaag
atggtgtatg aggacaccct gacactcttc ccattctctg gggaaactgt gttcatgagc
atggagaacc ctggactgtg gattctggga tgccacaact ctgacttcag aaacagggga
atgactgcac tgctcaaagt ctcctcctgt gacaagaaca ctggggacta ctatgaggac
tcttatgagg acatctctgc ctacctgctc agcaagaaca atgccattga gcccaga
(SEQ ID NO:24)
```

```
                                          g agatcaccag gacaaccctc
cagtctgacc aggaagagat tgactatgat gacaccattt ctgtggagat gaagaaggag
gactttgaca tctatgatga ggacgagaac cagtctccaa gatcattcca gaagaagaca
agacactact tcattgctgc tgtggaaaga ctgtgggact atggcatgtc ttcctctccc
catgtcctca ggaacagggc acagtctggc tctgtgccac agttcaagaa agtggtcttc
caggagttca ctgatggctc attcacccag ccctgtaca gaggggaact gaatgagcac
ctgggactcc tggaccata catcagggct gaggtggaag acaacatcat ggtgacattc
agaaaccagg cctccaggcc ctacagcttc tactcttccc tcatcagcta tgaggaagac
cagagacaag gggctgagcc aagaaagaac tttgtgaaac ccaatgaaac caagacctac
ttctggaaag tccagcacca catggcaccc accaaggatg agtttgactg caaggctgg
gcatacttct ctgatgtgga cctggagaaa gatgtgcact ctggcctgat tggcccactc
ctggtctgcc acaccaacac cctgaaccct gcacatggaa ggcaagtgac tgtgcaggag
tttgccctct tcttcaccat ctttgatgaa accaagtcat ggtacttcac tgagaacatg
gagagaaact gcagagcacc atgcaacatt cagatggaag ccccaccctt caaggagaac
tacaggttcc atgccatcaa tggctacatc atggacaccc tgcctgggct tgtcatggca
caggaccaga gaatcagatg gtacctgctt tctatgggat ccaatgagaa cattcactcc
atccacttct ctgggcatgt cttcactgtg agaaagaagg aggaatacaa gatggccctg
tacaacctct accctggggt ctttgagact gtggagatgc tgccctccaa agctggcatc
tggagggtgg aatgctcat tggggagcac ctgcatgctg gcatgtcaac cctgttcctg
gtctacagca caagtgcca gacaccctg ggaatggcct ctggccacat cagggacttc
cagatcactg cctctggcca gtatggccag tgggcaccca aactggccag gctccactac
tctggctcca tcaatgcatg gtcaaccaag gagccattct cttggatcaa ggtggacctg
ctggcaccca tgatcattca tggcatcaag acacaggggg caagacagaa attctcctct
ctgtacatct cacagttcat catcatgtac tctctggatg caagaagtg gcagacatac
agaggcaact ccactggcac cctcatggtc ttctttggca atgtggacag ctctggcatc
aagcacaaca tcttcaaccc tccatcatt gccagataca tcaggctgca cccacccac
tactcaatca gatcaaccct caggatggaa ctgatgggat gtgacctgaa ctcctgtca
atgccctgg aatggagag caaggccatt tctgatgccc agatcactgc atcctcttac
ttcaccaaca tgtttgccac ctggtcacca tcaaaagcca ggctgcacct ccagggaaga
agcaatgcct ggagacccca ggtcaacaac ccaaaggaat ggctgcaagt ggacttccag
aagacaatga aagtcactgg ggtgacaacc caggggtca gtctctgct cacctcaatg
tatgtgaagg agttcctgat ctcttcctca caggatggcc accagtggac actcttcttc
cagaatggca aagtcaaggt gttccagggc aaccaggact ctttcacacc tgtggtgaac
tcactggacc ccccctcct gacaagatac ctgagaattc accccagtc ttgggtccac
cagattgccc tgagaatgga agtcctggga tgtgaggcac aagacctgta c
(SEQ ID NO:25)
```

```
ATGCAGATTGAGCTGTCCACCTGCTTCTTTCTGTGCCTGCTGAGATTCTGCTTCTCTGCCACCAGGAGATAC
TACCTGGGGGCTGTGGAACTTTCTTGGGACTACATGCAGTCTGACCTGGGAGAGCTGCCTGTGGATGCCAGG
TTCCCACCCAGAGTGCCCAAGTCCTTCCCATTCAACACCTCTGTGGTCTACAAGAAGACACTCTTTGTGGAA
TTCACTGACCACCTGTTCAACATTGCAAAACCCAGACCACCCTGGATGGGACTCCTGGGACCCACCATTCAG
GCTGAGGTGTATGACACTGTGGTCATCACCCTCAAGAACATGGCATCCCACCCTGTGTCTCTGCATGCTGTG
GGAGTCTCATACTGGAAAGCCTCTGAAGGGGCTGAGTATGATGACCAGACATCCCAGAGAGAGAAGAGGAT
GACAAGGTGTTCCCTGGGGGATCTCACACCTATGTGTGGCAAGTCCTCAAGGAGAATGGACCCATGGCATCT
GACCCACTCTGCCTGACATACTCCTACCTTTCTCATGTGGACCTGGTCAAGGACCTCAACTCTGGACTGATT
GGGGCACTGCTGGTGTGCAGGGAAGGATCCCTGGCCAAGGAGAAAACCCAGACACTGCACAAGTTCATTCTC
CTGTTTGCTGTCTTTGATGAGGGCAAGTCTTGGCACTCTGAAACAAAGAACTCCCTGATGCAAGACAGGGAT
GCTGCCTCTGCCAGGGCATGGCCCAAGATGCACACTGTGAATGGCTATGTGAACAGATCACTGCCTGGACTC
ATTGGCTGCCACAGGAAATCTGTCTACTGGCATGTGATTGGCATGGGACAACCCCTGAAGTGCACTCCATT
TTCCTGGAGGGACACACCTTCCTGGTCAGGAACCACAGACAAGCCTCTCTGGAGATCTCTCCCATCACCTTC
CTCACTGCACAGACACTGCTGATGGACCTTGGACAGTTCCTGCTGTTCTGCCACATCTCTTCCCACCAGCAT
GATGGCATGGAAGCCTATGTCAAGGTGGACTCATGCCCTGAGGAACCACAGCTCAGGATGAAGAACAATGAG
GAGGCTGAGGACTATGATGATGACCTGACTGACTCTGAGATGGATGTGGTCAGATTTGATGATGACAACTCT
CCATCCTTCATTCAGATCAGGTCTGTGGCAAAGAAACACCCCAAGACATGGGTGCACTACATTGCTGCTGAG
GAAGAGGACTGGGACTATGCACCACTGGTCCTGGCCCCTGATGACAGGAGCTACAAGTCTCAGTACCTCAAC
AATGGCCCACAAAGAATTGGAAGAAAGTACAAGAAAGTCAGATTCATGGCCTACACTGATGAAACCTTCAAG
ACAAGAGAAGCCATTCAGCATGAGTCTGGCATTCTGGGACCACTCCTGTATGGGAAGTGGGAGACACCCTG
CTCATCATCTTCAAGAACCAGGCCTCCAGGCCCTACAACATCTACCCACATGGCATCACTGATGTCAGGCCC
CTGTACAGCAGGAGACTGCCAAAAGGGGTGAAACACCTCAAGGACTTCCCCATTCTGCCTGGAGAGATCTTC
AAGTACAAGTGGACTGTCACTGTGGAGGATGGACCAACAAAGTCTGACCCCAGGTGCCTCACCAGATACTAC
TCCTCTTTTGTGAACATGGAGAGAGACCTGGCATCTGGACTGATTGGACCACTGCTCATCTGCTACAAGGAG
TCTGTGGACCAGAGAGGCAACCAGATCATGTCTGACAAGAGAAATGTGATTCTGTTCTCTGTCTTTGATGAG
AACAGATCATGGTACCTGACTGAGAACATTCAGAGATTCCTGCCCCAACCCTGCTGGGGTGCAACTGGAAGAC
CCTGAGTTCCAGGCAAGCAACATCATGCACTCCATCAATGGCTATGTGTTTGACTCTCTCCAGCTTTCTGTC
TGCCTGCATGAGGTGGCCTACTGGTACATTCTTTCTATTGGGGCACAAACTGACTTCCTTTCTGTCTTCTTC
TCTGGATACACCTTCAAGCACAAGATGGTGTATGAGGACACCCTGACACTCTTCCCATTCTCTGGGGAAACT
GTGTTCATGAGCATGGAGAACCCTGGACTGTGGATTCTGGGATGCCACAACTCTGACTTCAGAAACAGGGGA
ATGACTGCACTGCTCAAAGTCTCCTCCTGTGACAAGAACACTGGGGACTACTATGAGGACTCTTATGAGGAC
ATCTCTGCCTACCTGCTCAGCAAGAACAATGCCATTGAGCCCAGAGAGATCACCAGGACAACCCTCCAGTCT
GACCAGGAAGAGATTGACTATGATGACACCATTTCTGTGGAGATGAAGAAGGAGGACTTTGACATCTATGAT
GAGGACGAGAACCAGTCTCCAAGATCATTCCAGAAGAAGACAAGACACTACTTCATTGCTGCTGTGGAAAGA
CTGTGGGACTATGGCATGTCTTCCTCTCCCATGTCCTCAGGAACAGGGCACAGTCTGGCTCTGTGCCACAG
TTCAAGAAAGTGGTCTTCCAGGAGTTCACTGATGGCTCATTCACCCAGCCCCTGTACAGAGGGAACTGAAT
GAGCACCTGGGACTCCTGGGACCATACATCAGGGCTGAGGTGGAAGACAACATCATGGTGACATTCAGAAAC
CAGGCCTCCAGGCCCTACAGCTTCTACTCTTCCCTCATCAGCTATGAGGAAGACCAGAGACAAGGGGCTGAG
CCAAGAAAGAACTTTGTGAAACCCAATGAAACCAAGACCTACTTCTGGAAAGTCCAGCACCACATGGCACCC
```

```
ACCAAGGATGAGTTTGACTGCAAGGCCTGGGCATACTTCTCTGATGTGGACCTGGAGAAAGATGTGCACTCT
GGCCTGATTGGCCCACTCCTGGTCTGCCACACCAACACCCTGAACCCTGCACATGGAAGGCAAGTGACTGTG
CAGGAGTTTGCCCTCTTCTTCACCATCTTTGATGAAACCAAGTCATGGTACTTCACTGAGAACATGGAGAGA
AACTGCAGAGCACCATGCAACATTCAGATGGAAGACCCCACCTTCAAGGAGAACTACAGGTTCCATGCCATC
AATGGCTACATCATGGACACCCTGCCTGGGCTTGTCATGGCACAGGACCAGAGAATCAGATGGTACCTGCTT
TCTATGGGATCCAATGAGAACATTCACTCCATCCACTTCTCTGGGCATGTCTTCACTGTGAGAAAGAAGGAG
GAATACAAGATGGCCCTGTACAACCTCTACCCTGGGGTCTTTGAGACTGTGGAGATGCTGCCCTCCAAAGCT
GGCATCTGGAGGGTGGAATGCCTCATTGGGGAGCACCTGCATGCTGGCATGTCAACCCTGTTCCTGGTCTAC
AGCAACAAGTGCCAGACACCCCTGGGAATGGCCTCTGGCCACATCAGGGACTTCCAGATCACTGCCTCTGGC
CAGTATGGCCAGTGGGCACCCAAACTGGCCAGGCTCCACTACTCTGGCTCCATCAATGCATGGTCAACCAAG
GAGCCATTCTCTTGGATCAAGGTGGACCTGCTGGCACCCATGATCATTCATGGCATCAAGACACAGGGGGCA
AGACAGAAATTCTCCTCTCTGTACATCTCACAGTTCATCATCATGTACTCTCTGGATGGCAAGAAGTGGCAG
ACATACAGAGGCAACTCCACTGGCACCCTCATGGTCTTCTTTGGCAATGTGGACAGCTCTGGCATCAAGCAC
AACATCTTCAACCCTCCCATCATTGCCAGATACATCAGGCTGCACCCCACCCACTACTCAATCAGATCAACC
CTCAGGATGGAACTGATGGGATGTGACCTGAACTCCTGCTCAATGCCCCTGGGAATGGAGAGCAAGGCCATT
TCTGATGCCCAGATCACTGCATCCTCTTACTTCACCAACATGTTTGCCACCTGGTCACCATCAAAAGCCAGG
CTGCACCTCCAGGGAAGAAGCAATGCCTGGAGACCCCAGGTCAACAACCCAAAGGAATGGCTGCAAGTGGAC
TTCCAGAAGACAATGAAAGTCACTGGGGTGACAACCCAGGGGGTCAAGTCTCTGCTCACCTCAATGTATGTG
AAGGAGTTCCTGATCTCTTCCTCACAGGATGGCCACCAGTGGACACTCTTCTTCCAGAATGGCAAAGTCAAG
GTGTTCCAGGGCAACCAGGACTCTTTCACACCTGTGGTGAACTCACTGGACCCCCCCCTCCTGACAAGATAC
CTGAGAATTCACCCCCAGTCTTGGGTCCACCAGATTGCCCTGAGAATGGAAGTCCTGGGATGTGAGGCACAA
GACCTGTACTGA   (SEQ ID NO:26)
```

ATGCAGATTGAGCTGTCCACCTGCTTCTTTCTGTGCCTGCTGAGATTCTGCTTCTCTGCCACCAGG
AGATACTACCTGGGGGCTGTGGAACTTTCTTGGGACTACATGCAGTCTGACCTGGGAGAGCTGCCT
GTGGATGCCAGGTTCCCACCCAGAGTGCCCAAGTCCTTCCCATTCAACACCTCTGTGGTCTACAAG
AAGCACTCTTTGTGGAATTCACTGACCACCTGTTCAACATTGCAAAACCCAGACCACCCTGGATG
GGACTCCTGGGACCCACCATTCAGGCTGAGGTGTATGACACTGTGGTCATCACCCTCAAGAACATG
GCATCCCACCCTGTGTCTCTGCATGCTGTGGGAGTCTCATACTGGAAAGCCTCTGAAGGGGCTGAG
TATGATGACCAGACATCCCAGAGAGAGAAAGAGGATGACAAGGTGTTCCCTGGGGGATCTCACACC
TATGTGTGGCAAGTCCTCAAGGAGAATGGACCCATGGCATCTGACCCACTCTGCCTGACATACTCC
TACCTTTCTCATGTGGACCTGGTCAAGGACCTCAACTCTGGACTGATTGGGGCACTGCTGGTGTGC
AGGGAAGGATCCCTGGCCAAGGAGAAAACCCAGACACTGCACAAGTTCATTCTCCTGTTTGCTGTC
TTTGATGAGGGCAAGTCTTGGCACTCTGAAACAAAGAACTCCCTGATGCAAGACAGGGATGCTGCC
TCTGCCAGGGCATGGCCCAAGATGCACACTGTGAATGGCTATGTGAACAGATCACTGCCTGGACTC
ATTGGCTGCCACAGGAAATCTGTCTACTGGCATGTGATTGGCATGGGGACAACCCCTGAAGTGCAC
TCCATTTTCCTGGAGGGACACACCTTCCTGGTCAGGAACCACAGACAAGCCTCTCTGGAGATCTCT
CCCATCACCTTCCTCACTGCACAGACACTGCTGATGGACCTTGGACAGTTCCTGCTGTTCTGCCAC
ATCTCTTCCCACCAGCATGATGGCATGGAAGCCTATGTCAAGGTGGACTCATGCCCTGAGGAACCA
CAGCTCAGGATGAAGAACAATGAGGAGGCTGAGGACTATGATGATGACCTGACTGACTCTGAGATG
GATGTGGTCAGATTTGATGATGACAACTCTCCATCCTTCATTCAGATCAGGTCTGTGGCAAAGAAA
CACCCCAAGACATGGGTGCACTACATTGCTGCTGAGGAAGAGGACTGGGACTATGCACCACTGGTC
CTGGCCCCTGATGACAGGAGCTACAAGTCTCAGTACCTCAACAATGGCCCACAAAGAATTGGAAGA
AAGTACAAGAAAGTCAGATTCATGGCCTACACTGATGAAACCTTCAAGACAAGAGAAGCCATTCAG
CATGAGTCTGGCATTCTGGGACCACTCCTGTATGGGAAGTGGGAGACACCCTGCTCATCATCTTC
AAGAACCAGGCCTCCAGGCCCTACAACATCTACCCACATGGCATCACTGATGTCAGGCCCCTGTAC
AGCAGGAGACTGCCAAAAGGGGTGAAACACCTCAAGGACTTCCCCATTCTGCCTGGAGAGATCTTC
AAGTACAAGTGGACTGTCACTGTGGAGGATGGACCAACAAAGTCTGACCCCAGGTGCCTCACCAGA
TACTACTCCTCTTTTGTGAACATGGAGAGAGACCTGGCATCTGGACTGATTGGACCACTGCTCATC
TGCTACAAGGAGTCTGTGGACCAGAGAGGCAACCAGATCATGTCTGACAAGAGAAATGTGATTCTG
TTCTCTGTCTTTGATGAGAACAGATCATGGTACCTGACTGAGAACATTCAGAGATTCCTGCCCAAC
CCTGCTGGGGTGCAACTGGAAGACCCTGAGTTCCAGGCAAGCAACATCATGCACTCCATCAATGGC
TATGTGTTTGACTCTCTCCAGCTTTCTGTCTGCCTGCATGAGGTGGCCTACTGGTACATTCTTTCT
ATTGGGGCACAAACTGACTTCCTTTCTGTCTTCTTCTCTGGATACACCTTCAAGCACAAGATGGTG
TATGAGGACACCCTGACACTCTTCCCATTCTCTGGGGAAACTGTGTTCATGAGCATGGAGAACCCT
GGACTGTGGATTCTGGGATGCCACAACTCTGACTTCAGAAACAGGGGAATGACTGCACTGCTCAAA
GTCTCCTCCTGTGACAAGAACACTGGGGACTACTATGAGGACTCTTATGAGGACATCTCTGCCTAC
CTGCTCAGCAAGAACAATGCCATTGAGCCCAGAAGCTTCTCTCAGAATTCCAGACACCCCAGCACC
AGGGAGATCACCAGGACAACCCTCCAGTCTGACCAGGAAGAGATTGACTATGATGACACCATTTCT
GTGGAGATGAAGAAGGAGGACTTTGACATCTATGATGAGGACGAGAACCAGTCTCCAAGATCATTC (Continued)

Figure 29A

```
CAGAAGAAGACAAGACACTACTTCATTGCTGCTGTGGAAAGACTGTGGGACTATGGCATGTCTTCC
TCTCCCCATGTCCTCAGGAACAGGGCACAGTCTGGCTCTGTGCCACAGTTCAAGAAAGTGGTCTTC
CAGGAGTTCACTGATGGCTCATTCACCCAGCCCTGTACAGAGGGGAACTGAATGAGCACCTGGGA
CTCCTGGGACCATACATCAGGGCTGAGGTGGAAGACAACATCATGGTGACATTCAGAAACCAGGCC
TCCAGGCCCTACAGCTTCTACTCTTCCCTCATCAGCTATGAGGAAGACCAGAGACAAGGGGCTGAG
CCAAGAAAGAACTTTGTGAAACCCAATGAAACCAAGACCTACTTCTGGAAAGTCCAGCACCACATG
GCACCCACCAAGGATGAGTTTGACTGCAAGGCCTGGGCATACTTCTCTGATGTGGACCTGGAGAAA
GATGTGCACTCTGGCCTGATTGGCCCACTCCTGGTCTGCCACACCAACACCCTGAACCCTGCACAT
GGAAGGCAAGTGACTGTGCAGGAGTTTGCCCTCTTCTTCACCATCTTTGATGAAACCAAGTCATGG
TACTTCACTGAGAACATGGAGAGAAACTGCAGAGCACCATGCAACATTCAGATGGAAGACCCCACC
TTCAAGGAGAACTACAGGTTCCATGCCATCAATGGCTACATCATGGACACCCTGCCTGGGCTTGTC
ATGGCACAGGACCAGAGAATCAGATGGTACCTGCTTTCTATGGGATCCAATGAGAACATTCACTCC
ATCCACTTCTCTGGGCATGTCTTCACTGTGAGAAGAAGGAGGAATACAAGATGGCCCTGTACAAC
CTCTACCCTGGGGTCTTTGAGACTGTGGAGATGCTGCCCTCCAAAGCTGGCATCTGGAGGGTGGAA
TGCCTCATTGGGGAGCACCTGCATGCTGGCATGTCAACCCTGTTCCTGGTCTACAGCAACAAGTGC
CAGACACCCCTGGGAATGGCCTCTGGCCACATCAGGGACTTCCAGATCACTGCCTCTGGCCAGTAT
GGCCAGTGGGCACCCAAACTGGCCAGGCTCCACTACTCTGGCTCCATCAATGCATGGTCAACCAAG
GAGCCATTCTCTTGGATCAAGGTGGACCTGCTGGCACCCATGATCATTCATGGCATCAAGACACAG
GGGGCAAGACAGAAATTCTCCTCTCTGTACATCTCACAGTTCATCATCATGTACTCTCTGGATGGC
AAGAAGTGGCAGACATACAGAGGCAACTCCACTGGCACCCTCATGGTCTTCTTTGGCAATGTGGAC
AGCTCTGGCATCAAGCACAACATCTTCAACCCTCCCATCATTGCCAGATACATCAGGCTGCACCCC
ACCCACTACTCAATCAGATCAACCCTCAGGATGGAACTGATGGGATGTGACCTGAACTCCTGCTCA
ATGCCCCTGGGAATGGAGAGCAAGGCCATTTCTGATGCCCAGATCACTGCATCCTCTTACTTCACC
AACATGTTTGCCACCTGGTCACCATCAAAAGCCAGGCTGCACCTCCAGGGAAGAAGCAATGCCTGG
AGACCCCAGGTCAACAACCCAAAGGAATGGCTGCAAGTGGACTTCCAGAAGACAATGAAAGTCACT
GGGGTGACAACCCAGGGGGTCAAGTCTCTGCTCACCTCAATGTATGTGAAGGAGTTCCTGATCTCT
TCCTCACAGGATGGCCACCAGTGGACACTCTTCTTCCAGAATGGCAAAGTCAAGGTGTTCCAGGGC
AACCAGGACTCTTTCACACCTGTGGTGAACTCACTGGACCCCCCCCTCCTGACAAGATACCTGAGA
ATTCACCCCCAGTCTTGGGTCCACCAGATTGCCCTGAGAATGGAAGTCCTGGGATGTGAGGCACAA
GACCTGTACTGA (SEQ ID NO:27)
```

ATGCAGATTGAGCTGAGCACCTGCTTCTTCCTGTGCCTGCTGAGGTTCTGCTTCTCTGCCACCAGGAGATAC
TACCTGGGCGCCGTGGAGCTGAGCTGGGACTACATGCAGTCTGACCTGGGCGAGCTGCCTGTGGACGCCAGG
TTCCCCCCCAGAGTGCCCAAGAGCTTCCCCTTCAACACCTCAGTGGTGTACAAGAAGACCCTGTTCGTGGAG
TTCACCGACCACCTGTTCAACATCGCCAAGCCCAGGCCCCCCTGGATGGGCCTGCTGGGCCCCACCATCCAG
GCCGAGGTGTACGACACCGTGGTGATCACCCTGAAGAACATGGCCAGCCACCCCGTGAGCCTGCACGCCGTG
GGCGTGAGCTACTGGAAGGCCTCTGAGGGCGCCGAGTATGACGACCAGACCAGCCAGAGGGAGAAGGAGGAC
GACAAGGTGTTCCCCGGCGGCAGCCACACCTACGTGTGGCAGGTGCTGAAGGAGAACGGCCCCATGGCCAGC
GACCCCCTGTGCCTGACCTACAGCTACCTGAGCCACGTGGACCTGGTGAAGGACCTGAACTCTGGCCTGATC
GGCGCCCTGCTGGTGTGCAGGGAGGGCAGCCTGGCCAAGGAGAAGACCCAGACCCTGCACAAGTTCATCCTG
CTGTTCGCCGTGTTCGATGAGGGCAAGAGCTGGCACAGCGAGACCAAGAACAGCCTGATGCAGGACAGGGAT
GCCGCCTCTGCCAGGGCCTGGCCCAAGATGCACACCGTGAACGGCTACGTGAACAGGAGCCTGCCCGGCCTG
ATCGGCTGCCACAGGAAGTCTGTGTACTGGCACGTGATCGGCATGGGCACCACCCCCGAGGTGCACAGCATC
TTCCTGGAGGGCCACACCTTCCTGGTGAGGAACCACAGGCAGGCCAGCCTGGAGATCAGCCCCATCACCTTC
CTGACCGCCCAGACCCTGCTGATGGACCTGGGCCAGTTCCTGCTGTTCTGCCACATCAGCAGCCACCAGCAC
GACGGCATGGAGGCCTACGTGAAGGTGGACAGCTGCCCCGAGGAGCCCCAGCTGAGGATGAAGAACAACGAG
GAGGCCGAGGACTATGATGATGACCTGACCGACTCTGAGATGGACGTGGTGAGGTTTGATGATGACAACAGC
CCCAGCTTCATCCAGATCAGGTCTGTGGCCAAGAAGCACCCCAAGACCTGGGTGCACTACATCGCCGCCGAG
GAGGAGGACTGGGACTACGCCCCCCTGGTGCTGGCCCCCGACGACAGGAGCTACAAGAGCCAGTACCTGAAC
AACGGCCCCCAGAGGATCGGCAGGAAGTACAAGAAGGTCAGATTCATGGCCTACACCGACGAGACCTTCAAG
ACCAGGGAGGCCATCCAGCACGAGTCTGGCATCCTGGGCCCCCTGCTGTACGGCGAGGTGGGCGACACCCTG
CTGATCATCTTCAAGAACCAGGCCAGCAGGCCCTACAACATCTACCCCACGGCATCACCGATGTGAGGCCC
CTGTACAGCAGGAGGCTGCCCAAGGGCGTGAAGCACCTGAAGGACTTCCCCATCCTGCCCGGCGAGATCTTC
AAGTACAAGTGGACCGTGACCGTGGAGGATGGCCCCACCAAGTCTGACCCCAGGTGCCTGACCAGGTACTAC
AGCAGCTTCGTGAACATGGAGAGGGACCTGGCCTCTGGCCTGATCGGCCCCCTGCTGATCTGCTACAAGGAG
AGCGTGGACCAGAGGGGCAACCAGATCATGTCTGACAAGAGGAACGTGATCCTGTTCTCTGTGTTCGATGAG
AACAGGAGCTGGTATCTGACCGAGAACATCCAGAGGTTCCTGCCCAACCCCGCCGGCGTGCAGCTGGAGGAC
CCCGAGTTCCAGGCCAGCAACATCATGCACAGCATCAACGGCTACGTGTTCGACAGCCTGCAGCTGTCTGTG
TGCCTGCACGAGGTGGCCTACTGGTACATCCTGAGCATCGGCGCCCAGACCGACTTCCTGTCTGTGTTCTTC
TCTGGCTACACCTTCAAGCACAAGATGGTGTACGAGGACACCCTGACCCTGTTCCCCTTCAGCGGCGAGACC
GTGTTCATGAGCATGGAGAACCCCGGCCTGTGGATCCTGGGCTGCCACAACAGCGACTTCAGGAACAGGGGC
ATGACCGCCCTGCTGAAAGTCAGCAGCTGCGACAAGAACACCGGCGACTACTACGAGGACAGCTACGAGGAC
ATCAGCGCCTACCTGCTGAGCAAGAACAACGCCATCGAGCCCAGGGAGATCACCAGGACCACCCTGCAGAGC
GACCAGGAGGAGATCGACTATGATGACACCATCAGCGTGGAGATGAAGAAGGAGGACTTCGACATCTACGAC
GAGGACGAGAACCAGAGCCCCAGGAGCTTCCAGAAGAAGACCAGGCACTACTTCATCGCCGCCGTGGAGAGG
CTGTGGGACTATGGCATGAGCAGCAGCCCCACGTGCTGAGGAACAGGGCCCAGAGCGGCAGCGTGCCCCAG
TTCAAGAAGGTGGTGTTCCAGGAGTTCACCGACGGCAGCTTCACCCAGCCCCTGTACAGAGGCGAGCTGAAC
GAGCACCTGGGCCTGCTGGGCCCCTACATCAGGGCCGAGGTGGAGGACAACATCATGGTGACCTTCAGGAAC
CAGGCCAGCAGGCCCTACAGCTTCTACAGCAGCCTGATCAGCTACGAGGAGGACCAGAGGCAGGGCGCCGAG (Continued)

Figure 30A

```
CCCAGGAAGAACTTCGTGAAGCCCAACGAGACCAAGACCTACTTCTGGAAGGTGCAGCACCACATGGCCCCC
ACCAAGGACGAGTTCGACTGCAAGGCCTGGGCCTACTTCTCTGATGTGGACCTGGAGAAGGACGTGCACAGC
GGCCTGATCGGCCCCCTGCTGGTGTGCCACACCAACACCCTGAACCCCGCCCACGGCAGGCAGGTGACCGTG
CAGGAGTTCGCCCTGTTCTTCACCATCTTCGACGAGACCAAGAGCTGGTACTTCACCGAGAACATGGAGAGG
AACTGCAGGGCCCCCTGCAACATCCAGATGGAGGACCCCACCTTCAAGGAGAACTACAGGTTCCACGCCATC
AACGGCTACATCATGGACACCCTGCCCGGCCTGGTGATGGCCCAGGACCAGAGGATCAGGTGGTATCTGCTG
AGCATGGGCAGCAACGAGAACATCCACAGCATCCACTTCAGCGGCCACGTGTTCACCGTGAGGAAGAAGGAG
GAGTACAAGATGGCCCTGTACAACCTGTACCCCGGCGTGTTCGAGACCGTGGAGATGCTGCCCAGCAAGGCC
GGCATCTGGAGGGTGGAGTGCCTGATCGGCGAGCACCTGCACGCCGGCATGAGCACCCTGTTCCTGGTGTAC
AGCAACAAGTGCCAGACCCCCCTGGGCATGGCCAGCGGCCACATCAGGGACTTCCAGATCACCGCCTCTGGC
CAGTACGGCCAGTGGGCCCCCAAGCTGGCCAGGCTGCACTACAGCGGCAGCATCAACGCCTGGAGCACCAAG
GAGCCCTTCAGCTGGATCAAGGTGGACCTGCTGGCCCCCATGATCATCCACGGCATCAAGACCCAGGGCGCC
AGGCAGAAGTTCAGCAGCCTGTACATCAGCCAGTTCATCATCATGTACAGCCTGGACGGCAAGAAGTGGCAG
ACCTACAGGGGCAACAGCACCGGCACCCTGATGGTGTTCTTCGGCAACGTGGACAGCAGCGGCATCAAGCAC
AACATCTTCAACCCCCCCATCATCGCCAGGTACATCAGGCTGCACCCCACCCACTACAGCATCAGGAGCACC
CTGCGGATGGAACTGATGGGCTGCGACCTGAACAGCTGCAGCATGCCCCTGGGCATGGAGAGCAAGGCCATC
TCTGACGCCCAGATCACCGCCAGCAGCTACTTCACCAACATGTTCGCCACCTGGAGCCCCAGCAAGGCCAGG
CTGCACCTGCAGGGCAGGAGCAACGCCTGGAGGCCCCAGGTGAACAACCCCAAGGAGTGGCTGCAGGTGGAC
TTCCAGAAGACCATGAAGGTGACCGGCGTGACCACCCAGGGCGTGAAGAGCCTGCTGACCAGCATGTACGTG
AAGGAGTTCCTGATCAGCAGCAGCCAGGACGGCCACCAGTGGACCCTGTTCTTCCAGAACGGCAAAGTGAAG
GTGTTCCAGGGCAACCAGGACAGCTTCACCCCCGTGGTGAACAGCCTGGACCCCCCCCTGCTGACCAGGTAT
CTGAGGATCCACCCCCAGAGCTGGGTGCACCAGATCGCCCTGAGAATGGAAGTGCTGGGATGCGAGGCCCAG
GACCTGTACTGA    (SEQ ID NO:28)
```

```
ATGCAGATTGAGCTGAGCACCTGCTTCTTCCTGTGCCTGCTGAGGTTCTGCTTCTCTGCCACCAGG
AGATACTACCTGGGCGCCGTGGAGCTGAGCTGGGACTACATGCAGTCTGACCTGGGCGAGCTGCCT
GTGGACGCCAGGTTCCCCCCCAGAGTGCCCAAGAGCTTCCCCTTCAACACCTCAGTGGTGTACAAG
AAGACCCTGTTCGTGGAGTTCACCGACCACCTGTTCAACATCGCCAAGCCCAGGCCCCCCTGGATG
GGCCTGCTGGGCCCCACCATCCAGGCCGAGGTGTACGACACCGTGGTGATCACCCTGAAGAACATG
GCCAGCCACCCCGTGAGCCTGCACGCCGTGGGCGTGAGCTACTGGAAGGCCTCTGAGGGCGCCGAG
TATGACGACCAGACCAGCCAGAGGGAGAAGGAGGACGACAAGGTGTTCCCCGGCGGCAGCCACACC
TACGTGTGGCAGGTGCTGAAGGAGAACGGCCCCATGGCCAGCGACCCCCTGTGCCTGACCTACAGC
TACCTGAGCCACGTGGACCTGGTGAAGGACCTGAACTCTGGCCTGATCGGCGCCCTGCTGGTGTGC
AGGGAGGGCAGCCTGGCCAAGGAGAAGACCCAGACCCTGCACAAGTTCATCCTGCTGTTCGCCGTG
TTCGATGAGGGCAAGAGCTGGCACAGCGAGACCAAGAACAGCCTGATGCAGGACAGGGATGCCGCC
TCTGCCAGGGCCTGGCCCAAGATGCACACCGTGAACGGCTACGTGAACAGGAGCCTGCCCGGCCTG
ATCGGCTGCCACAGGAAGTCTGTGTACTGGCACGTGATCGGCATGGGCACCACCCCCGAGGTGCAC
AGCATCTTCCTGGAGGGCCACACCTTCCTGGTGAGGAACCACAGGCAGGCCAGCCTGGAGATCAGC
CCCATCACCTTCCTGACCGCCCAGACCCTGCTGATGGACCTGGGCCAGTTCCTGCTGTTCTGCCAC
ATCAGCAGCCACCAGCACGACGGCATGGAGGCCTACGTGAAGGTGGACAGCTGCCCCGAGGAGCCC
CAGCTGAGGATGAAGAACAACGAGGAGGCCGAGGACTATGATGATGACCTGACCGACTCTGAGATG
GACGTGGTGAGGTTTGATGATGACAACAGCCCCAGCTTCATCCAGATCAGGTCTGTGGCCAAGAAG
CACCCCAAGACCTGGGTGCACTACATCGCCGCCGAGGAGGAGGACTGGGACTACGCCCCCCTGGTG
CTGGCCCCCGACGACAGGAGCTACAAGAGCCAGTACCTGAACAACGGCCCCCAGAGGATCGGCAGG
AAGTACAAGAAGGTCAGATTCATGGCCTACACCGACGAGACCTTCAAGACCAGGGAGGCCATCCAG
CACGAGTCTGGCATCCTGGGCCCCCTGCTGTACGGCGAGGTGGGCGACACCCTGCTGATCATCTTC
AAGAACCAGGCCAGCAGGCCCTACAACATCTACCCCCACGGCATCACCGATGTGAGGCCCCTGTAC
AGCAGGAGGCTGCCCAAGGGCGTGAAGCACCTGAAGGACTTCCCCATCCTGCCCGGCGAGATCTTC
AAGTACAAGTGGACCGTGACCGTGGAGGATGGCCCCACCAAGTCTGACCCCAGGTGCCTGACCAGG
TACTACAGCAGCTTCGTGAACATGGAGAGGGACCTGGCCTCTGGCCTGATCGGCCCCCTGCTGATC
TGCTACAAGGAGAGCGTGGACCAGAGGGGCAACCAGATCATGTCTGACAAGAGGAACGTGATCCTG
TTCTCTGTGTTCGATGAGAACAGGAGCTGGTATCTGACCGAGAACATCCAGAGGTTCCTGCCCAAC
CCCGCCGGCGTGCAGCTGGAGGACCCCGAGTTCCAGGCCAGCAACATCATGCACAGCATCAACGGC
TACGTGTTCGACAGCCTGCAGCTGTCTGTGTGCCTGCACGAGGTGGCCTACTGGTACATCCTGAGC
ATCGGCGCCCAGACCGACTTCCTGTCTGTGTTCTTCTCTGGCTACACCTTCAAGCACAAGATGGTG
TACGAGGACACCCTGACCCTGTTCCCCTTCAGCGGCGAGACCGTGTTCATGAGCATGGAGAACCCC
GGCCTGTGGATCCTGGGCTGCCACAACAGCGACTTCAGGAACAGGGGCATGACCGCCCTGCTGAAA
GTCAGCAGCTGCGACAAGAACACCGGCGACTACTACGAGGACAGCTACGAGGACATCAGCGCCTAC
CTGCTGAGCAAGAACAACGCCATCGAGCCCAGGAGCTTCAGCCAGAACTCCAGACACCCCAGCACC
```

```
AGGGAGATCACCAGGACCACCCTGCAGAGCGACCAGGAGGAGATCGACTATGATGACACCATCAGC
GTGGAGATGAAGAAGGAGGACTTCGACATCTACGACGAGGACGAGAACCAGAGCCCCAGGAGCTTC
CAGAAGAAGACCAGGCACTACTTCATCGCCGCCGTGGAGAGGCTGTGGGACTATGGCATGAGCAGC
AGCCCCACGTGCTGAGGAACAGGGCCCAGAGCGGCAGCGTGCCCCAGTTCAAGAAGGTGGTGTTC
CAGGAGTTCACCGACGGCAGCTTCACCCAGCCCCTGTACAGAGGCGAGCTGAACGAGCACCTGGGC
CTGCTGGGCCCCTACATCAGGGCCGAGGTGGAGGACAACATCATGGTGACCTTCAGGAACCAGGCC
AGCAGGCCCTACAGCTTCTACAGCAGCCTGATCAGCTACGAGGAGGACCAGAGGCAGGGCGCCGAG
CCCAGGAAGAACTTCGTGAAGCCCAACGAGACCAAGACCTACTTCTGGAAGGTGCAGCACCACATG
GCCCCCACCAAGGACGAGTTCGACTGCAAGGCCTGGGCCTACTTCTCTGATGTGGACCTGGAGAAG
GACGTGCACAGCGGCCTGATCGGCCCCCTGCTGGTGTGCCACACCAACACCCTGAACCCCGCCCAC
GGCAGGCAGGTGACCGTGCAGGAGTTCGCCCTGTTCTTCACCATCTTCGACGAGACCAAGAGCTGG
TACTTCACCGAGAACATGGAGAGGAACTGCAGGGCCCCCTGCAACATCCAGATGGAGGACCCCACC
TTCAAGGAGAACTACAGGTTCCACGCCATCAACGGCTACATCATGGACACCCTGCCCGGCCTGGTG
ATGGCCCAGGACCAGAGGATCAGGTGGTATCTGCTGAGCATGGGCAGCAACGAGAACATCCACAGC
ATCCACTTCAGCGGCCACGTGTTCACCGTGAGGAAGAAGGAGGAGTACAAGATGGCCCTGTACAAC
CTGTACCCCGGCGTGTTCGAGACCGTGGAGATGCTGCCCAGCAAGGCCGGCATCTGGAGGGTGGAG
TGCCTGATCGGCGAGCACCTGCACGCCGGCATGAGCACCCTGTTCCTGGTGTACAGCAACAAGTGC
CAGACCCCCCTGGGCATGGCCAGCGGCCACATCAGGGACTTCCAGATCACCGCCTCTGGCCAGTAC
GGCCAGTGGGCCCCCAAGCTGGCCAGGCTGCACTACAGCGGCAGCATCAACGCCTGGAGCACCAAG
GAGCCCTTCAGCTGGATCAAGGTGGACCTGCTGGCCCCCATGATCATCCACGGCATCAAGACCCAG
GGCGCCAGGCAGAAGTTCAGCAGCCTGTACATCAGCCAGTTCATCATCATGTACAGCCTGGACGGC
AAGAAGTGGCAGACCTACAGGGGCAACAGCACCGGCACCCTGATGGTGTTCTTCGGCAACGTGGAC
AGCAGCGGCATCAAGCACAACATCTTCAACCCCCCCATCATCGCCAGGTACATCAGGCTGCACCCC
ACCCACTACAGCATCAGGAGCACCCTGCGGATGGAACTGATGGGCTGCGACCTGAACAGCTGCAGC
ATGCCCCTGGGCATGGAGAGCAAGGCCATCTCTGACGCCCAGATCACCGCCAGCAGCTACTTCACC
AACATGTTCGCCACCTGGAGCCCCAGCAAGGCCAGGCTGCACCTGCAGGGCAGGAGCAACGCCTGG
AGGCCCCAGGTGAACAACCCCAAGGAGTGGCTGCAGGTGGACTTCCAGAAGACCATGAAGGTGACC
GGCGTGACCACCCAGGGCGTGAAGAGCCTGCTGACCAGCATGTACGTGAAGGAGTTCCTGATCAGC
AGCAGCCAGGACGGCCACCAGTGGACCCTGTTCTTCCAGAACGGCAAAGTGAAGGTGTTCCAGGGC
AACCAGGACAGCTTCACCCCCGTGGTGAACAGCCTGGACCCCCCCTGCTGACCAGGTATCTGAGG
ATCCACCCCAGAGCTGGGTGCACCAGATCGCCCTGAGAATGGAAGTGCTGGGATGCGAGGCCCAG
GACCTGTACTGA  (SEQ ID NO:29)
```

Figure 31B

VIRAL VECTORS ENCODING RECOMBINANT FVIII VARIANTS WITH INCREASED EXPRESSION FOR GENE THERAPY OF HEMOPHILIA A

CROSS REFERENCE TO RELATED APPLICATIONS

This application claims priority to U.S. Provisional Patent Application No. 62/255,323, filed Nov. 13, 2015, the content of which is hereby incorporated by reference in its entirety for all purposes.

SEQUENCE LISTING

The instant application contains a Sequence Listing which has been submitted electronically in ASCII format and is hereby incorporated by reference in its entirety. Said ASCII copy, created on Nov. 7, 2016, is named 008073_5115_US_Sequence_Listing.txt and is 183,311 bytes in size.

BACKGROUND OF THE DISCLOSURE

Blood coagulation proceeds through a complex and dynamic biological pathway of interdependent biochemical reactions, referred to as the coagulation cascade. Coagulation Factor VIII (FVIII) is a key component in the cascade. Factor VIII is recruited to bleeding sites, and forms a Xase complex with activated Factor IX (FIXa) and Factor X (FX). The Xase complex activates FX, which in turn activates prothrombin to thrombin, which then activates other components in the coagulation cascade to generate a stable clot (reviewed in Saenko et al., *Trends Cardiovasc. Med.*, 9:185-192 (1999); Lenting et al., *Blood*, 92:3983-3996 (1998)).

Hemophilia A is a congenital X-linked bleeding disorder characterized by a deficiency in Factor VIII activity. Diminished Factor VIII activity inhibits a positive feedback loop in the coagulation cascade. This causes incomplete coagulation, which manifests as bleeding episodes with increased duration, extensive bruising, spontaneous oral and nasal bleeding, joint stiffness and chronic pain, and possibly internal bleeding and anemia in severe cases (Zhang et al., *Clinic. Rev. Allerg. Immunol.*, 37:114-124 (2009)).

Conventionally, hemophilia A is treated by Factor VIII replacement therapy, which consists of administering Factor VIII protein (e.g., plasma-derived or recombinantly-produced Factor VIII) to an individual with hemophilia A. Factor VIII is administered prophylactically to prevent or reduce frequency of bleeding episodes, in response to an acute bleeding episode, and/or perioperatively to manage bleeding during surgery. However, there are several undesirable features of Factor VIII replacement therapy.

First, Factor VIII replacement therapy is used to treat or manage hemophilia A, but does not cure the underlying Factor VIII deficiency. Because of this, individuals with hemophilia A require Factor VIII replacement therapy for the duration of their lives. Continuous treatment is expensive and requires the individual to maintain strict compliance, as missing only a few prophylactic doses can have serious consequences for individuals with severe hemophilia A.

Second, because Factor VIII has a relatively short half-life in vivo, conventional prophylactic Factor VIII replacement therapy requires administration every second or third day. This places a burden on the individual to maintain compliance throughout their life. While third generation "long-acting" Factor VIII drugs may reduce the frequency of administration, prophylactic Factor FVIII replacement therapy with these drugs still requires monthly, weekly, or more frequent administration in perpetuity. For example, prophylactic treatment with ELOCTATE™ [Antihemophilic Factor (Recombinant), Fc Fusion Protein] requires administration every three to five days (ELOCTATE™ Prescribing Information, Biogen Idec Inc., (2015)). Moreover, the long-term effects of chemically modified biologics (e.g., pegylated polypeptides) are not yet fully understood.

Third, between 15% and 30% of all individuals receiving Factor VIII replacement therapy form anti-Factor VIII inhibitor antibodies, rendering the therapy inefficient. Factor VIII bypass therapy (e.g., administration of plasma-derived or recombinantly-produced prothrombin complex concentrates) can be used to treat hemophilia in individuals that form inhibitor antibodies. However, Factor VIII bypass therapy is less effective than Factor VIII replacement therapy (Mannucci P. M., J Thromb Haemost., 1(7):1349-55 (2003)) and may be associated with an increased risk of cardiovascular complication (Luu and Ewenstein, Haemophilia, 10 Suppl. 2:10-16 (2004)).

Somatic gene therapy holds great promise for the treatment of hemophilia A because it would remedy the underlying under-expression functional Factor VIII activity (e.g., due to missense or nonsense mutations), rather than provide a one-time dose of Factor VIII activity to the individual. Because of this difference in the mechanism of action, as compared to Factor VIII replacement therapy, one-time administration of a Factor VIII gene therapy vector may provide an individual with Factor VIII for several years, reducing the cost of treatment and eliminating the need for continued patient compliance.

Coagulation Factor IX (FIX) gene therapy has been used effectively to treat individuals with hemophilia B, a related blood coagulation condition characterized by diminished Factor IX activity (Manno C. S., et al., Nat Med., 12(3):342-47 (2006)). However, Factor VIII gene therapy presents several unique challenges. For example, the full-length, wild-type Factor VIII polypeptide (2351 amino acids; UniProt accession number P00451) is five times larger than the full-length, wild-type Factor IX polypeptide (461 amino acids; UniProt accession number P00740). As such, the coding sequence of wild-type Factor VIII is 7053 base pairs, which is too large to be packaged in conventional AAV gene therapy vectors. Further, reported recombinant expression of B-domain deleted variants of Factor VIII (BDD-FVIII) has been poor. As such, several groups have attempted to alter the codon usage of BDD-FVIII constructs, with limited success.

BRIEF SUMMARY OF DISCLOSURE

Accordingly, there is a need for Factor VIII variants whose coding sequences are more efficiently packaged into, and delivered via, gene therapy vectors. There is also a need for synthetic, codon-altered nucleic acids which express Factor VIII more efficiently. Such Factor VIII variants and codon-altered nucleic acids allow for improved treatment of Factor VIII deficiencies (e.g., hemophilia A). The above deficiencies and other problems associated with the treatment of Factor VIII deficiencies (e.g., hemophilia A) are reduced or eliminated by the disclosed codon-altered Factor VIII variants.

In accordance with some embodiments, the present disclosure provides nucleic acids encoding Factor VIII variants that have high sequence identity to the disclosed codon-altered sequences of the Factor VIII heavy chain (e.g., CS01-HC-NA, CS04-HC-NA, or CS23-HC-NA) and light chain (CS01-LC-NA, CS04-LC-NA, or CS23-LC-NA). In some embodiments, these nucleic acids further include a sequence encoding a linker sequence that replaces the native Factor VIII B-domain (e.g., a linker sequences comprising a furin cleavage site), between the sequences coding for the Factor VIII heavy and light chains.

In one aspect, the disclosure provides a polynucleotide including a nucleotide sequence encoding a Factor VIII polypeptide. The Factor VIII polypeptide includes a light chain, a heavy chain, and a polypeptide linker joining the C-terminus of the heavy chain to the N-terminus of the light chain. The heavy chain of the Factor VIII polypeptide is encoded by a first nucleotide sequence having at least 95% identity to CS04-HC-NA (SEQ ID NO: 3). The light chain of the Factor FVIII polypeptide is encoded by a second nucleotide sequence having at least 95% identity to CS04-LC-NA (SEQ ID NO: 4). The polypeptide linker comprises a furin cleavage site.

In one embodiment of the polynucleotides described above, the polypeptide linker is encoded by a third nucleotide sequence having at least 95% identity to BDLO04 (SEQ ID NO: 6).

In one aspect, the disclosure provides a polynucleotide including a nucleotide sequence encoding a Factor VIII polypeptide. The Factor VIII polypeptide includes a light chain, a heavy chain, and a polypeptide linker joining the C-terminus of the heavy chain to the N-terminus of the light chain. The heavy chain of the Factor VIII polypeptide is encoded by a first nucleotide sequence having at least 95% identity to CS01-HC-NA (SEQ ID NO: 24). The light chain of the Factor FVIII polypeptide is encoded by a second nucleotide sequence having at least 95% identity to CS01-LC-NA (SEQ ID NO: 25). The polypeptide linker comprises a furin cleavage site.

In one embodiment of the polynucleotides described above, the polypeptide linker is encoded by a third nucleotide sequence having at least 95% identity to BDLO01 (SEQ ID NO: 5).

In one aspect, the disclosure provides a polynucleotide including a nucleotide sequence encoding a Factor VIII polypeptide. The Factor VIII polypeptide includes a light chain, a heavy chain, and a polypeptide linker joining the C-terminus of the heavy chain to the N-terminus of the light chain. The heavy chain of the Factor VIII polypeptide is encoded by a first nucleotide sequence having at least 95% identity to CS23-HC-NA (SEQ ID NO: 22). The light chain of the Factor FVIII polypeptide is encoded by a second nucleotide sequence having at least 95% identity to CS23-LC-NA (SEQ ID NO: 23). The polypeptide linker comprises a furin cleavage site.

In one embodiment of the polynucleotides described above, the polypeptide linker is encoded by a third nucleotide sequence having at least 95% identity to BDLO23 (SEQ ID NO: 7).

In one embodiment of the polynucleotides described above, the first nucleotide sequence encoding the heavy chain of the Factor VIII polypeptide has at least 96% identity to the respective heavy chain sequence (e.g., CS04-HC-NA (SEQ ID NO: 3), CS01-HC-NA (SEQ ID NO: 24), or CS23-HC-NA (SEQ ID NO: 22)), and the second nucleotide sequence encoding the light chain of the Factor FVIII polypeptide has at least 96% identity to the respective light chain sequence (e.g., CS04-LC-NA (SEQ ID NO: 4), CS01-LC-NA (SEQ ID NO: 25), or CS23-LC-NA (SEQ ID NO: 23)).

In one embodiment of the polynucleotides described above, the first nucleotide sequence encoding the heavy chain of the Factor VIII polypeptide has at least 97% identity to the respective heavy chain sequence (e.g., CS04-HC-NA (SEQ ID NO: 3), CS01-HC-NA (SEQ ID NO: 24), or CS23-HC-NA (SEQ ID NO: 22)), and the second nucleotide sequence encoding the light chain of the Factor FVIII polypeptide has at least 97% identity to the respective light chain sequence (e.g., CS04-LC-NA (SEQ ID NO: 4), CS01-LC-NA (SEQ ID NO: 25), or CS23-LC-NA (SEQ ID NO: 23)).

In one embodiment of the polynucleotides described above, the first nucleotide sequence encoding the heavy chain of the Factor VIII polypeptide has at least 98% identity to the respective heavy chain sequence (e.g., CS04-HC-NA (SEQ ID NO: 3), CS01-HC-NA (SEQ ID NO: 24), or CS23-HC-NA (SEQ ID NO: 22)), and the second nucleotide sequence encoding the light chain of the Factor FVIII polypeptide has at least 98% identity to the respective light chain sequence (e.g., CS04-LC-NA (SEQ ID NO: 4), CS01-LC-NA (SEQ ID NO: 25), or CS23-LC-NA (SEQ ID NO: 23)).

In one embodiment of the polynucleotides described above, the first nucleotide sequence encoding the heavy chain of the Factor VIII polypeptide has at least 99% identity to the respective heavy chain sequence (e.g., CS04-HC-NA (SEQ ID NO: 3), CS01-HC-NA (SEQ ID NO: 24), or CS23-HC-NA (SEQ ID NO: 22)), and the second nucleotide sequence encoding the light chain of the Factor FVIII polypeptide has at least 99% identity to the respective light chain sequence (e.g., CS04-LC-NA (SEQ ID NO: 4), CS01-LC-NA (SEQ ID NO: 25), or CS23-LC-NA (SEQ ID NO: 23)).

In one embodiment of the polynucleotides described above, the first nucleotide sequence encoding the heavy chain of the Factor VIII polypeptide has at least 99.5% identity to the respective heavy chain sequence (e.g., CS04-HC-NA (SEQ ID NO: 3), CS01-HC-NA (SEQ ID NO: 24), or CS23-HC-NA (SEQ ID NO: 22)), and the second nucleotide sequence encoding the light chain of the Factor FVIII polypeptide has at least 99.5% identity to the respective light chain sequence (e.g., CS04-LC-NA (SEQ ID NO: 4), CS01-LC-NA (SEQ ID NO: 25), or CS23-LC-NA (SEQ ID NO: 23)).

In one embodiment of the polynucleotides described above, the first nucleotide sequence encoding the heavy chain of the Factor VIII polypeptide has at least 99.9% identity to the respective heavy chain sequence (e.g., CS04-HC-NA (SEQ ID NO: 3), CS01-HC-NA (SEQ ID NO: 24), or CS23-HC-NA (SEQ ID NO: 22)), and the second nucleotide sequence encoding the light chain of the Factor FVIII polypeptide has at least 99.9% identity to the respective light chain sequence (e.g., CS04-LC-NA (SEQ ID NO: 4), CS01-LC-NA (SEQ ID NO: 25), or CS23-LC-NA (SEQ ID NO: 23)).

In one embodiment of the polynucleotides described above, the first nucleotide sequence encoding the heavy chain of the Factor VIII polypeptide is CS04-HC-NA (SEQ ID NO: 3), and the second nucleotide sequence encoding the light chain of the Factor FVIII polypeptide is CS04-LC-NA (SEQ ID NO: 4).

In one embodiment of the polynucleotides described above, the first nucleotide sequence encoding the heavy chain of the Factor VIII polypeptide is CS01-HC-NA (SEQ ID NO: 24), and the second nucleotide sequence encoding the light chain of the Factor FVIII polypeptide is CS01-LC-NA (SEQ ID NO: 25).

In one embodiment of the polynucleotides described above, the first nucleotide sequence encoding the heavy chain of the Factor VIII polypeptide is CS23-HC-NA (SEQ ID NO: 22), and the second nucleotide sequence encoding the light chain of the Factor FVIII polypeptide is CS23-LC-NA (SEQ ID NO: 23).

In one aspect, the disclosure provides a polynucleotide comprising a nucleotide sequence having at least 95% identity to CS04-FL-NA, wherein the polynucleotide encodes a Factor VIII polypeptide.

In one aspect, the disclosure provides a polynucleotide comprising a nucleotide sequence having at least 95% identity to CS01-FL-NA, wherein the polynucleotide encodes a Factor VIII polypeptide.

In one aspect, the disclosure provides a polynucleotide comprising a nucleotide sequence having at least 95% identity to CS23-FL-NA, wherein the polynucleotide encodes a Factor VIII polypeptide.

In one embodiment of the polynucleotides described above, the nucleotide sequence has at least 96% identity to the respective full-length polynucleotide sequence (e.g., CS04-FL-NA (SEQ ID NO: 1), CS01-FL-NA (SEQ ID NO: 13), or CS23-FL-NA (SEQ ID NO: 20)).

In one embodiment of the polynucleotides described above, the nucleotide sequence has at least 97% identity to the respective full-length polynucleotide sequence (e.g., CS04-FL-NA (SEQ ID NO: 1), CS01-FL-NA (SEQ ID NO: 13), or CS23-FL-NA (SEQ ID NO: 20)).

In one embodiment of the polynucleotides described above, the nucleotide sequence has at least 98% identity to the respective full-length polynucleotide sequence (e.g., CS04-FL-NA (SEQ ID NO: 1), CS01-FL-NA (SEQ ID NO: 13), or CS23-FL-NA (SEQ ID NO: 20)).

In one embodiment of the polynucleotides described above, the nucleotide sequence has at least 99% identity to the respective full-length polynucleotide sequence (e.g., CS04-FL-NA (SEQ ID NO: 1), CS01-FL-NA (SEQ ID NO: 13), or CS23-FL-NA (SEQ ID NO: 20)).

In one embodiment of the polynucleotides described above, the nucleotide sequence has at least 99.5% identity to the respective full-length polynucleotide sequence (e.g., CS04-FL-NA (SEQ ID NO: 1), CS01-FL-NA (SEQ ID NO: 13), or CS23-FL-NA (SEQ ID NO: 20)).

In one embodiment of the polynucleotides described above, the nucleotide sequence has at least 99.9% identity to the respective full-length polynucleotide sequence (e.g., CS04-FL-NA (SEQ ID NO: 1), CS01-FL-NA (SEQ ID NO: 13), or CS23-FL-NA (SEQ ID NO: 20)).

In one embodiment of the polynucleotides described above, the nucleotide sequence is CS04-FL-NA (SEQ ID NO: 1).

In one embodiment of the polynucleotides described above, the nucleotide sequence is CS01-FL-NA (SEQ ID NO: 13).

In one embodiment of the polynucleotides described above, the nucleotide sequence is CS23-FL-NA (SEQ ID NO: 20).

In one embodiment of the polynucleotides described above, the polynucleotide encodes a Factor VIII polypeptide comprising an amino acid sequence having at least 95% identity to CS04-FL-AA (SEQ ID NO: 2).

In one embodiment of the polynucleotides described above, the polynucleotide encodes a Factor VIII polypeptide comprising an amino acid sequence having at least 96% identity to CS04-FL-AA (SEQ ID NO: 2).

In one embodiment of the polynucleotides described above, the polynucleotide encodes a Factor VIII polypeptide comprising an amino acid sequence having at least 97% identity to CS04-FL-AA (SEQ ID NO: 2).

In one embodiment of the polynucleotides described above, the polynucleotide encodes a Factor VIII polypeptide comprising an amino acid sequence having at least 98% identity to CS04-FL-AA (SEQ ID NO: 2).

In one embodiment of the polynucleotides described above, the polynucleotide encodes a Factor VIII polypeptide comprising an amino acid sequence having at least 99% identity to CS04-FL-AA (SEQ ID NO: 2).

In one embodiment of the polynucleotides described above, the polynucleotide encodes a Factor VIII polypeptide comprising an amino acid sequence having at least 99.5% identity to CS04-FL-AA (SEQ ID NO: 2).

In one embodiment of the polynucleotides described above, the polynucleotide encodes a Factor VIII polypeptide comprising an amino acid sequence having at least 99.9% identity to CS04-FL-AA (SEQ ID NO: 2).

In one embodiment of the polynucleotides described above, the polynucleotide encodes a Factor VIII polypeptide comprising the amino acid sequence of CS04-FL-AA (SEQ ID NO: 2).

In one aspect, the disclosure provides a polynucleotide comprising a nucleotide sequence having at least 95% identity to CS04-SC1-NA (SEQ ID NO: 9), wherein the polynucleotide encodes a single-chain Factor VIII polypeptide.

In one aspect, the disclosure provides a polynucleotide comprising a nucleotide sequence having at least 95% identity to CS04-SC2-NA (SEQ ID NO: 11), wherein the polynucleotide encodes a single-chain Factor VIII polypeptide.

In one aspect, the disclosure provides a polynucleotide comprising a nucleotide sequence having at least 95% identity to CS01-SC1-NA (SEQ ID NO: 26), wherein the polynucleotide encodes a single-chain Factor VIII polypeptide.

In one aspect, the disclosure provides a polynucleotide comprising a nucleotide sequence having at least 95% identity to CS01-SC2-NA (SEQ ID NO: 27), wherein the polynucleotide encodes a single-chain Factor VIII polypeptide.

In one aspect, the disclosure provides a polynucleotide comprising a nucleotide sequence having at least 95% identity to CS23-SC1-NA (SEQ ID NO: 28), wherein the polynucleotide encodes a single-chain Factor VIII polypeptide.

In one aspect, the disclosure provides a polynucleotide comprising a nucleotide sequence having at least 95% identity to CS23-SC2-NA (SEQ ID NO: 29), wherein the polynucleotide encodes a single-chain Factor VIII polypeptide.

In one embodiment of the polynucleotides described above, the nucleotide sequence has at least 96% identity to the respective full-length polynucleotide sequence (e.g., CS04-SC1-NA (SEQ ID NO: 9), CS04-SC2-NA (SEQ ID NO: 11), CS01-SC1-NA (SEQ ID NO: 26), CS01-SC2-NA (SEQ ID NO: 27), CS23-SC1-NA (SEQ ID NO: 28), or CS23-SC2-NA (SEQ ID NO: 29)).

In one embodiment of the polynucleotides described above, the nucleotide sequence has at least 97% identity to the respective full-length polynucleotide sequence (e.g., CS04-SC1-NA (SEQ ID NO: 9), CS04-SC2-NA (SEQ ID NO: 11), CS01-SC1-NA (SEQ ID NO: 26), CS01-SC2-NA (SEQ ID NO: 27), CS23-SC1-NA (SEQ ID NO: 28), or CS23-SC2-NA (SEQ ID NO: 29)).

In one embodiment of the polynucleotides described above, the nucleotide sequence has at least 98% identity to the respective full-length polynucleotide sequence (e.g., CS04-SC1-NA (SEQ ID NO: 9), CS04-SC2-NA (SEQ ID NO: 11), CS01-SC1-NA (SEQ ID NO: 26), CS01-SC2-NA (SEQ ID NO: 27), CS23-SC1-NA (SEQ ID NO: 28), or CS23-SC2-NA (SEQ ID NO: 29)).

In one embodiment of the polynucleotides described above, the nucleotide sequence has at least 99% identity to the respective full-length polynucleotide sequence (e.g., CS04-SC1-NA (SEQ ID NO: 9), CS04-SC2-NA (SEQ ID NO: 11), CS01-SC1-NA (SEQ ID NO: 26), CS01-SC2-NA (SEQ ID NO: 27), CS23-SC1-NA (SEQ ID NO: 28), or CS23-SC2-NA (SEQ ID NO: 29)).

In one embodiment of the polynucleotides described above, the nucleotide sequence has at least 99.5% identity to the respective full-length polynucleotide sequence (e.g., CS04-SC1-NA (SEQ ID NO: 9), CS04-SC2-NA (SEQ ID NO: 11), CS01-SC1-NA (SEQ ID NO: 26), CS01-SC2-NA (SEQ ID NO: 27), CS23-SC1-NA (SEQ ID NO: 28), or CS23-SC2-NA (SEQ ID NO: 29)).

In one embodiment of the polynucleotides described above, the nucleotide sequence has at least 99.9% identity to the respective full-length polynucleotide sequence (e.g., CS04-SC1-NA (SEQ ID NO: 9), CS04-SC2-NA (SEQ ID NO: 11), CS01-SC1-NA (SEQ ID NO: 26), CS01-SC2-NA (SEQ ID NO: 27), CS23-SC1-NA (SEQ ID NO: 28), or CS23-SC2-NA (SEQ ID NO: 29)).

In one embodiment of the polynucleotides described above, the nucleotide sequence is CS04-SC1-NA (SEQ ID NO: 9).

In one embodiment of the polynucleotides described above, the nucleotide sequence is CS04-SC2-NA (SEQ ID NO: 11).

In one embodiment of the polynucleotides described above, the nucleotide sequence is CS01-SC1-NA (SEQ ID NO: 26).

In one embodiment of the polynucleotides described above, the nucleotide sequence is CS01-SC2-NA (SEQ ID NO: 27).

In one embodiment of the polynucleotides described above, the nucleotide sequence is CS23-SC1-NA (SEQ ID NO: 28).

In one embodiment of the polynucleotides described above, the nucleotide sequence is CS23-SC2-NA (SEQ ID NO: 29).

In one embodiment of the polynucleotides described above, the nucleotide sequence has at least 95% identity to a sequence selected from the group consisting of CS01-FL-NA, CS01-HC-NA, CS01-LC-NA, CS04-FL-NA, CS04-HC-NA, CS04-LC-NA, CS23-FL-NA, CS23-HC-NA, CS23-LC-NA, CS01-SC1-NA, CS04-SC1-NA, CS23-SC1-NA, CS01-SC2-NA, CS04-SC2-NA, and CS23-SC2-NA.

In one embodiment of the polynucleotides described above, the nucleotide sequence has at least 96% identity to a sequence selected from the group consisting of CS01-FL-NA, CS01-HC-NA, CS01-LC-NA, CS04-FL-NA, CS04-HC-NA, CS04-LC-NA, CS23-FL-NA, CS23-HC-NA, CS23-LC-NA, CS01-SC1-NA, CS04-SC1-NA, CS23-SC1-NA, CS01-SC2-NA, CS04-SC2-NA, and CS23-SC2-NA.

In one embodiment of the polynucleotides described above, the nucleotide sequence has at least 97% identity to a sequence selected from the group consisting of CS01-FL-NA, CS01-HC-NA, CS01-LC-NA, CS04-FL-NA, CS04-HC-NA, CS04-LC-NA, CS23-FL-NA, CS23-HC-NA, CS23-LC-NA, CS01-SC1-NA, CS04-SC1-NA, CS23-SC1-NA, CS01-SC2-NA, CS04-SC2-NA, and CS23-SC2-NA.

In one embodiment of the polynucleotides described above, the nucleotide sequence has at least 98% identity to a sequence selected from the group consisting of CS01-FL-NA, CS01-HC-NA, CS01-LC-NA, CS04-FL-NA, CS04-HC-NA, CS04-LC-NA, CS23-FL-NA, CS23-HC-NA, CS23-LC-NA, CS01-SC1-NA, CS04-SC1-NA, CS23-SC1-NA, CS01-SC2-NA, CS04-SC2-NA, and CS23-SC2-NA.

In one embodiment of the polynucleotides described above, the nucleotide sequence has at least 99% identity to a sequence selected from the group consisting of CS01-FL-NA, CS01-HC-NA, CS01-LC-NA, CS04-FL-NA, CS04-HC-NA, CS04-LC-NA, CS23-FL-NA, CS23-HC-NA, CS23-LC-NA, CS01-SC1-NA, CS04-SC1-NA, CS23-SC1-NA, CS01-SC2-NA, CS04-SC2-NA, and CS23-SC2-NA.

In one embodiment of the polynucleotides described above, the nucleotide sequence has at least 99.5% identity to a sequence selected from the group consisting of CS01-FL-NA, CS01-HC-NA, CS01-LC-NA, CS04-FL-NA, CS04-HC-NA, CS04-LC-NA, CS23-FL-NA, CS23-HC-NA, CS23-LC-NA, CS01-SC1-NA, CS04-SC1-NA, CS23-SC1-NA, CS01-SC2-NA, CS04-SC2-NA, and CS23-SC2-NA.

In one embodiment of the polynucleotides described above, the nucleotide sequence has at least 99.5% identity to a sequence selected from the group consisting of CS01-FL-NA, CS01-HC-NA, CS01-LC-NA, CS04-FL-NA, CS04-HC-NA, CS04-LC-NA, CS23-FL-NA, CS23-HC-NA, CS23-LC-NA, CS01-SC1-NA, CS04-SC1-NA, CS23-SC1-NA, CS01-SC2-NA, CS04-SC2-NA, and CS23-SC2-NA.

In one embodiment of the polynucleotides described above, the nucleotide sequence is selected from the group consisting of CS01-FL-NA, CS01-HC-NA, CS01-LC-NA, CS04-FL-NA, CS04-HC-NA, CS04-LC-NA, CS23-FL-NA, CS23-HC-NA, CS23-LC-NA, CS01-SC1-NA, CS04-SC1-NA, CS23-SC1-NA, CS01-SC2-NA, CS04-SC2-NA, and CS23-SC2-NA.

In one embodiment of the polynucleotides described above, the encoded Factor VIII polypeptide comprises a glycosylation polypeptide positioned between two consecutive amino acids.

In one embodiment of the polynucleotides described above, the polynucleotide also includes a promoter element operably linked to the polynucleotide encoding the Factor VIII polypeptide.

In one embodiment of the polynucleotides described above, the polynucleotide also includes an enhancer element operably linked to the polynucleotide encoding the Factor VIII polypeptide.

In one embodiment of the polynucleotides described above, the polynucleotide also includes a polyadenylation element operably linked to the polynucleotide encoding the Factor VIII polypeptide.

In one embodiment of the polynucleotides described above, the polynucleotide also includes an intron operatively linked to the nucleotide sequence encoding the Factor VIII polypeptide.

In one embodiment of the polynucleotides described above, the intron is positioned between a promoter element and the translation initiation site (e.g., the first coding ATG) of the nucleotide sequence encoding a Factor VIII polypeptide.

In another aspect, the disclosure provides a mammalian gene therapy vector including a polynucleotide as described above.

In one embodiment of the mammalian gene therapy vector described above, the mammalian gene therapy vector is an adeno-associated virus (AAV) vector.

In one embodiment of the mammalian gene therapy vector described above, the AAV vector is an AAV-8 vector.

In another aspect, the disclosure provides a method for treating hemophilia A including administering, to a patient in need thereof, a mammalian gene therapy vector as described above.

In another aspect, the disclosure provides a mammalian gene therapy vector as described above for treating hemophilia A.

In another aspect, the disclosure provides the use of a mammalian gene therapy vector as described above for the manufacture of a medicament for treating hemophilia A.

BRIEF DESCRIPTION OF DRAWINGS

FIGS. 2A and 2B show the CS04 codon-altered nucleotide sequence (SEQ ID NO: 1) encoding a Factor VIII variant in accordance with some embodiments ("CS04-FL-NA" for full-length coding sequence).

FIG. 3 shows the Factor VIII variant amino acid sequence (SEQ ID NO: 2) encoded by the CS04 codon-altered nucleotide sequence in accordance with some embodiments ("CS04-FL-AA" for full-length amino acid sequence).

FIG. 4 shows the portion of the CS04 codon-altered nucleotide sequence (SEQ ID NO: 3) encoding the heavy chain of a Factor VIII variant in accordance with some embodiments ("CS04-HC-NA").

FIG. 5 shows the portion of the CS04 codon-altered nucleotide sequence (SEQ ID NO: 4) encoding the light chain of a Factor VIII variant in accordance with some embodiments ("CS04-LC-NA").

FIG. 6 shows exemplary coding sequences (SEQ ID NOS: 5-7) for B-domain substituted linkers in accordance with some embodiments. BDLO01 (SEQ ID NO: 5), BDLO04 (SEQ ID NO: 6), and BDLO23 (SEQ ID NO: 7) are the respective portions of the CS01, CS04, and CS23 codon-altered nucleotide sequences that encode a B-domain substituted linker, respectively.

FIGS. 7A, 7B, and 7C show an AAV vector sequence (SEQ ID NO: 8) containing an CS04 codon-altered nucleotide sequence in accordance with some embodiments ("CS04-AV-NA").

FIGS. 8A and 8B show the CS04Δ(760-1667) (SPI; CS04Δ(741-1648), SPE) codon-altered nucleotide sequence (SEQ ID NO: 9) encoding a single-chain Factor VIII variant in accordance with some embodiments ("CS04-SC1-NA").

FIG. 9 shows the Factor VIII variant amino acid sequence (SEQ ID NO: 10) encoded by the CS01Δ(760-1667) (SPI; CS01Δ(741-1648), SPE), CS04Δ(760-1667) (SPI; CS04Δ(741-1648), SPE), and CS23Δ(760-1667) (SPI; CS23Δ(741-1648), SPE) codon-altered nucleotide sequences in accordance with some embodiments ("CS01-SC1-AA," "CS04-SC1-AA," and "CS23-SC1-AA," respectively).

FIGS. 10A and 10B show the CS04Δ(772-1667) (SPI; CS04Δ(753-1648), SPE) codon-altered nucleotide sequence (SEQ ID NO: 11) encoding a single-chain Factor VIII variant in accordance with some embodiments ("CS04-SC2-NA").

FIG. 11 shows the Factor VIII variant amino acid sequence (SEQ ID NO: 12) encoded by the CS01Δ(772-1667) (SPI; CS01Δ(753-1648), SPE), CS04Δ(772-1667) (SPI; CS04Δ(753-1648), SPE), and CS23Δ(772-1667) (SPI; CS23Δ(753-1648), SPE) codon-altered nucleotide sequences in accordance with some embodiments ("CS01-SC2-AA," "CS04-SC2-AA," and "CS23-SC2-AA," respectively).

FIGS. 12A and 12B show the CS01 codon-altered nucleotide sequence (SEQ ID NO: 13) encoding a Factor VIII variant in accordance with some embodiments ("CS01-FL-NA").

FIGS. 13A and 13B show the CS08 codon-altered nucleotide sequence (SEQ ID NO: 14) encoding a Factor VIII variant in accordance with some embodiments ("CS08-FL-NA").

FIGS. 14A and 14B show the CS10 codon-altered nucleotide sequence (SEQ ID NO: 15) encoding a Factor VIII variant in accordance with some embodiments ("CS10-FL-NA").

FIGS. 15A and 15B show the CS11 codon-altered nucleotide sequence (SEQ ID NO: 16) encoding a Factor VIII variant in accordance with some embodiments ("CS11-FL-NA").

FIGS. 16A and 16B show the CS40 wild-type ReFacto coding sequence (SEQ ID NO: 17), in accordance with some embodiments ("CS40-FL-NA").

FIGS. 17A and 17B show the CH25 codon-altered nucleotide sequence (SEQ ID NO: 18) encoding a Factor VIII variant in accordance with some embodiments ("CH25-FL-NA").

FIG. 18 shows a wild-type human Factor VIII amino acid sequence (SEQ ID NO: 19), in accordance with some embodiments ("FVIII-FL-AA").

FIGS. 22A and 22B show the CS23 codon-altered nucleotide sequence (SEQ ID NO: 20) encoding a Factor VIII variant in accordance with some embodiments ("CS23-FL-NA").

FIG. 23 shows the Factor VIII variant amino acid sequence (SEQ ID NO: 21) encoded by the CS23 codon-altered nucleotide sequence in accordance with some embodiments ("CS23-FL-AA").

FIG. 24 shows the portion of the CS23 codon-altered nucleotide sequence (SEQ ID NO: 22) encoding the heavy chain of a Factor VIII variant in accordance with some embodiments ("CS23-HC-NA").

FIG. 25 shows the portion of the CS23 codon-altered nucleotide sequence (SEQ ID NO: 23) encoding the light chain of a Factor VIII variant in accordance with some embodiments("CS23-LC-NA").

FIG. 26 shows the portion of the CS01 codon-altered nucleotide sequence (SEQ ID NO: 24) encoding the heavy chain of a Factor VIII variant in accordance with some embodiments ("CS01-HC-NA").

FIG. 27 shows the portion of the CS01 codon-altered nucleotide sequence (SEQ ID NO: 25) encoding the light chain of a Factor VIII variant in accordance with some embodiments ("CS01-LC-NA").

FIGS. 28A and 28B show the CS01Δ(760-1667) (SPI; CS01Δ(741-1648), SPE) codon-altered nucleotide sequence (SEQ ID NO: 26) encoding a single-chain Factor VIII variant in accordance with some embodiments ("CS01-SC1-NA").

FIGS. 29A and 29B show the CS01Δ(772-1667) (SPI; CS01Δ(753-1648), SPE) codon-altered nucleotide sequence (SEQ ID NO: 27) encoding a single-chain Factor VIII variant in accordance with some embodiments ("CS01-SC2-NA").

FIGS. 30A and 30B show the CS23Δ(760-1667) (SPI; CS23Δ(741-1648), SPE) codon-altered nucleotide sequence (SEQ ID NO: 28) encoding a single-chain Factor VIII variant in accordance with some embodiments ("CS23-SC1-NA").

FIGS. 31A and 31B show the CS23Δ(772-1667) (SPI; CS23Δ(753-1648), SPE) codon-altered nucleotide sequence (SEQ ID NO: 29) encoding a single-chain Factor VIII variant in accordance with some embodiments ("CS23-SC2-NA").

DETAILED DESCRIPTION OF DISCLOSURE

I. Introduction

Figure 1:
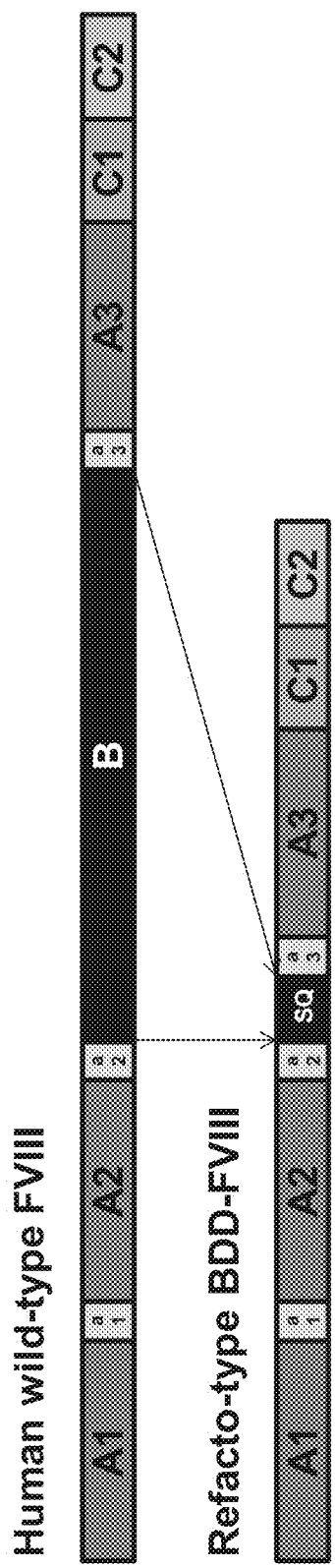
FIG. 1 shows schematic illustrations of the wild-type and ReFacto-type human Factor VIII protein constructs.

AAV-based gene therapy holds great promise for the treatment of hemophiliacs. For hemophilia B, first clinical data are encouraging in that FIX levels of about 10% can be maintained in at least some patients for more than 1 year. For hemophilia A however, achieving therapeutic expression levels of 5-10% with AAV vectors remains challenging for various reasons. First, the Factor VIII coding sequence is too large for conventional AAV-based vectors. Second, engineered B-domain deleted or truncated Factor VIII constructs suffer from poor expression in vivo, even when codon-optimized. Third, these B-domain deleted or truncated Factor VIII variant constructs have short half-lives in vivo, exacerbating the effects of poor expression. Fourth, even when expressed, FVIII is not efficiently secreted from cells, as are other coagulation factors, such as Factor IX.

Moreover, these challenges cannot be addressed by simply administering higher doses of the gene therapy construct. According to current knowledge, the vector dose of an AAV-based gene therapy vector should be increased above $2\times10^{12}$ vg/kg bodyweight. This is because at such high doses a T cell immune response is triggered, which destroys transduced cells and, as a consequence, transgene expression is reduced or even eliminated. Therefore, strategies to improve the expression of FVIII are needed to make FVIII gene therapy a viable therapeutic option for hemophilia A patients.

The present disclosure relates to the discovery of codon-altered Factor VIII variant coding sequences that solve these and other problems associated with Factor VIII gene therapy. For example, the polynucleotides disclosed herein provide markedly improved expression in mammalian cells, and display improved virion packaging due to stabilized packing interactions. In some implementations, these advantages are realized by using coding sequences for the heavy and light chains of Factor VIII with high sequence identity to the codon altered CS01, CS04, and CS23 constructs (e.g., with high sequence identity to one of the CS01-HC, CS04-HC, and CS23-HC heavy chain coding sequences and high sequence identity to one of the CS01-LC, CS04-LC, and CS23-LC light chain coding sequences).

In some implementations, the Factor VIII molecules encoded by the polynucleotides described herein have been shortened by truncating, deleting, or replacing the wild-type B-domain. As such, the polynucleotides are better suited for expressing Factor VIII via conventional gene therapy vectors, which inefficiently express larger polypeptides, such as the wild-type Factor VIII.

Advantageously, it is shown herein that the CS01, CS04, and CS23 codon-altered Factor VIII variant coding sequences provide superior expression of a B-domain deleted Factor VIII construct in vivo. For example, it is demonstrated in Example 2 and Table 4 that intravenous administration of AAV-based gene therapy vectors having the CS01 (SEQ ID NO: 13), CS04 (SEQ ID NO: 1), and CS23 (SEQ ID NO: 20) coding sequence provide 18-fold, 74-fold, and 30-fold increases in Factor VIII expression, relative to the corresponding CS40 construct encoded with the wild-type polynucleotide sequence (SEQ ID NO: 17), in Factor VIII knock-out mice (Table 4).

Further, it also shown herein that the CS01 and CS04 codon-altered Factor VIII variant coding sequences provide superior virion packaging and virus production. For example, it is demonstrated in Example 1 that AAV vector constructs containing the CS01 and CS04 constructs provided 5 to 7-fold greater viral yield, relative to the corresponding CS40 construct encoded with the wild-type polynucleotide sequence, when isolated from the same amount of cell pellet.

II. Definitions

As used herein, the following terms have the meanings ascribed to them unless specified otherwise.

As used herein, the terms "Factor VIII" and "FVIII" are used interchangeably, and refer to any protein with Factor VIII activity (e.g., active FVIII, often referred to as FVIIIa) or protein precursor (e.g., pro-protein or pre-pro-protein) of a protein with Factor VIII activity, particularly Factor IXa cofactor activity. In an exemplary embodiment, a Factor VIII polypeptide refers to a polypeptide that has sequences with high sequence identity (e.g., at least 70%, 75%, 80%, 85%, 90%, 95%, 99%, or more) to the heavy and light chains of a wild type Factor VIII polypeptide. In some embodiments, the B-domain of a Factor VIII polypeptide is deleted, truncated, or replaced with a linker polypeptide to reduce the size of the polynucleotide encoding the Factor VIII polypeptide. In an exemplary embodiment, amino acids 20-1457 of CS04-FL-AA constitute a Factor VIII polypeptide.

Non-limiting examples of wild type Factor VIII polypeptides include human pre-pro-Factor VIII (e.g., GenBank accession nos. AAA52485, CAA25619, AAA58466, AAA52484, AAA52420, AAV85964, BAF82636, BAG36452, CAI41660, CAI41666, CAI41672, CAI43241, CAO03404, EAW72645, AAH22513, AAH64380, AAH98389, AAI11968, AAI11970, or AAB61261), corresponding pro-Factor VIII, and natural variants thereof; porcine pre-pro-Factor VIII (e.g., UniProt accession nos. F1RZ36 or K7GSZ5), corresponding pro-Factor VIII, and natural variants thereof; mouse pre-pro-Factor VIII (e.g., GenBank accession nos. AAA37385, CAM15581, CAM26492, or EDL29229), corresponding pro-Factor VIII, and natural variants thereof; rat pre-pro-Factor VIII (e.g., GenBank accession no. AAQ21580), corresponding pro-Factor VIII, and natural variants thereof; rat pre-pro-Factor VIII; and other mammalian Factor VIII homologues (e.g., monkey, ape, hamster, guinea pig, etc.).

As used herein, a Factor VIII polypeptide includes natural variants and artificial constructs with Factor IX cofactor activity. As used in the present disclosure, Factor VIII encompasses any natural variants, alternative sequences, isoforms, or mutant proteins that retain some basal Factor IX cofactor activity (e.g., at least 5%, 10%, 25%, 50%, 75%, or more of the corresponding wild type activity). Examples of Factor VIII amino acid variations (relative to FVIII-FL-AA (SEQ ID NO: 19)) found in the human population include, without limitation, S19R, R22T, Y24C, Y25C, L26P/R, E30V, W33G, Y35C/H, G41C, R48C/K, K67E/N, L69P, E72K, D75E/V/Y, P83R, G89D/V, G92A/V, A97P, E98K, V99D, D101G/H/V, V104D, K108T, M110V, A111T/V, H113R/Y, L117F/R, G121S, E129V, G130R, E132D, Y133C, D135G/Y, T137A/I, S138R, E141K, D145H, V147D, Y155H, V159A, N163K, G164D/V, P165S, C172W, S176P, S179P, V181E/M, K185T, D186G/N/Y, S189L, L191F, G193R, L195P, C198G, S202N/R, F214V, L217H, A219D/T, V220G, D222Y, E223K, G224W, T252I, V253F, N254I, G255V, L261P, P262L, G263S, G266F, C267Y, W274C, H275L, G278R, G280D, E284K, V285G, E291G/K, T294I, F295L, V297A, N299I, R301C/H/L, A303E/P, 1307S, S308L, F312S, T314A/I, A315V, G323E, L326P, L327P/V, C329F, I331V, M339T, E340K, V345A/L, C348R/S/Y, Y365C, R391C/H/P, S392L/P, A394S, W401G, I405F/S, E409G, W412G/R, K427I, L431F/S, R437P/W, I438F, G439D/S/V, Y442C, K444R, Y450D/N, T454I, F455C, G466E, P470L/R/T, G474E/R/V, E475K, G477V, D478N, T479R, F484C, A488G, R490G, Y492C/H, Y492H, I494T, P496R, G498R, R503H, G513S/V, I522Y, K529E, W532G, P540T, T541S, D544N, R546W, R550C/G/H, S553P, S554C/G, V556D, R560T, D561G/H/Y, I567T, P569R, S577F, V578A, D579A/H, N583S, Q584H/K/R, I585R/T, M586V, D588G/Y, L594Q, S596P, N601D/K, R602G, S603I/R, W604C, Y605H/S, N609I, R612C, N631K/S, M633I, S635N, N637D/I/S, Y639C, L644V, L650F, V653A/M, L659P, A663Y, Q664P, F677L, M681I, V682F, Y683C/N, T686R, F698L, M699T/V, M701I, G705V, G710W, N713I, R717L/W, G720D/S, M721I/L, A723T, L725Q, V727F, E739K, Y742C, R795G, P947R, V1012L, E1057K, H1066Y, D1260E, K1289Q, Q1336K, N1460K, L1481P, A1610S, I1698T, Y1699C/F, E1701K, Q1705H, R1708C/H, T1714S, R1715G, A1720V, E1723K, D1727V, Y1728C, R1740G, K1751Q, F1762L, R1768H, G1769R, L1771P, L1775F/V, L1777P, G1779E/R, P1780L, I1782R, D1788H, M1791T, A1798P, S1799H, R1800C/G/H, P1801A, Y1802C, S1803Y, F1804S, L1808F, M1842I, P1844S, T1845P, E1848G, A1853T/V, S1858C, K1864E, D1865N/Y, H1867P/R, G1869D/V, G1872E, P1873R, L1875P, V1876L, C1877R/Y, L1882P, R1888I, E1894G, 11901F, E1904D/K, S1907C/R, W1908L, Y1909C, A1939T/V, N1941D/S, G1942A, M1945V, L1951F, R1960L/Q, L1963P, S1965I, M1966I/V, G1967D, S1968R, N1971T, H1973L, G1979V, H1980P/Y, F1982I, R1985Q, L1994P, Y1998C, G2000A, T2004R, M2007I, G2013R, W2015C, R2016P/W, E2018G, G2022D, G2028R, S2030N, V2035A, Y2036C, N2038S, 2040Y, G2045E/V, I2051S, I2056N, A2058P, W2065R, P2067L, A2070V, S2082N, S2088F, D2093G/Y, H2101D, T2105N, Q2106E/P/R, G2107S, R2109C, I2117F/S, Q2119R, F2120C/L, Y2124C, R2135P, S2138Y, T2141N, M2143V, F2145C, N2148S, N2157D, P2162L, R2169C/H, P2172L/Q/R, T2173A/I, H2174D, R2178C/H/L, R2182C/H/P, M2183R/V, L2185S/W, S2192I, C2193G, P2196R, G2198V, E2200D, I2204T, I2209N, A2211P, A2220P, P2224L, R2228G/L/P/Q, L2229F, V2242M, W2248C/S, V2251A/E, M2257V, T2264A, Q2265R, F2279C/I, I2281T, D2286G, W2290L, G2304V, D2307A, P2319L/S, R2323C/G/H/L, R2326G/L/P/Q, Q2330P, W2332R, I2336F, R2339T, G2344C/D/S, and C2345S/Y. Factor VIII proteins also include polypeptides containing post-translational modifications.

Generally, polynucleotides encoding Factor VIII encode for an inactive single-chain polypeptide (e.g., a pre-pro-protein) that undergoes post-translational processing to form an active Factor VIII protein (e.g., FVIIIa). For example, referring to FIG. 1, the wild type human Factor VIII pre-pro-protein is first cleaved to release the encoded signal peptide (not shown), forming a first single-chain pro-protein (shown as "human wild-type FVIII). The pro-protein is then cleaved between the B and A3 domains to form a first polypeptide that includes the Factor VIII heavy chain (e.g., the A1 and A2 domains) and B-domain, and a second polypeptide that includes the Factor VIII light chain (e.g., including the A3, C1, and C3 domains). The first polypeptide is further cleaved to remove the B-domain, and also to separate the A1 and A2 domains, which remain associated with the Factor VIII light chain in the mature Factor VIIIa protein. For review of the Factor VIII maturation process, see Graw et al., Nat Rev Genet., 6(6):488-501 (2005), the content of which is incorporated herein by reference in its entirety for all purposes.

However, in some embodiments, the Factor VIII polypeptide is a single-chain Factor VIII polypeptide. Single-chain Factor VIII polypeptides are engineered to remove natural cleavage sites, and optionally remove, truncate, or replace the B-domain of Factor VIII. As such, they are not matured by cleavage (other than cleavage of an optional signal and/or leader peptide), and are active as a single chain. Non-limiting examples of single-chain Factor VIII polypeptides are described in Zollner et al. (Thromb Res, 134(1):125-31 (2014)) and Donath et al. (Biochem J., 312 (1):49-55 (1995)), the disclosures of which are hereby incorporated by reference in their entireties for all purposes.

As used herein, the terms "Factor VIII heavy chain," or simply "heavy chain," refers to the aggregate of the A1 and A2 domains of a Factor VIII polypeptide. In an exemplary embodiment, amino acids 20-759 of CS04-FL-AA (SEQ ID NO: 2) constitute a Factor VIII heavy chain.

As used herein, the term "Factor VIII light chain," or simply "light chain," refers to the aggregate of the A3, C1, and C2 domains of a Factor VIII polypeptide. In an exemplary embodiment, amino acids 774-1457 CS04-FL-AA (SEQ ID NO: 2) constitute a Factor VIII light chain. In some embodiments, a Factor VIII light chain excludes the acidic a3 peptide, which is released during maturation in vivo.

Generally, Factor VIII heavy and light chains are expressed as a single polypeptide chain, e.g., along with an optional B-domain or B-domain substituted linker. However, in some embodiments, a Factor VIII heavy chain and Factor VIII light chain are expressed as separate polypeptide chains (e.g., co-expressed), and reconstituted to form a Factor VIII protein (e.g., in vivo or in vitro).

As used herein, the terms "B-domain substituted linker" and "Factor VIII linker" are used interchangeably, and refer to truncated versions of a wild type Factor VIII B-domain (e.g., amino acids 760-1667 of FVIII-FL-AA (SEQ ID NO: 19)) or peptides engineered to replace the B-domain of a Factor VIII polypeptide. As used herein, a Factor VIII linker is positioned between the C-terminus of a Factor VIII heavy chain and the N-terminus of a Factor VIII light chain in a Factor VIII variant polypeptide in accordance with some embodiments. Non-limiting examples of B-domain substituted linkers are disclosed in U.S. Pat. Nos. 4,868,112, 5,112,950, 5,171,844, 5,543,502, 5,595,886, 5,610,278, 5,789,203, 5,972,885, 6,048,720, 6,060,447, 6,114,148, 6,228,620, 6,316,226, 6,346,513, 6,458,563, 6,924,365, 7,041,635, and 7,943,374; U.S. Patent Application Publication Nos. 2013/024960, 2015/0071883, and 2015/0158930; and PCT Publication Nos. WO 2014/064277 and WO 2014/127215, the disclosures of which are hereby incorporated by reference, in their entireties, for all purposes.

Unless otherwise specified herein, the numbering of Factor VIII amino acids refers to the corresponding amino acid in the full-length, wild-type human Factor VIII sequence (FVIII-FL-AA), presented as SEQ ID NO: 19 in FIG. 18. As such, when referring to an amino acid substitution in a Factor VIII variant protein disclosed herein, the recited amino acid number refers to the analogous (e.g., structurally or functionally equivalent) and/or homologous (e.g., evolutionarily conserved in the primary amino acid sequence) amino acid in the full-length, wild-type Factor VIII sequence. For example, a T2105N amino acid substitution refers to a T to N substitution at position 2105 of the full-length, wild-type human Factor VIII sequence (FVIII-FL-AA; SEQ ID NO: 19) and a T to N substitution at position 1211 of the Factor VIII variant protein encoded by CS04 (CS04-FL-AA; SEQ ID NO: 2).

As described herein, the Factor VIII amino acid numbering system is dependent on whether the Factor VIII signal peptide (e.g., amino acids 1-19 of the full-length, wild-type human Factor VIII sequence) is included. Where the signal peptide is included, the numbering is referred to as "signal peptide inclusive" or "SPI". Where the signal peptide is not included, the numbering is referred to as "signal peptide exclusive" or "SPE." For example, F328S is SPI numbering for the same amino acid as F309S, in SPE numbering. Unless otherwise indicated, all amino acid numbering refers to the corresponding amino acid in the full-length, wild-type human Factor VIII sequence (FVIII-FL-AA), presented as SEQ ID NO: 19 in FIG. 18.

As described herein, the codon-altered polynucleotides provide increased expression of transgenic Factor VIII in vivo (e.g., when administered as part of a gene therapy vector), as compared to the level of Factor VIII expression provided by a natively-coded Factor VIII construct (e.g., a polynucleotide encoding the same Factor VIII construct using the wild-type human codons). As used herein, the term "increased expression" refers to an increased level of transgenic Factor VIII activity in the blood of an animal administered the codon-altered polynucleotide encoding Factor VIII, as compared to the level of transgenic Factor VIII activity in the blood of an animal administered a natively-coded Factor VIII construct. The activity levels can be measured using any Factor VIII activity known in the art. An exemplary assay for determining Factor VIII activity is the Technochrome FVIII assay (Technoclone, Vienna, Austria).

In some embodiments, increased expression refers to at least 25% greater transgenic Factor VIII activity in the blood of an animal administered the codon-altered Factor VIII polynucleotide, as compared to the level of transgenic Factor VIII activity in the blood of an animal administered a natively coded Factor VIII polynucleotide. In some embodiments, increased expression refers to at least 50% greater, at least 75% greater, at least 100% greater, at least 3-fold greater, at least 4-fold greater, at least 5-fold greater, at least 6-fold greater, at least 7-fold greater, at least 8-fold greater, at least 9-fold greater, at least 10-fold greater, at least 15-fold greater, at least 20-fold greater, at least 25-fold greater, at least 30-fold greater, at least 40-fold greater, at least 50-fold greater, at least 60-fold greater, at least 70-fold greater, at least 80-fold greater, at least 90-fold greater, at least 100-fold greater, at least 125-fold greater, at least 150-fold greater, at least 175-fold greater, at least 200-fold greater, at least 225-fold greater, or at least 250-fold greater transgenic Factor VIII activity in the blood of an animal administered the codon-altered Factor VIII polynucleotide, as compared to the level of transgenic Factor VIII activity in the blood of an animal administered a natively coded Factor VIII polynucleotide.

As described herein, the codon-altered polynucleotides provide increased vector production, as compared to the level of vector production provided by a natively-coded Factor VIII construct (e.g., a polynucleotide encoding the same Factor VIII construct using the wild-type human codons). As used herein, the term "increased virus production" refers to an increased vector yield in cell culture (e.g., titer per liter culture) inoculated with the codon-altered polynucleotide encoding Factor VIII, as compared to the vector yield in cell culture inoculated with a natively-coded Factor VIII construct. The vector yields can be measured using any vector titer assay known in the art. An exemplary assay for determining vector yield (e.g., of an AAV vector) is qPCR targeting the AAV2 inverted terminal repeats (Aurnhammer, Human Gene Therapy Methods: Part B 23:18-28 (2012)).

In some embodiments, increased virus production refers to at least 25% greater codon-altered vector yield, as compared to the yield of a natively-coded Factor VIII construct in the same type of culture. In some embodiments, increased vector production refers to at least 50% greater, at least 75% greater, at least 100% greater, at least 3-fold greater, at least 4-fold greater, at least 5-fold greater, at least 6-fold greater, at least 7-fold greater, at least 8-fold greater, at least 9-fold greater, at least 10-fold greater, at least 15-fold greater, or at least 20-fold greater codon-altered vector yield, as compared to the yield of a natively-coded Factor VIII construct in the same type of culture.

As used herein, the term "hemophilia" refers to a group of disease states broadly characterized by reduced blood clotting or coagulation. Hemophilia may refer to Type A, Type B, or Type C hemophilia, or to the composite of all three diseases types. Type A hemophilia (hemophilia A) is caused by a reduction or loss of factor VIII (FVIII) activity and is the most prominent of the hemophilia subtypes. Type B hemophilia (hemophilia B) results from the loss or reduction of factor IX (FIX) clotting function. Type C hemophilia (hemophilia C) is a consequence of the loss or reduction in factor XI (FXI) clotting activity. Hemophilia A and B are X-linked diseases, while hemophilia C is autosomal. Conventional treatments for hemophilia include both prophylactic and on-demand administration of clotting factors, such as FVIII, FIX, including Bebulin®-VH, and FXI, as well as FEIBA-VH, desmopressin, and plasma infusions.

As used herein, the term "FVIII gene therapy" includes any therapeutic approach of providing a nucleic acid encoding Factor VIII to a patient to relieve, diminish, or prevent the reoccurrence of one or more symptoms (e.g., clinical factors) associated with hemophilia. The term encompasses administering any compound, drug, procedure, or regimen comprising a nucleic acid encoding a Factor VIII molecule, including any modified form of Factor VIII (e.g., Factor VIII variant), for maintaining or improving the health of an individual with hemophilia. One skilled in the art will appreciate that either the course of FVIII therapy or the dose of a FVIII therapeutic agent can be changed, e.g., based upon the results obtained in accordance with the present disclosure.

As used herein, the term "bypass therapy" includes any therapeutic approach of providing non-Factor VIII hemostatic agents, compounds or coagulation factors to a patient to relieve, diminish, or prevent the reoccurrence of one or more symptoms (e.g., clinical factors) associated with hemophilia. Non-Factor VIII compounds and coagulation factors include, but are not limited to, Factor VIII Inhibitor Bypass Activity (FEIBA), recombinant activated factor VII (FVIIa), prothrombin complex concentrates, and activated prothrombin complex concentrates. These non-Factor VIII compounds and coagulation factors may be recombinant or plasma-derived. One skilled in the art will appreciate that either the course of bypass therapy or the dose of bypass therapy can be changed, e.g., based upon the results obtained in accordance with the present disclosure.

As used herein, a "combination therapy" including administration of a nucleic acid encoding a Factor VIII molecule and a conventional hemophilia A therapeutic agent includes any therapeutic approach of providing both a nucleic acid encoding a Factor VIII molecule and a Factor VIII molecule and/or non-Factor VIII hemostatic agent (e.g., bypass therapeutic agent) to a patient to relieve, diminish, or prevent the reoccurrence of one or more symptoms (e.g., clinical factors) associated with hemophilia. The term encompasses administering any compound, drug, procedure, or regimen including a nucleic acid encoding a Factor VIII molecule, including any modified form of factor VIII, which is useful for maintaining or improving the health of an individual with hemophilia and includes any of the therapeutic agents described herein.

The terms "therapeutically effective amount or dose" or "therapeutically sufficient amount or dose" or "effective or sufficient amount or dose" refer to a dose that produces therapeutic effects for which it is administered. For example, a therapeutically effective amount of a drug useful for treating hemophilia can be the amount that is capable of preventing or relieving one or more symptoms associated with hemophilia. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, Dosage *Calculations* (1999); and *Remington: The Science and Practice of Pharmacy*, 20th Edition, 2003, Gennaro, Ed., Lippincott, Williams & Wilkins).

As used herein, the term "gene" refers to the segment of a DNA molecule that codes for a polypeptide chain (e.g., the coding region). In some embodiments, a gene is positioned by regions immediately preceding, following, and/or intervening the coding region that are involved in producing the polypeptide chain (e.g., regulatory elements such as a promoter, enhancer, polyadenylation sequence, 5'-untranslated region, 3'-untranslated region, or intron).

As used herein, the term "regulatory elements" refers to nucleotide sequences, such as promoters, enhancers, terminators, polyadenylation sequences, introns, etc, that provide for the expression of a coding sequence in a cell.

As used herein, the term "promoter element" refers to a nucleotide sequence that assists with controlling expression of a coding sequence. Generally, promoter elements are located 5' of the translation start site of a gene. However, in certain embodiments, a promoter element may be located within an intron sequence, or 3' of the coding sequence. In some embodiments, a promoter useful for a gene therapy vector is derived from the native gene of the target protein (e.g., a Factor VIII promoter). In some embodiments, a promoter useful for a gene therapy vector is specific for expression in a particular cell or tissue of the target organism (e.g., a liver-specific promoter). In yet other embodiments, one of a plurality of well characterized promoter elements is used in a gene therapy vector described herein. Non-limiting examples of well-characterized promoter elements include the CMV early promoter, the (β-actin promoter, and the methyl CpG binding protein 2 (MeCP2) promoter. In some embodiments, the promoter is a constitutive promoter, which drives substantially constant expression of the target protein. In other embodiments, the promoter is an inducible promoter, which drives expression of the target protein in response to a particular stimulus (e.g., exposure to a particular treatment or agent). For a review of designing promoters for AAV-mediated gene therapy, see Gray et al. (Human Gene Therapy 22:1143-53 (2011)), the contents of which are expressly incorporated by reference in their entirety for all purposes.

As used herein, the term "vector" refers to any vehicle used to transfer a nucleic acid (e.g., encoding a Factor VIII gene therapy construct) into a host cell. In some embodiments, a vector includes a replicon, which functions to replicate the vehicle, along with the target nucleic acid. Non-limiting examples of vectors useful for gene therapy include plasmids, phages, cosmids, artificial chromosomes, and viruses, which function as autonomous units of replication in vivo. In some embodiments, a vector is a viral vehicle for introducing a target nucleic acid (e.g., a codon-altered polynucleotide encoding a Factor VIII variant). Many modified eukaryotic viruses useful for gene therapy are known in the art. For example, adeno-associated viruses (AAVs) are particularly well suited for use in human gene therapy because humans are a natural host for the virus, the native viruses are not known to contribute to any diseases, and the viruses illicit a mild immune response.

As used herein, the term "CpG island" refers to a region within a polynucleotide having a statistically elevated density of CpG dinucleotides. As used herein, a region of a polynucleotide (e.g., a polynucleotide encoding a codon-altered Factor VIII protein) is a CpG island if, over a 200-base pair window: (i) the region has GC content of greater than 50%, and (ii) the ratio of observed CpG dinucleotides per expected CpG dinucleotides is at least 0.6, as defined by the relationship:

$$\frac{N[CpG] * [\text{length of window}]}{N[C] * N[G]} \geq 0.6.$$

For additional information on methods for identifying CpG islands, see Gardiner-Garden M. et al., J Mol Biol., 196(2): 261-82 (1987), the content of which is expressly incorporated herein by reference, in its entirety, for all purposes.

As used herein, the term "nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, and peptide-nucleic acids (PNAs).

The term "amino acid" refers to naturally occurring and non-natural amino acids, including amino acid analogs and amino acid mimetics that function in a manner similar to the naturally occurring amino acids. Naturally occurring amino acids include those encoded by the genetic code, as well as those amino acids that are later modified, e.g., hydroxyproline, y-carboxyglutamate, and O-phosphoserine. Naturally occurring amino acids can include, e.g., D- and L-amino acids. The amino acids used herein can also include non-natural amino acids. Amino acid analogs refer to compounds that have the same basic chemical structure as a naturally occurring amino acid, i.e., any carbon that is bound to a hydrogen, a carboxyl group, an amino group, and an R group, e.g., homoserine, norleucine, methionine sulfoxide, or methionine methyl sulfonium. Such analogs have modified R groups (e.g., norleucine) or modified peptide backbones, but retain the same basic chemical structure as a naturally occurring amino acid. Amino acid mimetics refer to chemical compounds that have a structure that is different from the general chemical structure of an amino acid, but that function in a manner similar to a naturally occurring amino acid. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

As to amino acid sequences, one of ordinary skill in the art will recognize that individual substitutions, deletions or additions to a nucleic acid or peptide sequence that alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the disclosure.

Conservative amino acid substitutions providing functionally similar amino acids are well known in the art. Dependent on the functionality of the particular amino acid, e.g., catalytic, structural, or sterically important amino acids, different groupings of amino acid may be considered conservative substitutions for each other. Table 1 provides groupings of amino acids that are considered conservative substitutions based on the charge and polarity of the amino acid, the hydrophobicity of the amino acid, the surface exposure/structural nature of the amino acid, and the secondary structure propensity of the amino acid.

TABLE 1

Groupings of conservative amino acid substitutions based on the functionality of the residue in the protein.

| Important Feature | Conservative Groupings |
|---|---|
| Charge/Polarity | 1. H, R, and K |
| | 2. D and E |
| | 3. C, T, S, G, N, Q, and Y |
| | 4. A, P, M, L, I, V, F, and W |
| Hydrophobicity | 1. D, E, N, Q, R, and K |
| | 2. C, S, T, P, G, H, and Y |
| | 3. A, M, I, L, V, F, and W |
| Structural/Surface Exposure | 1. D, E, N, Q, H, R, and K |
| | 2. C, S, T, P, A, G, W, and Y |
| | 3. M, I, L, V, and F |
| Secondary Structure Propensity | 1. A, E, Q, H, K, M, L, and R |
| | 2. C, T, I, V, F, Y, and W |
| | 3. S, G, P, D, and N |

TABLE 1-continued

Groupings of conservative amino acid substitutions based on the functionality of the residue in the protein.

| Important Feature | Conservative Groupings |
|---|---|
| Evolutionary Conservation | 1. D and E |
| | 2. H, K, and R |
| | 3. N and Q |
| | 4. S and T |
| | 5. L, I, and V |
| | 6. F, Y, and W |
| | 7. A and G |
| | 8. M and C |

The terms "identical" or percent "identity," in the context of two or more nucleic acids or peptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using, e.g., a BLAST or BLAST 2.0 sequence comparison algorithms with default parameters described below, or by manual alignment and visual inspection.

As is known in the art, a number of different programs may be used to identify whether a protein (or nucleic acid as discussed below) has sequence identity or similarity to a known sequence. Sequence identity and/or similarity is determined using standard techniques known in the art, including, but not limited to, the local sequence identity algorithm of Smith & Waterman, Adv. Appl. Math., 2:482 (1981), by the sequence identity alignment algorithm of Needleman & Wunsch, J. Mol. Biol., 48:443 (1970), by the search for similarity method of Pearson & Lipman, Proc. Natl. Acad. Sci. U.S.A., 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., Nucl. Acid Res., 12:387-395 (1984), preferably using the default settings, or by inspection. Preferably, percent identity is calculated by FastDB based upon the following parameters: mismatch penalty of 1; gap penalty of 1; gap size penalty of 0.33; and joining penalty of 30, "Current Methods in Sequence Comparison and Analysis," Macromolecule Sequencing and Synthesis, Selected Methods and Applications, pp 127-149 (1988), Alan R. Liss, Inc, all of which are incorporated by reference.

An example of a useful algorithm is PILEUP. PILEUP creates a multiple sequence alignment from a group of related sequences using progressive, pair wise alignments. It may also plot a tree showing the clustering relationships used to create the alignment. PILEUP uses a simplification of the progressive alignment method of Feng & Doolittle, J. Mol. Evol. 35:351-360 (1987); the method is similar to that described by Higgins & Sharp CABIOS 5:151-153 (1989), both incorporated by reference. Useful PILEUP parameters including a default gap weight of 3.00, a default gap length weight of 0.10, and weighted end gaps.

Another example of a useful algorithm is the BLAST algorithm, described in: Altschul et al., J. Mol. Biol. 215, 403-410, (1990); Altschul et al., Nucleic Acids Res. 25:3389-3402 (1997); and Karlin et al., Proc. Natl. Acad. Sci. U.S.A. 90:5873-5787 (1993), both incorporated by reference. A particularly useful BLAST program is the WU-BLAST-2 program which was obtained from Altschul et al., Methods in Enzymology, 266:460-480 (1996); http://blast.wustl/edu/blast/README.html]. WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST, as reported by Altschul et al., Nucl. Acids Res., 25:3389-3402, incorporated by reference. Gapped BLAST uses BLOSUM-62 substitution scores; threshold T parameter set to 9; the two-hit method to trigger ungapped extensions; charges gap lengths of k a cost of 10+k; Xu set to 16, and Xg set to 40 for database search stage and to 67 for the output stage of the algorithms. Gapped alignments are triggered by a score corresponding to ~22 bits.

A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored). In a similar manner, "percent (%) nucleic acid sequence identity" with respect to the coding sequence of the polypeptides identified is defined as the percentage of nucleotide residues in a candidate sequence that are identical with the nucleotide residues in the coding sequence of the cell cycle protein. A preferred method utilizes the BLASTN module of WU-BLAST-2 set to the default parameters, with overlap span and overlap fraction set to 1 and 0.125, respectively.

The alignment may include the introduction of gaps in the sequences to be aligned. In addition, for sequences which contain either more or fewer amino acids than the protein encoded by the sequence of FIG. 2 (SEQ ID NO:1), it is understood that in one embodiment, the percentage of sequence identity will be determined based on the number of identical amino acids or nucleotides in relation to the total number of amino acids or nucleotides. Thus, for example, sequence identity of sequences shorter than that shown in FIG. 2 (SEQ ID NO:1), as discussed below, will be determined using the number of nucleotides in the shorter sequence, in one embodiment. In percent identity calculations relative weight is not assigned to various manifestations of sequence variation, such as, insertions, deletions, substitutions, etc.

In one embodiment, only identities are scored positively (+1) and all forms of sequence variation including gaps are assigned a value of "0", which obviates the need for a weighted scale or parameters as described below for sequence similarity calculations. Percent sequence identity may be calculated, for example, by dividing the number of matching identical residues by the total number of residues of the "shorter" sequence in the aligned region and multiplying by 100. The "longer" sequence is the one having the most actual residues in the aligned region.

The term "allelic variants" refers to polymorphic forms of a gene at a particular genetic locus, as well as cDNAs derived from mRNA transcripts of the genes, and the polypeptides encoded by them. The term "preferred mammalian codon" refers a subset of codons from among the set of codons encoding an amino acid that are most frequently used in proteins expressed in mammalian cells as chosen from the following list: Gly (GGC, GGG); Glu (GAG); Asp (GAC); Val (GTG, GTC); Ala (GCC, GCT); Ser (AGC, TCC); Lys (AAG); Asn (AAC); Met (ATG); Ile (ATC); Thr (ACC); Trp (TGG); Cys (TGC); Tyr (TAT, TAC); Leu (CTG); Phe (TTC); Arg (CGC, AGG, AGA); Gln (CAG); His (CAC); and Pro (CCC).

As used herein, the term codon-altered refers to a polynucleotide sequence encoding a polypeptide (e.g., a Factor VIII variant protein), where at least one codon of the native polynucleotide encoding the polypeptide has been changed to improve a property of the polynucleotide sequence. In some embodiments, the improved property promotes increased transcription of mRNA coding for the polypeptide, increased stability of the mRNA (e.g., improved mRNA half-life), increased translation of the polypeptide, and/or increased packaging of the polynucleotide within the vector. Non-limiting examples of alterations that can be used to achieve the improved properties include changing the usage and/or distribution of codons for particular amino acids, adjusting global and/or local GC content, removing AT-rich sequences, removing repeated sequence elements, adjusting global and/or local CpG dinucleotide content, removing cryptic regulatory elements (e.g., TATA box and CCAAT box elements), removing of intron/exon splice sites, improving regulatory sequences (e.g., introduction of a Kozak consensus sequence), and removing sequence elements capable of forming secondary structure (e.g., stem-loops) in the transcribed mRNA.

As discussed herein, there are various nomenclatures to refer to components of the disclosure herein. "CS-number" (e.g. "CS04", "CS01", "CS 23", etc.) refer to codon altered polynucleotides encoding FVIII polypeptides and/or the encoded polypeptides, including variants. For example, CS01-FL refers to the Full Length codon altered CS01 polynucleotide sequence or amino acid sequence (sometimes referred to herein as "CS01-FL-AA" for the Amino Acid sequence and "CS01-FL-NA" for the Nucleic Acid sequence) encoded by the CS01 polynucleotide sequence. Similarly, "CS01-LC" refers to either the codon altered nucleic acid sequence ("CS01-LC-NA") encoding the light chain of a FVIII polypeptide or the amino acid sequence (also sometimes referred to herein as "CS01-LC-AA") of the FVIII light chain encoded by the CS01 polynucleotide sequence. Likewise, CS01-HC, CS01-HC-AA and CS01-HC-NA are the same for the FVIII heavy chain. As will be appreciated by those in the art, for constructs such as CS01, CS04, CS23, etc., that are only codon-altered (e.g. they do not contain additional amino acid substitutions as compared to Refacto), the amino acid sequences will be identical, as the amino acid sequences are not altered by the codon optimization. Thus, sequence constructs of the disclosure include, but are not limited to, CS01-FL-NA, CS01-FL-AA, CS01-LC-NA, CS01-LC-AA, CS01-HC-AA, CS01-HC-NA, CS04-FL-NA, CS04-FL-AA, CS04-LC-NA, CS04-LC-AA, CS04-HC-AA, CS04-HC-NA, CS23-FL-NA, CS23-FL-AA, CS23-LC-NA, CS23-LC-AA, CS23-HC-AA and CS23-HC-NA.

III. Codon-Altered Factor VIII Variants

In some embodiments, the present disclosure provides codon-altered polynucleotides encoding Factor VIII variants. These codon-altered polynucleotides provide markedly improved expression of Factor VIII when administered in an AAV-based gene therapy construct. The codon-altered polynucleotides also demonstrate improved AAV-virion packaging, as compared to conventionally codon-optimized constructs. As demonstrated in Example 2 and Table 4, Applicants have achieve these advantages through the discovery of three codon-altered polynucleotides (CS01-FL-NA, CS04-FL-NA, and CS23-FL-NA) encoding a Factor VIII polypeptide with human wild-type Factor VIII heavy and light chains, and a short, 14 amino acid, B-domain substituted linker (the "SQ" linker) containing a furin cleavage site to facilitate maturation of an active FVIIIa protein in vivo.

In one embodiment, a codon-altered polynucleotide provided herein has nucleotide sequences with high sequence identity to at least the sequences within CS01, CS04, or CS23 (SEQ ID NOS 13, 1, and 20, respectively) encoding the Factor VIII heavy chain and Factor VIII light chains. As known in the art, the B-domain of Factor VIII is dispensable for activity in vivo. Thus, in some embodiments, the codon-altered polynucleotides provided herein completely lack a Factor VIII B-domain. In some embodiments, the native Factor VIII B-domain is replaced with a short amino acid linker containing a furin cleavage site, e.g., the "SQ" linker consisting of amino acids 760-773 of the CS01, CS04, or CS23 (SEQ ID NOS 2, 2, and 21, respectively) constructs. The "SQ" linker is also referred to as BDLO04, (–AA for the amino acid sequence and –NA for the nucleotide sequence).

In one embodiment, the Factor VIII heavy and light chains encoded by the codon-altered polynucleotide are human Factor VIII heavy and light chains, respectively. In other embodiments, the Factor VIII heavy and light chains encoded by the codon-altered polynucleotide are heavy and light chain sequences from another mammal (e.g., porcine Factor VIII). In yet other embodiments, the Factor VIII heavy and light chains are chimeric heavy and light chains (e.g., a combination of human and a second mammalian sequence). In yet other embodiments, the Factor VIII heavy and light chains are humanized version of the heavy and light chains from another mammal, e.g., heavy and light chain sequences from another mammal in which human residues are substituted at select positions to reduce the immunogenicity of the resulting peptide when administered to a human.

The GC content of human genes varies widely, from less than 25% to greater than 90%. However, in general, human genes with higher GC contents are expressed at higher levels. For example, Kudla et al. (PLoS Biol., 4(6):80 (2006)) demonstrate that increasing a gene's GC content increases expression of the encoded polypeptide, primarily by increasing transcription and effecting a higher steady state level of the mRNA transcript. Generally, the desired GC content of a codon-optimized gene construct is equal or greater than 60%. However, native AAV genomes have GC contents of around 56%.

Accordingly, in some embodiments, the codon-altered polynucleotides provided herein have a CG content that more closely matches the GC content of native AAV virions (e.g., around 56% GC), which is lower than the preferred CG contents of polynucleotides that are conventionally codon-optimized for expression in mammalian cells (e.g., at or above 60% GC). As outlined in Example 1, CS04-FL-NA (SEQ ID NO: 1), which has a GC content of about 56%, has improved virion packaging as compared to similarly codon-altered coding sequences with higher GC content.

Thus, in some embodiments, the overall GC content of a codon-altered polynucleotide encoding a Factor VIII polypeptide is less than 60%. In some embodiments, the overall GC content of a codon-altered polynucleotide encoding a Factor VIII polypeptide is less than 59%. In some embodiments, the overall GC content of a codon-altered polynucleotide encoding a Factor VIII polypeptide is less than 58%. In some embodiments, the overall GC content of a codon-altered polynucleotide encoding a Factor VIII polypeptide is less than 57%. In some embodiments, the overall GC content of a codon-altered polynucleotide encoding a Factor VIII polypeptide is no more than 56%.

In some embodiments, the overall GC content of a codon-altered polynucleotide encoding a Factor VIII polypeptide is from 54% to 59%. In some embodiments, the overall GC content of a codon-altered polynucleotide encoding a Factor VIII polypeptide is from 55% to 59%. In some embodiments, the overall GC content of a codon-altered polynucleotide encoding a Factor VIII polypeptide is from 56% to 59%. In some embodiments, the overall GC content of a codon-altered polynucleotide encoding a Factor VIII polypeptide is from 54% to 58%. In some embodiments, the overall GC content of a codon-altered polynucleotide encoding a Factor VIII polypeptide is from 55% to 58%. In some embodiments, the overall GC content of a codon-altered polynucleotide encoding a Factor VIII polypeptide is from 56% to 58%. In some embodiments, the overall GC content of a codon-altered polynucleotide encoding a Factor VIII polypeptide is from 54% to 57%. In some embodiments, the overall GC content of a codon-altered polynucleotide encoding a Factor VIII polypeptide is from 55% to 57%. In some embodiments, the overall GC content of a codon-altered polynucleotide encoding a Factor VIII polypeptide is from 56% to 57%. In some embodiments, the overall GC content of a codon-altered polynucleotide encoding a Factor VIII polypeptide is from 54% to 56%. In some embodiments, the overall GC content of a codon-altered polynucleotide encoding a Factor VIII polypeptide is from 55% to 56%.

In some embodiments, the overall GC content of a codon-altered polynucleotide encoding a Factor VIII polypeptide is 56±0.5%. In some embodiments, the overall GC content of a codon-altered polynucleotide encoding a Factor VIII polypeptide is 56±0.4%. In some embodiments, the overall GC content of a codon-altered polynucleotide encoding a Factor VIII polypeptide is 56±0.3%. In some embodiments, the overall GC content of a codon-altered polynucleotide encoding a Factor VIII polypeptide is 56±0.2%. In some embodiments, the overall GC content of a codon-altered polynucleotide encoding a Factor VIII polypeptide is 56±0.1%. In some embodiments, the overall GC content of a codon-altered polynucleotide encoding a Factor VIII polypeptide is 56%.

A. Factor VIII B-Domain Substituted Linkers

In some embodiments, the linkage between the FVIII heavy chain and the light chain (e.g., the B-domain in wild-type Factor VIII) is further altered. Due to size constraints of AAV packaging capacity, B-domain deleted, truncated, and or linker substituted variants should improve the efficacy of the FVIII gene therapy construct. The most conventionally used B-domain substituted linker is that of SQ FVIII, which retains only 14 amino acids of the B domain as linker sequence. Another variant of porcine VIII ("OBI-1," described in U.S. Pat. No. 6,458,563) is well expressed in CHO cells, and has a slightly longer linker of 24 amino acids. In some embodiments, the Factor VIII constructs encoded by the codon-altered polynucleotides described herein include an SQ-type B-domain linker sequence. In other embodiments, the Factor VIII constructs encoded by the codon-altered polynucleotides described herein include an OBI-1-type B-domain linker sequence.

In some embodiments, the encoded Factor VIII polypeptides described herein include an SQ-type B-domain linker (SFSQNPPVLKRHQR; BDL-SQ-AA; SEQ ID NO: 30), including amino acids 760-762/1657-1667 of the wild-type human Factor VIII B-domain (FVIII-FL-AA; SEQ ID NO: 19) (Sandberg et al. Thromb. Haemost. 85:93 (2001)). In some embodiments, the SQ-type B-domain linker has one amino acid substitution relative to the corresponding wild-type sequence. In some embodiments, the SQ-type B-domain linker has two amino acid substitutions relative to the corresponding wild-type sequence.

In some embodiments, the encoded Factor VIII polypeptides described herein include a Greengene-type B-domain linker, including amino acids 760/1582-1667 of the wild-type human Factor VIII B-domain (FVIII-FL-AA; SEQ ID NO: 19) (Oh et al., Biotechnol. Prog., 17:1999 (2001)). In some embodiments, the Greengene-type B-domain linker has one amino acid substitution relative to the corresponding wild-type sequence. In some embodiments, the Greengene-type B-domain linker has two amino acid substitutions relative to the corresponding wild-type sequence.

In some embodiments, the encoded Factor VIII polypeptides described herein include an extended SQ-type B-domain linker, including amino acids 760-769/1657-1667 of the wild-type human Factor VIII B-domain (FVIII-FL-AA; SEQ ID NO: 19) (Thim et al., Haemophilia, 16:349 (2010)). In some embodiments, the extended SQ-type B-domain linker has one amino acid substitution relative to the corresponding wild-type sequence. In some embodiments, the extended SQ-type B-domain linker has two amino acid substitutions relative to the corresponding wild-type sequence.

In some embodiments, the encoded Factor VIII polypeptides described herein include a porcine OBI-1-type B-domain linker, including the amino acids SFAQNSR-PPSASAPKPPVLRRHQR (SEQ ID NO: 31) from the wild-type porcine Factor VIII B-domain (Toschi et al., Curr. Opin. Mol. Ther. 12:517 (2010)). In some embodiments, the porcine OBI-1-type B-domain linker has one amino acid substitution relative to the corresponding wild-type sequence. In some embodiments, the porcine OBI-1-type B-domain linker has two amino acid substitutions relative to the corresponding wild-type sequence.

In some embodiments, the encoded Factor VIII polypeptides described herein include a human OBI-1-type B-domain linker, including amino acids 760-772/1655-1667 of the wild-type human Factor VIII B-domain (FVIII-FL-AA; SEQ ID NO: 19). In some embodiments, the human OBI-1-type B-domain linker has one amino acid substitution relative to the corresponding wild-type sequence. In some embodiments, the human OBI-1-type B-domain linker has two amino acid substitutions relative to the corresponding wild-type sequence.

In some embodiments, the encoded Factor VIII polypeptides described herein include an O8-type B-domain linker, including the amino acids SFSQNSRHQAYRYRRG (SEQ ID NO: 32) from the wild-type porcine Factor VIII B-domain (Toschi et al., Curr. Opin. Mol. Ther. 12:517 (2010)). In some embodiments, the porcine OBI-1-type B-domain linker has one amino acid substitution relative to the corresponding wild-type sequence. In some embodiments, the porcine OBI-1-type B-domain linker has two amino acid substitutions relative to the corresponding wild-type sequence.

Removal of the B-domain from Factor VIII constructs does not appear to affect the activity of the activated enzyme (e.g., FVIIIa), presumably because the B-domain is removed during activation. However, the B-domain of Factor VIII contains several residues that are post-translationally modified, e.g., by N- or O-linked glycosylation. In silico analysis (Prediction of N-glycosylation sites in human proteins, R. Gupta, E. Jung and S. Brunak, in preparation (2004)) of the wild-type Factor VIII B-domain predicts that at least four of these sites are glycosylated in vivo. It is thought that these modifications within the B-domain contribute to the post-translational regulation and/or half-life of Factor VIII in vivo.

While the Factor VIII B-domain is absent in mature Factor VIIIa protein, glycosylation within the B-domain of the precursor Factor VIII molecule may increase the circulating half-life of the protein prior to activation. Thus, in some embodiments, the polypeptide linker of the encoded Factor VIII constructs described herein includes one or more glycosylation sequences, to allow for glycosylation in vivo. In some embodiments, the polypeptide linker includes at least one consensus glycosylation sequence (e.g., an N- or O-linked glycosylation consensus sequence). In some embodiments, the polypeptide linker includes at least two consensus glycosylation sequences. In some embodiments, the polypeptide linker includes at least three consensus glycosylation sequences. In some embodiments, the polypeptide linker includes at least four consensus glycosylation sequences. In some embodiments, the polypeptide linker includes at least five consensus glycosylation sequences. In some embodiments, the polypeptide linker includes at least 6, 7, 8, 9, 10, or more consensus glycosylation sequences.

In some embodiments, the polypeptide linker contains at least one N-linked glycosylation sequence N-X-S/T, where X is any amino acid other than P, S, or T. In some embodiments, the polypeptide linker contains at least two N-linked glycosylation sequences N-X-S/T, where X is any amino acid other than P, S, or T. In some embodiments, the polypeptide linker contains at least three N-linked glycosylation sequences N-X-S/T, where X is any amino acid other than P, S, or T. In some embodiments, the polypeptide linker contains at least four N-linked glycosylation sequences N-X-S/T, where X is any amino acid other than P, S, or T. In some embodiments, the polypeptide linker contains at least five N-linked glycosylation sequences N-X-S/T, where X is any amino acid other than P, S, or T. In some embodiments, the polypeptide linker contains at least 6, 7, 8, 9, 10, or more N-linked glycosylation sequences N-X-S/T, where X is any amino acid other than P, S, or T.

B. Codon-altered Polynucleotides Encoding a Factor VIII Variant with a Cleavable Linker CS04 Codon Altered Polynucleotides In one embodiment, the codon-altered polynucleotides provided herein include a nucleotide sequence encoding a Factor VIII variant polypeptide with a linker that is cleavable in vivo. The Factor VIII polypeptide includes a Factor VIII light chain, a Factor VIII heavy chain, and a polypeptide linker joining the C-terminus of the heavy chain to the N-terminus of the light chain. The heavy chain of the Factor VIII polypeptide is encoded by a first nucleotide sequence having high sequence identity to CS04-HC-NA (SEQ ID NO: 3), which is the portion of CS04-FL-NA (SEQ ID NO: 1) encoding for a Factor VIII heavy chain. The light chain of the Factor VIII polypeptide is encoded by a second nucleotide sequence with high sequence identity to CS04-LC-NA (SEQ ID NO: 4), which is the portion of CS04-FL-NA (SEQ ID NO: 1) encoding for a Factor VIII light chain. The polypeptide linker includes a furin cleavage site, which allows for maturation in vivo (e.g., after expression in vivo or administration of the precursor polypeptide).

In some embodiments, the first and second nucleotide sequences have at least 95% sequence identity to CS04-HC-NA and CS04-LC-NA (SEQ ID NOS 3 and 4), respectively.

In some embodiments, the first and second nucleotide sequences have at least 96% sequence identity to CS04-HC-NA and CS04-LC-NA (SEQ ID NOS 3 and 4), respectively. In some embodiments, the first and second nucleotide sequences have at least 97% sequence identity to CS04-HC-NA and CS04-LC-NA (SEQ ID NOS 3 and 4), respectively. In some embodiments, the first and second nucleotide sequences have at least 98% sequence identity to CS04-HC-NA and CS04-LC-NA (SEQ ID NOS 3 and 4), respectively. In some embodiments, the first and second nucleotide sequences have at least 99% sequence identity to CS04-HC-NA and CS04-LC-NA (SEQ ID NOS 3 and 4), respectively. In some embodiments, the first and second nucleotide sequences have at least 99.5% sequence identity to CS04-HC-NA and CS04-LC-NA (SEQ ID NOS 3 and 4), respectively. In some embodiments, the first and second nucleotide sequences have at least 99.9% sequence identity to CS04-HC-NA and CS04-LC-NA (SEQ ID NOS 3 and 4), respectively. In some embodiments, the first and second nucleotide sequences are identical to CS04-HC-NA and CS04-LC-NA (SEQ ID NOS 3 and 4), respectively.

In some embodiments, the polypeptide linker of the Factor VIII construct is encoded by a third nucleotide sequence having high sequence identity to BDLO04 (SEQ ID NO: 6), which encodes the 14-amino acid linker corresponding to amino acids 760-773 of CS04-FL-AA (SEQ ID NO: 2). In some embodiments, the third nucleotide sequence has at least 95% identity to BDLO04 (SEQ ID NO: 6). In some embodiments, the third nucleotide sequence has at least 96% identity to BDLO04 (SEQ ID NO: 6). In some embodiments, the third nucleotide sequence has at least 97% identity to BDLO04 (SEQ ID NO: 6). In some embodiments, the third nucleotide sequence has at least 98% identity to BDLO04 (SEQ ID NO: 6). In some embodiments, the third nucleotide sequence is identical to BDLO04 (SEQ ID NO: 6).

In some embodiments, the codon-altered polynucleotide has a nucleotide sequence with high sequence identity to CS04-FL-NA (SEQ ID NO: 1). In some embodiments, the nucleotide sequence has at least 95% identity to CS04-FL-NA (SEQ ID NO: 1). In some embodiments, the nucleotide sequence has at least 96% identity to CS04-FL-NA (SEQ ID NO: 1). In some embodiments, the nucleotide sequence has at least 97% identity to CS04-FL-NA (SEQ ID NO: 1). In some embodiments, the nucleotide sequence has at least 98% identity to CS04-FL-NA (SEQ ID NO: 1). In some embodiments, the nucleotide sequence has at least 99% identity to CS04-FL-NA (SEQ ID NO: 1). In some embodiments, the nucleotide sequence has at least 99.5% identity to CS04-FL-NA (SEQ ID NO: 1). In some embodiments, the nucleotide sequence has at least 99.9% identity to CS04-FL-NA (SEQ ID NO: 1). In some embodiments, the nucleotide sequence is identical to CS04-FL-NA (SEQ ID NO: 1).

In some embodiments, the Factor VIII variant encoded by the codon-altered polynucleotide has an amino acid sequence with high sequence identity to CS04-FL-AA (SEQ ID NO: 2). In some embodiments, the amino acid sequence has at least 97% identity to CS04-FL-AA (SEQ ID NO: 2). In some embodiments, the amino acid sequence has at least 98% identity to CS04-FL-AA (SEQ ID NO: 2). In some embodiments, the amino acid sequence has at least 99% identity to CS04-FL-AA (SEQ ID NO: 2). In some embodiments, the amino acid sequence has at least 99.5% identity to CS04-FL-AA (SEQ ID NO: 2). In some embodiments, the amino acid sequence has at least 99.9% identity to CS04-FL-AA (SEQ ID NO: 2). In some embodiments, the amino acid sequence is identical to CS04-FL-AA (SEQ ID NO: 2).

CS01 Codon Altered Polynucleotides

In one embodiment, the codon-altered polynucleotides provided herein include a nucleotide sequence encoding a Factor VIII variant polypeptide with a linker that is cleavable in vivo. The Factor VIII polypeptide includes a Factor VIII light chain, a Factor VIII heavy chain, and a polypeptide linker joining the C-terminus of the heavy chain to the N-terminus of the light chain. The heavy chain of the Factor VIII polypeptide is encoded by a first nucleotide sequence having high sequence identity to CS01-HC-NA (SEQ ID NO: 24), which is the portion of CS01-FL-NA (SEQ ID NO: 13) encoding for a Factor VIII heavy chain. The light chain of the Factor VIII polypeptide is encoded by a second nucleotide sequence with high sequence identity to CS01-LC-NA (SEQ ID NO: 25), which is the portion of CS01-FL-NA (SEQ ID NO: 13) encoding for a Factor VIII light chain. The polypeptide linker includes a furin cleavage site, which allows for maturation in vivo (e.g., after expression in vivo or administration of the precursor polypeptide).

In some embodiments, the first and second nucleotide sequences have at least 95% sequence identity to CS01-HC-NA and CS01-LC-NA (SEQ ID NOS 24 and 25), respectively. In some embodiments, the first and second nucleotide sequences have at least 96% sequence identity to CS01-HC-NA and CS01-LC-NA (SEQ ID NOS 24 and 25), respectively. In some embodiments, the first and second nucleotide sequences have at least 97% sequence identity to CS01-HC-NA and CS01-LC-NA (SEQ ID NOS 24 and 25), respectively. In some embodiments, the first and second nucleotide sequences have at least 98% sequence identity to CS01-HC-NA and CS01-LC-NA (SEQ ID NOS 24 and 25), respectively. In some embodiments, the first and second nucleotide sequences have at least 99% sequence identity to CS01-HC-NA and CS01-LC-NA (SEQ ID NOS 24 and 25), respectively. In some embodiments, the first and second nucleotide sequences have at least 99.5% sequence identity to CS01-HC-NA and CS01-LC-NA (SEQ ID NOS 24 and 25), respectively. In some embodiments, the first and second nucleotide sequences have at least 99.9% sequence identity to CS01-HC-NA and CS01-LC-NA (SEQ ID NOS 24 and 25), respectively. In some embodiments, the first and second nucleotide sequences are identical to CS01-HC-NA and CS01-LC-NA (SEQ ID NOS 24 and 25), respectively.

In some embodiments, the polypeptide linker of the Factor VIII construct is encoded by a third nucleotide sequence having high sequence identity to BDLO04 (SEQ ID NO: 6), which encodes the 14-amino acid linker corresponding to amino acids 760-773 of CS01-FL-AA (SEQ ID NO: 2). In some embodiments, the third nucleotide sequence has at least 95% identity to BDLO04 (SEQ ID NO: 6). In some embodiments, the third nucleotide sequence has at least 96% identity to BDLO04 (SEQ ID NO: 6). In some embodiments, the third nucleotide sequence has at least 97% identity to BDLO04 (SEQ ID NO: 6). In some embodiments, the third nucleotide sequence has at least 98% identity to BDLO04 (SEQ ID NO: 6). In some embodiments, the third nucleotide sequence is identical to BDLO04 (SEQ ID NO: 6).

In some embodiments, the codon-altered polynucleotide has a nucleotide sequence with high sequence identity to CS01-FL-NA (SEQ ID NO: 13). In some embodiments, the nucleotide sequence has at least 95% identity to CS01-FL-NA (SEQ ID NO: 13). In some embodiments, the nucleotide sequence has at least 96% identity to CS01-FL-NA (SEQ ID NO: 13). In some embodiments, the nucleotide sequence has at least 97% identity to CS01-FL-NA (SEQ ID NO: 13). In some embodiments, the nucleotide sequence has at least 98% identity to CS01-FL-NA (SEQ ID NO: 13). In some embodiments, the nucleotide sequence has at least 99% identity to CS01-FL-NA (SEQ ID NO: 13). In some embodiments, the nucleotide sequence has at least 99.5% identity to CS01-FL-NA (SEQ ID NO: 13). In some embodiments, the nucleotide sequence has at least 99.9% identity to CS01-FL-NA (SEQ ID NO: 13). In some embodiments, the nucleotide sequence is identical to CS01-FL-NA (SEQ ID NO: 13).

In some embodiments, the Factor VIII variant encoded by the codon-altered polynucleotide has an amino acid sequence with high sequence identity to CS01-FL-AA (SEQ ID NO: 2). In some embodiments, the amino acid sequence has at least 97% identity to CS01-FL-AA (SEQ ID NO: 2). In some embodiments, the amino acid sequence has at least 98% identity to CS01-FL-AA (SEQ ID NO: 2). In some embodiments, the amino acid sequence has at least 99% identity to CS01-FL-AA (SEQ ID NO: 2). In some embodiments, the amino acid sequence has at least 99.5% identity to CS01-FL-AA (SEQ ID NO: 2). In some embodiments, the amino acid sequence has at least 99.9% identity to CS01-FL-AA (SEQ ID NO: 2). In some embodiments, the amino acid sequence is identical to CS01-FL-AA (SEQ ID NO: 2).

CS23 Codon Altered Polynucleotides

In one embodiment, the codon-altered polynucleotides provided herein include a nucleotide sequence encoding a Factor VIII variant polypeptide with a linker that is cleavable in vivo. The Factor VIII polypeptide includes a Factor VIII light chain, a Factor VIII heavy chain, and a polypeptide linker joining the C-terminus of the heavy chain to the N-terminus of the light chain. The heavy chain of the Factor VIII polypeptide is encoded by a first nucleotide sequence having high sequence identity to CS23-HC-NA (SEQ ID NO: 22), which is the portion of CS23-FL-NA (SEQ ID NO: 20) encoding for a Factor VIII heavy chain. The light chain of the Factor VIII polypeptide is encoded by a second nucleotide sequence with high sequence identity to CS23-LC-NA (SEQ ID NO: 23), which is the portion of CS23-FL-NA (SEQ ID NO: 20) encoding for a Factor VIII light chain. The polypeptide linker includes a furin cleavage site, which allows for maturation in vivo (e.g., after expression in vivo or administration of the precursor polypeptide).

In some embodiments, the first and second nucleotide sequences have at least 95% sequence identity to CS23-HC-NA and CS23-LC-NA (SEQ ID NOS 22 and 23), respectively. In some embodiments, the first and second nucleotide sequences have at least 96% sequence identity to CS23-HC-NA and CS23-LC-NA (SEQ ID NOS 22 and 23), respectively. In some embodiments, the first and second nucleotide sequences have at least 97% sequence identity to CS23-HC-NA and CS23-LC-NA (SEQ ID NOS 22 and 23), respectively. In some embodiments, the first and second nucleotide sequences have at least 98% sequence identity to CS23-HC-NA and CS23-LC-NA (SEQ ID NOS 22 and 23), respectively. In some embodiments, the first and second nucleotide sequences have at least 99% sequence identity to CS23-HC-NA and CS23-LC-NA (SEQ ID NOS 22 and 23), respectively. In some embodiments, the first and second nucleotide sequences have at least 99.5% sequence identity to CS23-HC-NA and CS23-LC-NA (SEQ ID NOS 22 and 23), respectively. In some embodiments, the first and second nucleotide sequences have at least 99.9% sequence identity to CS23-HC-NA and CS23-LC-NA (SEQ ID NOS 22 and 23), respectively. In some embodiments, the first and second nucleotide sequences are identical to CS23-HC-NA and CS23-LC-NA (SEQ ID NOS 22 and 23), respectively.

In some embodiments, the polypeptide linker of the Factor VIII construct is encoded by a third nucleotide sequence having high sequence identity to BDLO04 (SEQ ID NO: 6), which encodes the 14-amino acid linker corresponding to amino acids 760-773 of CS23-FL-AA (SEQ ID NO: 21). In some embodiments, the third nucleotide sequence has at least 95% identity to BDLO04 (SEQ ID NO: 6). In some embodiments, the third nucleotide sequence has at least 96% identity to BDLO04 (SEQ ID NO: 6). In some embodiments, the third nucleotide sequence has at least 97% identity to BDLO04 (SEQ ID NO: 6). In some embodiments, the third nucleotide sequence has at least 98% identity to BDLO04 (SEQ ID NO: 6). In some embodiments, the third nucleotide sequence is identical to BDLO04 (SEQ ID NO: 6).

In some embodiments, the codon-altered polynucleotide has a nucleotide sequence with high sequence identity to CS23-FL-NA (SEQ ID NO: 20). In some embodiments, the nucleotide sequence has at least 95% identity to CS23-FL-NA (SEQ ID NO: 20). In some embodiments, the nucleotide sequence has at least 96% identity to CS23-FL-NA (SEQ ID NO: 20). In some embodiments, the nucleotide sequence has at least 97% identity to CS23-FL-NA (SEQ ID NO: 20). In some embodiments, the nucleotide sequence has at least 98% identity to CS23-FL-NA (SEQ ID NO: 20). In some embodiments, the nucleotide sequence has at least 99% identity to CS23-FL-NA (SEQ ID NO: 20). In some embodiments, the nucleotide sequence has at least 99.5% identity to CS23-FL-NA (SEQ ID NO: 20). In some embodiments, the nucleotide sequence has at least 99.9% identity to CS23-FL-NA (SEQ ID NO: 20). In some embodiments, the nucleotide sequence is identical to CS23-FL-NA (SEQ ID NO: 20).

In some embodiments, the Factor VIII variant encoded by the codon-altered polynucleotide has an amino acid sequence with high sequence identity to CS23-FL-AA (SEQ ID NO: 21). In some embodiments, the amino acid sequence has at least 97% identity to CS23-FL-AA (SEQ ID NO: 21). In some embodiments, the amino acid sequence has at least 98% identity to CS23-FL-AA (SEQ ID NO: 21). In some embodiments, the amino acid sequence has at least 99% identity to CS23-FL-AA (SEQ ID NO: 21). In some embodiments, the amino acid sequence has at least 99.5% identity to CS23-FL-AA (SEQ ID NO: 21). In some embodiments, the amino acid sequence has at least 99.9% identity to CS23-FL-AA (SEQ ID NO: 21). In some embodiments, the amino acid sequence is identical to CS23-FL-AA (SEQ ID NO: 21).

C. Codon-altered Polynucleotides Encoding a Single-chain Factor VIII Protein

Factor VIII constructs in which the furin cleavage site located at the C-terminal end of the B-domain is removed retain activity as a single chain polypeptide, despite that normal maturation of the Factor VIII molecule cannot occur (Leyte et al. (1991)). Similarly, a B-domain deleted Factor VIII construct with an attenuated furin site (containing an R1664H amino acid substitution) is more biologically active than the corresponding Factor VIII construct with a wild-type furin cleavage site (Siner et al. (2013)). Accordingly, in some embodiments, the codon-altered polynucleotides provided herein include a nucleotide sequence encoding a single-chain Factor VIII variant polypeptide. The single-chain Factor VIII polypeptide includes a Factor VIII light chain, a Factor VIII heavy chain, and a polypeptide linker joining the C-terminus of the heavy chain to the N-terminus of the light chain. The polypeptide linker does not include a furin cleavage site.

Single-chain CS04 Codon Altered Polynucleotides

In one embodiment, the codon-altered polynucleotides provided herein include a nucleotide sequence encoding a single-chain Factor VIII variant polypeptide. The Factor VIII polypeptide includes a Factor VIII light chain, a Factor VIII heavy chain, and an optional polypeptide linker joining the C-terminus of the heavy chain to the N-terminus of the light chain. The heavy chain of the Factor VIII polypeptide is encoded by a first nucleotide sequence having high sequence identity to CS04-HC-NA (SEQ ID NO: 3), which is the portion of CS04-FL-NA (SEQ ID NO: 1) encoding for a Factor VIII heavy chain. The light chain of the Factor VIII polypeptide is encoded by a second nucleotide sequence with high sequence identity to CS04-LC-NA (SEQ ID NO: 4), which is the portion of CS04-FL-NA (SEQ ID NO: 1) encoding for a Factor VIII light chain. The optional polypeptide linker does not include a furin cleavage site.

In some embodiments, the first and second nucleotide sequences have at least 95% sequence identity to CS04-HC-NA and CS04-LC-NA (SEQ ID NOS 3 and 4), respectively. In some embodiments, the first and second nucleotide sequences have at least 96% sequence identity to CS04-HC-NA and CS04-LC-NA (SEQ ID NOS 3 and 4), respectively. In some embodiments, the first and second nucleotide sequences have at least 97% sequence identity to CS04-HC-NA and CS04-LC-NA (SEQ ID NOS 3 and 4), respectively. In some embodiments, the first and second nucleotide sequences have at least 98% sequence identity to CS04-HC-NA and CS04-LC-NA (SEQ ID NOS 3 and 4), respectively. In some embodiments, the first and second nucleotide sequences have at least 99% sequence identity to CS04-HC-NA and CS04-LC-NA (SEQ ID NOS 3 and 4), respectively. In some embodiments, the first and second nucleotide sequences have at least 99.5% sequence identity to CS04-HC-NA and CS04-LC-NA (SEQ ID NOS 3 and 4), respectively. In some embodiments, the first and second nucleotide sequences have at least 99.9% sequence identity to CS04-HC-NA and CS04-LC-NA (SEQ ID NOS 3 and 4), respectively. In some embodiments, the first and second nucleotide sequences are identical to CS04-HC-NA and CS04-LC-NA (SEQ ID NOS 3 and 4), respectively.

In some embodiments, the codon-altered polynucleotide has a nucleotide sequence with high sequence identity to CS04-SC1-NA (SEQ ID NO: 9). In some embodiments, the nucleotide sequence has at least 95% identity to CS04-SC1-NA (SEQ ID NO: 9). In some embodiments, the nucleotide sequence has at least 96% identity to CS04-SC1-NA (SEQ ID NO: 9). In some embodiments, the nucleotide sequence has at least 97% identity to CS04-SC1-NA (SEQ ID NO: 9). In some embodiments, the nucleotide sequence has at least 98% identity to CS04-SC1-NA (SEQ ID NO: 9). In some embodiments, the nucleotide sequence has at least 99% identity to CS04-SC1-NA (SEQ ID NO: 9). In some embodiments, the nucleotide sequence has at least 99.5% identity to CS04-SC1-NA (SEQ ID NO: 9). In some embodiments, the nucleotide sequence has at least 99.9% identity to CS04-SC1-NA (SEQ ID NO: 9). In some embodiments, the nucleotide sequence is identical to CS04-SC1-NA (SEQ ID NO: 9).

In some embodiments, the codon-altered polynucleotide has a nucleotide sequence with high sequence identity to CS04-SC2-NA (SEQ ID NO: 11). In some embodiments, the nucleotide sequence has at least 95% identity to CS04-SC2-NA (SEQ ID NO: 11). In some embodiments, the nucleotide sequence has at least 96% identity to CS04-SC2-NA (SEQ ID NO: 11). In some embodiments, the nucleotide sequence has at least 97% identity to CS04-SC2-NA (SEQ ID NO: 11). In some embodiments, the nucleotide sequence has at least 98% identity to CS04-SC2-NA (SEQ ID NO: 11). In some embodiments, the nucleotide sequence has at least 99% identity to CS04-SC2-NA (SEQ ID NO: 11). In some embodiments, the nucleotide sequence has at least 99.5% identity to (CS04-SC2-NA (SEQ ID NO: 11). In some embodiments, the nucleotide sequence has at least 99.9% identity to CS04-SC2-NA (SEQ ID NO: 11). In some embodiments, the nucleotide sequence is identical to CS04-SC2-NA (SEQ ID NO: 11).

In some embodiments, the single-chain Factor VIII variant encoded by the codon-altered polynucleotide has an amino acid sequence with high sequence identity to CS04-SC1-AA (SEQ ID NO: 10; human Factor VIIIΔ(760-1667) (SPI; HsFVIIIΔ(741-1648), SPE)). In some embodiments, the Factor VIII variant encoded by the codon-altered polynucleotide has an amino acid sequence with high sequence identity to CS04-SC1-AA (SEQ ID NO: 10). In some embodiments, the amino acid sequence has at least 97% identity to CS04-SC1-AA (SEQ ID NO: 10). In some embodiments, the amino acid sequence has at least 98% identity to CS04-SC1-AA (SEQ ID NO: 10). In some embodiments, the amino acid sequence has at least 99% identity to CS04-SC1-AA (SEQ ID NO: 10). In some embodiments, the amino acid sequence has at least 99.5% identity to CS04-SC1-AA (SEQ ID NO: 10). In some embodiments, the amino acid sequence has at least 99.9% identity to CS04-SC1-AA (SEQ ID NO: 10). In some embodiments, the amino acid sequence is identical to CS04-SC1-AA (SEQ ID NO: 10).

In some embodiments, the single-chain Factor VIII variant encoded by the codon-altered polynucleotide has an amino acid sequence with high sequence identity to CS04-SC2-AA (SEQ ID NO: 12; human Factor VIIIΔ (772-1667) (SPI; HsFVIIIΔ (753-1648), SPE)). In some embodiments, the Factor VIII variant encoded by the codon-altered polynucleotide has an amino acid sequence with high sequence identity to CS04-SC2-AA (SEQ ID NO: 12). In some embodiments, the amino acid sequence has at least 97% identity to CS04-SC2-AA (SEQ ID NO: 12). In some embodiments, the amino acid sequence has at least 98% identity to CS04-SC2-AA (SEQ ID NO: 12). In some embodiments, the amino acid sequence has at least 99% identity to CS04-SC2-AA (SEQ ID NO: 12). In some embodiments, the amino acid sequence has at least 99.5% identity to CS04-SC2-AA (SEQ ID NO: 12). In some embodiments, the amino acid sequence has at least 99.9% identity to CS04-SC2-AA (SEQ ID NO: 12). In some embodiments, the amino acid sequence is identical to CS04-SC2-AA (SEQ ID NO: 12).

Single-chain CS01 Codon Altered Polynucleotides

In one embodiment, the codon-altered polynucleotides provided herein include a nucleotide sequence encoding a single-chain Factor VIII variant polypeptide. The Factor VIII polypeptide includes a Factor VIII light chain, a Factor VIII heavy chain, and an optional polypeptide linker joining the C-terminus of the heavy chain to the N-terminus of the light chain. The heavy chain of the Factor VIII polypeptide is encoded by a first nucleotide sequence having high sequence identity to CS01-HC-NA (SEQ ID NO: 24), which is the portion of CS01-FL-NA (SEQ ID NO: 13) encoding for a Factor VIII heavy chain. The light chain of the Factor VIII polypeptide is encoded by a second nucleotide sequence with high sequence identity to CS01-LC-NA (SEQ ID NO: 25), which is the portion of CS01-FL-NA (SEQ ID NO: 13) encoding for a Factor VIII light chain. The optional polypeptide linker does not include a furin cleavage site.

In some embodiments, the first and second nucleotide sequences have at least 95% sequence identity to CS01-HC-NA and CS01-LC-NA (SEQ ID NOS 24 and 25), respectively. In some embodiments, the first and second nucleotide sequences have at least 96% sequence identity to CS01-HC-NA and CS01-LC-NA (SEQ ID NOS 24 and 25), respectively. In some embodiments, the first and second nucleotide sequences have at least 97% sequence identity to CS01-HC-NA and CS01-LC-NA (SEQ ID NOS 24 and 25), respectively. In some embodiments, the first and second nucleotide sequences have at least 98% sequence identity to CS01-HC-NA and CS01-LC-NA (SEQ ID NOS 24 and 25), respectively. In some embodiments, the first and second nucleotide sequences have at least 99% sequence identity to CS01-HC-NA and CS01-LC-NA (SEQ ID NOS 24 and 25), respectively. In some embodiments, the first and second nucleotide sequences have at least 99.5% sequence identity to CS01-HC-NA and CS01-LC-NA (SEQ ID NOS 24 and 25), respectively. In some embodiments, the first and second nucleotide sequences have at least 99.9% sequence identity to CS01-HC-NA and CS01-LC-NA (SEQ ID NOS 24 and 25), respectively. In some embodiments, the first and second nucleotide sequences are identical to CS01-HC-NA and CS01-LC-NA (SEQ ID NOS 24 and 25), respectively.

In some embodiments, the codon-altered polynucleotide has a nucleotide sequence with high sequence identity to CS01-SC1-NA (SEQ ID NO: 26). In some embodiments, the nucleotide sequence has at least 95% identity to CS01-SC1-NA (SEQ ID NO: 26). In some embodiments, the nucleotide sequence has at least 96% identity to CS01-SC1-NA (SEQ ID NO: 26). In some embodiments, the nucleotide sequence has at least 97% identity to CS01-SC1-NA (SEQ ID NO: 26). In some embodiments, the nucleotide sequence has at least 98% identity to CS01-SC1-NA (SEQ ID NO: 26). In some embodiments, the nucleotide sequence has at least 99% identity CS01-SC1-NA (SEQ ID NO: 26). In some embodiments, the nucleotide sequence has at least 99.5% identity to CS01-SC1-NA (SEQ ID NO: 26). In some embodiments, the nucleotide sequence has at least 99.9% identity to CS01-SC1-NA (SEQ ID NO: 26). In some embodiments, the nucleotide sequence is identical to CS01-SC1-NA (SEQ ID NO: 26).

In some embodiments, the codon-altered polynucleotide has a nucleotide sequence with high sequence identity to CS01-SC2-NA (SEQ ID NO: 27). In some embodiments, the nucleotide sequence has at least 95% identity to CS01-SC2-NA (SEQ ID NO: 27). In some embodiments, the nucleotide sequence has at least 96% identity to CS01-SC2-NA (SEQ ID NO: 27). In some embodiments, the nucleotide sequence has at least 97% identity to CS01-SC2-NA (SEQ ID NO: 27). In some embodiments, the nucleotide sequence has at least 98% identity to CS01-SC2-NA (SEQ ID NO: 27). In some embodiments, the nucleotide sequence has at least 99% identity to CS01-SC2-NA (SEQ ID NO: 27). In some embodiments, the nucleotide sequence has at least 99.5% identity to CS01-SC2-NA (SEQ ID NO: 27). In some embodiments, the nucleotide sequence has at least 99.9% identity to CS01-SC2-NA (SEQ ID NO: 27). In some embodiments, the nucleotide sequence is identical to CS01-SC2-NA (SEQ ID NO: 27).

In some embodiments, the single-chain Factor VIII variant encoded by the codon-altered polynucleotide has an amino acid sequence with high sequence identity to CS01-SC1-AA (SEQ ID NO: 10; human Factor VIIIΔ (760-1667) (SPI; HsFVIIIΔ (741-1648), SPE)). In some embodiments, the Factor VIII variant encoded by the codon-altered polynucleotide has an amino acid sequence with high sequence identity to CS01-SC1-AA (SEQ ID NO: 10). In some embodiments, the amino acid sequence has at least 97% identity to CS01-SC1-AA (SEQ ID NO: 10). In some embodiments, the amino acid sequence has at least 98% identity to CS01-SC1-AA (SEQ ID NO: 10). In some embodiments, the amino acid sequence has at least 99% identity to CS01-SC1-AA (SEQ ID NO: 10). In some embodiments, the amino acid sequence has at least 99.5% identity to CS01-SC1-AA (SEQ ID NO: 10). In some embodiments, the amino acid sequence has at least 99.9% identity to CS01-SC1-AA (SEQ ID NO: 10). In some embodiments, the amino acid sequence is identical to CS01-SC1-AA (SEQ ID NO: 10).

In some embodiments, the single-chain Factor VIII variant encoded by the codon-altered polynucleotide has an amino acid sequence with high sequence identity to CS01-SC2-AA (SEQ ID NO: 12; human Factor VIIIΔ (772-1667) (SPI; HsFVIIIΔ (753-1648), SPE)). In some embodiments, the Factor VIII variant encoded by the codon-altered polynucleotide has an amino acid sequence with high sequence identity to CS01-SC2-AA (SEQ ID NO: 12). In some embodiments, the amino acid sequence has at least 97% identity to CS01-SC2-AA (SEQ ID NO: 12). In some embodiments, the amino acid sequence has at least 98% identity to CS01-SC2-AA (SEQ ID NO: 12). In some embodiments, the amino acid sequence has at least 99% identity to CS01-SC2-AA (SEQ ID NO: 12). In some embodiments, the amino acid sequence has at least 99.5% identity to CS01-SC2-AA (SEQ ID NO: 12). In some embodiments, the amino acid sequence has at least 99.9% identity to CS01-SC2-AA (SEQ ID NO: 12). In some embodiments, the amino acid sequence is identical to CS01-SC2-AA (SEQ ID NO: 12).

Single-chain CS23 Codon Altered Polynucleotides

In one embodiment, the codon-altered polynucleotides provided herein include a nucleotide sequence encoding a single-chain Factor VIII variant polypeptide. The Factor VIII polypeptide includes a Factor VIII light chain, a Factor VIII heavy chain, and an optional polypeptide linker joining the C-terminus of the heavy chain to the N-terminus of the light chain. The heavy chain of the Factor VIII polypeptide is encoded by a first nucleotide sequence having high sequence identity to CS23-HC-NA (SEQ ID NO: 22), which is the portion of CS23-FL-NA (SEQ ID NO: 20) encoding for a Factor VIII heavy chain. The light chain of the Factor VIII polypeptide is encoded by a second nucleotide sequence with high sequence identity to CS23-LC-NA (SEQ ID NO: 23), which is the portion of CS23-FL-NA (SEQ ID NO: 20) encoding for a Factor VIII light chain. The optional polypeptide linker does not include a furin cleavage site.

In some embodiments, the first and second nucleotide sequences have at least 95% sequence identity to CS23-HC-NA and CS23-LC-NA (SEQ ID NOS 22 and 23), respectively. In some embodiments, the first and second nucleotide sequences have at least 96% sequence identity to CS23-HC-NA and CS23-LC-NA (SEQ ID NOS 22 and 23), respectively. In some embodiments, the first and second nucleotide sequences have at least 97% sequence identity to CS23-HC-NA and CS23-LC-NA (SEQ ID NOS 22 and 23), respectively. In some embodiments, the first and second nucleotide sequences have at least 98% sequence identity to CS23-HC-NA and CS23-LC-NA (SEQ ID NOS 22 and 23), respectively. In some embodiments, the first and second nucleotide sequences have at least 99% sequence identity to CS23-HC-NA and CS23-LC-NA (SEQ ID NOS 22 and 23), respectively. In some embodiments, the first and second nucleotide sequences have at least 99.5% sequence identity to CS23-

HC-NA and CS23-LC-NA (SEQ ID NOS 22 and 23), respectively. In some embodiments, the first and second nucleotide sequences have at least 99.9% sequence identity to CS23-HC-NA and CS23-LC-NA (SEQ ID NOS 22 and 23), respectively. In some embodiments, the first and second nucleotide sequences are identical to CS23-HC-NA and CS23-LC-NA (SEQ ID NOS 22 and 23), respectively.

In some embodiments, the codon-altered polynucleotide has a nucleotide sequence with high sequence identity to CS23-SC1-NA (SEQ ID NO: 28). In some embodiments, the nucleotide sequence has at least 95% identity to CS23-SC1-NA (SEQ ID NO: 28). In some embodiments, the nucleotide sequence has at least 96% identity to CS23-SC1-NA (SEQ ID NO: 28). In some embodiments, the nucleotide sequence has at least 97% identity to CS23-SC1-NA (SEQ ID NO: 28). In some embodiments, the nucleotide sequence has at least 98% identity to CS23-SC1-NA (SEQ ID NO: 28). In some embodiments, the nucleotide sequence has at least 99% identity to CS23-SC1-NA (SEQ ID NO: 28). In some embodiments, the nucleotide sequence has at least 99.5% identity to CS23-SC1-NA (SEQ ID NO: 28). In some embodiments, the nucleotide sequence has at least 99.9% identity to CS23-SC1-NA (SEQ ID NO: 28). In some embodiments, the nucleotide sequence is identical to CS23-SC1-NA (SEQ ID NO: 28).

In some embodiments, the codon-altered polynucleotide has a nucleotide sequence with high sequence identity to CS23-SC2-NA (SEQ ID NO: 29). In some embodiments, the nucleotide sequence has at least 95% identity to CS23-SC2-NA (SEQ ID NO: 29). In some embodiments, the nucleotide sequence has at least 96% identity to CS23-SC2-NA (SEQ ID NO: 29). In some embodiments, the nucleotide sequence has at least 97% identity to CS23-SC2-NA (SEQ ID NO: 29). In some embodiments, the nucleotide sequence has at least 98% identity to CS23-SC2-NA (SEQ ID NO: 29). In some embodiments, the nucleotide sequence has at least 99% identity to CS23-SC2-NA (SEQ ID NO: 29). In some embodiments, the nucleotide sequence has at least 99.5% identity to CS23-SC2-NA (SEQ ID NO: 29). In some embodiments, the nucleotide sequence has at least 99.9% identity to CS23-SC2-NA (SEQ ID NO: 29). In some embodiments, the nucleotide sequence is identical to CS23-SC2-NA (SEQ ID NO: 29).

In some embodiments, the single-chain Factor VIII variant encoded by the codon-altered polynucleotide has an amino acid sequence with high sequence identity to CS23-SC1-AA (SEQ ID NO: 10; human Factor VIIIΔ (760-1667) (SPI; HsFVIIIΔ (741-1648), SPE)). In some embodiments, the Factor VIII variant encoded by the codon-altered polynucleotide has an amino acid sequence with high sequence identity to CS23-SC1-AA (SEQ ID NO: 10). In some embodiments, the amino acid sequence has at least 97% identity to CS23-SC1-AA (SEQ ID NO: 10). In some embodiments, the amino acid sequence has at least 98% identity to CS23-SC1-AA (SEQ ID NO: 10). In some embodiments, the amino acid sequence has at least 99% identity to CS23-SC1-AA (SEQ ID NO: 10). In some embodiments, the amino acid sequence has at least 99.5% identity to CS23-SC1-AA (SEQ ID NO: 10). In some embodiments, the amino acid sequence has at least 99.9% identity to CS23-SC1-AA (SEQ ID NO: 10). In some embodiments, the amino acid sequence is identical to CS23-SC1-AA (SEQ ID NO: 10).

In some embodiments, the single-chain Factor VIII variant encoded by the codon-altered polynucleotide has an amino acid sequence with high sequence identity to CS23-SC2-AA (SEQ ID NO: 12; human Factor VIIIΔ (772-1667) (SPI; HsFVIIIΔ (753-1648), SPE)). In some embodiments, the Factor VIII variant encoded by the codon-altered polynucleotide has an amino acid sequence with high sequence identity to CS23-SC2-AA (SEQ ID NO: 12). In some embodiments, the amino acid sequence has at least 97% identity to CS23-SC2-AA (SEQ ID NO: 12). In some embodiments, the amino acid sequence has at least 98% identity to CS23-SC2-AA (SEQ ID NO: 12). In some embodiments, the amino acid sequence has at least 99% identity to CS23-SC2-AA (SEQ ID NO: 12). In some embodiments, the amino acid sequence has at least 99.5% identity to CS23-SC2-AA (SEQ ID NO: 12). In some embodiments, the amino acid sequence has at least 99.9% identity to CS23-SC2-AA (SEQ ID NO: 12). In some embodiments, the amino acid sequence is identical to CS23-SC2-AA (SEQ ID NO: 12).

D. Factor VIII Expression Vectors

In some embodiments, the codon-altered polynucleotides described herein are integrated into expression vectors. Non-limiting examples of expression vectors include viral vectors (e.g., vectors suitable for gene therapy), plasmid vectors, bacteriophage vectors, cosmids, phagemids, artificial chromosomes, and the like.

Non-limiting examples of viral vectors include: retrovirus, e.g., Moloney murine leukemia virus (MMLV), Harvey murine sarcoma virus, murine mammary tumor virus, and Rous sarcoma virus; adenoviruses, adeno-associated viruses; SV40-type viruses; polyomaviruses; Epstein-Barr viruses; papilloma viruses; herpes viruses; vaccinia viruses; and polio viruses.

In some embodiments, the codon-altered polynucleotides described herein are integrated into a gene therapy vector. In some embodiments, the gene therapy vector is a retrovirus, and particularly a replication-deficient retrovirus. Protocols for the production of replication-deficient retroviruses are known in the art. For review, see Kriegler, M., Gene Transfer and Expression, A Laboratory Manual, W.H. Freeman Co., New York (1990) and Murry, E. J., Methods in Molecular Biology, Vol. 7, Humana Press, Inc., Cliffton, N.J. (1991).

In one embodiment, the gene therapy vector is an adeno-associated virus (AAV) based gene therapy vector. AAV systems have been described previously and are generally well known in the art (Kelleher and Vos, *Biotechniques*, 17(6):1110-17 (1994); Cotten et al., *Proc Natl Acad Sci USA*, 89(13):6094-98 (1992); Curiel, *Nat Immun*, 13(2-3): 141-64 (1994); Muzyczka, *Curr Top Microbiol Immunol*, 158:97-129 (1992); and Asokan A, et al., Mol. Ther., 20(4): 699-708 (2012), each incorporated herein by reference in their entireties for all purposes). Details concerning the generation and use of rAAV vectors are described, for example, in U.S. Pat. Nos. 5,139,941 and 4,797,368, each incorporated herein by reference in their entireties for all purposes. In a particular embodiment, the AAV vector is an AAV-8 vector.

In some embodiments, the codon-altered polynucleotides described herein are integrated into a retroviral expression vector. These systems have been described previously, and are generally well known in the art (Mann et al., *Cell*, 33:153-159, 1983; Nicolas and Rubinstein, In: Vectors: A survey of molecular cloning vectors and their uses, Rodriguez and Denhardt, eds., Stoneham: Butterworth, pp. 494-513, 1988; Temin, In: Gene Transfer, Kucherlapati (ed.), New York: Plenum Press, pp. 149-188, 1986). In a specific embodiment, the retroviral vector is a lentiviral vector (see, for example, Naldini et al., *Science*, 272(5259):263-267, 1996; Zufferey et al., *Nat Biotechnol*, 15(9):871-875, 1997;

Blomer et al., *J Virol.,* 71(9):6641-6649, 1997; U.S. Pat. Nos. 6,013,516 and 5,994,136).

A wide variety of vectors can be used for the expression of a Factor VIII polypeptide from a codon-altered polypeptide in cell culture, including eukaryotic and prokaryotic expression vectors. In certain embodiments, a plasmid vector is contemplated for use in expressing a Factor VIII polypeptide in cell culture. In general, plasmid vectors containing replicon and control sequences which are derived from species compatible with the host cell are used in connection with these hosts. The vector can carry a replication site, as well as marking sequences which are capable of providing phenotypic selection in transformed cells. The plasmid will include the codon-altered polynucleotide encoding the Factor VIII polypeptide, operably linked to one or more control sequences, for example, a promoter.

Non-limiting examples of vectors for prokaryotic expression include plasmids such as pRSET, pET, pBAD, etc., wherein the promoters used in prokaryotic expression vectors include lac, trc, trp, recA, araBAD, etc. Examples of vectors for eukaryotic expression include: (i) for expression in yeast, vectors such as pAO, pPIC, pYES, pMET, using promoters such as AOX1, GAP, GAL1, AUG1, etc; (ii) for expression in insect cells, vectors such as pMT, pAc5, pIB, pMIB, pBAC, etc., using promoters such as PH, p10, MT, Ac5, OpIE2, gp64, po1h, etc., and (iii) for expression in mammalian cells, vectors such as pSVL, pCMV, pRc/RSV, pcDNA3, pBPV, etc., and vectors derived from viral systems such as vaccinia virus, adeno-associated viruses, herpes viruses, retroviruses, etc., using promoters such as CMV, SV40, EF-1, UbC, RSV, ADV, BPV, and β-actin.

IV. Examples

Example 1

Construction of a Codon Altered Factor VIII Variant Expression Sequence

Two hurdles had to be overcome in order to create a Factor VIII coding sequence that is effective for gene therapy of hemophilia A. First, because of the genomic size limitations of conventional gene therapy delivery vectors (e.g., AAV virions), the encoded Factor VIII polypeptide had to be shortened considerably. Second, the coding sequence had to be altered to: (i) stabilize packaging interactions within the delivery vector, (ii) stabilize the mRNA intermediary, and (iii) improve the robustness of transcription/translation of the mRNA.

To achieve the first objective, Applicants started with a B-domain deleted Factor VIII variant construct, referred to herein as "FVIII-BDD-SQ." In this construct, the B-domain is replaced with a fourteen amino acid sequence referred to as the "SQ" sequence. Recombinant FVIII-BDD-SQ is sold under the trade name REFACTO®, and has been shown to be effective for the management of hemophilia A. However, the native coding sequence for FVIII-BDD-SQ, which includes human wild-type nucleic acid sequences for the Factor VIII heavy and light chains, is ineffectively expressed in gene therapy vectors.

To address the poor expression of the native FVIII-BDD-SQ, the codon optimization algorithm described in Fath et al. (PLoS ONE, 6:e17596 (2011)), modified as described in Ward et al. (Blood, 117:798 (2011)) and in McIntosh et al. (Blood, 121, 3335-3344 (2013)) was applied to the FVIII-BDD-SQ sequence to create first intermediate coding sequence CS04a. However, Applicants recognized that the CS04a sequence created using the modified algorithm could be improved by further modifying the sequence. Accordingly, Applicants re-introduced CpG dinucleotides, re-introduced the CGC codon for arginine, changed the leucine and serine codon distributions, re-introduced highly conserved codon pairs, and removed cryptic TATA box, CCAAT box, and splice site elements, while avoiding CpG islands and local overrepresentation of AT-rich and GC-rich stretches.

First, the modified algorithm systematically replaces codons containing CpG-dinucleotides (e.g., arginine codons) with non-CpG-dinucleotide codons, and eliminates/avoids CpG-dinucleotides created by neighboring codons. This strict avoidance of CpG dinucleotides is usually done to prevent TLR-induced immunity after intramuscular injection of DNA vaccines. However, doing so limits the codon optimization possibilities. For example, the modified algorithm excludes use of the complete set of CGX arginine codons. This is particularly disruptive in the coding of genes for expression in human cells, because CGC is the most frequently used arginine codon in highly expressed human genes. Additionally, avoiding the creation of CpGs by neighboring codons further limits the optimization possibilities (e.g., limits the number of codon pairs that may be used together).

Because TLR-induced immunity is not expected to be a problem associated with liver-directed, AAV-based gene therapy, codons including CpGs, and neighboring codons creating CpGs, were re-introduced into intermediate coding sequence CS04a, preferentially in the sequence coding for the Factor VIII light chain (e.g., at the 3' end of the FVIII-BDD-SQ coding sequence). This allowed for more frequent use of preferred human codons, particularly those for arginine. Care was taken, however, to avoid creation of CpG islands, which are regions of coding sequence having a high frequency of CpG sites. This is contrary to the teachings of Krinner et al. (Nucleic Acids Res., 42(6):3551-64 (2014)), which suggests that CpG domains downstream of transcriptional start sites promote high levels of gene expression.

Second, the modified algorithm applies certain codons exclusively, such as CTG for leucine, GTG for valine, and CAG for glutamine. However, this offends the principles of balanced codon use, for example, as proposed in Haas et al. (Current Biology, 6(3):315-24 (1996)). To account for the overuse of preferred codons by the modified algorithm, alternate leucine codons were re-introduced where allowed by the other rules applied to the codon alteration (e.g., CpG frequency and GC content).

Third, the modified algorithm replaces codon pairs without regard to how conserved they are in nature, when certain criteria (e.g., the presence of CG-dinucleotides) are met. To account for beneficial properties which may have been conserved by evolution, the most conserved codon pairs that were replaced by the algorithm and the most conserved preferred codon pairs, e.g., as described in Tats et al. (BMC Genomics 9:463 (2008)), were analyzed and adjusted where allowed by the other rules applied to the codon alteration (e.g., CpG frequency and GC content).

Fourth, serine codons used in the intermediate coding sequence were also re-engineered. Specifically, AGC, TCC, and TCT serine codons were introduced into the modified coding sequence with higher frequency, to better match overall for human codon usage (Haas et al., supra).

Fifth, TATA box, CCAAT box elements, and intron/exon splice sites were screened and removed from the modified coding sequence. When modifying the coding sequence, care was taken to avoid local overrepresentation of AT-rich or GC rich stretches.

Finally, in addition to optimizing the codon usage within the coding sequence, the structural requirements of the underlying AAV virion were considered when further refining the intermediate coding sequence CS04a. AAV vectors (e.g., the nucleic acid portion of an AAV virion) are packaged as single stranded DNA molecules into their capsids (for review, see, Daya and Berns, Clin. Microbiol Rev., 21(4):583-93 (2008)). The GC content of the vector is therefore likely to influence packaging of the genome and, thus, vector yields during production. Like many algorithms, the modified algorithm used here creates an optimized gene sequence with a GC content of at least 60% (see, Fath et al., PLoS One, 6(3):e17596 (2011) (erratum in: PLoS One, (6)3 (2011)). However, the AAV8 capsid protein is encoded by a nucleotide sequence having a lower GC content of about 56%. Thus, to better mimic the native AAV8 capsid protein coding sequence, the GC content of the intermediate coding sequence CS04a was reduced to 56%.

The resulting CS04 coding sequence, shown in FIG. 2, has an overall GC content of 56%. The CpG-dinucleotide content of the sequence is moderate. However, CpG dinucleotides are predominantly in the downstream portion of the coding sequence, e.g., the portion coding for the Factor VIII light chain. The CS04 sequence has 79.77% nucleotide sequence identity to the corresponding coding sequences in wild-type Factor VIII (Genbank accession M14113).

For comparison purposes, several other codon-optimized, ReFacto constructs were prepared. CS01 was constructed by applying the codon-optimization algorithm of Fath et al., as modified by Ward et al., as done for CS04. However, unlike CS04, the CS01 construct does not contain any CpG islands. The CS08 ReFacto construct was codon-optimized as described in Radcliff P. M. et al., Gene Therapy, 15:289-97 (2008), the content of which is hereby expressly incorporated by reference herein, in its entirety, for all purposes. The CS10 codon-optimized ReFacto construct was obtained from Eurofins Genomics (Ebersberg, Germany). The CS11 codon-optimized ReFacto construct was obtained from Integrated DNA Technologies, Inc. (Coralville, USA). The CH25 codon-optimized ReFacto construct was obtained from ThermoFischer Scientific's GeneArt services (Regensburg, Germany). The CS40 ReFacto construct consists of the wild type Factor VIII coding sequence. The algorithm used to construct CS23 is based on the JCAT tool (www.jcat.de), an on-line tool for codon-optimizations (Grote et al., 2005; Nucl. Acids Res. W526-31). The sequence was further modified to more reflect the codon usage of the albumin superfamily (Mirsafian et al. 2014: Sc. Word Journal 2014, ID 639682). The sequence identities shared between each of the ReFacto coding sequences is shown in Table 2, below.

Figure 19:
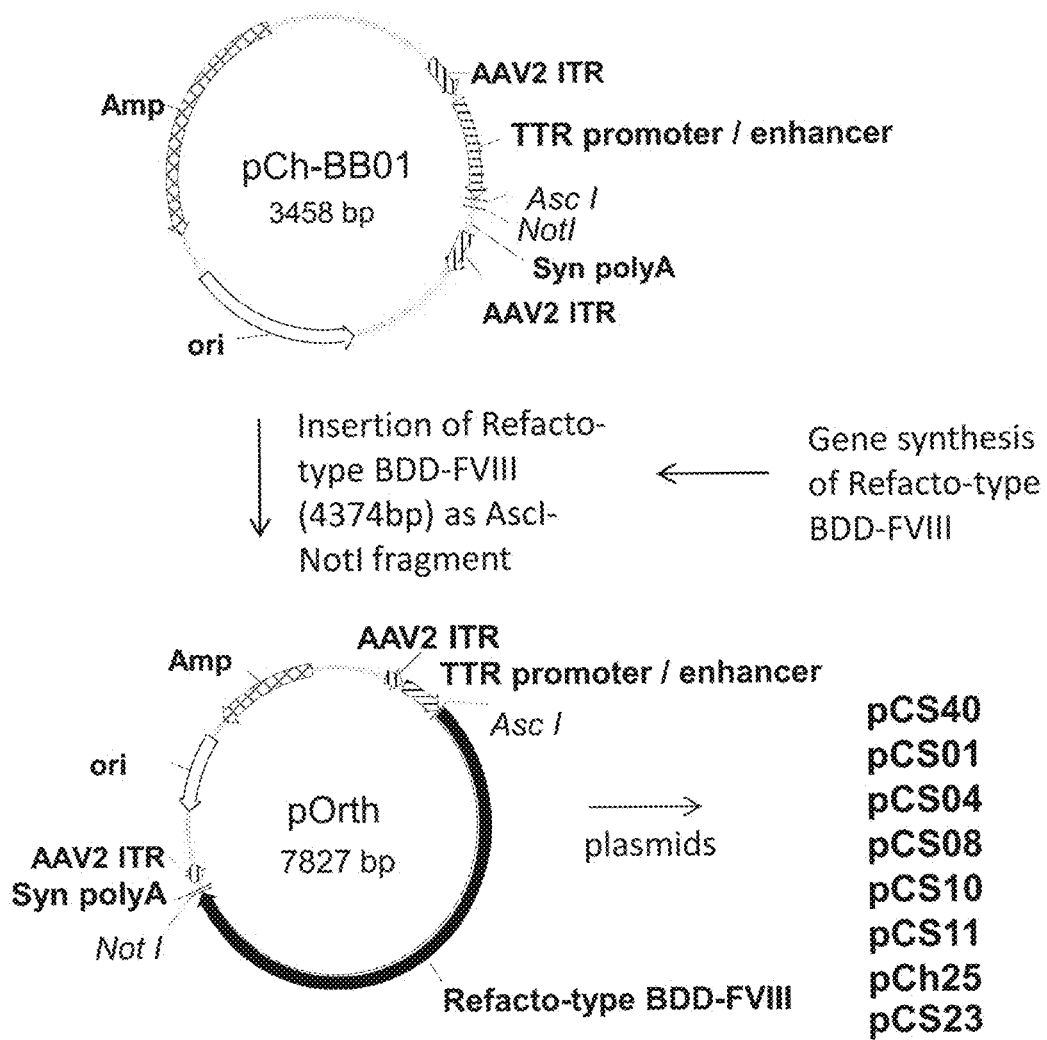
FIG. 19 illustrates the scheme for cloning the pCS40, pCS01, pCS04, pCS08, pCS10, pCS11, and pCh25 constructs, by inserting synthetic Refacto-type BDD-FVIII DNA sequences into the vector backbone pCh-BB01 via AscI and NotI restriction sites.

Plasmids of each construct were constructed by cloning different synthetic DNA fragments into the same vector backbone plasmid (pCh-BB01). DNA synthesis of the Refacto-type BDD-FVIII fragments with flanking AscI and NotI enzyme restriction sites were done by ThermoFischer Scientific (Regensburg, Germany). The vector backbone contains two flanking AAV2-derived inverted terminal repeats (ITRs) that encompass a promoter/enhancer sequence derived from the liver-specific murine transthyretin gene, AscI and NotI enzyme restriction sites for insertion of the respective Refacto-type BDD-FVIII and a synthetic polyA site. After ligation of the prepared vector backbone and inserts via the AscI and NotI sites, the resulting plasmids were amplified in milligram scale. The Refacto-type BDD-FVIII sequences of the constructs were verified by direct sequencing (Microsynth, Balgach, Switzerland). The cloning resulted in seven different plasmid constructs named pCS40, pCS01, pCS04, pCS08, pCS10, pCS11, pCh25, and pCS23 (FIG. 19). The constructs have the same vector backbone and encode the same B-domain deleted FVIII protein (Refacto-type BDD-FVIII), but differ in their FVIII coding sequence.

AAV8-based vectors were prepared by the three plasmid transfection method, as described in Grieger J C, et al. (Virus Vectors Using Suspension HEK293 Cells and Continuous Harvest of Vector From the Culture Media for GMP FIX and FLT1 Clinical Vector, Mol Ther., Oct. 6. (2015) doi: 10.1038/mt.2015.187. [Epub ahead of print]), the content of which is hereby expressly incorporated by reference herein, in its entirety, for all purposes. HEK293 suspensions cells were used for plasmid transfections using the corresponding FVIII vector plasmid, the helper plasmid pXX6-80 (carrying adenoviral helper genes), and the packaging plasmid pGSK$^{2}/_{8}$(contributing the rep2 and cap8 genes). To isolate the AAV8 constructs, the cell pellets of one liter cultures were processed using iodixanol gradients, as described in Grieger et al. (2015, Supra). The procedure resulted in vector preparations called vCS01, vCS04, vCS08, vCS10, vCS11, and vCH25. Vectors were quantified by qPCR using the universal qPCR procedure targeting the AAV2 inverted terminal repeats (Aurnhammer, Human Gene Therapy Methods: Part B 23:18-28 (2012)). A control vector plasmid carrying AAV2 inverted terminal repeats served for preparing the standard curve. The resulting vCS04 construct is presented as SEQ ID NO: 8 in FIGS. 7A-7C.

The integrity of the vector genomes was analyzed by AAV agarose gel electrophoresis. The electrophoresis was performed as described in Fagone et al., Human Gene Therapy Methods 23:1-7 (2012). Briefly, AAV vector preparations were incubated at 75° C. for 10 minutes in the presence of 0.5% SDS and then cooled down to room temperature. Approximately 1.5E10 vector genomes (vg) were loaded per lane on a 1% 1×TAE agarose gel and electrophoresed for 60 min at 7 V/cm of gel length. The gel was then stained in

TABLE 2

Percent identity matrix for codon-altered Factor VIII constructs.

| | CS01 | CS04 | CS08 | CS10 | CS11 | CS40 | CH25 | CS23 |
|---|---|---|---|---|---|---|---|---|
| CS01 | 100% | | | | | | | |
| CS04 | 93.0% | 100% | | | | | | |
| CS08 | 80.7% | 82.2.% | 100% | | | | | |
| CS10 | 79.1% | 79.4% | 78.4% | 100% | | | | |
| CS11 | 78.3% | 78.3% | 78.1% | 77.5% | 100% | | | |
| CS40 | 79.6% | 79.8% | 76.7% | 77.6% | 75.4% | 100% | | |
| CH25 | 81.3% | 85.1% | 85.0% | 79.9% | 79.4% | 75.8% | 100% | |
| CS23 | 84.3% | 89.2% | 85.1% | 80.3% | 79.9 | 76.5% | 93.2% | 100% |

Figure 20:
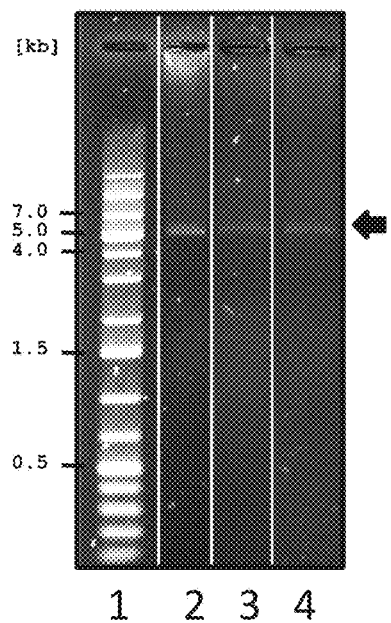
FIG. 20 shows the integrity of AAV vector genome preparations, as analyzed by agarose gel electrophoresis. Lane 1, DNA marker; lane 2, vCS40; lane 3, vCS01; lane 4, vCS04. The AAV vectors have all the same-sized genomes, migrating at approximately 5 kb (arrow, right side). The scale on the left side indicates size of the DNA fragments in kilobases (kb).

2×GelRed (Biotium Cat#41003) solution and imaged by ChemiDocTMMP (Biorad). The results shown in FIG. 20 demonstrate that the vCS01, vCS04, and vCS40 viral vectors have the same-sized genome, indicated by a distinct band in the 5kb range (FIG. 20, lanes 2-4). Despite a vector size of approx. 5.2 kb, the genome is a homogenous band confirming correct packaging of the somewhat oversized genome (relative to an AAV wild-type genome of 4.7 kb). All other vCS vector preparations show the same genomic size (data not shown).

Figure 21:
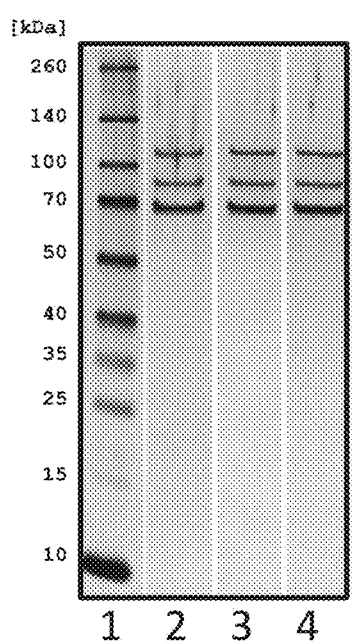
FIG. 21 shows the protein analysis of AAV vector preparations by PAGE and silver staining. Lane 1, protein marker (M); lane 2, vCS40, lane 3, vCS01; and lane 4, vCS04. The constructs all have the same AAV8 capsids consisting of VP1, VP2, and VP3 (arrows right side). The scale on the left side indicates size of the protein marker in kilodaltons (kDa).

In order to confirm the expected pattern of capsid proteins, SDS PAGE followed by silver staining was performed with the vectors vCS01, vCS04, and vCS40 (FIG. 21). As shown in the figure, the downstream purification procedure resulted in highly purified material displaying the expected protein pattern of VP1, VP2 and VP3 (FIG. 21, lanes 2-4). The same pattern was seen with all other viral preparations (not shown). The SDS-PAGE procedure of AAV preparations was done according to standard procedures. Each lane contained 1E10 vg of the respective viral construct, and were separated on a 4-12% Bis-Tris (NuPAGE® Novex, Life Technologies) gel as per manufacturer's instructions. Silver staining was performed with a SilverQuest™ kit (Novex, Life Technologies) according to the manufacturer's instructions.

Surprisingly, AAV vectors vCS01 and vCS04 had higher virion packaging, measured by higher yields in AAV virus production, as compared to the vCS40 wild-type coding construct and the other codon-optimized constructs. As shown in Table 3, the vCS01 and vCS04 vectors replicated substantially better than vCS40, providing a 5-7 fold yield increase in AAV titer.

TABLE 3

Yields per liter cell culture obtained with AAV vector constructs vCS01, vCS04, and vCD40, as purified from cell pellets.

| Construct | Vector concentration [vg/ml] × 10E12 | Yields [vg/liter] × 10E12 | Fold increase vs wt |
|---|---|---|---|
| vCS40 | 2.0 | 11.0 | — |
| vCS01 | 9.2 | 51.4 | 4.7 |
| vCS04 - Sample 1 | 17.6 | 79.2 | 7.2 |
| vCS04 - Sample 2 | 15.9 | 58.8 | 5.4 |

Example 2

In Vivo Expression of Codon Altered Factor VIII Variant Expression Sequences

To test the biological potency of the codon-altered Factor VIII variant sequences, the ReFacto-type FVIII constructs described in Example 1 were administered to mice lacking Factor VIII. Briefly, the assays were performed in C57Bl/6 FVIII knock-out (ko) mice (with 6-8 animals per group) by tail vein injection of 4E12 vector genomes (vg) per kilogram body weight of mouse. Blood was drawn 14 days after injection by retroorbital puncture and plasma was prepared and frozen using standard procedures. Expression levels at day 14 were chosen because there is minimal influence of inhibitory antibodies at this time, which are seen in some animals of this mouse model at later times. FVIII activity in the mouse plasma was determined using the Technochrome FVIII assay performed, with only minor modifications, as suggested by the manufacture (Technoclone, Vienna, Austria). For the assay, the plasma samples were appropriately diluted and mixed with assay reagents, containing thrombin, activated factor IX (FIXa), phospholipids, factor X and calcium. Following FVIII activation by thrombin a complex with FIXa, phospholipids and calcium is formed. This complex activates FX to activated FX (FXa) which in turn cleaves para-nitroanilide (pNA) from the chromogenic substrate. The kinetics of pNA formation is measured at 405 nm. The rate is directly proportional to the FVIII concentration in the sample. FVIII concentrations are read from a reference curve and results are given in IU FVIII/milliliter.

The results, presented in Table 4 below, demonstrate that the codon-altered sequences designed using commercial algorithms (CS10, CS11, and CH25) provided only a modest increase in BDD-Factor VIII (3-4 fold) as compared to the wild-type BDD-Factor VIII construct (CS40). Similarly, the codon-altered BDD-Factor VIII construct prepared as described in Radcliffe et al. (CS08), only provided a 3-4 fold increase in BDD-FVIII expression. This result is consistent with the results reported in Radcliff et al. Surprisingly, the CS01, CS04, and CS23 constructs provided much higher BDD-FVIII expression in the in-vivo biopotency assays (18-, 74-, and 30-fold increases, respectively).

TABLE 4

Expression of FVIII in the plasma of FVIII-knock-out mice induced by the different AAV vector constructs.

| Construct | Codon Algorithm | Average FVIII Expression at Day 14 [IU/ml] | Standard deviation | Number of mice | Fold increase vs wt |
|---|---|---|---|---|---|
| vCS40 | Human wild-type | 0.03 | 0.03 | 12 | — |
| vCS01 | Applicants' | 0.55 | 0.28 | 22 | 18.3 |
| vCS04 | Applicants' | 2.21 | 1.20 | 55 | 73.7 |
| vCS08 | Radcliffe et al. | 0.11 | 0.01 | 6 | 3.6 |
| vCS10 | Eurofins | 0.09 | 0.01 | 7 | 3.0 |
| vCS11 | IDT | 0.08 | 0.02 | 8 | 2.7 |
| vCH25 | GeneArt | 0.13 | 0.12 | 18 | 4.3 |
| vCS23 | Applicants' | 0.91 | 0.32 | 5 | 30.3 |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed:

1. A polynucleotide comprising the nucleotide sequence of SEQ ID NO:1, wherein the polynucleotide encodes a Factor VIII polypeptide.

2. The polynucleotide of claim 1, further comprising a promoter element operably linked to the polynucleotide encoding the Factor VIII polypeptide.

3. The polynucleotide of claim 2, wherein the promoter element is a liver-specific promoter sequence upstream of the nucleotide sequence encoding the Factor VIII polypeptide.

4. The polynucleotide of claim 3, further comprising an intron sequence positioned between the liver-specific promoter sequence and the nucleotide sequence encoding the Factor VIII polypeptide.

5. An adeno-associated virus (AAV) vector comprising a polynucleotide of claim 1.

6. An adeno-associated virus (AAV) particle comprising a polynucleotide of claim 1.

7. A host cell infected with an adeno-associated virus (AAV) particle comprising a polynucleotide of claim 1.

8. A method for producing an adeno-associated virus (AAV) particle comprising introducing a polynucleotide of claim 1 into a mammalian host cell, wherein the polynucleotide is competent for replication in the mammalian host cell.

9. A method for treating hemophilia A comprising administering, to a patient in need thereof, an adeno-associated virus (AAV) particle according to claim 6.

10. A method for transducing a host cell comprising contacting the host cell with an adeno-associated virus (AAV) particle according to claim 6.

* * * * *

SEQUENCE LISTING

<160> NUMBER OF SEQ ID NOS: 32

<210> SEQ ID NO 1
<211> LENGTH: 4374

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
atgcagattg agctgagcac ctgcttcttc ctgtgcctgc tgaggttctg cttctctgcc      60
accaggagat actacctggg ggctgtggag ctttcttggg actacatgca gtctgacctg     120
ggggagctgc ctgtggatgc caggttccca cccagagtgc ccaaatcctt cccattcaac     180
acctctgtgg tctacaagaa gaccctcttt gtggagttca ctgaccacct gttcaacatt     240
gccaaaccca ggccaccctg gatgggactc ctgggaccca ccattcaggc tgaggtgtat     300
gacactgtgg tcatcaccct caagaacatg gcctcccacc ctgtgagcct gcatgctgtg     360
ggggtcagct actggaaggc ctctgagggg gctgagtatg atgaccagac ctcccagagg     420
gagaaggagg atgacaaagt gttccctggg ggcagccaca cctatgtgtg gcaggtcctc     480
aaggagaatg gccccatggc ctctgaccca ctctgcctga cctactccta cctttctcat     540
gtggacctgg tcaaggacct caactctgga ctgattgggg ccctgctggt gtgcagggag     600
ggctccctgg ccaaagagaa gacccagacc tgcacaagt tcattctcct gtttgctgtc      660
tttgatgagg gcaagagctg gcactctgaa accaagaact ccctgatgca ggacagggat     720
gctgcctctg ccagggcctg gcccaagatg cacactgtga atggctatgt gaacaggagc     780
ctgcctggac tcattggctg ccacaggaaa tctgtctact ggcatgtgat tggcatgggg     840
acaacccctg aggtgcactc catttttctg gagggccaca ccttcctggt caggaaccac     900
agacaggcca gcctggagat cagcccaatc accttcctca ctgcccagac cctgctgatg     960
gacctcggac agttcctgct gttctgccac atcagctccc accagcatga tggcatggag    1020
gcctatgtca aggtggacag ctgccctgag agccacagc tcaggatgaa gaacaatgag     1080 gaggctgagac actatgatga tgacctgact gactctgaga tggatgtggt ccgctttgat    1140
gatgacaaca gccatccctt cattcagatc aggtctgtgg ccaagaaaca ccccaagacc    1200
tgggtgcact acattgctgc tgaggaggag gactgggact atgccccact ggtcctggcc    1260
cctgatgaca ggagctacaa gagccagtac ctcaacaatg gcccacagag gattggacgc    1320
aagtacaaga agtcaggtt catggcctac actgatgaaa ccttcaagac cagggaggcc    1380
attcagcatg agtctggcat cctgggccca ctcctgtatg ggaggtgggg ggacaccctg    1440
ctcatcatct tcaagaacca ggcctccagg ccctacaaca tctacccaca tggcatcact    1500
gatgtcaggc ccctgtacag ccgcaggctg ccaaaggggg tgaaacacct caaggacttc    1560
cccattctgc tggggagat cttcaagtac aagtggactg tcactgtgga ggatggacca    1620
accaaatctg accccaggtg cctcaccaga tactactcca gctttgtgaa catggagagg    1680
gacctggcct ctggcctgat tggcccactg ctcatctgct acaaggagtc tgtggaccag    1740
aggggaaacc agatcatgtc tgacaagagg aatgtgattc tgttctctgt ctttgatgag    1800
aacaggagct ggtacctgac tgagaacatt cagcgcttcc tgcccaaccc tgctggggtg    1860
cagctggagg accctgagtt ccaggccagc aacatcatgc actccatcaa tggctatgtg    1920
tttgacagcc tccagctttc tgtctgcctg catgaggtgg cctactggta cattctttct    1980
attggggccc agactgactt cctttctgtc ttcttctctg gctacacctt caaacacaag    2040
atggtgtatg aggacaccct gaccctcttc ccattctctg ggagactgt gttcatgagc    2100 atggagaacc tggcctgtg gattctggga tgccacaact ctgacttccg caacaggggc    2160
```

-continued

```
atgactgccc tgctcaaagt ctcctcctgt gacaagaaca ctggggacta ctatgaggac    2220
agctatgagg acatctctgc ctacctgctc agcaagaaca atgccattga gcccaggagc    2280
ttcagccaga atccacctgt cctgaaacgc caccagaggg agatcaccag gaccaccctc    2340
cagtctgacc aggaggagat tgactatgat gacaccattt ctgtggagat gaagaaagag    2400
gactttgaca tctatgacga ggacgagaac cagagcccaa ggagcttcca gaagaagacc    2460
aggcactact tcattgctgc tgtggagcgc ctgtgggact atggcatgag ctccagcccc    2520
catgtcctca ggaacagggc ccagtctggc tctgtgccac agttcaagaa agtggtcttc    2580
caagagttca ctgatggcag cttcacccag cccctgtaca gggggagct gaatgagcac    2640 ctgggactcc tgggcccata catcagggct gaggtggagg acaacatcat ggtgaccttc    2700
cgcaaccagg cctccaggcc ctacagcttc tacagctccc tcatcagcta tgaggaggac    2760
cagaggcagg gggctgagcc acgcaagaac tttgtgaaac ccaatgaaac caagacctac    2820
ttctggaaag tccagcacca catggccccc accaaggatg agtttgactg caaggcctgg    2880
gcctacttct ctgatgtgga cctggagaag gatgtgcact ctggcctgat tggcccactc    2940
ctggtctgcc acaccaacac cctgaaccct gcccatggaa ggcaagtgac tgtgcaggag    3000
tttgccctct tcttcaccat cttttgatgaa accaagagct ggtacttcac tgagaacatg    3060
gagcgcaact gcagggcccc atgcaacatt cagatggagg accccacctt caaagagaac    3120
taccgcttcc atgccatcaa tggctacatc atggacaccc tgcctgggct tgtcatggcc    3180
caggaccaga ggatcaggtg gtacctgctt tctatgggct ccaatgagaa cattcactcc    3240
atccacttct ctgggcatgt cttcactgtg cgcaagaagg aggagtacaa gatggccctg    3300
tacaacctct accctggggt cttttgagact gtggagatgc tgccctccaa agctggcatc    3360
tggagggtgg agtgcctcat tggggagcac ctgcatgctg catgagcac cctgttcctg    3420 gtctacagca acaagtgcca gaccccctg ggaatggcct ctggccacat cagggacttc    3480
cagatcactg cctctggcca gtatggccag tgggccccca agctggccag gctccactac    3540
tctggatcca tcaatgcctg gagccaccaag gagccattca gctggatcaa agtggacctg    3600 ctggcccca tgatcatcca tggcatcaag acccagggg ccaggcagaa gttctccagc    3660
ctgtacatca gccagttcat catcatgtac agcctggatg gcaagaaatg cagacctac    3720 agaggcaact ccactggaac actcatggtc ttctttggca atgtggacag ctctggcatc    3780
aagcacaaca tcttcaaccc cccaatcatc gccagataca tcaggctgca ccccacccac    3840
tacagcatcc gcagcaccct caggatggag ctgatgggct gtgacctgaa ctcctgcagc    3900
atgcccctgg gcatggagag caaggccatt tctgatgccc agatcactgc ctccagctac    3960
ttcaccaaca tgtttgccac ctggagccca agcaaggca ggctgcacct ccagggaagg    4020
agcaatgcct ggaggcccca ggtcaacaac ccaaaggagt ggctgcaggt ggacttccag    4080
aagaccatga aggtcactgg ggtgaccacc caggggtca agagcctgct caccagcatg    4140
tatgtgaagg agttcctgat cagctccagc caggatggcc accagtggac cctcttcttc    4200
cagaatggca aggtcaaggt gttccagggc aaccaggaca gcttcacccc tgtggtgaac    4260
agcctggacc cccccctcct gaccagatac ctgaggattc accccagag ctgggtccac    4320 cagattgccc tgaggatgga ggtcctggga tgtgaggccc aggacctgta ctga         4374
```

<210> SEQ ID NO 2
<211> LENGTH: 1457
<212> TYPE: PRT

-continued

<213> ORGANISM: Artificial Sequence
<220> FEATURE:
<223> OTHER INFORMATION: Description of Artificial Sequence: Synthetic
      polypeptide

<400> SEQUENCE: 2

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
370                 375                 380
```

-continued

```
Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Pro Pro Val Leu
        755                 760                 765

Lys Arg His Gln Arg Glu Ile Thr Arg Thr Thr Leu Gln Ser Asp Gln
770                 775                 780

Glu Glu Ile Asp Tyr Asp Asp Thr Ile Ser Val Glu Met Lys Lys Glu
785                 790                 795                 800

Asp Phe Asp Ile Tyr Asp Glu Asp Glu Asn Gln Ser Pro Arg Ser Phe
```

-continued

```
                805                 810                 815
Gln Lys Lys Thr Arg His Tyr Phe Ile Ala Ala Val Glu Arg Leu Trp
            820                 825                 830
Asp Tyr Gly Met Ser Ser Pro His Val Leu Arg Asn Arg Ala Gln
        835                 840                 845
Ser Gly Ser Val Pro Gln Phe Lys Lys Val Val Phe Gln Glu Phe Thr
    850                 855                 860
Asp Gly Ser Phe Thr Gln Pro Leu Tyr Arg Gly Glu Leu Asn Glu His
865                 870                 875                 880
Leu Gly Leu Leu Gly Pro Tyr Ile Arg Ala Glu Val Glu Asp Asn Ile
            885                 890                 895
Met Val Thr Phe Arg Asn Gln Ala Ser Arg Pro Tyr Ser Phe Tyr Ser
            900                 905                 910
Ser Leu Ile Ser Tyr Glu Glu Asp Gln Arg Gln Gly Ala Glu Pro Arg
            915                 920                 925
Lys Asn Phe Val Lys Pro Asn Glu Thr Lys Thr Tyr Phe Trp Lys Val
        930                 935                 940
Gln His His Met Ala Pro Thr Lys Asp Glu Phe Asp Cys Lys Ala Trp
945                 950                 955                 960
Ala Tyr Phe Ser Asp Val Asp Leu Glu Lys Asp Val His Ser Gly Leu
                965                 970                 975
Ile Gly Pro Leu Leu Val Cys His Thr Asn Thr Leu Asn Pro Ala His
            980                 985                 990
Gly Arg Gln Val Thr Val Gln Glu Phe Ala Leu Phe Phe Thr Ile Phe
            995                 1000                1005
Asp Glu Thr Lys Ser Trp Tyr Phe Thr Glu Asn Met Glu Arg Asn
        1010                1015                1020
Cys Arg Ala Pro Cys Asn Ile Gln Met Glu Asp Pro Thr Phe Lys
        1025                1030                1035
Glu Asn Tyr Arg Phe His Ala Ile Asn Gly Tyr Ile Met Asp Thr
        1040                1045                1050
Leu Pro Gly Leu Val Met Ala Gln Asp Gln Arg Ile Arg Trp Tyr
        1055                1060                1065
Leu Leu Ser Met Gly Ser Asn Glu Asn Ile His Ser Ile His Phe
        1070                1075                1080
Ser Gly His Val Phe Thr Val Arg Lys Lys Glu Glu Tyr Lys Met
        1085                1090                1095
Ala Leu Tyr Asn Leu Tyr Pro Gly Val Phe Glu Thr Val Glu Met
        1100                1105                1110
Leu Pro Ser Lys Ala Gly Ile Trp Arg Val Glu Cys Leu Ile Gly
        1115                1120                1125
Glu His Leu His Ala Gly Met Ser Thr Leu Phe Leu Val Tyr Ser
        1130                1135                1140
Asn Lys Cys Gln Thr Pro Leu Gly Met Ala Ser Gly His Ile Arg
        1145                1150                1155
Asp Phe Gln Ile Thr Ala Ser Gly Gln Tyr Gly Gln Trp Ala Pro
        1160                1165                1170
Lys Leu Ala Arg Leu His Tyr Ser Gly Ser Ile Asn Ala Trp Ser
        1175                1180                1185
Thr Lys Glu Pro Phe Ser Trp Ile Lys Val Asp Leu Leu Ala Pro
        1190                1195                1200
Met Ile Ile His Gly Ile Lys Thr Gln Gly Ala Arg Gln Lys Phe
        1205                1210                1215
```

```
Ser Ser Leu Tyr Ile Ser Gln Phe Ile Ile Met Tyr Ser Leu Asp
    1220                1225                1230

Gly Lys Lys Trp Gln Thr Tyr Arg Gly Asn Ser Thr Gly Thr Leu
    1235                1240                1245

Met Val Phe Phe Gly Asn Val Asp Ser Ser Gly Ile Lys His Asn
    1250                1255                1260

Ile Phe Asn Pro Pro Ile Ile Ala Arg Tyr Ile Arg Leu His Pro
    1265                1270                1275

Thr His Tyr Ser Ile Arg Ser Thr Leu Arg Met Glu Leu Met Gly
    1280                1285                1290

Cys Asp Leu Asn Ser Cys Ser Met Pro Leu Gly Met Glu Ser Lys
    1295                1300                1305

Ala Ile Ser Asp Ala Gln Ile Thr Ala Ser Ser Tyr Phe Thr Asn
    1310                1315                1320

Met Phe Ala Thr Trp Ser Pro Ser Lys Ala Arg Leu His Leu Gln
    1325                1330                1335

Gly Arg Ser Asn Ala Trp Arg Pro Gln Val Asn Asn Pro Lys Glu
    1340                1345                1350

Trp Leu Gln Val Asp Phe Gln Lys Thr Met Lys Val Thr Gly Val
    1355                1360                1365

Thr Thr Gln Gly Val Lys Ser Leu Leu Thr Ser Met Tyr Val Lys
    1370                1375                1380

Glu Phe Leu Ile Ser Ser Ser Gln Asp Gly His Gln Trp Thr Leu
    1385                1390                1395

Phe Phe Gln Asn Gly Lys Val Lys Val Phe Gln Gly Asn Gln Asp
    1400                1405                1410

Ser Phe Thr Pro Val Val Asn Ser Leu Asp Pro Pro Leu Leu Thr
    1415                1420                1425

Arg Tyr Leu Arg Ile His Pro Gln Ser Trp Val His Gln Ile Ala
    1430                1435                1440

Leu Arg Met Glu Val Leu Gly Cys Glu Ala Gln Asp Leu Tyr
    1445                1450                1455
```

<210> SEQ ID NO 3
<211> LENGTH: 2220
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 3

```
gccaccagga gatactacct gggggctgtg gagctttctt gggactacat gcagtctgac      60
ctgggggagc tgcctgtgga tgccaggttc ccacccagag tgcccaaatc cttcccattc     120
aacacctctg tggtctacaa gaagaccctc tttgtggagt tcactgacca cctgttcaac     180
attgccaaac ccaggccacc ctggatggga ctcctgggac ccaccattca ggctgaggtg     240
tatgacactg tggtcatcac cctcaagaac atggcctccc accctgtgag cctgcatgct     300 gtggggtca gctactggaa ggcctctgag ggggctgagt atgatgacca gaccttccag     360
agggagaagg aggatgacaa agtgttccct gggggcagcc acacctatgt gtggcaggtc     420
ctcaaggaga atggcccat ggcctctgac ccactctgcc tgacctactc ctacctttct     480
catgtggacc tggtcaagga cctcaactct ggactgattg ggcccctgct ggtgtgcagg     540
gagggctccc tggccaaaga gaagacccag acccctgcaca agttcattct cctgtttgct     600
```

-continued

```
gtctttgatg agggcaagag ctggcactct gaaaccaaga actccctgat gcaggacagg      660
gatgctgcct ctgccagggc ctggcccaag atgcacactg tgaatggcta tgtgaacagg      720
agcctgcctg gactcattgg ctgccacagg aaatctgtct actggcatgt gattggcatg      780
gggacaaccc ctgaggtgca ctccattttc ctggagggcc acaccttcct ggtcaggaac      840
cacagacagg ccagcctgga gatcagcccc atcaccttcc tcactgccca gaccctgctg      900
atggacctcg gacagttcct gctgttctgc cacatcagct cccaccagca tgatggcatg      960
gaggcctatg tcaaggtgga cagctgccct gaggagccac agctcaggat gaagaacaat     1020
gaggaggctg aggactatga tgatgacctg actgactctg gatggatgt ggtccgcttt      1080
gatgatgaca acagcccatc cttcattcag atcaggtctg tggccaagaa acaccccaag     1140
acctgggtgc actacattgc tgctgaggag gaggactggg actatgcccc actggtcctg     1200
gcccctgatg acaggagcta caagagccag tacctcaaca atgcccacag gaggattgga     1260
cgcaagtaca agaaagtcag gttcatggcc tacactgatg aaaaccttcaa gaccagggag     1320
gccattcagc atgagtctgg catcctgggc ccactcctgt atggggaggt ggggacacc      1380
ctgctcatca tcttcaagaa ccaggcctcc aggccctaca catctaccc acatggcatc     1440
actgatgtca ggcccctgta cagccgcagg ctgccaaagg gggtgaaaca cctcaaggac     1500
ttccccattc tgcctgggga gatcttcaag tacaagtgga ctgtcactgt ggaggatgga     1560
ccaaccaaat ctgaccccag gtgcctcacc agatactact ccagctttgt gaacatggag     1620
agggacctgg cctctggcct gattggccca ctgctcatct gctacaagga gtctgtggac     1680
cagaggggaa accagatcat gtctgacaag aggaatgtga ttctgttctc tgtctttgat     1740
gagaacagga gctggtacct gactgagaac attcagcgct tcctgcccaa ccctgctggg     1800
gtgcagctgg aggaccctga gttccaggcc agcaacatca tgcactccat caatggctat     1860
gtgtttgaca gcctccagct ttctgtctgc ctgcatgagg tggcctactg gtacattctt     1920
tctattgggg cccagactga cttcctttct gtcttcttct ctggctacac cttcaaacac     1980
aagatggtgt atgaggacac cctgaccctc ttcccattct ctggggagac tgtgttcatg     2040
agcatggaga accctggcct gtggattctg ggatgccaca ctctgactt ccgcaacagg      2100
ggcatgactg ccctgctcaa agtctcctcc tgtgacaaga acactgggga ctactatgag     2160
gacagctatg aggacatctc tgcctacctg ctcagcaaga caatgccat tgagcccagg      2220
```

<210> SEQ ID NO 4
<211> LENGTH: 2052
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 4

```
gagatcacca ggaccaccct ccagtctgac caggaggaga ttgactatga tgacaccatt       60
tctgtggaga tgaagaaaga ggactttgac atctatgacg aggacgagaa ccagagccca      120
aggagcttcc agaagaagac caggcactac ttcattgctg ctgtggagcg cctgtgggac      180
tatggcatga gctccagccc ccatgtcctc aggaacaggg cccagtctgg ctctgtgcca      240
cagttcaaga agtggtctt ccaagagttc actgatggca gcttcaccca gccccctgtac      300
agaggggagc tgaatgagca cctgggactc ctgggcccat acatcaggc tgaggtggag       360
gacaacatca tggtgacctt ccgcaaccag gcctccaggc cctacagctt ctacagctcc      420
```

```
ctcatcagct atgaggagga ccagaggcag ggggctgagc cacgcaagaa ctttgtgaaa      480
cccaatgaaa ccaagaccta cttctggaaa gtccagcacc acatggcccc caccaaggat      540
gagtttgact gcaaggcctg ggcctacttc tctgatgtgg acctggagaa ggatgtgcac      600
tctggcctga ttggcccact cctggtctgc cacaccaaca ccctgaaccc tgcccatgga      660
aggcaagtga ctgtgcagga gtttgccctc ttcttcacca tctttgatga aaccaagagc      720
tggtacttca ctgagaacat ggagcgcaac tgcagggccc catgcaacat tcagatggag      780
gaccccacct tcaaagagaa ctaccgcttc catgccatca atggctacat catggacacc      840
ctgcctgggc ttgtcatggc ccaggaccag aggatcaggt ggtacctgct ttctatgggc      900
tccaatgaga acattcactc catccacttc tctgggcatg tcttcactgt gcgcaagaag      960
gaggagtaca gatggccct gtacaacctc taccctgggg tctttgagac tgtggagatg     1020
ctgccctcca agctggcat ctggagggtg gagtgcctca ttggggagca cctgcatgct     1080
ggcatgagca ccctgttcct ggtctacagc aacaagtgcc agacccccct gggaatggcc     1140
tctggccaca tcagggactt ccagatcact gcctctggcc agtatggcca gtgggccccc     1200
aagctggcca ggctccacta ctctggatcc atcaatgcct ggagcaccaa ggagccattc     1260
agctggatca aagtggacct gctggccccc atgatcatcc atggcatcaa gacccagggg     1320
gccaggcaga agttctccag cctgtacatc agccagttca tcatcatgta cagcctggat     1380
ggcaagaaat ggcagaccta cagaggcaac tccactggaa cactcatggt cttctttggc     1440
aatgtggaca gctctggcat caagcacaac atcttcaacc ccccaatcat cgccagatac     1500
atcaggctgc accccaccca ctacagcatc cgcagcaccc tcaggatgga gctgatgggc     1560
tgtgacctga actcctgcag catgcccctg ggcatggaga gcaaggccat ttctgatgcc     1620
cagatcactg cctccagcta cttcaccaac atgtttgcca cctggagccc aagcaaggcc     1680
aggctgcacc tccagggaag gagcaatgcc tggaggcccc aggtcaacaa cccaaaggag     1740
tggctgcagg tggacttcca gaagaccatg aaggtcactg gggtgaccac ccagggggtc     1800
aagagcctgc tcaccagcat gtatgtgaag gagttcctga tcagctccag ccaggatggc     1860
caccagtgga ccctcttctt ccagaatggc aaggtcaagg tgttccaggg caaccaggac     1920
agcttcaccc ctgtggtgaa cagcctggac ccccccctcc tgaccagata cctgaggatt     1980 caccccccaga gctgggtcca ccagattgcc ctgaggatgg aggtcctggg atgtgaggcc     2040
caggacctgt ac                                                          2052
```

<210> SEQ ID NO 5
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5

```
agcttctctc agaatccacc tgtcctgaag agacaccaga ga                          42
```

<210> SEQ ID NO 6
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 6
agcttcagcc agaatccacc tgtcctgaaa cgccaccaga gg        42

<210> SEQ ID NO 7
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
agcttcagcc agaacccccc cgtgctgaag aggcaccaga gg        42

<210> SEQ ID NO 8
<211> LENGTH: 7827
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg   120
ttggcgggtg tcgggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt cctcgagatt taaatgacgt    420
tggccactcc ctctctgcgc gctcgctcgc tcactgaggc cgggcgacca aggtcgccc    480 gacgcccggg ctttgcccgg gcggcctcag tgagcgagcg agcgcgcaga gagggagtgg    540
ccaactccat cactaggggt tcctgagttt aaacttcgtc gacgattcga gcttgggctg    600
caggtcgagg gcactgggag gatgttgagt aagatggaaa actactgatg acccttgcag    660
agacagagta ttaggacatg tttgaacagg ggccgggcga tcagcaggta gctctagagg    720
atccccgtct gtctgcacat ttcgtagagc gagtgttccg atactctaat ctccctaggc    780
aaggttcata tttgtgtagg ttacttattc tccttttgtt gactaagtca ataatcagaa    840
tcagcaggtt tggagtcagc ttggcaggga tcagcagcct gggttggaag aggggggtat    900
aaaagcccct tcaccaggag aagccgtcac acagactagg cgcgccaccg ccaccatgca    960
gattgagctg agcaccttgct tcttcctgtg cctgctgagg ttctgcttct ctgccaccag   1020 agatactac ctgggggctg tggagctttc ttgggactac atgcagtctg acctggggga   1080
gctgcctgtg gatgccaggt tcccacccag agtgcccaaa tccttcccat tcaacacctc   1140
tgtggtctac aagaagaccc tctttgtgga gttcactgac cacctgttca acattgccaa   1200
acccaggcca ccctggatgg gactcctggg accaccatt caggctgagg tgtatgacac   1260
tgtggtcatc accctcaaga acatggcctc ccaccctgtg agcctgcatg ctgtgggggt   1320
cagctactgg aaggcctctg aggggctga gtatgatgac cagacctccc agagggagaa   1380
ggaggatgac aaagtgttcc ctgggggcag ccacacctat gtgtggcagg tcctcaagga   1440
gaatggcccc atggcctctg acccactctg cctgacctac tcctaccttt ctcatgtgga   1500
cctggtcaag gacctcaact ctggactgat tggggccctg ctggtgtgca gggagggctc   1560
```

```
cctggccaaa gagaagaccc agaccctgca caagttcatt ctcctgtttg ctgtctttga   1620
tgagggcaag agctggcact ctgaaaccaa gaactccctg atgcaggaca gggatgctgc   1680
ctctgccagg gcctggccca agatgcacac tgtgaatggc tatgtgaaca ggagcctgcc   1740
tggactcatt ggctgccaca ggaaatctgt ctactggcat gtgattggca tggggacaac   1800
ccctgaggtg cactccattt tcctggaggg ccacaccttc ctggtcagga accacagaca   1860
ggccagcctg gagatcagcc ccatcacctt cctcactgcc cagaccctgc tgatggacct   1920
cggacagttc ctgctgttct gccacatcag ctcccaccag catgatggca tggaggccta   1980
tgtcaaggtg gacagctgcc ctgaggagcc acagctcagg atgaagaaca atgaggaggc   2040
tgaggactat gatgatgacc tgactgactc tgagatggat gtggtccgct ttgatgatga   2100
caacagccca tccttcattc agatcaggtc tgtggccaag aaacaccccc agacctgggt   2160
gcactacatt gctgctgagg aggaggactg ggactatgcc ccactggtcc tggcccctga   2220
tgacaggagc tacaagagcc agtacctcaa caatggccca cagaggattg gacgcaagta   2280
caagaaagtc aggttcatgg cctacactga tgaaaccttc aagaccaggg aggccattca   2340
gcatgagtct ggcatcctgg gcccactcct gtatggggag gtgggggaca ccctgctcat   2400
catcttcaag aaccaggcct ccaggcccta caacatctac ccacatggca tcactgatgt   2460
caggcccctg tacagccgca ggctgccaaa ggggtgaaa cacctcaagg acttccccat   2520
tctgcctggg gagatcttca gtacaagtg gactgtcact gtggaggatg gaccaaccaa   2580 atctgaccc aggtgcctca ccagatacta ctccagcttt gtgaacatgg agagggacct   2640
ggcctctggc ctgattggcc cactgctcat ctgctacaag gagtctgtgg accagagggg   2700
aaaccagatc atgtctgaca gaggaatgt gattctgttc tctgtctttg atgagaacag   2760
gagctggtac ctgactgaga acattcagcg cttcctgccc aaccctgctg gggtgcagct   2820
ggaggaccct gagttccagg ccagcaacat catgcactcc atcaatggct atgtgtttga   2880
cagcctccag ctttctgtct gcctgcatga ggtggcctac tggtacattc tttctattgg   2940
ggcccagact gacttccttt ctgtcttctt ctctggctac accttcaaac acaagatggt   3000
gtatgaggac accctgaccc tcttcccatt ctctggggag actgtgttca tgagcatgga   3060
gaaccctggc ctgtggattc tgggatgcca caactctgac ttccgcaaca ggggcatgac   3120
tgccctgctc aaagtctcct cctgtgacaa gaacactggg gactactatg aggacagcta   3180
tgaggacatc tctgcctacc tgctcagcaa gaacaatgcc attgagccca ggagcttcag   3240
ccagaatcca cctgtcctga acgccacca gagggagatc accaggacca ccctccagtc   3300
tgaccaggag gagattgact atgatgacac catttctgtg gagatgaaga agaggacttt   3360
tgacatctat gacgaggacg agaaccagag cccaaggagc ttccagaaga gaccaggca   3420 ctacttcatt gctgctgtgg agcgcctgtg ggactatggc atgagctcca gccccatgt   3480 cctcaggaac agggcccagt ctggctctgt gccacagttc aagaaagtgg tcttccaaga   3540
gttcactgat ggcagcttca cccagccct gtacagaggg gagctgaatg agcacctggg   3600
actcctgggc ccatacatca gggctgaggt ggaggacaac atcatggtga ccttccgcaa   3660
ccaggcctcc aggccctaca gcttctacag ctccctcatc agctatgagg aggaccagag   3720
gcagggggct gagccacgca agaactttgt gaaacccaat gaaaccaaga cctacttctg   3780
gaaagtccag caccacatgg cccccaccaa ggatgagttt gactgcaagg cctgggccta   3840
cttctctgat gtggacctgg agaaggatgt gcactctggc ctgattggcc cactcctggt   3900
```

```
ctgccacacc aacaccctga accctgccca tggaaggcaa gtgactgtgc aggagtttgc    3960
cctcttcttc accatctttg atgaaaccaa gagctggtac ttcactgaga acatggagcg    4020
caactgcagg gccccatgca acattcagat ggaggacccc accttcaaag agaactaccg    4080
cttccatgcc atcaatggct acatcatgga caccctgcct gggcttgtca tggcccagga    4140
ccagaggatc aggtggtacc tgctttctat gggctccaat gagaacattc actccatcca    4200
cttctctggg catgtcttca ctgtgcgcaa gaaggaggag tacaagatgg ccctgtacaa    4260
cctctaccct ggggtctttg agactgtgga gatgctgccc tccaaagctg gcatctggag    4320
ggtggagtgc ctcattgggg agcacctgca tgctggcatg agcaccctgt tcctggtcta    4380
cagcaacaag tgccagaccc ccctgggaat ggcctctggc cacatcaggg acttccagat    4440
cactgcctct ggccagtatg ccagtgggc ccccaagctg ccaggctcc actactctgg    4500
atccatcaat gcctggagca ccaaggagcc attcagctgg atcaaagtgg acctgctggc    4560
ccccatgatc atccatggca tcaagaccca ggggccagg cagaagttct ccagcctgta    4620
catcagccag ttcatcatca tgtacagcct ggatggcaag aaatggcaga cctacagagg    4680
caactccact ggaacactca tggtcttctt tggcaatgtg gacagctctg gcatcaagca    4740
caacatcttc aaccccccaa tcatcgccag atacatcagg ctgcaccca cccactacag    4800
catccgcagc accctcagga tggagctgat gggctgtgac ctgaactcct gcagcatgcc    4860
cctgggcatg gagagcaagg ccatttctga tgcccagatc actgcctcca gctacttcac    4920
caacatgttt gccacctgga gcccaagcaa ggccaggctg cacctccagg gaaggagcaa    4980
tgcctggagg ccccaggtca acaacccaaa ggagtggctg caggtggact tccagaagac    5040
catgaaggtc actggggtga ccacccaggg ggtcaagagc ctgctcacca gcatgtatgt    5100
gaaggagttc ctgatcagct ccagccagga tggccaccag tggaccctct tcttccagaa    5160
tggcaaggtc aaggtgttcc agggcaacca ggacagcttc acccctgtgg tgaacagcct    5220
ggacccccc ctcctgacca gatacctgag gattcacccc cagagctggg tccaccagat    5280
tgccctgagg atggaggtcc tgggatgtga ggcccaggac ctgtactgat gacgagcggc    5340
cgctcttagt agcagtatcg ataataaaag atctttattt tcattagatc tgtgtgttgg    5400
ttttttgtgt gttaattaag ctcgcgaagg aaccccctagt gatggagttg ccactccct    5460
ctctgcgcgc tcgctcgctc actgaggccg ggcgaccaaa ggtcgcccga cgccccgggct    5520
ttgcccgggc ggcctcagtg agcgagcgag cgcgcagaga gggagtggcc aagacgattt    5580
aaatgacaag cttggcgtaa tcatggtcat agctgtttcc tgtgtgaaat tgttatccgc    5640
tcacaattcc acacaacata cgagccggaa gcataaagtg taaagcctgg ggtgcctaat    5700
gagtgagcta actcacatta attgcgttgc gctcactgcc cgctttccag tcgggaaacc    5760
tgtcgtgcca gctgcattaa tgaatcggcc aacgcgcggg gagaggcggt ttgcgtattg    5820
ggcgctcttc cgcttcctcg ctcactgact cgctgcgctc ggtcgttcgg ctgcggcgag    5880
cggtatcagc tcactcaaag gcggtaatac ggttatccac agaatcaggg gataacgcag    5940
gaaagaacat gtgagcaaaa ggccagcaaa aggccaggaa ccgtaaaaag gccgcgttgc    6000
tggcgttttt ccataggctc cgcccccctg acgagcatca caaaaatcga cgctcaagtc    6060
agaggtggcg aaacccgaca ggactataaa gataccaggc gtttccccct ggaagctccc    6120
tcgtgcgctc tcctgttccg accctgccgc ttaccggata cctgtccgcc tttctccctt    6180
cgggaagcgt ggcgctttct catagctcac gctgtaggta tctcagttcg gtgtaggtcg    6240
ttcgctccaa gctgggctgt gtgcacgaac ccccgttca gcccgaccgc tgcgccttat    6300
```

```
ccggtaacta tcgtcttgag tccaacccgg taagacacga cttatcgcca ctggcagcag    6360
ccactggtaa caggattagc agagcgaggt atgtaggcgg tgctacagag ttcttgaagt    6420
ggtggcctaa ctacggctac actagaagaa cagtatttgg tatctgcgct ctgctgaagc    6480
cagttacctt cggaaaaaga gttggtagct cttgatccgg caaacaaacc accgctggta    6540
gcggtggttt ttttgtttgc aagcagcaga ttacgcgcag aaaaaaagga tctcaagaag    6600
atcctttgat cttttctacg gggtctgacg ctcagtggaa cgaaaactca cgttaaggga    6660
ttttggtcat gagattatca aaaggatctc acctagatcc ttttaaatta aaaatgaa    6720 gttttaaatc aatctaaagt atatatgagt aaacttggtc tgacagttac caatgcttaa    6780
tcagtgaggc acctatctca gcgatctgtc tatttcgttc atccatagtt gcctgactcc    6840
ccgtcgtgta gataactacg atacgggagg gcttaccatc tggccccagt gctgcaatga    6900
taccgcgaga cccacgctca ccggctccag atttatcagc aataaaccag ccagccggaa    6960
gggccgagcg cagaagtggt cctgcaactt tatccgcctc catccagtct attaattgtt    7020
gccgggaagc tagagtaagt agttcgccag ttaatagttt gcgcaacgtt gttgccattg    7080
ctacaggcat cgtggtgtca cgctcgtcgt ttggtatggc ttcattcagc tccggttccc    7140
aacgatcaag gcgagttaca tgatccccca tgttgtgcaa aaaagcggtt agctccttcg    7200
gtcctccgat cgttgtcaga agtaagttgg ccgcagtgtt atcactcatg gttatggcag    7260
cactgcataa ttctcttact gtcatgccat ccgtaagatg cttttctgtg actggtgagt    7320
actcaaccaa gtcattctga atagtgta tgcggcgacc gagttgctct tgcccggcgt    7380
caatacggga taataccgcg ccacatagca gaactttaaa agtgctcatc attggaaaac    7440
gttcttcggg gcgaaaactc tcaaggatct taccgctgtt gagatccagt tcgatgtaac    7500
ccactcgtgc acccaactga tcttcagcat cttttacttt caccagcgtt tctgggtgag    7560
caaaaacagg aaggcaaaat gccgcaaaaa agggaataag ggcgacacgg aaatgttgaa    7620
tactcatact cttcctttt caatattatt gaagcattta tcagggttat tgtctcatga    7680
gcggatacat atttgaatgt atttagaaaa ataaacaaat aggggttccg cgcacatttc    7740
cccgaaaagt gccacctgac gtctaagaaa ccattattat catgacatta acctataaaa    7800
ataggcgtat cacgaggccc tttcgtc                                        7827
```

<210> SEQ ID NO 9
<211> LENGTH: 4332
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9

```
atgcagattg agctgagcac ctgcttcttc ctgtgcctgc tgaggttctg cttctctgcc      60
accaggagat actacctggg ggctgtggag ctttcttggg actacatgca gtctgacctg     120
ggggagctgc ctgtggatgc caggttccca cccagagtgc ccaaatcctt cccattcaac     180
acctctgtgg tctacaagaa gacccttctt gtggagttca ctgaccacct gttcaacatt     240
gccaaaccca ggccaccctg gatgggactc ctgggaccca ccattcaggc tgaggtgtat     300
gacactgtgg tcatcacccc tcaagaacat gcctcccacc ctgtgagcct gcatgctgtg     360
ggggtcagct actggaaggc ctctgagggg ctgagtatg atgaccagac ctcccagagg     420
gagaaggagg atgacaaagt gttccctggg ggcagccaca cctatgtgtg gcaggtcctc     480
```

```
aaggagaatg gccccatggc ctctgaccca ctctgcctga cctactccta cctttctcat    540
gtggacctgg tcaaggacct caactctgga ctgattgggg ccctgctggt gtgcagggag    600
ggctccctgg ccaaagagaa gacccagacc ctgcacaagt tcattctcct gtttgctgtc    660
tttgatgagg gcaagagctg gcactctgaa accaagaact ccctgatgca ggacagggat    720
gctgcctctg ccagggcctg gcccaagatg cacactgtga atggctatgt gaacaggagc    780
ctgcctggac tcattggctg ccacaggaaa tctgtctact ggcatgtgat tggcatgggg    840
acaacccctg aggtgcactc cattttcctg gagggccaca ccttcctggt caggaaccac    900
agacaggcca gcctggagat cagccccatc accttcctca ctgcccagac cctgctgatg    960
gacctcggac agttcctgct gttctgccac atcagctccc accagcatga tggcatggag   1020
gcctatgtca aggtggacag ctgccctgag gagccacagc tcaggatgaa gaacaatgag   1080
gaggctgagg actatgatga tgacctgact gactctgaga tggatgtggt ccgctttgat   1140
gatgacaaca gcccatcctt cattcagatc aggtctgtgg ccaagaaaca ccccaagacc   1200
tgggtgcact acattgctgc tgaggaggag gactgggact atgccccact ggtcctggcc   1260
cctgatgaca ggagctacaa gagccagtac ctcaacaatg cccacagag gattggacgc   1320 aagtacaaga aagtcaggtt catggcctac actgatgaaa ccttcaagac cagggaggcc   1380
attcagcatg agtctggcat cctgggccca ctcctgtatg gggaggtggg ggacaccctg   1440
ctcatcatct tcaagaacca ggcctccagg ccctacaaca tctacccaca tggcatcact   1500
gatgtcaggc cctgtacag ccgcaggctg ccaaagggg tgaaacacct caaggacttc   1560
cccattctgc ctggggagat cttcaagtac aagtggactg tcactgtgga ggatggacca   1620
accaaatctg accccaggtg cctcaccaga tactactcca gctttgtgaa catggagagg   1680
gacctggcct ctggcctgat tggcccactg ctcatctgct acaaggagtc tgtggaccag   1740
aggggaaacc agatcatgtc tgacaagagg aatgtgattc tgttctctgt ctttgatgag   1800
aacaggagct ggtacctgac tgagaacatt cagcgcttcc tgcccaaccc tgctggggtg   1860
cagctggagg accctgagtt ccaggccagc aacatcatgc actccatcaa tggctatgtg   1920
tttgacagcc tccagctttc tgtctgcctg catgaggtgg cctactggta cattcttttct   1980 attgggccc agactgactt cctttctgtc ttcttctctg gctacacctt caaacacaag   2040
atggtgtatg aggacaccct gaccctcttc ccattctctg gggagactgt gttcatgagc   2100
atggagaacc ctggcctgtg gattctggga tgccacaact ctgacttccg caacaggggc   2160
atgactgccc tgctcaaagt ctcctcctgt gacaagaaca ctggggacta ctatgaggac   2220
agctatgagg acatctctgc ctacctgctc agcaagaaca atgccattga gcccagggag   2280
atcaccagga ccaccctcca gtctgaccag gaggagattg actatgatga caccattct   2340 gtggagatga agaaagagga ctttgacatc tatgacgagg acgagaacca gagcccaagg   2400
agcttccaga gaagaccag gcactactt attgctgctg tggagcgcct gtgggactat   2460
ggcatgagct ccagccccca tgtcctcagg aacagggccc agtctggctc tgtgccacag   2520
ttcaagaaag tggtcttcca agagttcact gatggcagct tcacccagcc cctgtacaga   2580
ggggagctga atgagcacct gggactcctg gcccatacag tcagggctga ggtggaggac   2640
aacatcatgg tgaccttccg caaccaggcc tccaggccct acagcttcta cagctccctc   2700
atcagctatg aggaggacca gaggcagggg gctgagccac gcaagaactt tgtgaaaccc   2760
aatgaaacca gacctactt ctggaaagtc cagcaccaca tggccccccac caaggatgag   2820
```

```
tttgactgca aggcctgggc ctacttctct gatgtggacc tggagaagga tgtgcactct    2880
ggcctgattg cccactcct ggtctgccac accaacaccc tgaaccctgc ccatggaagg     2940
caagtgactg tgcaggagtt tgccctcttc ttcaccatct ttgatgaaac caagagctgg    3000
tacttcactg agaacatgga gcgcaactgc agggccccat gcaacattca gatggaggac    3060
cccaccttca agagaactac cgcttccat gccatcaatg ctacatcat ggacaccctg      3120 cctgggcttg tcatggccca ggaccagagg atcaggtggt acctgctttc tatgggctcc    3180
aatgagaaca ttcactccat ccacttctct gggcatgtct tcactgtgcg caagaaggag    3240
gagtacaaga tggccctgta caacctctac cctggggtct ttgagactgt ggagatgctg    3300
ccctccaaag ctggcatctg gagggtggag tgcctcattg gggagcacct gcatgctggc    3360
atgagcaccc tgttcctggt ctacagcaac aagtgccaga ccccctggg aatggcctct    3420 ggccacatca gggacttcca gatcactgcc tctggccagt atggccagtg ggcccccaag    3480
ctggccaggc tccactactc tggatccatc aatgcctgga gcaccaagga gccattcagc    3540
tggatcaaag tggacctgct ggcccccatg atcatccatg catcaagac ccaggggcc      3600 aggcagaagt tctccagcct gtacatcagc cagttcatca tcatgtacag cctggatggc    3660
aagaaatggc agacctacag aggcaactcc actggaacac tcatggtctt ctttggcaat    3720
gtggacagct ctggcatcaa gcacaacatc ttcaaccccc aatcatcgc cagatacatc     3780 aggctgcacc ccacccacta cagcatccgc agcaccctca ggatggagct gatgggctgt    3840
gacctgaact cctgcagcat gccctgggc atggagagca aggccatttc tgatgcccag    3900
atcactgcct ccagctactt caccaacatg tttgccacct ggagcccaag caaggccagg    3960
ctgcacctcc agggaaggag caatgcctgg aggccccagg tcaacaaccc aaaggagtgg    4020
ctgcaggtgg acttccagaa gaccatgaag gtcactgggg tgaccaccca gggggtcaag    4080
agcctgctca ccagcatgta tgtgaaggag ttcctgatca gctccagcca ggatggccac    4140
cagtggaccc tcttcttcca gaatggcaag gtcaaggtgt tccagggcaa ccaggacagc    4200
ttcacccctg tggtgaacag cctggacccc cccctcctga ccagatacct gaggattcac    4260
ccccagagct gggtccacca gattgccctg aggatggagg tcctgggatg tgaggcccag    4320
gacctgtact ga                                                        4332
```

<210> SEQ ID NO 10
<211> LENGTH: 1443
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
                20                  25                  30

Trp Asp Tyr Met Gln Ser Asp Leu Gly Glu Leu Pro Val Asp Ala Arg
            35                  40                  45

Phe Pro Pro Arg Val Pro Lys Ser Phe Pro Phe Asn Thr Ser Val Val
        50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
```

-continued

```
                    85                  90                  95
Ala Glu Val Tyr Asp Thr Val Val Ile Thr Leu Lys Asn Met Ala Ser
                100                 105                 110

His Pro Val Ser Leu His Ala Val Gly Val Ser Tyr Trp Lys Ala Ser
                115                 120                 125

Glu Gly Ala Glu Tyr Asp Asp Gln Thr Ser Gln Arg Glu Lys Glu Asp
            130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
                180                 185                 190

Gly Ala Leu Leu Val Cys Arg Glu Gly Ser Leu Ala Lys Glu Lys Thr
                195                 200                 205

Gln Thr Leu His Lys Phe Ile Leu Leu Phe Ala Val Phe Asp Glu Gly
            210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
                260                 265                 270

Tyr Trp His Val Ile Gly Met Gly Thr Thr Pro Glu Val His Ser Ile
                275                 280                 285

Phe Leu Glu Gly His Thr Phe Leu Val Arg Asn His Arg Gln Ala Ser
            290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
                340                 345                 350

Gln Leu Arg Met Lys Asn Asn Glu Glu Ala Glu Asp Tyr Asp Asp Asp
            355                 360                 365

Leu Thr Asp Ser Glu Met Asp Val Val Arg Phe Asp Asp Asp Asn Ser
370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
                420                 425                 430

Asn Gly Pro Gln Arg Ile Gly Arg Lys Tyr Lys Lys Val Arg Phe Met
            435                 440                 445

Ala Tyr Thr Asp Glu Thr Phe Lys Thr Arg Glu Ala Ile Gln His Glu
                450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
                500                 505                 510
```

-continued

Gly Val Lys His Leu Lys Asp Phe Pro Ile Leu Pro Gly Glu Ile Phe
           515                 520                 525

Lys Tyr Lys Trp Thr Val Thr Val Glu Asp Gly Pro Thr Lys Ser Asp
       530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
               565                 570                 575

Ser Val Asp Gln Arg Gly Asn Gln Ile Met Ser Asp Lys Arg Asn Val
               580                 585                 590

Ile Leu Phe Ser Val Phe Asp Glu Asn Arg Ser Trp Tyr Leu Thr Glu
           595                 600                 605

Asn Ile Gln Arg Phe Leu Pro Asn Pro Ala Gly Val Gln Leu Glu Asp
       610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
               645                 650                 655

Tyr Ile Leu Ser Ile Gly Ala Gln Thr Asp Phe Leu Ser Val Phe Phe
               660                 665                 670

Ser Gly Tyr Thr Phe Lys His Lys Met Val Tyr Glu Asp Thr Leu Thr
           675                 680                 685

Leu Phe Pro Phe Ser Gly Glu Thr Val Phe Met Ser Met Glu Asn Pro
       690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
               725                 730                 735

Tyr Tyr Glu Asp Ser Tyr Glu Asp Ile Ser Ala Tyr Leu Leu Ser Lys
               740                 745                 750

Asn Asn Ala Ile Glu Pro Arg Glu Ile Thr Arg Thr Thr Leu Gln Ser
           755                 760                 765

Asp Gln Glu Glu Ile Asp Tyr Asp Asp Thr Ile Ser Val Glu Met Lys
       770                 775                 780

Lys Glu Asp Phe Asp Ile Tyr Asp Glu Asp Glu Asn Gln Ser Pro Arg
785                 790                 795                 800

Ser Phe Gln Lys Lys Thr Arg His Tyr Phe Ile Ala Ala Val Glu Arg
               805                 810                 815

Leu Trp Asp Tyr Gly Met Ser Ser Ser Pro His Val Leu Arg Asn Arg
               820                 825                 830

Ala Gln Ser Gly Ser Val Pro Gln Phe Lys Lys Val Val Phe Gln Glu
           835                 840                 845

Phe Thr Asp Gly Ser Phe Thr Gln Pro Leu Tyr Arg Gly Glu Leu Asn
       850                 855                 860

Glu His Leu Gly Leu Leu Gly Pro Tyr Ile Arg Ala Glu Val Glu Asp
865                 870                 875                 880

Asn Ile Met Val Thr Phe Arg Asn Gln Ala Ser Arg Pro Tyr Ser Phe
               885                 890                 895

Tyr Ser Ser Leu Ile Ser Tyr Glu Glu Asp Gln Arg Gln Gly Ala Glu
           900                 905                 910

Pro Arg Lys Asn Phe Val Lys Pro Asn Glu Thr Lys Thr Tyr Phe Trp
       915                 920                 925

```
Lys Val Gln His His Met Ala Pro Thr Lys Asp Glu Phe Asp Cys Lys
    930                 935                 940

Ala Trp Ala Tyr Phe Ser Asp Val Asp Leu Glu Lys Asp Val His Ser
945                 950                 955                 960

Gly Leu Ile Gly Pro Leu Leu Val Cys His Thr Asn Thr Leu Asn Pro
                965                 970                 975

Ala His Gly Arg Gln Val Thr Val Gln Glu Phe Ala Leu Phe Phe Thr
                980                 985                 990

Ile Phe Asp Glu Thr Lys Ser Trp Tyr Phe Thr Glu Asn Met Glu Arg
                995                1000                1005

Asn Cys Arg Ala Pro Cys Asn Ile Gln Met Glu Asp Pro Thr Phe
    1010                1015                1020

Lys Glu Asn Tyr Arg Phe His Ala Ile Asn Gly Tyr Ile Met Asp
    1025                1030                1035

Thr Leu Pro Gly Leu Val Met Ala Gln Asp Gln Arg Ile Arg Trp
    1040                1045                1050

Tyr Leu Leu Ser Met Gly Ser Asn Glu Asn Ile His Ser Ile His
    1055                1060                1065

Phe Ser Gly His Val Phe Thr Val Arg Lys Lys Glu Glu Tyr Lys
    1070                1075                1080

Met Ala Leu Tyr Asn Leu Tyr Pro Gly Val Phe Glu Thr Val Glu
    1085                1090                1095

Met Leu Pro Ser Lys Ala Gly Ile Trp Arg Val Glu Cys Leu Ile
    1100                1105                1110

Gly Glu His Leu His Ala Gly Met Ser Thr Leu Phe Leu Val Tyr
    1115                1120                1125

Ser Asn Lys Cys Gln Thr Pro Leu Gly Met Ala Ser Gly His Ile
    1130                1135                1140

Arg Asp Phe Gln Ile Thr Ala Ser Gly Gln Tyr Gly Gln Trp Ala
    1145                1150                1155

Pro Lys Leu Ala Arg Leu His Tyr Ser Gly Ser Ile Asn Ala Trp
    1160                1165                1170

Ser Thr Lys Glu Pro Phe Ser Trp Ile Lys Val Asp Leu Leu Ala
    1175                1180                1185

Pro Met Ile Ile His Gly Ile Lys Thr Gln Gly Ala Arg Gln Lys
    1190                1195                1200

Phe Ser Ser Leu Tyr Ile Ser Gln Phe Ile Ile Met Tyr Ser Leu
    1205                1210                1215

Asp Gly Lys Lys Trp Gln Thr Tyr Arg Gly Asn Ser Thr Gly Thr
    1220                1225                1230

Leu Met Val Phe Phe Gly Asn Val Asp Ser Ser Gly Ile Lys His
    1235                1240                1245

Asn Ile Phe Asn Pro Pro Ile Ile Ala Arg Tyr Ile Arg Leu His
    1250                1255                1260

Pro Thr His Tyr Ser Ile Arg Ser Thr Leu Arg Met Glu Leu Met
    1265                1270                1275

Gly Cys Asp Leu Asn Ser Cys Ser Met Pro Leu Gly Met Glu Ser
    1280                1285                1290

Lys Ala Ile Ser Asp Ala Gln Ile Thr Ala Ser Ser Tyr Phe Thr
    1295                1300                1305

Asn Met Phe Ala Thr Trp Ser Pro Ser Lys Ala Arg Leu His Leu
    1310                1315                1320

Gln Gly Arg Ser Asn Ala Trp Arg Pro Gln Val Asn Asn Pro Lys
```

| | | | | | | | | | | | |
|---|---|---|---|---|---|---|---|---|---|---|---|
| | | | | 1325 | | | | 1330 | | | 1335 |

Glu Trp Leu Gln Val Asp Phe Gln Lys Thr Met Lys Val Thr Gly
    1340                1345                1350

Val Thr Thr Gln Gly Val Lys Ser Leu Leu Thr Ser Met Tyr Val
    1355                1360                1365

Lys Glu Phe Leu Ile Ser Ser Gln Asp Gly His Gln Trp Thr
    1370                1375                1380

Leu Phe Phe Gln Asn Gly Lys Val Lys Val Phe Gln Gly Asn Gln
    1385                1390                1395

Asp Ser Phe Thr Pro Val Val Asn Ser Leu Asp Pro Pro Leu Leu
    1400                1405                1410

Thr Arg Tyr Leu Arg Ile His Pro Gln Ser Trp Val His Gln Ile
    1415                1420                1425

Ala Leu Arg Met Glu Val Leu Gly Cys Glu Ala Gln Asp Leu Tyr
    1430                1435                1440

<210> SEQ ID NO 11
<211> LENGTH: 4368
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11

```
atgcagattg agctgagcac ctgcttcttc ctgtgcctgc tgaggttctg cttctctgcc      60
accaggagat actacctggg ggctgtggag cttttcttgg gactacatgca gtctgacctg     120 ggggagctgc ctgtggatgc caggttccca cccagagtgc caaatccttt cccattcaac     180
acctctgtgg tctacaagaa gaccctcttt gtggagttca ctgaccacct gttcaacatt     240
gccaaaccca ggccacctg atgggactc ctgggaccca ccattcaggc tgaggtgtat     300
gacactgtgg tcatcaccct caagaacatg gcctcccacc ctgtgagcct gcatgctgtg     360
ggggtcagct actggaaggc ctctgagggg gctgagtatg atgaccagac ctcccagagg     420
gagaaggagg atgacaaagt gttccctggg ggcagccaca cctatgtgtg gcaggtcctc     480
aaggagaatg gccccatggc ctctgaccca ctctgcctga cctactccta cctttctcat     540
gtggacctgg tcaaggacct caactctgga ctgattgggg ccctgctggt gtgcagggag     600
ggctccctgg ccaaagagaa gacccagacc ctgcacaagt tcattctcct gtttgctgtc     660
tttgatgagg gcaagagctg gcactctgaa accaagaact ccctgatgca ggacagggat     720
gctgcctctg ccagggcctg gcccaagatg cacactgtga atggctatgt gaacaggagc     780
ctgcctggac tcattggctg ccacaggaaa tctgtctact ggcatgtgat tggcatgggg     840 acaaccctg aggtgcactc cattttcctg gagggccaca ccttcctggt caggaaccac     900
agacaggcca gctggagat cagccccatc accttcctca ctgcccagac cctgctgatg     960
gacctcggac agttcctgct gttctgccac atcagctccc accagcatga tggcatggag    1020
gcctatgtca aggtggacag ctgccctgag agccacagc tcaggatgaa gaacaatgag    1080
gaggctgagg actatgatga tgacctgact gactctgaga tggatgtggt ccgctttgat    1140
gatgacaaca gcccatcctt cattcagatc aggtctgtgg ccaagaaaca ccccaagacc    1200
tgggtgcact acattgctgc tgaggaggag gactgggact atgccccact ggtcctggcc    1260
cctgatgaca gagagctacaa gagccagtac ctcaacaatg gccacagag gattggacgc    1320 aagtacaaga agtcaggtt catggcctac actgatgaaa ccttcaagac cagggaggcc    1380
```

```
attcagcatg agtctggcat cctgggccca ctcctgtatg gggaggtggg ggacaccctg    1440
ctcatcatct tcaagaacca ggcctccagg ccctacaaca tctacccaca tggcatcact    1500
gatgtcaggc ccctgtacag ccgcaggctg ccaaaggggg tgaaacacct caaggacttc    1560
cccattctgc ctgggagat cttcaagtac aagtggactg tcactgtgga ggatggacca    1620
accaaatctg accccaggtg cctcaccaga tactactcca gctttgtgaa catggagagg    1680
gacctggcct ctggcctgat tggcccactg ctcatctgct acaaggagtc tgtggaccag    1740
aggggaaacc agatcatgtc tgacaagagg aatgtgattc tgttctctgt ctttgatgag    1800
aacaggagct ggtacctgac tgagaacatt cagcgcttcc tgcccaaccc tgctggggtg    1860
cagctggagg accctgagtt ccaggccagc aacatcatgc actccatcaa tggctatgtg    1920
tttgacagcc tccagctttc tgtctgcctg catgaggtgg cctactggta cattctttct    1980
attggggccc agactgactt cctttctgtc ttcttctctg gctacacctt caaacacaag    2040
atggtgtatg aggacaccct gaccctcttc ccattctctg gggagactgt gttcatgagc    2100
atggagaacc ctggcctgtg gattctggga tgccacaact ctgacttccg caacaggggc    2160
atgactgccc tgctcaaagt ctcctcctgt gacaagaaca ctggggacta ctatgaggac    2220
agctatgagg acatctctgc ctacctgctc agcaagaaca atgccattga gcccaggagc    2280
ttcagccaga attccagaca ccccagcacc agggagatca ccaggaccac cctccagtct    2340
gaccaggagg agattgacta tgatgacacc atttctgtgg agatgaagaa agaggacttt    2400
gacatctatg acgaggacga gaaccagagc ccaaggagct tccagaagaa gaccaggcac    2460
tacttcattg ctgctgtgga gcgcctgtgg gactatggca tgagctccag cccccatgtc    2520
ctcaggaaca gggcccagtc tggctctgtg ccacagttca gaaaagtggt cttccaagag    2580
ttcactgatg gcagcttcac ccagcccctg tacagagggg agctgaatga gcacctggga    2640
ctcctgggcc catacatcag gctgaggtg gaggacaaca tcatggtgac cttccgcaac    2700
caggcctcca ggccctacag cttctacagc tccctcatca gctatgagga ggaccagagg    2760 caggggctg agccacgcaa gaactttgtg aaacccaatg aaaccaagac ctacttctgg    2820
aaagtccagc accacatggc ccccaccaag gatgagtttg actgcaaggc ctgggcctac    2880
ttctctgatg tggacctgga aaggatgtg cactctggcc tgattggccc actcctggtc    2940
tgccacacca cacccctgaa ccctgcccat ggaaggcaag tgactgtgca ggagtttgcc    3000
ctcttcttca ccatctttga tgaaaccaag agctggtact tcactgagaa catggagcgc    3060
aactgcaggc cccatgcaa cattcagatg gaggaccca ccttcaaaga gaactaccgc    3120
ttccatgcca tcaatggcta catcatggac accctgcctg gcttgtcat ggcccaggac    3180 cagaggatca ggtggtacct gctttctatg ggctccaatg aaacattca ctccatccac    3240 ttctctgggc atgtcttcac tgtgcgcaag aaggaggagt acaagatggc cctgtacaac    3300
ctctaccctg ggtctttga gactgtggag atgctgccct ccaaagctgg catctggagg    3360
gtggagtgcc tcattgggga gcacctgcat gctggcatga gcaccctgtt cctggtctac    3420
agcaacaagt gccagacccc cctgggaatg gcctctggcc acatcaggga cttccagatc    3480
actgcctctg ccagtatgg ccagtgggcc cccaagctgg ccaggctcca ctactctgga    3540
tccatcaatg cctggagcac caaggagcca ttcagctgga tcaaagtgga cctgctggcc    3600
cccatgatca tccatggcat caagacccag ggggccaggc agaagttctc cagcctgtac    3660
atcagccagt tcatcatcat gtacagcctg gatggcaaga atggcagac ctacagaggc    3720
```

```
aactccactg gaacactcat ggtcttcttt ggcaatgtgg acagctctgg catcaagcac    3780
aacatcttca acccccaat catcgccaga tacatcaggc tgcaccccac ccactacagc     3840
atccgcagca ccctcaggat ggagctgatg ggctgtgacc tgaactcctg cagcatgccc    3900
ctgggcatgg agagcaaggc catttctgat gcccagatca ctgcctccag ctacttcacc    3960
aacatgtttg ccacctggag cccaagcaag gccaggctgc acctccaggg aaggagcaat    4020
gcctggaggc cccaggtcaa caacccaaag gagtggctgc aggtggactt ccagaagacc    4080
atgaaggtca ctggggtgac cacccagggg gtcaagagcc tgctcaccag catgtatgtg    4140
aaggagttcc tgatcagctc cagccaggat ggccaccagt ggaccctctt cttccagaat    4200
ggcaaggtca aggtgttcca gggcaaccag gacagcttca cccctgtggt gaacagcctg    4260 gaccccccc tcctgaccag atacctgagg attcaccccc agagctgggt ccaccagatt     4320
gccctgagga tggaggtcct gggatgtgag gcccaggacc tgtactga                 4368
```

<210> SEQ ID NO 12
<211> LENGTH: 1455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
```

```
                    245                 250                 255
        Val Asn Arg Ser Leu Pro Gly Leu Ile Gly Cys His Arg Lys Ser Val
                        260                 265                 270
        Tyr Trp His Val Ile Gly Met Gly Thr Thr Pro Glu Val His Ser Ile
                        275                 280                 285
        Phe Leu Glu Gly His Thr Phe Leu Val Arg Asn His Arg Gln Ala Ser
                        290                 295                 300
        Leu Glu Ile Ser Pro Ile Thr Phe Leu Thr Ala Gln Thr Leu Leu Met
        305                 310                 315                 320
        Asp Leu Gly Gln Phe Leu Leu Phe Cys His Ile Ser Ser His Gln His
                        325                 330                 335
        Asp Gly Met Glu Ala Tyr Val Lys Val Asp Ser Cys Pro Glu Glu Pro
                        340                 345                 350
        Gln Leu Arg Met Lys Asn Asn Glu Glu Ala Glu Asp Tyr Asp Asp Asp
                        355                 360                 365
        Leu Thr Asp Ser Glu Met Asp Val Val Arg Phe Asp Asp Asp Asn Ser
                        370                 375                 380
        Pro Ser Phe Ile Gln Ile Arg Ser Val Ala Lys Lys His Pro Lys Thr
        385                 390                 395                 400
        Trp Val His Tyr Ile Ala Ala Glu Glu Glu Asp Trp Asp Tyr Ala Pro
                        405                 410                 415
        Leu Val Leu Ala Pro Asp Asp Arg Ser Tyr Lys Ser Gln Tyr Leu Asn
                        420                 425                 430
        Asn Gly Pro Gln Arg Ile Gly Arg Lys Tyr Lys Lys Val Arg Phe Met
                        435                 440                 445
        Ala Tyr Thr Asp Glu Thr Phe Lys Thr Arg Glu Ala Ile Gln His Glu
                        450                 455                 460
        Ser Gly Ile Leu Gly Pro Leu Leu Tyr Gly Glu Val Gly Asp Thr Leu
        465                 470                 475                 480
        Leu Ile Ile Phe Lys Asn Gln Ala Ser Arg Pro Tyr Asn Ile Tyr Pro
                        485                 490                 495
        His Gly Ile Thr Asp Val Arg Pro Leu Tyr Ser Arg Arg Leu Pro Lys
                        500                 505                 510
        Gly Val Lys His Leu Lys Asp Phe Pro Ile Leu Pro Gly Glu Ile Phe
                        515                 520                 525
        Lys Tyr Lys Trp Thr Val Thr Val Glu Asp Gly Pro Thr Lys Ser Asp
                        530                 535                 540
        Pro Arg Cys Leu Thr Arg Tyr Tyr Ser Ser Phe Val Asn Met Glu Arg
        545                 550                 555                 560
        Asp Leu Ala Ser Gly Leu Ile Gly Pro Leu Leu Ile Cys Tyr Lys Glu
                        565                 570                 575
        Ser Val Asp Gln Arg Gly Asn Gln Ile Met Ser Asp Lys Arg Asn Val
                        580                 585                 590
        Ile Leu Phe Ser Val Phe Asp Glu Asn Arg Ser Trp Tyr Leu Thr Glu
                        595                 600                 605
        Asn Ile Gln Arg Phe Leu Pro Asn Pro Ala Gly Val Gln Leu Glu Asp
                        610                 615                 620
        Pro Glu Phe Gln Ala Ser Asn Ile Met His Ser Ile Asn Gly Tyr Val
        625                 630                 635                 640
        Phe Asp Ser Leu Gln Leu Ser Val Cys Leu His Glu Val Ala Tyr Trp
                        645                 650                 655
        Tyr Ile Leu Ser Ile Gly Ala Gln Thr Asp Phe Leu Ser Val Phe Phe
                        660                 665                 670
```

```
Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
        690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                    725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Ser Arg His Pro
                755                 760                 765

Ser Thr Arg Glu Ile Thr Arg Thr Thr Leu Gln Ser Asp Gln Glu Glu
770                 775                 780

Ile Asp Tyr Asp Asp Thr Ile Ser Val Glu Met Lys Lys Glu Asp Phe
785                 790                 795                 800

Asp Ile Tyr Asp Glu Asp Glu Asn Gln Ser Pro Arg Ser Phe Gln Lys
                805                 810                 815

Lys Thr Arg His Tyr Phe Ile Ala Ala Val Glu Arg Leu Trp Asp Tyr
            820                 825                 830

Gly Met Ser Ser Ser Pro His Val Leu Arg Asn Arg Ala Gln Ser Gly
        835                 840                 845

Ser Val Pro Gln Phe Lys Lys Val Val Phe Gln Glu Phe Thr Asp Gly
850                 855                 860

Ser Phe Thr Gln Pro Leu Tyr Arg Gly Glu Leu Asn Glu His Leu Gly
865                 870                 875                 880

Leu Leu Gly Pro Tyr Ile Arg Ala Glu Val Glu Asp Asn Ile Met Val
                885                 890                 895

Thr Phe Arg Asn Gln Ala Ser Arg Pro Tyr Ser Phe Tyr Ser Ser Leu
            900                 905                 910

Ile Ser Tyr Glu Glu Asp Gln Arg Gln Gly Ala Glu Pro Arg Lys Asn
        915                 920                 925

Phe Val Lys Pro Asn Glu Thr Lys Thr Tyr Phe Trp Lys Val Gln His
        930                 935                 940

His Met Ala Pro Thr Lys Asp Glu Phe Asp Cys Lys Ala Trp Ala Tyr
945                 950                 955                 960

Phe Ser Asp Val Asp Leu Glu Lys Asp Val His Ser Gly Leu Ile Gly
                965                 970                 975

Pro Leu Leu Val Cys His Thr Asn Thr Leu Asn Pro Ala His Gly Arg
            980                 985                 990

Gln Val Thr Val Gln Glu Phe Ala Leu Phe Phe Thr Ile Phe Asp Glu
        995                 1000                1005

Thr Lys Ser Trp Tyr Phe Thr Glu Asn Met Glu Arg Asn Cys Arg
    1010                1015                1020

Ala Pro Cys Asn Ile Gln Met Glu Asp Pro Thr Phe Lys Glu Asn
    1025                1030                1035

Tyr Arg Phe His Ala Ile Asn Gly Tyr Ile Met Asp Thr Leu Pro
    1040                1045                1050

Gly Leu Val Met Ala Gln Asp Gln Arg Ile Arg Trp Tyr Leu Leu
    1055                1060                1065

Ser Met Gly Ser Asn Glu Asn Ile His Ser Ile His Phe Ser Gly
    1070                1075                1080
```

His Val Phe Thr Val Arg Lys Lys Glu Glu Tyr Lys Met Ala Leu
1085                1090                1095

Tyr Asn Leu Tyr Pro Gly Val Phe Glu Thr Val Glu Met Leu Pro
1100                1105                1110

Ser Lys Ala Gly Ile Trp Arg Val Glu Cys Leu Ile Gly Glu His
1115                1120                1125

Leu His Ala Gly Met Ser Thr Leu Phe Leu Val Tyr Ser Asn Lys
1130                1135                1140

Cys Gln Thr Pro Leu Gly Met Ala Ser Gly His Ile Arg Asp Phe
1145                1150                1155

Gln Ile Thr Ala Ser Gly Gln Tyr Gly Gln Trp Ala Pro Lys Leu
1160                1165                1170

Ala Arg Leu His Tyr Ser Gly Ser Ile Asn Ala Trp Ser Thr Lys
1175                1180                1185

Glu Pro Phe Ser Trp Ile Lys Val Asp Leu Leu Ala Pro Met Ile
1190                1195                1200

Ile His Gly Ile Lys Thr Gln Gly Ala Arg Gln Lys Phe Ser Ser
1205                1210                1215

Leu Tyr Ile Ser Gln Phe Ile Ile Met Tyr Ser Leu Asp Gly Lys
1220                1225                1230

Lys Trp Gln Thr Tyr Arg Gly Asn Ser Thr Gly Thr Leu Met Val
1235                1240                1245

Phe Phe Gly Asn Val Asp Ser Ser Gly Ile Lys His Asn Ile Phe
1250                1255                1260

Asn Pro Pro Ile Ile Ala Arg Tyr Ile Arg Leu His Pro Thr His
1265                1270                1275

Tyr Ser Ile Arg Ser Thr Leu Arg Met Glu Leu Met Gly Cys Asp
1280                1285                1290

Leu Asn Ser Cys Ser Met Pro Leu Gly Met Glu Ser Lys Ala Ile
1295                1300                1305

Ser Asp Ala Gln Ile Thr Ala Ser Ser Tyr Phe Thr Asn Met Phe
1310                1315                1320

Ala Thr Trp Ser Pro Ser Lys Ala Arg Leu His Leu Gln Gly Arg
1325                1330                1335

Ser Asn Ala Trp Arg Pro Gln Val Asn Asn Pro Lys Glu Trp Leu
1340                1345                1350

Gln Val Asp Phe Gln Lys Thr Met Lys Val Thr Gly Val Thr Thr
1355                1360                1365

Gln Gly Val Lys Ser Leu Leu Thr Ser Met Tyr Val Lys Glu Phe
1370                1375                1380

Leu Ile Ser Ser Ser Gln Asp Gly His Gln Trp Thr Leu Phe Phe
1385                1390                1395

Gln Asn Gly Lys Val Lys Val Phe Gln Gly Asn Gln Asp Ser Phe
1400                1405                1410

Thr Pro Val Val Asn Ser Leu Asp Pro Pro Leu Leu Thr Arg Tyr
1415                1420                1425

Leu Arg Ile His Pro Gln Ser Trp Val His Gln Ile Ala Leu Arg
1430                1435                1440

Met Glu Val Leu Gly Cys Glu Ala Gln Asp Leu Tyr
1445                1450                1455

<210> SEQ ID NO 13
<211> LENGTH: 4374
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 13

```
atgcagattg agctgtccac ctgcttcttt ctgtgcctgc tgagattctg cttctctgcc      60
accaggagat actacctggg ggctgtggaa ctttcttggg actacatgca gtctgacctg     120
ggagagctgc ctgtggatgc caggttccca cccagagtgc ccaagtcctt cccattcaac     180
acctctgtgg tctacaagaa gacactcttt gtggaattca ctgaccacct gttcaacatt     240
gcaaaaccca gaccaccctg gatgggactc tgggaccca ccattcaggc tgaggtgtat      300
gacactgtgg tcatcaccct caagaacatg gcatcccacc ctgtgtctct gcatgctgtg     360
ggagtctcat actggaaagc ctctgaaggg gctgagtatg atgaccagac atcccagaga     420
gagaaagagg atgacaaggt gttccctggg ggatctcaca cctatgtgtg caagtcctc      480
aaggagaatg acccatggc atctgaccca ctctgcctga catactccta cctttctcat      540
gtggacctgg tcaaggacct caactctgga ctgattgggg cactgctggt gtgcagggaa     600
ggatccctgg ccaaggagaa aacccagaca ctgcacaagt tcattctcct gtttgctgtc     660
tttgatgagg gcaagtcttg gcactctgaa acaaagaact ccctgatgca agacagggat     720
gctgcctctg ccagggcatg gcccaagatg cacactgtga atggctatgt gaacagatca     780
ctgcctggac tcattggctg ccacaggaaa tctgtctact ggcatgtgat tggcatgggg     840
acaacccctg aagtgcactc cattttcctg gagggacaca ccttcctggt caggaaccac     900
agacaagcct ctctggagat ctctcccatc accttcctca ctgcacagac actgctgatg     960
gaccttggac agttcctgct gttctgccac atctcttccc accagcatga tggcatggaa    1020
gcctatgtca aggtggactc atgccctgag gaaccacagc tcaggatgaa gaacaatgag    1080
gaggctgagg actatgatga tgacctgact gactctgaga tggatgtggt cagatttgat    1140
gatgacaact ctccatcctt cattcagatc aggtctgtgg caaagaaaca ccccaagaca    1200
tgggtgcact acattgctgc tgaggaagag gactgggact atgcaccact ggtcctggcc    1260
cctgatgaca ggagctacaa gtctcagtac ctcaacaatg gccacaaag aattggaaga    1320
aagtacaaga agtcagatt catggcctac actgatgaaa ccttcaagac aagagaagcc    1380
attcagcatg agtctggcat tctgggacca ctcctgtatg gggaagtggg agacaccctg    1440
ctcatcatct tcaagaacca ggcctccagg ccctacaaca tctacccaca tggcatcact    1500
gatgtcaggc cctgtacag caggagactg ccaaaagggg tgaaacacct caaggacttc    1560
cccattctgc ctggagagat cttcaagtac aagtggactg tcactgtgga ggatggacca    1620
acaaagtctg accccaggtg cctcaccaga tactactcct cttttgtgaa catggagaga    1680
gacctggcat ctggactgat tggaccactg ctcatctgct acaaggagtc tgtggaccag    1740
agaggcaacc agatcatgtc tgacaagaga aatgtgattc tgttctctgt ctttgatgag    1800
aacagatcat ggtacctgac tgagaacatt cagagattcc tgcccaaccc tgctggggtg    1860
caactggaag accctgagtt ccaggcaagc aacatcatgc actccatcaa tggctatgtg    1920
tttgactctc tccagctttc tgtctgcctg catgaggtgg cctactggta cattcttttct   1980
attggggcac aaactgactt cctttctgtc ttcttctctg gatacacctt caagcacaag    2040
atggtgtatg aggacaccct gacactcttc ccattctctg ggaaactgt gttcatgagc    2100
atggagaacc ctggactgtg gattctggga tgccacaact ctgacttcag aaacagggga    2160
```

| | |
|---|---|
| atgactgcac tgctcaaagt ctcctcctgt gacaagaaca ctggggacta ctatgaggac | 2220 |
| tcttatgagg acatctctgc ctacctgctc agcaagaaca atgccattga gcccagaagc | 2280 |
| ttctctcaga atccacctgt cctgaagaga caccagagag agatcaccag acaaccctc | 2340 |
| cagtctgacc aggaagagat tgactatgat gacaccattt ctgtggagat gaagaaggag | 2400 |
| gactttgaca tctatgatga ggacgagaac cagtctccaa gatcattcca gaagaagaca | 2460 |
| agacactact tcattgctgc tgtggaaaga ctgtgggact atggcatgtc ttcctctccc | 2520 |
| catgtcctca ggaacagggc acagtctggc tctgtgccac agttcaagaa agtggtcttc | 2580 |
| caggagttca ctgatggctc attcacccag cccctgtaca gagggaact gaatgagcac | 2640 |
| ctgggactcc tgggaccata catcagggct gaggtggaag acaacatcat ggtgacattc | 2700 |
| agaaaccagg cctccaggcc ctacagcttc tactcttccc tcatcagcta tgaggaagac | 2760 |
| cagagacaag gggctgagcc aagaaagaac tttgtgaaac ccaatgaaac caagacctac | 2820 |
| ttctggaaag tccagcacca catggcaccc accaaggatg agtttgactg caaggcctgg | 2880 |
| gcatacttct ctgatgtgga cctggagaaa gatgtgcact ctggcctgat tggcccactc | 2940 |
| ctggtctgcc acaccaacac cctgaaccct gcacatggaa ggcaagtgac tgtgcaggag | 3000 |
| tttgccctct tcttcaccat cttttgatgaa accaagtcat ggtacttcac tgagaacatg | 3060 |
| gagagaaact gcagagcacc atgcaacatt cagatggaag accccaccct caaggagaac | 3120 |
| tacaggttcc atgccatcaa tggctacatc atggacaccc tgcctgggct tgtcatggca | 3180 |
| caggaccaga gaatcagatg gtacctgctt tctatgggat ccaatgagaa cattcactcc | 3240 |
| atccacttct ctgggcatgt cttcactgtg agaaagaagg aggaatacaa gatggccctg | 3300 |
| tacaacctct accctgggt ctttgagact gtggagatgc tgccctccaa gctggcatc | 3360 |
| tggagggtgg aatgcctcat tggggagcac ctgcatgctg gcatgtcaac cctgttcctg | 3420 |
| gtctacagca acaagtgcca gacaccctg ggaatggcct ctggccacat cagggacttc | 3480 |
| cagatcactg cctctggcca gtatggccag tgggcaccca aactggccag gctccactac | 3540 |
| tctggctcca tcaatgcatg gtcaaccaag gagccattct cttggatcaa ggtggacctg | 3600 |
| ctggcaccca tgatcattca tggcatcaag acacaggggg caagacagaa attctcctct | 3660 |
| ctgtacatct cacagttcat catcatgtac tctctggatg gcaagaagtg gcagacatac | 3720 |
| agaggcaact ccactggcac cctcatggtc ttctttggca atgtggacag ctctggcatc | 3780 |
| aagcacaaca tcttcaaccc tccatcatt gccagataca tcaggctgca ccccacccac | 3840 |
| tactcaatca gatcaaccct caggatgaa ctgatgggat gtgacctgaa ctcctgctca | 3900 |
| atgcccctgg gaatggagag caaggccatt tctgatgccc agatcactgc atcctcttac | 3960 |
| ttcaccaaca tgtttgccac ctggtcacca tcaaaagcca ggctgcacct ccagggaaga | 4020 |
| agcaatgcct ggagacccca ggtcaacaac ccaaaggaat ggctgcaagt ggacttccag | 4080 |
| aagacaatga agtcactgg ggtgacaacc caggggtca gtctctgct cacctcaatg | 4140 |
| tatgtgaagg agttcctgat ctcttcctca caggatggcc accagtggac actcttcttc | 4200 |
| cagaatggca aagtcaaggt gttccagggc aaccaggact ctttcacacc tgtggtgaac | 4260 |
| tcactggacc ccccctcct gacaagatac ctgagaattc accccagtc ttgggtccac | 4320 |
| cagattgccc tgagaatgga agtcctggga tgtgaggcac aagacctgta ctga | 4374 |

<210> SEQ ID NO 14
<211> LENGTH: 4374
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 14

```
atgcagatcg aactgagcac ttgcttcttc ctgtgtctcc tgcgcttttg cttctccgcc      60
acaaggagat actatctcgg tgccgtggag ctcagctggg actacatgca gagcgacttg     120
ggtgaactgc ctgtggacgc caggtttcca ccccgcgtgc caagagtttt cccgttcaac     180
accagtgtcg tgtacaagaa aaccctcttc gtggaattca ccgaccacct gttcaacatc     240
gccaaaccgc gccctccctg gatggggctg ctcggcccga cgatccaggc tgaggtctat     300
gacacggtgg tgattaccct caagaacatg gctagccacc cggtgagcct gcacgccgtg     360
ggcgtgtcct attggaaagc gtccgagggt gcggagtacg atgaccagac ttcacagcgg     420
gagaaggaag acgacaaagt gttccccggg ggttcccaca cctatgtctg gcaggtcctg     480
aaggagaatg gtcctatggc ctccgaccca ttgtgcctca cctactctta cctaagccat     540
gtggatctcg tcaaggacct gaactcgggg ctgatcggcg ccctgctcgt gtgccgggag     600
ggctcactgg ccaaggagaa gacccaaact ctgcacaagt tcatcctgct gttcgcggta     660
ttcgacgagg ggaagtcctg gcactccgag accaagaaca gcctgatgca ggaccgcgac     720
gcagcctcgg cccgtgcgtg gccaaagatg cacaccgtga acggctacgt taacaggagc     780
ctacccggcc tgatcggctg ccaccgcaaa tcggtctact ggcatgtgat cggaatgggc     840
acaacgcccg aggtccacag tatcttcctc gagggccaca ctttcctggt ccggaatcac     900
cgccaggcca gctggagat cagccccata acctttctga cggcgcagac cttactcatg     960
gatctcggcc agttcctcct gttctgccac atttcgtccc accagcacga tgggatggaa    1020
gcatatgtga agtggactc ctgccccgag gaacccagc ttaggatgaa gaacaatgag    1080
gaggccgagg actacgacga tgaccttacc gattcagaaa tggacgtagt acgctttgac    1140
gacgacaact ctccatcctt catacagatt cgctccgtcg ccaagaagca ccctaagact    1200
tgggtgcact acatcgcggc cgaggaggag gactgggatt atgctcccct ggtgctggcc    1260
cccgacgacc gcagctacaa gagccagtac ctgaataacg gccccagcg catcggccgg    1320
aagtacaaga aagtgcggtt catggcttac acggacgaga ccttcaagac ccgggaggct    1380
atccagcatg agagcggcat cttggggccc ctcctgtacg gcgaagttgg agacacactg    1440
ctgatcatct tcaagaacca ggcgagcagg ccctacaaca tctacccca cggcattacc    1500
gatgtccggc cgttgtacag ccgacggctg cccaagggcg tgaagcacct gaaggacttt    1560
ccgatcctgc cgggcgagat cttcaagtac aagtggactg tgaccgtgga ggatgggccg    1620
accaagagcg atccgcgctg cctgacccgt tactactcca gctttgtcaa tatggagcgc    1680
gacctcgcta gcggcttgat tggccctctg ctgatctgct acaaggagtc cgtggaccag    1740
aggggggaatc agatcatgag tgacaagagg aacgtgatcc tgttctccgt gttcgacgaa    1800
aaccgcagct ggtatctcac cgagaatatc cagcgcttcc tgcccaaccc ggccggtgtg    1860
cagctggagg accccgagtt tcaggccagc aacatcatgc attctatcaa cggatatgtg    1920
tttgattccc tgcagctctc agtgtgtctg cacgaggtcg cctactggta tatcctcagc    1980
attgggcac agaccgactt cctgagcgtg ttcttctccg ggtataccttt caagcacaag    2040
atggtgtacg aggatcccct gaccctgttc cccctttagcg gcgaaaccgt gtttatgtct    2100
atggagaacc ccgggctctg gatccttggc tgccataact ccgacttccg caaccgcgga    2160
atgaccgcgc tcctgaaagt gtcgagttgt gacaagaaca ccggcgacta ttacgaggac    2220
```

```
agttacgagg acatctctgc gtacctcctt agcaagaata acgccatcga gccaagatcc    2280
ttcagccaga acccccagt gctgaagagg catcagcggg agatcacccg cacgaccctg    2340
cagtcggatc aggaggagat tgattacgac gacacgatca gtgtggagat gaagaaggag    2400
gacttcgaca tctacgacga agatgaaaac cagtcccctc ggtccttcca aaagaagacc    2460
cggcactact tcatcgccgc tgtggaacgc ctgtgggact atggaatgtc ttctagccct    2520
cacgttttga ggaaccgcgc ccagtcgggc agcgtgcccc agttcaagaa agtggtgttc    2580
caggagttca ccgacggctc cttcacccag ccactttacc ggggcgagct caatgaacat    2640
ctgggcctgc tggaccccta catcagggct gaggtgagg acaacatcat ggtgacattc    2700
cggaatcagg ccagcagacc atacagtttc tacagttcac tcatctccta cgaggaggac    2760
cagcgccagg gggctgaacc ccgtaagaac ttcgtgaagc caaacgaaac aaagacctac    2820
ttctggaagg tccagcacca catggcacct accaaggacg agttcgattg caaggcctgg    2880
gcctacttct ccgacgtgga cctggagaaa gatgtgcaca cgcggcctgat tggccctctg    2940
ctggtgtgtc acacgaacac actcaaccct gcacacgggc ggcaggtcac tgtgcaggaa    3000
ttcgccctgt tctttaccat cttgatgag acgaagtcct ggtatttcac cgaaaacatg    3060
gagaggaact gccgcgcacc ctgcaacatc cagatggaag atccgacatt caaggagaac    3120
taccggttcc atgccatcaa tggctacatc atggacaccc tgcctggcct cgtgatggcc    3180
caagaccagc gtatccgctg gtatctgctg tcgatgggct ccaacgagaa catccatagt    3240
atccacttca gcgggcatgt cttcacggtg aggaaaaagg aggagtacaa gatggcactg    3300
tacaacctct atcccggcgt gttcgagacc gtggagatgc tgccctccaa ggccggcatc    3360
tggagagtgg aatgcctgat cggcgagcac ctccacgctg ggatgtccac gctgttcctc    3420
gtttacagca ataagtgcca gaccctctg ggcatggcga gcggccacat ccgcgacttc    3480
cagattacag ccagcggcca gtacggtcag tgggctccaa agctggcccg tctgcactac    3540
tccggatcca tcaacgcctg gtccaccaag gaaccgttct cctggatcaa agtagacctg    3600
ctagccccca tgatcattca cggcatcaag acacaaggcg cccgacagaa gttctcgagc    3660
ctctatatct cccagttcat catcatgtat agcctggacg gaaagaagtg gcagacttac    3720
cgcggaaact cgacagggac cctgatggta ttcttcggta acgtggacag ctccggaatc    3780
aagcacaaca tcttcaaccc acccattatc gcccgctaca tccgcctgca ccccactcac    3840
tatagcatta ggtccaccct gcgaatggag ctcatgggct gtgacctgaa cagctgtagc    3900
atgccctcg gcatggagtc taaggcgatc tccgacgcac agataacggc atcatcctac    3960
tttaccaaca tgttcgctac ctggtccccc tccaaggccc gactccacct gcaagggaga    4020
tccaacgcct ggcggccaca ggtcaacaat cccaaggagt ggctgcaagt ggactttcag    4080
aaaactatga agtcaccgg agtgaccaca cagggagtga agtctctgct gaccagcatg    4140
tacgtgaagg agttcctcat ctccagttcg caggatggcc accagtggac gttgttcttc    4200
caaaacggta aagtcaaagt cttccaaggg aaccaggaca gctttacacc cgtcgtgaac    4260
tccctggacc ccccgcttct cactagatac ctccgcatcc accctcagag ctgggtgcac    4320
cagattgccc tgcgcatgga ggttctgggg tgtgaagccc aggacctgta ctaa    4374
```

<210> SEQ ID NO 15
<211> LENGTH: 4374
<212> TYPE: DNA
<213> ORGANISM: Artificial Sequence
<220> FEATURE:

<223> OTHER INFORMATION: Description of Artificial Sequence: Synthetic polynucleotide

<400> SEQUENCE: 15

```
atgcagattg agctctccac ctgcttcttt ctctgccttc ttcgcttctg cttttctgcc     60
acacgcaggt actatttggg agcagtggaa ctgagctggg attacatgca gagtgacctt    120
ggtgaacttc ctgtggacgc tcgttttcca cctagagttc ccaagtcctt ccccttcaac    180
acctcagtgg tctacaagaa aacgctgttt gtggagttca ctgaccacct cttcaacatt    240
gccaaaccaa gaccccttg gatgggattg ctgggaccca caatacaagc agaagtctac    300
gacacggtgt tgattaccct gaagaacatg gcgtcacacc ctgtttcact tcacgctgtt    360
ggggtcagtt attggaaagc ctcagagggt gcggaatacg atgatcaaac cagccagagg    420
gagaaggaag atgacaaggt cttttcctggg ggtagccata cctatgtttg gcaggtgctg    480
aaagagaatg ggcctatggc ctctgatccc ttgtgcctca catactctta cctgagtcac    540
gtcgacctgg tgaaagacct gaatagcggt ctgattggtg cactgcttgt ttgtagagag    600
gggagtttgg ccaaggagaa aactcagact ctccacaagt ttatcctcct gtttgctgtg    660
ttcgacgagg gcaagtcttg gcactctgaa acaaagaact ccctgatgca ggacagagat    720
gctgcatctg caagggcttg gccaaaaatg cacacagtga acggctatgt gaatcgatca    780
ctgccaggac tgataggctg tcatcgcaag tcagtgtatt ggcacgttat cgggatggga    840
acaactccag aagtgcacag catcttcctt gagggccaca cttccctggt tcggaatcat    900
agacaggcca gccttgagat cagcccaatc acctttctga ctgcccaaac cttgctgatg    960
gatctgggac agttcctcct gttttgtcac atctcctccc accaacatga cgggatggag   1020
gcttatgtga aggtcgatag ctgtccggag gaaccacaac tgaggatgaa gaacaacgaa   1080
gaggcagagg actatgacga cgatctgact gacagtgaaa tggacgtggt tcggttcgac   1140
gatgacaatt ctccttcatt tatccagatc cgttccgtgg ccaagaagca ccccaagact   1200
tgggttcatt acatcgctgc tgaggaggag gattgggact acgcgccctt ggtgttggcc   1260
ccagacgatc gctcatacaa gagccagtac cttaacaatg gtccacaaag gatcggccgg   1320
aagtacaaga aggttagatt tatggcttat accgacgaga cttttaaaac tagggaagca   1380
attcagcatg aaagtggcat tcttggaccc ctgctgtatg gcgaggttgg cgacaccctg   1440
ctgattatct ttaagaacca ggcaagccgg ccctacaaca tctacccgca cggcataacc   1500
gatgtacgac ccctgtacag tcgcagactt cctaaagggg tgaaacacct gaaggacttc   1560
ccaattctgc ccggggagat cttcaagtat aaatggaccg tgacggttga ggatggtccc   1620
acaaagtccg atccgagatg ccttacccga tattattcca gcttcgtgaa catggaaagg   1680
gacctggcca gcgggctgat tggcccactg ctgatttgtt acaaggagtc tgtcgatcaa   1740
agaggaaacc aaataatgag cgacaaacgt aacgtcatcc tgttcagcgt ctttgatgag   1800
aatagaagct ggtacctcac agaaaatatt cagcggtttc tgcctaaccc cgcaggcgtc   1860
cagctggaag atcccgagtt ccaagcctca acatcatgc atagcatcaa cggatacgta   1920
ttcgatagcc tgcagctgtc cgtctgtctc catgaagtgg catattggta catcctgagt   1980
atcggggcgc agaccgactt cctgagcgtg ttctttctg atacacgtt caaacacaaa   2040
atggtctatg aagataccct gactctgttt ccattctcag agagacagt ctttatgagt   2100
atggaaaatc ctggactgtg gatcctgggc tgtcacaatt ctgattttcg gaacagaggc   2160
atgacagccc tgcttaaagt gagctcatgc gacaagaaca ccggtgatta ctacgaagat   2220
```

```
agctatgagg acatcagtgc gtatttgctc tccaagaaca acgctatcga gccacggtct    2280
ttcagtcaga atcctcccgt tctgaagcgg catcagcgcg aaataacacg cacaacccct    2340
cagtcagacc aagaggaaat cgactacgat gatactatct ctgtggagat gaagaaggag    2400
gatttcgaca tttacgacga ggacgagaat cagtccccaa ggagctttca gaagaaaaca    2460
agacactatt tcattgccgc cgtggagcga ctgtgggact acggcatgtc tagctctccg    2520
catgtactta gaaatagggc acaaagcgga tccgtgcctc agtttaagaa agttgtcttt    2580
caggagttta cagatggctc cttcacccag cccttgtatc gcggggaact caatgaacac    2640
ctgggcctcc tggtccttta tattagggcc gaagtcgagg acaatatcat ggtgaccttt    2700
aggaaccagg catctagacc ttactctttc tactcctccc tgatatccta tgaggaggac    2760
cagcggcaag gcgctgagcc tcggaagaac tttgtgaagc caaatgaaac caaaacatac    2820
ttttggaaag ttcagcacca catggctccc acgaaggacg aatttgactg taaagcctgg    2880
gcctacttct cagatgtaga tctcgagaaa gacgtgcact cagggctcat tggtcccctc    2940
ctggtctgtc atactaatac cctcaatcca gcacacggac gtcaggtaac cgtccaggaa    3000
tttgccctgt tctttaccat tttcgatgag actaaatcct ggtactttac cgaaaacatg    3060
gagaggaatt gcagagcccc atgcaacatc cagatggagg accctacctt caaagagaac    3120
tatcgcttcc atgccattaa cggttacatt atggatactc tcccaggact tgtgatggca    3180
caggatcagc ggataagatg gtatctgttg agcatgggct ccaacgagaa tattcacagc    3240
atccatttct ccggtcacgt gtttacagtg agaaagaaag aagagtacaa gatggctctg    3300
tataatctct atccaggcgt attcgaaacg gtggagatgt tgcctagcaa ggccggcatt    3360
tggcgagtag aatgccttat cggggaacat ctgcatgccg gaatgagcac gctcttcctg    3420
gtgtatagta acaagtgcca gactccgctg ggcatggcat ctggccatat acgggacttt    3480
cagattacgg ctagcgggca gtatgggcag tgggcaccca aacttgcgcg actgcactat    3540
tcaggctcta tcaatgcatg gtccaccaag gaacccttct cttggattaa ggtggacctt    3600
ttggcgccca tgataatcca tgggatcaaa acccagggcg ctcgtcagaa attctcatca    3660
ctctacatct ctcagttcat aataatgtat tcactggatg ggaagaaatg gcagacttac    3720
agaggaaaca gcaccgggac gctgatggtg ttctttggca acgtggacag cagcggcatc    3780
aaacacaaca tcttcaatcc tcccattatt gcccgttata ttagactgca tcccactcac    3840
tactctatac gcagcacact taggatggag ctcatgggat gcgacctgaa cagttgtagt    3900
atgcccttgg ggatggagtc caaagctata agcgacgcac aaattacagc tagctcttac    3960
tttacgaata tgttcgccac gtggagccca agcaaagccc ggctgcattt gcagggtcgg    4020
agtaatgctt ggcgcccaca ggtgaataac cctaaggaat ggttgcaagt agatttccag    4080
aaaactatga aggtaaccgg cgtcactaca cagggagtca agtccctctt gacctctatg    4140
tacgtcaagg agttcctgat tagcagcagt caggatgggc accaatggac actgttcttc    4200
cagaatggga aagttaaagt atttcagggt aaccaggact cctttacacc tgtggtgaat    4260
agcctcgacc caccccctgct gacacgatac ctccgcatcc accctcagtc ttgggtgcat    4320
caaattgccc tgcgaatgga ggtgttggga tgcgaagctc aggacctcta ctga         4374
```

<210> SEQ ID NO 16
<211> LENGTH: 4374
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 16

| | | | | | |
|---|---|---|---|---|---|
| atgcagatcg | aactctctac | ttgcttcttc | ctgtgccttc | tgaggttctg | cttctctgcc | 60 |
| actcgccgat | attacctcgg | ggccgtggag | ttgagttggg | actacatgca | atcagatctg | 120 |
| ggcgaactcc | ctgtggatgc | ccgattccca | ccgcgcgtgc | ccaagtcttt | cccatttaat | 180 |
| acttctgtgg | tgtacaagaa | gacattgttt | gtggagttta | ccgatcacct | gttcaacatc | 240 |
| gccaaaccgc | ggcccccatg | gatgggtctg | cttgggccca | ccattcaagc | ggaggtctat | 300 |
| gatacagtgg | tgataacgct | taagaacatg | gcgagccacc | cagtgtctct | gcatgccgtt | 360 |
| ggtgtatcat | attggaaggc | cagcgaagga | gcggagtacg | atgaccagac | ctctcagaga | 420 |
| gagaaggaag | acgataaggt | ttttcctggc | ggaagtcata | catatgtatg | gcaggtcctg | 480 |
| aaagagaatg | ggccgatggc | ttctgacccc | ctttgtctta | cctatagtta | tctgagccac | 540 |
| gtggacctgg | tcaaggacct | caacagtggt | ctgattgggg | ctctgcttgt | ttgtagagag | 600 |
| ggtagcttgg | ctaaggagaa | aacccaaaca | ctccataagt | tcattttgct | gttcgcggtg | 660 |
| ttcgacgagg | gaaagagttg | gcacagcgaa | acaaagaatt | cactgatgca | agacagggac | 720 |
| gccgcttccg | caagggcttg | gcctaagatg | catacggtga | atgggtatgt | gaaccggagc | 780 |
| ctcccggggc | tgatcgggtg | ccatcgcaag | tctgtttact | ggcacgtcat | tggaatgggg | 840 |
| acaacgccag | aggtacatag | tatatttctt | gaaggccaca | cgttcctcgt | acggaaccac | 900 |
| cgacaggctt | ccctggagat | aagcccccatt | acctttctga | ccgctcagac | tctgctgatg | 960 |
| gaccttggcc | agtttctcct | gttctgccat | attagcagcc | accagcacga | cggtatggaa | 1020 |
| gcatacgtga | agtcgatag | ctgtcctgag | gagcctcagc | tcagaatgaa | gaacaacgag | 1080 |
| gaggccgaag | actatgacga | tgaccttaca | gattccgaga | tggacgtggt | gcgctttgac | 1140 |
| gacgataaca | gtcctagttt | cattcaaatc | agatccgtag | ccaaaaagca | tccaaagaca | 1200 |
| tgggtgcatt | acattgcagc | cgaagaggag | gattgggatt | atgcgcccct | tgttctggct | 1260 |
| ccagatgaca | ggagctataa | gtcccagtac | ttgaacaacg | ggccacagcg | aatcggtaga | 1320 |
| aaatataaga | aggtaagatt | catggcctac | actgacgaaa | catttaaaac | cagggaagct | 1380 |
| atccaacacg | aatctggaat | tctcggccct | ctgctctacg | gtgaggtggg | ggacaccttg | 1440 |
| ctgatcattt | tcaaaaatca | ggcatccagg | ccttacaaca | tatacccccca | tggcatcacc | 1500 |
| gatgtccgcc | cgctgtattc | cagaagactc | cccaagggag | tgaaacatct | gaaagatttt | 1560 |
| cccatcctgc | cgggcgagat | ctttaaatac | aaatggactg | tgactgtaga | ggacgggcct | 1620 |
| acaaaatcag | acccacggtg | cctgacaagg | tattacagta | gcttcgtcaa | catggaacgc | 1680 |
| gacctcgcca | gcggactcat | tggcccactg | ttgatctgtt | acaaagagtc | agtggatcag | 1740 |
| agggaaaatc | agatcatgag | cgataagaga | aacgttatcc | tgtttagtgt | cttcgacgag | 1800 |
| aaccggtctt | ggtaccttac | tgagaacatc | cagaggttcc | tgccgaatcc | ggctggcgtt | 1860 |
| cagctcgagg | acccagagtt | ccaggccagt | aatataatgc | actcaatcaa | cggttatgtg | 1920 |
| ttcgatagcc | tgcagctgag | cgtctgcctc | cacgaggtag | cctattggta | catattgtcc | 1980 |
| atcgggctc | agaccgattt | tctgtccgtg | ttctttagcg | ggtataccttt | taaacataaa | 2040 |
| atggtctatg | aagacacccct | gaccctgttc | ccattctccg | gtgagactgt | gttcatgtcc | 2100 |
| atggagaacc | cagggctgtg | gatcctgggg | tgtcacaata | gtgactttag | gaatcgggga | 2160 |
| atgacggcac | tgctgaaggt | gagttcttgc | gataaaaata | caggagatta | ctatgaggat | 2220 |
| agttacgagg | atatcagtgc | ctatctgctt | tcaaaaaaca | acgcaattga | gccccggtct | 2280 |

```
ttctcacaaa accccccggt gctgaagcgc caccagcgcg aaattacccg gacaaccttg      2340
cagtccgacc aggaggaaat cgattatgac gatactatca gtgtagaaat gaaaaaggag      2400
gattttgata tttacgacga agacgagaac cagtctccgc gaagttttca gaagaaaacg      2460
cgacactact ttatagctgc cgtggaacga ctctgggatt atggcatgtc ctccagccct      2520
catgtcctta ggaatcgagc gcagagtggc tctgtgcctc agttcaaaaa ggttgtgttc      2580
caggaattca ccgacggctc atttacccag ccgctgtaca gaggcgaact caacgaacac      2640
cttgggctgc ttgggccata tattcgagca gaggtggaag ataatatcat ggtaaccttt      2700
agaaaccagg cgtcaagacc ctattccttc tacagttctc tgatcagcta cgaggaggac      2760
caaagacagg gagctgaacc caggaagaac tttgtgaaac ctaatgagac caagacctac      2820
ttctggaagg tccagcacca tatggcccca actaaagatg aattcgattg caaggcctgg      2880
gcttatttca gcgacgtgga tctcgaaaag gatgtgcaca gcgggttgat cggaccgctt      2940
ttggtgtgcc acacaaatac cctcaatcct gcccacgggc ggcaggtcac agttcaagag      3000
tttgcactct tctttacaat atttgacgag acaaagtcat ggtattttac agagaatatg      3060
gagagaaatt gtcgcgcacc ttgcaacatt cagatggagg accccacatt taaggagaat      3120
tacagatttc atgctatcaa tgggtacatt atggatactc tgcctggtct ggtcatggcc      3180
caggatcagc gcataaggtg gtacttgctg agcatgggat ctaatgagaa tatacacagc      3240
attcacttca gtggccacgt ttttactgtt agaaagaagg aggagtacaa aatggcgctc      3300 tacaacctttt acccgggtgt gtttgagaca gtggagatgc tgccaagcaa ggcaggcatc      3360
tggagggttg agtgtcttat tggggagcat ctgcatgctg aatgtccac cctctttctt      3420 gtgtacagca ataagtgcca gacaccgctt ggcatggcca gcggccacat tagggacttt      3480
cagataactg ccagtggaca gtacggccag tgggctccca agcttgcaag actccactac      3540
tccggaagca taaacgcatg gagcaccaag gaacccttct cttggattaa ggtgacctg      3600 ctggcgccaa tgatcattca cggcataaaa acccaagggg cacgacagaa attttcatct      3660
ttgtatatta gtcagtttat catcatgtac agcttggatg gaaagaagtg gcagacgtac      3720
aggggcaatt ctacaggaac acttatggtg tttttggga atgtcgattc cagcgggatc      3780
aaacataaca tcttcaatcc tcctattatc gcccgatata tccgcctgca ccctacgcat      3840
tactccatca ggtccacatt gagaatgaaa ctgatggggt gcgacctgaa tagttgtagt      3900
atgccactgg gcatggagtc taaagccatc agcgatgcac agatcactgc cagctcttac      3960
ttcaccaaca tgtttgcaac ttggtccccc tctaaagctc gcctgcatct gcagggacgc      4020
tcaaatgcat ggcgaccaca ggtgaacaat ccaaaagagt ggctccaggt cgactttcag      4080
aagacaatga aggtaacagg agtgacaacc cagggtgtaa aaagcctcct tacgagtatg      4140
tacgttaagg agtttctgat ttctagctcc caggacggac accagtggac tctgttcttc      4200
cagaacggca aagtgaaggt atttcaggga aaccaggatt cttttacccc ggtagtgaat      4260
agcctggatc caccgttgct gacccgctat ctgagaattc atccacaatc ctgggtgcat      4320
cagattgccc tccggatgga agtgctcggc tgtgaagctc aggatctgta ttag           4374
```

<210> SEQ ID NO 17
<211> LENGTH: 4374
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 17

```
atgcaaatag agctctccac ctgcttcttt ctgtgccttt tgcgattctg ctttagtgcc      60
accagaagat actacctggg tgcagtggaa ctgtcatggg actatatgca aagtgatctc     120
ggtgagctgc ctgtgacgc aagatttcct cctagagtgc caaaatcttt tccattcaac     180
acctcagtcg tgtacaaaaa gactctgttt gtagaattca cggatcaccct tttcaacatc    240
gctaagccaa ggccaccctg gatgggtctg ctaggtccta ccatccaggc tgaggtttat     300
gatacagtgg tcattacact taagaacatg gcttcccatc ctgtcagtct tcatgctgtt    360
ggtgtatcct actggaaagc ttctgaggga gctgaatatg atgatcagac cagtcaaagg    420
gagaaagaag atgataaagt cttccctggt ggaagccata catatgtctg gcaggtcctg    480
aaagagaatg gtccaatggc ctctgaccca ctgtgcctta cctactcata tctttctcat     540
gtggacctgg taaaagactt gaattcaggc ctcattggag ccctactagt atgtagagaa    600
gggagtctgg ccaaggaaaa gacacagacc ttgcacaaat ttatactact ttttgctgta    660
tttgatgaag ggaaaagttg gcactcagaa acaaagaact ccttgatgca ggatagggat    720
gctgcatctg ctcgggcctg gcctaaaatg cacacagtca atggttatgt aaacaggtct    780
ctgccaggtc tgattggatg ccacaggaaa tcagtctatt ggcatgtgat tggaatgggc    840
accactcctg aagtgcactc aatattcctc gaaggtcaca catttcttgt gaggaaccat    900
cgccaggcgt ccttggaaat ctcgccaata actttcctta ctgctcaaac actcttgatg    960
gaccttggac agtttctact gttttgtcat atctcttccc accaacatga tggcatggaa   1020
gcttatgtca agtagacag ctgtccagag gaaccccaac tacgaatgaa aaataatgaa    1080
gaagcggaag actatgatga tgatcttact gattctgaaa tggatgtggt caggtttgat   1140
gatgacaact ctccttcctt tatccaaatt cgctcagttg ccaagaagca tcctaaaact   1200
tgggtacatt acattgctgc tgaagaggag gactgggact atgctccctt agtcctcgcc   1260
cccgatgaca gaagttataa aagtcaatat ttgaacaatg gccctcagcg gattggtagg   1320
aagtacaaaa aagtccgatt tatggcatac acagatgaaa cctttaagac tcgtgaagct   1380
attcagcatg aatcaggaat cttgggacct ttactttatg gggaagttgg agacacactg   1440
ttgattatat ttaagaatca agcaagcaga ccatataaca tctaccctca cggaatcact   1500
gatgtccgtc ctttgtattc aaggagatta ccaaaaggtg taaaacattt gaaggatttt   1560
ccaattctgc caggagaaat attcaaatat aaatggacag tgactgtaga agatgggcca   1620
actaaatcag atcctcggtg cctgacccgc tattactcta gtttcgttaa tatggagaga   1680
gatctagctt caggactcat tggccctctc ctcatctgct acaaagaatc tgtagatcaa   1740
agaggaaacc agataatgtc agacaagagg aatgtcatcc tgttttctgt atttgatgag   1800
aaccgaagct ggtacctcac agagaatata caacgctttc tccccaatcc agctggagtg   1860
cagcttgagg atccagagtt ccaagcctcc aacatcatgc acagcatcaa tggctatgtt   1920
tttgatagtt tgcagttgtc agtttgtttg catgaggtgg catactggta cattctaagc   1980
attggagcac agactgactt cctttctgtc ttcttctctg gatataccttcaaacacaaa   2040
atggtctatg aagacacact caccctattc ccattctcag agaaactgt cttcatgtcg   2100
atggaaaacc caggtctatg gattctgggg tgccacaact cagactttcg gaacagaggc   2160
atgaccgcct tactgaaggt ttctagttgt gacaagaaca ctggtgatta ttacgaggac   2220
agttatgaag atatttcagc atacttgctg agtaaaaaca atgccattga accaagaagc   2280
```

```
ttctcccaga atccaccagt cttgaaacgc atcaacggg aaataactcg tactactctt    2340
cagtcagatc aagaggaaat tgactatgat gataccatat cagttgaaat gaagaaggaa    2400
gattttgaca tttatgatga ggatgaaaat cagagccccc gcagctttca aaagaaaaca    2460
cgacactatt ttattgctgc agtggagagg ctctgggatt atgggatgag tagctcccca    2520
catgttctaa gaaacagggc tcagagtggc agtgtccctc agttcaagaa agttgttttc    2580
caggaattta ctgatggctc ctttactcag cccttatacc gtggagaact aaatgaacat    2640
ttgggactcc tggggccata tataagagca gaagttgaag ataatatcat ggtaactttc    2700
agaaatcagg cctctcgtcc ctattccttc tattctagcc ttatttctta tgaggaagat    2760
cagaggcaag gagcagaacc tagaaaaaac tttgtcaagc ctaatgaaac caaaacttac    2820
ttttggaaag tgcaacatca tatggcaccc actaaagatg agtttgactg caaagcctgg    2880
gcttatttct ctgatgttga cctggaaaaa gatgtgcact caggcctgat tggaccccct    2940
ctggtctgcc acactaacac actgaaccct gctcatggga gacaagtgac agtacaggaa    3000
tttgctctgt ttttcaccat ctttgatgag accaaaagct ggtacttcac tgaaaatatg    3060
gaaagaaact gcagggctcc ctgcaatatc cagatggaag atcccacttt taaagagaat    3120
tatcgcttcc atgcaatcaa tggctacata atggatacac tacctggctt agtaatggct    3180
caggatcaaa ggattcgatg gtatctgctc agcatgggca gcaatgaaaa catccattct    3240
attcatttca gtggacatgt gttcactgta cgaaaaaaag aggagtataa aatggcactg    3300
tacaatctct atccaggtgt ttttgagaca gtggaaatgt taccatccaa agctggaatt    3360
tggcgggtgg aatgccttat tggcgagcat ctacatgctg ggatgagcac acttttctg    3420
gtgtacagca ataagtgtca gactcccctg gaatggcttc tggacacat tagagatttt    3480
cagattacag cttcaggaca atatggacag tgggccccaa agctggccag acttcattat    3540
tccggatcaa tcaatgcctg gagcaccaag gagccctttt cttggatcaa ggtggatctg    3600
ttggcaccaa tgattattca cggcatcaag acccagggtg cccgtcagaa gttctccagc    3660
ctctacatct ctcagtttat catcatgtat agtcttgatg gaagaagtg cagacttat    3720
cgaggaaatt ccactggaac cttaatggtc ttctttggca atgtggattc atctgggata    3780
aaacacaata ttttttaaccc tccaattatt gctcgataca tccgtttgca cccaactcat    3840
tatagcattc gcagcactct tcgcatggag ttgatgggct gtgatttaaa tagttgcagc    3900
atgccattgg gaatggagag taaagcaata tcagatgcac agattactgc ttcatcctac    3960
tttaccaata tgtttgccac ctggtctcct tcaaaagctc gacttcacct ccaagggagg    4020
agtaatgcct ggagacctca ggtgaataat ccaaaagagt ggctgcaagt ggacttccag    4080
aagacaatga agtcacagg agtaactact cagggagtaa aatctctgct taccagcatg    4140
tatgtgaagg agttcctcat ctccagcagt caagatggcc atcagtggac tctcttttt    4200
cagaatggca agtaaaggt ttttcaggga aatcaagact ccttcacacc tgtggtgaac    4260
tctctagacc caccgttact gactcgctac cttcgaattc acccccagag ttgggtgcac    4320
cagattgccc tgaggatgga ggttctgggc tgcgaggcac aggacctcta ctga          4374
```

<210> SEQ ID NO 18
<211> LENGTH: 4374
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 18

```
atgcagatcg agctgtccac atgcttttt ctgtgcctgc tgcggttctg cttcagcgcc      60
acccggcggt actacctggg cgccgtggag ctgtcctggg actacatgca gagcgacctg     120
ggcgagctgc ccgtggacgc ccggttcccc cccagagtgc ccaagagctt cccccttcaac    180
accagcgtgg tgtacaagaa aaccctgttc gtggagttca ccgaccacct gttcaacatc     240
gccaagccca ggcccccctg gatgggcctg ctgggcccca ccatccaggc cgaggtgtac     300
gacaccgtgg tgatcaccct gaagaacatg gccagccacc ccgtgagcct gcacgccgtg     360
ggcgtgagct actggaaggc ctccgagggc gccgagtacg acgaccagac cagccagcgg     420
gagaaagagg acgacaaagt cttcctggc ggcagccaca cctacgtgtg gcaggtcctg      480
aaagaaaacg gccccatggc ctccgacccc ctgtgcctga cctacagcta cctgagccac     540
gtggacctgg tgaaggacct gaacagcggg ctgattgggg ccctgctggt ctgccgggag     600
ggcagcctgg ccaaagagaa acccagacc ctgcacaagt tcatcctgct gttcgccgtg      660
ttcgacgagg gcaagagctg gcacagcgag accaagaaca gcctgatgca ggaccgggac     720
gccgcctctg ccagagcctg gcccaagatg cacaccgtga acggctacgt gaacagaagc     780
ctgcccggcc tgattggctg ccaccggaag agcgtgtact ggcacgtgat cggcatgggc     840
accacacccg aggtgcacag catctttctg gaagggcaca cctttctggt gcggaaccac     900
cggcaggcca gcctggaaat cagccctatc accttcctga ccgcccagac actgctgatg     960
gacctgggcc agttcctgct gttttgccac atcagctctc accagcacga cggcatggaa    1020
gcctacgtga aggtggactc ctgccccgag gaaccccagc tgcggatgaa gaacaacgag    1080
gaagccgagg actacgacga cgacctgacc gacagcgaga tggacgtggt gcggttcgac    1140
gacgacaaca gccccagctt catccagatc agaagcgtgg ccaagaagca ccccaagacc    1200
tgggtgcact acatcgccgc cgaggaagag gactgggact acgccccct ggtgctggcc     1260
cccgacgaca gaagctacaa gagccagtac ctgaacaatg gccccccagcg gatcggccgg    1320
aagtacaaga agtgcggtt catggcctac accgacgaga ccttcaagac ccggggggcc    1380
atccagcacg agagcggcat cctgggcccc ctgctgtacg gcgaagtggg cgacacactg    1440
ctgatcatct tcaagaacca ggccagccgg ccctacaaca tctaccccca cggcatcacc    1500
gacgtgcggc ccctgtacag caggcggctg cccaagggcg tgaagcacct gaaggacttc    1560
cccatcctgc ccggcgagat cttcaagtac aagtggaccg tgaccgtgga ggacggcccc    1620
accaagagcg accccagatg cctgacccgg tactacagca gcttcgtgaa catggaacgg    1680
gacctggcct ccgggctgat cggacctctg ctgatctgct acaaagaaag cgtggaccag    1740
cggggcaacc agatcatgag cgacaagcgg aacgtgatcc tgttcagcgt gttcgatgag    1800
aaccggtcct ggtatctgac cgagaacatc cagcggtttc tgcccaaccc tgccggggtg    1860
cagctggaag atcccgagtt ccaggccagc aacatcatgc actccatcaa tggctacgtg    1920
ttcgacagcc tgcagctgtc cgtgtgtctg cacgaggtgg cctactggta tatcctgagc    1980
atcggcgccc agaccgactt cctgagcgtg ttcttcagcg gctacacctt caagcacaag    2040
atggtgtacg aggacaccct gaccctgttc cctttcagcg gcgagaccgt gttcatgagc    2100
atggaaaacc ccggcctgtg gatcctgggc tgccacaaca gcgacttccg gaaccggggc    2160
atgaccgccc tgctgaaggt gtccagctgc gacaagaaca ccggcgacta ctacgaggac    2220
agctacgagg atatcagcgc ctacctgctg tccaagaaca acgccatcga gcccagaagc    2280
ttcagccaga accccctgt gctgaagcgg caccagagag agatcacccg gaccaccctg    2340
```

```
cagtccgacc aggaagagat cgattacgac gacaccatca gcgtggagat gaaaaaagaa   2400
gatttcgaca tctacgacga ggacgagaac cagagccccc ggtccttcca gaagaaaacc   2460
cggcactact ttatcgccgc cgtggagcgg ctgtgggact acggcatgag cagcagcccc   2520
cacgtgctgc ggaaccgggc ccagagcggc agcgtgcccc agttcaagaa agtggtgttc   2580
caggaattca ccgacggcag cttcacccag cccctgtacc ggggcgagct gaacgagcac   2640
ctggggctgc tggggcccta catcaggggcc gaagtggagg acaacatcat ggtgaccttc   2700
cggaatcagg ccagcagacc ctactccttc tacagcagcc tgatcagcta cgaagaggac   2760
cagcggcagg gcgctgaacc ccggaagaac ttcgtgaagc ccaatgagac caagacctac   2820
ttctggaaag tgcagcacca catggccccc accaaggacg agttcgactg caaggcctgg   2880
gcctacttca gcgacgtgga tctggaaaag gacgtgcact ctggactgat ggccctctg   2940
ctggtgtgcc acaccaacac cctgaacccc gccacggcc ggcaggtgac cgtgcaggaa   3000
ttcgccctgt tcttcaccat cttcgacgag accagtcct ggtacttcac cgagaatatg   3060
gaacggaact gcagagcccc ctgcaacatc cagatggaag atcctaccct caaagagaac   3120
taccggttcc acgccatcaa cggctacatc atggacaccc tgcctggcct ggtgatggcc   3180
caggaccaga ggatccggtg gtatctgctg tccatgggca gcaacgagaa tatccacagc   3240
atccacttca gcggccacgt gttcaccgtg aggaagaaag aagagtacaa gatggccctg   3300
tacaacctgt accccggcgt gttcgagacc gtggagatgc tgcccagcaa ggccggcatc   3360
tggcgggtgg agtgtctgat cggcgagcac ctgcatgccg ggatgagcac cctgttctg   3420
gtgtacagca acaagtgcca gacccccctg gcatggccca gcggccacat ccgggacttc   3480
cagatcaccg cctccggcca gtacggccag tgggcccccca agctggcccg gctgcactac   3540
agcggcagca tcaacgcctg gtccaccaaa gagcccttca gctggatcaa ggtggacctg   3600
ctggccccta tgatcatcca cggcattaag acccagggcg ccaggcagaa gttcagcagc   3660
ctgtacatca gccagttcat catcatgtac agcctggacg gcaagaagtg gcagacctac   3720
cggggcaaca gcaccggcac cctgatggtg ttcttcggca acgtggacag cagcggcatc   3780
aagcacaaca tcttcaaccc ccccatcatc gcccggtaca tccggctgca ccccaaccac   3840
tacagcatca gatccaccct gcggatggaa ctgatgggct gcgacctgaa ctcctgcagc   3900
atgcctctgg gcatggaaag caaggccatc agcgacgccc agatcacagc cagcagctac   3960
ttcaccaaca tgttcgccac ctggtcccccc tccaaggcca ggctgcacct gcagggccgg   4020
tccaacgcct ggcggcctca ggtgaacaac cccaaagaat ggctgcaggt ggactttcag   4080
aaaaccatga aggtgaccgg cgtgaccacc cagggcgtga aaagcctgct gaccagcatg   4140
tacgtgaaag agtttctgat cagcagcagc caggacggcc accagtggac cctgttcttt   4200
cagaacggca aggtgaaagt gttccagggc aaccaggact ccttcacccc cgtggtgaac   4260
tccctggacc ccccccctgct gacccgctac ctgcggatcc accccagtc ttgggtgcac   4320
cagatcgccc tgaggatgga agtgctggga tgtgaggccc aggatctgta ctga         4374
```

<210> SEQ ID NO 19
<211> LENGTH: 2351
<212> TYPE: PRT
<213> ORGANISM: Homo sapiens

<400> SEQUENCE: 19

```
Met Gln Ile Glu Leu Ser Thr Cys Phe Phe Leu Cys Leu Leu Arg Phe
1               5                   10                  15
```

```
Cys Phe Ser Ala Thr Arg Arg Tyr Tyr Leu Gly Ala Val Glu Leu Ser
         20                  25                  30

Trp Asp Tyr Met Gln Ser Asp Leu Gly Glu Leu Pro Val Asp Ala Arg
         35                  40                  45

Phe Pro Pro Arg Val Pro Lys Ser Phe Pro Phe Asn Thr Ser Val Val
 50                  55                  60

Tyr Lys Lys Thr Leu Phe Val Glu Phe Thr Asp His Leu Phe Asn Ile
 65                  70                  75                  80

Ala Lys Pro Arg Pro Pro Trp Met Gly Leu Leu Gly Pro Thr Ile Gln
                 85                  90                  95

Ala Glu Val Tyr Asp Thr Val Val Ile Thr Leu Lys Asn Met Ala Ser
                 100                 105                 110

His Pro Val Ser Leu His Ala Val Gly Val Ser Tyr Trp Lys Ala Ser
                 115                 120                 125

Glu Gly Ala Glu Tyr Asp Asp Gln Thr Ser Gln Arg Glu Lys Glu Asp
 130                 135                 140

Asp Lys Val Phe Pro Gly Gly Ser His Thr Tyr Val Trp Gln Val Leu
145                  150                 155                 160

Lys Glu Asn Gly Pro Met Ala Ser Asp Pro Leu Cys Leu Thr Tyr Ser
                 165                 170                 175

Tyr Leu Ser His Val Asp Leu Val Lys Asp Leu Asn Ser Gly Leu Ile
                 180                 185                 190

Gly Ala Leu Leu Val Cys Arg Glu Gly Ser Leu Ala Lys Glu Lys Thr
                 195                 200                 205

Gln Thr Leu His Lys Phe Ile Leu Leu Phe Ala Val Phe Asp Glu Gly
                 210                 215                 220

Lys Ser Trp His Ser Glu Thr Lys Asn Ser Leu Met Gln Asp Arg Asp
225                  230                 235                 240

Ala Ala Ser Ala Arg Ala Trp Pro Lys Met His Thr Val Asn Gly Tyr
                 245                 250                 255

Val Asn Arg Ser Leu Pro Gly Leu Ile Gly Cys His Arg Lys Ser Val
                 260                 265                 270

Tyr Trp His Val Ile Gly Met Gly Thr Thr Pro Glu Val His Ser Ile
                 275                 280                 285

Phe Leu Glu Gly His Thr Phe Leu Val Arg Asn His Arg Gln Ala Ser
 290                 295                 300

Leu Glu Ile Ser Pro Ile Thr Phe Leu Thr Ala Gln Thr Leu Leu Met
305                  310                 315                 320

Asp Leu Gly Gln Phe Leu Leu Phe Cys His Ile Ser Ser His Gln His
                 325                 330                 335

Asp Gly Met Glu Ala Tyr Val Lys Val Asp Ser Cys Pro Glu Glu Pro
                 340                 345                 350

Gln Leu Arg Met Lys Asn Asn Glu Glu Ala Glu Asp Tyr Asp Asp Asp
                 355                 360                 365

Leu Thr Asp Ser Glu Met Asp Val Val Arg Phe Asp Asp Asp Asn Ser
                 370                 375                 380

Pro Ser Phe Ile Gln Ile Arg Ser Val Ala Lys Lys His Pro Lys Thr
385                  390                 395                 400

Trp Val His Tyr Ile Ala Ala Glu Glu Glu Asp Trp Asp Tyr Ala Pro
                 405                 410                 415

Leu Val Leu Ala Pro Asp Asp Arg Ser Tyr Lys Ser Gln Tyr Leu Asn
                 420                 425                 430
```

-continued

Asn Gly Pro Gln Arg Ile Gly Arg Lys Tyr Lys Lys Val Arg Phe Met
                435                 440                 445

Ala Tyr Thr Asp Glu Thr Phe Lys Thr Arg Glu Ala Ile Gln His Glu
450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
                500                 505                 510

Gly Val Lys His Leu Lys Asp Phe Pro Ile Leu Pro Gly Glu Ile Phe
            515                 520                 525

Lys Tyr Lys Trp Thr Val Thr Val Glu Asp Gly Pro Thr Lys Ser Asp
530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
            595                 600                 605

Asn Ile Gln Arg Phe Leu Pro Asn Pro Ala Gly Val Gln Leu Glu Asp
            610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
                660                 665                 670

Ser Gly Tyr Thr Phe Lys His Lys Met Val Tyr Glu Asp Thr Leu Thr
            675                 680                 685

Leu Phe Pro Phe Ser Gly Glu Thr Val Phe Met Ser Met Glu Asn Pro
690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Ser Arg His Pro
            755                 760                 765

Ser Thr Arg Gln Lys Gln Phe Asn Ala Thr Thr Ile Pro Glu Asn Asp
770                 775                 780

Ile Glu Lys Thr Asp Pro Trp Phe Ala His Arg Thr Pro Met Pro Lys
785                 790                 795                 800

Ile Gln Asn Val Ser Ser Ser Asp Leu Leu Met Leu Leu Arg Gln Ser
                805                 810                 815

Pro Thr Pro His Gly Leu Ser Leu Ser Asp Leu Gln Glu Ala Lys Tyr
            820                 825                 830

Glu Thr Phe Ser Asp Asp Pro Ser Pro Gly Ala Ile Asp Ser Asn Asn
            835                 840                 845

Ser Leu Ser Glu Met Thr His Phe Arg Pro Gln Leu His His Ser Gly

```
                850                 855                 860
Asp Met Val Phe Thr Pro Glu Ser Gly Leu Gln Leu Arg Leu Asn Glu
865                 870                 875                 880

Lys Leu Gly Thr Thr Ala Ala Thr Glu Leu Lys Lys Leu Asp Phe Lys
                885                 890                 895

Val Ser Ser Thr Ser Asn Asn Leu Ile Ser Thr Ile Pro Ser Asp Asn
                900                 905                 910

Leu Ala Ala Gly Thr Asp Asn Thr Ser Ser Leu Gly Pro Pro Ser Met
            915                 920                 925

Pro Val His Tyr Asp Ser Gln Leu Asp Thr Thr Leu Phe Gly Lys Lys
        930                 935                 940

Ser Ser Pro Leu Thr Glu Ser Gly Gly Pro Leu Ser Leu Ser Glu Glu
945                 950                 955                 960

Asn Asn Asp Ser Lys Leu Leu Glu Ser Gly Leu Met Asn Ser Gln Glu
                965                 970                 975

Ser Ser Trp Gly Lys Asn Val Ser Ser Thr Glu Ser Gly Arg Leu Phe
            980                 985                 990

Lys Gly Lys Arg Ala His Gly Pro Ala Leu Leu Thr Lys Asp Asn Ala
        995                 1000                1005

Leu Phe Lys Val Ser Ile Ser Leu Leu Lys Thr Asn Lys Thr Ser
    1010                1015                1020

Asn Asn Ser Ala Thr Asn Arg Lys Thr His Ile Asp Gly Pro Ser
    1025                1030                1035

Leu Leu Ile Glu Asn Ser Pro Ser Val Trp Gln Asn Ile Leu Glu
    1040                1045                1050

Ser Asp Thr Glu Phe Lys Lys Val Thr Pro Leu Ile His Asp Arg
    1055                1060                1065

Met Leu Met Asp Lys Asn Ala Thr Ala Leu Arg Leu Asn His Met
    1070                1075                1080

Ser Asn Lys Thr Thr Ser Ser Lys Asn Met Glu Met Val Gln Gln
    1085                1090                1095

Lys Lys Glu Gly Pro Ile Pro Pro Asp Ala Gln Asn Pro Asp Met
    1100                1105                1110

Ser Phe Phe Lys Met Leu Phe Leu Pro Glu Ser Ala Arg Trp Ile
    1115                1120                1125

Gln Arg Thr His Gly Lys Asn Ser Leu Asn Ser Gly Gln Gly Pro
    1130                1135                1140

Ser Pro Lys Gln Leu Val Ser Leu Gly Pro Glu Lys Ser Val Glu
    1145                1150                1155

Gly Gln Asn Phe Leu Ser Glu Lys Asn Lys Val Val Val Gly Lys
    1160                1165                1170

Gly Glu Phe Thr Lys Asp Val Gly Leu Lys Glu Met Val Phe Pro
    1175                1180                1185

Ser Ser Arg Asn Leu Phe Leu Thr Asn Leu Asp Asn Leu His Glu
    1190                1195                1200

Asn Asn Thr His Asn Gln Glu Lys Lys Ile Gln Glu Glu Ile Glu
    1205                1210                1215

Lys Lys Glu Thr Leu Ile Gln Glu Asn Val Val Leu Pro Gln Ile
    1220                1225                1230

His Thr Val Thr Gly Thr Lys Asn Phe Met Lys Asn Leu Phe Leu
    1235                1240                1245

Leu Ser Thr Arg Gln Asn Val Glu Gly Ser Tyr Asp Gly Ala Tyr
    1250                1255                1260
```

-continued

```
Ala Pro Val Leu Gln Asp Phe Arg Ser Leu Asn Asp Ser Thr Asn
    1265                1270                1275

Arg Thr Lys Lys His Thr Ala His Phe Ser Lys Lys Gly Glu Glu
    1280                1285                1290

Glu Asn Leu Glu Gly Leu Gly Asn Gln Thr Lys Gln Ile Val Glu
    1295                1300                1305

Lys Tyr Ala Cys Thr Thr Arg Ile Ser Pro Asn Thr Ser Gln Gln
    1310                1315                1320

Asn Phe Val Thr Gln Arg Ser Lys Arg Ala Leu Lys Gln Phe Arg
    1325                1330                1335

Leu Pro Leu Glu Glu Thr Glu Leu Glu Lys Arg Ile Ile Val Asp
    1340                1345                1350

Asp Thr Ser Thr Gln Trp Ser Lys Asn Met Lys His Leu Thr Pro
    1355                1360                1365

Ser Thr Leu Thr Gln Ile Asp Tyr Asn Glu Lys Glu Lys Gly Ala
    1370                1375                1380

Ile Thr Gln Ser Pro Leu Ser Asp Cys Leu Thr Arg Ser His Ser
    1385                1390                1395

Ile Pro Gln Ala Asn Arg Ser Pro Leu Pro Ile Ala Lys Val Ser
    1400                1405                1410

Ser Phe Pro Ser Ile Arg Pro Ile Tyr Leu Thr Arg Val Leu Phe
    1415                1420                1425

Gln Asp Asn Ser Ser His Leu Pro Ala Ala Ser Tyr Arg Lys Lys
    1430                1435                1440

Asp Ser Gly Val Gln Glu Ser Ser His Phe Leu Gln Gly Ala Lys
    1445                1450                1455

Lys Asn Asn Leu Ser Leu Ala Ile Leu Thr Leu Glu Met Thr Gly
    1460                1465                1470

Asp Gln Arg Glu Val Gly Ser Leu Gly Thr Ser Ala Thr Asn Ser
    1475                1480                1485

Val Thr Tyr Lys Lys Val Glu Asn Thr Val Leu Pro Lys Pro Asp
    1490                1495                1500

Leu Pro Lys Thr Ser Gly Lys Val Glu Leu Leu Pro Lys Val His
    1505                1510                1515

Ile Tyr Gln Lys Asp Leu Phe Pro Thr Glu Thr Ser Asn Gly Ser
    1520                1525                1530

Pro Gly His Leu Asp Leu Val Glu Gly Ser Leu Leu Gln Gly Thr
    1535                1540                1545

Glu Gly Ala Ile Lys Trp Asn Glu Ala Asn Arg Pro Gly Lys Val
    1550                1555                1560

Pro Phe Leu Arg Val Ala Thr Glu Ser Ser Ala Lys Thr Pro Ser
    1565                1570                1575

Lys Leu Leu Asp Pro Leu Ala Trp Asp Asn His Tyr Gly Thr Gln
    1580                1585                1590

Ile Pro Lys Glu Glu Trp Lys Ser Gln Glu Lys Ser Pro Glu Lys
    1595                1600                1605

Thr Ala Phe Lys Lys Lys Asp Thr Ile Leu Ser Leu Asn Ala Cys
    1610                1615                1620

Glu Ser Asn His Ala Ile Ala Ala Ile Asn Glu Gly Gln Asn Lys
    1625                1630                1635

Pro Glu Ile Glu Val Thr Trp Ala Lys Gln Gly Arg Thr Glu Arg
    1640                1645                1650
```

| | | | | | | | | | | | |
|---|---|---|---|---|---|---|---|---|---|---|---|
| Leu | Cys | Ser | Gln | Asn | Pro | Val | Leu | Lys | Arg | His | Gln | Arg | Glu |
| | 1655 | | | | 1660 | | | | 1665 | | |

| Ile | Thr | Arg | Thr | Thr | Leu | Gln | Ser | Asp | Gln | Glu | Glu | Ile | Asp | Tyr |
|---|---|---|---|---|---|---|---|---|---|---|---|---|---|---|
| | 1670 | | | | 1675 | | | | 1680 | | |

Asp Asp Thr Ile Ser Val Glu Met Lys Lys Glu Asp Phe Asp Ile
    1685            1690            1695

Tyr Asp Glu Asp Glu Asn Gln Ser Pro Arg Ser Phe Gln Lys Lys
    1700            1705            1710

Thr Arg His Tyr Phe Ile Ala Ala Val Glu Arg Leu Trp Asp Tyr
    1715            1720            1725

Gly Met Ser Ser Ser Pro His Val Leu Arg Asn Arg Ala Gln Ser
    1730            1735            1740

Gly Ser Val Pro Gln Phe Lys Lys Val Val Phe Gln Glu Phe Thr
    1745            1750            1755

Asp Gly Ser Phe Thr Gln Pro Leu Tyr Arg Gly Glu Leu Asn Glu
    1760            1765            1770

His Leu Gly Leu Leu Gly Pro Tyr Ile Arg Ala Glu Val Glu Asp
    1775            1780            1785

Asn Ile Met Val Thr Phe Arg Asn Gln Ala Ser Arg Pro Tyr Ser
    1790            1795            1800

Phe Tyr Ser Ser Leu Ile Ser Tyr Glu Glu Asp Gln Arg Gln Gly
    1805            1810            1815

Ala Glu Pro Arg Lys Asn Phe Val Lys Pro Asn Glu Thr Lys Thr
    1820            1825            1830

Tyr Phe Trp Lys Val Gln His His Met Ala Pro Thr Lys Asp Glu
    1835            1840            1845

Phe Asp Cys Lys Ala Trp Ala Tyr Phe Ser Asp Val Asp Leu Glu
    1850            1855            1860

Lys Asp Val His Ser Gly Leu Ile Gly Pro Leu Leu Val Cys His
    1865            1870            1875

Thr Asn Thr Leu Asn Pro Ala His Gly Arg Gln Val Thr Val Gln
    1880            1885            1890

Glu Phe Ala Leu Phe Phe Thr Ile Phe Asp Glu Thr Lys Ser Trp
    1895            1900            1905

Tyr Phe Thr Glu Asn Met Glu Arg Asn Cys Arg Ala Pro Cys Asn
    1910            1915            1920

Ile Gln Met Glu Asp Pro Thr Phe Lys Glu Asn Tyr Arg Phe His
    1925            1930            1935

Ala Ile Asn Gly Tyr Ile Met Asp Thr Leu Pro Gly Leu Val Met
    1940            1945            1950

Ala Gln Asp Gln Arg Ile Arg Trp Tyr Leu Leu Ser Met Gly Ser
    1955            1960            1965

Asn Glu Asn Ile His Ser Ile His Phe Ser Gly His Val Phe Thr
    1970            1975            1980

Val Arg Lys Lys Glu Glu Tyr Lys Met Ala Leu Tyr Asn Leu Tyr
    1985            1990            1995

Pro Gly Val Phe Glu Thr Val Glu Met Leu Pro Ser Lys Ala Gly
    2000            2005            2010

Ile Trp Arg Val Glu Cys Leu Ile Gly Glu His Leu His Ala Gly
    2015            2020            2025

Met Ser Thr Leu Phe Leu Val Tyr Ser Asn Lys Cys Gln Thr Pro
    2030            2035            2040

Leu Gly Met Ala Ser Gly His Ile Arg Asp Phe Gln Ile Thr Ala

| | | | | | | | | | | | |
|---|---|---|---|---|---|---|---|---|---|---|---|
| | | 2045 | | | 2050 | | | 2055 | | | |
| Ser | Gly | Gln | Tyr | Gly | Gln | Trp | Ala | Pro | Lys | Leu | Ala | Arg | Leu | His |
| | | 2060 | | | | 2065 | | | | 2070 | |
| Tyr | Ser | Gly | Ser | Ile | Asn | Ala | Trp | Ser | Thr | Lys | Glu | Pro | Phe | Ser |
| | | 2075 | | | | 2080 | | | | 2085 | |
| Trp | Ile | Lys | Val | Asp | Leu | Leu | Ala | Pro | Met | Ile | Ile | His | Gly | Ile |
| | | 2090 | | | | 2095 | | | | 2100 | |
| Lys | Thr | Gln | Gly | Ala | Arg | Gln | Lys | Phe | Ser | Ser | Leu | Tyr | Ile | Ser |
| | | 2105 | | | | 2110 | | | | 2115 | |
| Gln | Phe | Ile | Ile | Met | Tyr | Ser | Leu | Asp | Gly | Lys | Lys | Trp | Gln | Thr |
| | | 2120 | | | | 2125 | | | | 2130 | |
| Tyr | Arg | Gly | Asn | Ser | Thr | Gly | Thr | Leu | Met | Val | Phe | Phe | Gly | Asn |
| | | 2135 | | | | 2140 | | | | 2145 | |
| Val | Asp | Ser | Ser | Gly | Ile | Lys | His | Asn | Ile | Phe | Asn | Pro | Pro | Ile |
| | | 2150 | | | | 2155 | | | | 2160 | |
| Ile | Ala | Arg | Tyr | Ile | Arg | Leu | His | Pro | Thr | His | Tyr | Ser | Ile | Arg |
| | | 2165 | | | | 2170 | | | | 2175 | |
| Ser | Thr | Leu | Arg | Met | Glu | Leu | Met | Gly | Cys | Asp | Leu | Asn | Ser | Cys |
| | | 2180 | | | | 2185 | | | | 2190 | |
| Ser | Met | Pro | Leu | Gly | Met | Glu | Ser | Lys | Ala | Ile | Ser | Asp | Ala | Gln |
| | | 2195 | | | | 2200 | | | | 2205 | |
| Ile | Thr | Ala | Ser | Ser | Tyr | Phe | Thr | Asn | Met | Phe | Ala | Thr | Trp | Ser |
| | | 2210 | | | | 2215 | | | | 2220 | |
| Pro | Ser | Lys | Ala | Arg | Leu | His | Leu | Gln | Gly | Arg | Ser | Asn | Ala | Trp |
| | | 2225 | | | | 2230 | | | | 2235 | |
| Arg | Pro | Gln | Val | Asn | Asn | Pro | Lys | Glu | Trp | Leu | Gln | Val | Asp | Phe |
| | | 2240 | | | | 2245 | | | | 2250 | |
| Gln | Lys | Thr | Met | Lys | Val | Thr | Gly | Val | Thr | Thr | Gln | Gly | Val | Lys |
| | | 2255 | | | | 2260 | | | | 2265 | |
| Ser | Leu | Leu | Thr | Ser | Met | Tyr | Val | Lys | Glu | Phe | Leu | Ile | Ser | Ser |
| | | 2270 | | | | 2275 | | | | 2280 | |
| Ser | Gln | Asp | Gly | His | Gln | Trp | Thr | Leu | Phe | Phe | Gln | Asn | Gly | Lys |
| | | 2285 | | | | 2290 | | | | 2295 | |
| Val | Lys | Val | Phe | Gln | Gly | Asn | Gln | Asp | Ser | Phe | Thr | Pro | Val | Val |
| | | 2300 | | | | 2305 | | | | 2310 | |
| Asn | Ser | Leu | Asp | Pro | Pro | Leu | Leu | Thr | Arg | Tyr | Leu | Arg | Ile | His |
| | | 2315 | | | | 2320 | | | | 2325 | |
| Pro | Gln | Ser | Trp | Val | His | Gln | Ile | Ala | Leu | Arg | Met | Glu | Val | Leu |
| | | 2330 | | | | 2335 | | | | 2340 | |
| Gly | Cys | Glu | Ala | Gln | Asp | Leu | Tyr | | | | |
| | | 2345 | | | | 2350 | | | | | |

<210> SEQ ID NO 20
<211> LENGTH: 4374
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 20
atgcagattg agctgagcac ctgcttcttc ctgtgcctgc tgaggttctg cttctctgcc      60
accaggagat actacctggg cgccgtggag ctgagctggg actacatgca gtctgacctg     120
ggcgagctgc ctgtggacgc caggttcccc cccagagtgc ccaagagctt ccccttcaac     180

```
acctcagtgg tgtacaagaa gaccctgttc gtggagttca ccgaccacct gttcaacatc    240
gccaagccca ggccccctg  gatgggcctg ctgggcccca ccatccaggc cgaggtgtac    300
gacaccgtgg tgatcaccct gaagaacatg gccagccacc ccgtgagcct gcacgccgtg    360
ggcgtgagct actggaaggc ctctgagggc gccgagtatg acgaccagac cagccagagg    420
gagaaggagg acgacaaggt gttccccggc ggcagccaca cctacgtgtg gcaggtgctg    480
aaggagaacg gccccatggc cagcgacccc ctgtgcctga cctacagcta cctgagccac    540
gtggacctgg tgaaggacct gaactctggc ctgatcggcg ccctgctggt gtgcagggag    600
ggcagcctgg ccaaggagaa gacccagacc ctgcacaagt tcatcctgct gttcgccgtg    660
ttcgatgagg gcaagagctg gcacagcgag accaagaaca gcctgatgca ggacagggat    720
gccgcctctg ccagggcctg gcccaagatg cacaccgtga acggctacgt gaacaggagc    780
ctgcccggcc tgatcggctg ccacaggaag tctgtgtact ggcacgtgat cggcatgggc    840
accacccccg aggtgcacag catcttcctg gagggccaca ccttcctggt gaggaaccac    900
aggcaggcca gcctggagat cagccccatc accttcctga ccgcccagac cctgctgatg    960
gacctgggcc agttcctgct gttctgccac atcagcagcc accagcacga cggcatggag   1020
gcctacgtga aggtggacag ctgccccgag gagccccagc tgaggatgaa gaacaacgag   1080
gaggccgagg actatgatga tgacctgacc gactctgaga tggacgtggt gaggtttgat   1140
gatgacaaca gccccagctt catccagatc aggtctgtgg ccaagaagca ccccaagacc   1200
tgggtgcact acatcgccgc cgaggaggag gactgggact acgccccct  ggtgctggcc   1260 cccgacgaca ggagctacaa gagccagtac ctgaacaacg gcccccagag gatcggcagg   1320
aagtacaaga aggtcagatt catggcctac accgacgaga ccttcaagac cagggaggcc   1380
atccagcacg agtctggcat cctgggcccc ctgctgtacg gcgaggtggg cgacaccctg   1440
ctgatcatct tcaagaacca ggccagcagg ccctacaaca tctaccccca cggcatcacc   1500
gatgtgaggc ccctgtacag caggaggctg cccaagggcg tgaagcacct gaaggacttc   1560
cccatcctgc ccggcgagat cttcaagtac aagtggaccg tgaccgtgga ggatggcccc   1620
accaagtctg accccaggtg cctgaccagg tactacagca gcttcgtgaa catggagagg   1680
gacctggcct ctggcctgat cggccccctg ctgatctgct acaaggagag cgtggaccag   1740
aggggcaacc agatcatgtc tgacaagagg aacgtgatcc tgttctctgt gttcgatgag   1800
aacaggagct ggtatctgac cgagaacatc cagaggttcc tgcccaaccc cgccggcgtg   1860
cagctggagg accccgagtt ccaggccagc aacatcatgc acagcatcaa cggctacgtg   1920
ttcgacagcc tgcagctgtc tgtgtgcctg cacgaggtgg cctactggta catcctgagc   1980
atcggcgccc agaccgactt cctgtctgtg ttcttctctg gctacacctt caagcacaag   2040
atggtgtacg aggacaccct gaccctgttc cccttcagcg gcgagaccgt gttcatgagc   2100
atggagaacc ccggcctgtg gatcctgggc tgccacaaca gcgacttcag gaacaggggc   2160
atgaccgccc tgctgaaagt cagcagctgc gacaagaaca ccggcgacta ctacgaggac   2220
agctacgagg acatcagcgc ctacctgctg agcaagaaca acgccatcga gcccaggagc   2280
ttcagccaga ccccccccgt gctgaagagg caccagaggg gatcaccag  gaccacactg    2340 cagagcgacc aggaggagat cgactatgat gacaccatca gcgtggagat gaagaaggag   2400
gacttcgaca tctacgacga ggacgagaac cagagcccca ggagcttcca agaagaagacc   2460 aggcactact tcatcgccgc cgtggagagg ctgtgggact atggcatgag cagcagcccc   2520
cacgtgctga ggaacagggc ccagagcggc agcgtgcccc agttcaagaa ggtggtgttc    2580
```

-continued

```
caggagttca ccgacggcag cttcacccag ccctgtaca gaggcgagct gaacgagcac   2640
ctgggcctgc tgggcccta catcagggcc gaggtggagg acaacatcat ggtgaccttc   2700
aggaaccagg ccagcaggcc ctacagcttc tacagcagcc tgatcagcta cgaggaggac   2760
cagaggcagg gcgccgagcc caggaagaac ttcgtgaagc ccaacgagac caagacctac   2820
ttctggaagg tgcagcacca catggccccc accaaggacg agttcgactg caaggcctgg   2880
gcctacttct ctgatgtgga cctggagaag gacgtgcaca cgggcctgat cggccccctg   2940
ctggtgtgcc acaccaacac cctgaacccc gcccacggca ggcaggtgac cgtgcaggag   3000
ttcgccctgt tcttcaccat cttcgacgag accaagagct ggtacttcac cgagaacatg   3060
gagaggaact gcagggcccc ctgcaacatc agatggagg accccacctt caaggagaac   3120
tacaggttcc acgccatcaa cggctacatc atggacaccc tgcccggcct ggtgatggcc   3180
caggaccaga ggatcaggtg gtatctgctg agcatgggca gcaacgagaa catccacagc   3240
atccacttca gcggccacgt gttcaccgtg aggaagaagg aggagtacaa gatggccctg   3300
tacaacctgt accccggcgt gttcgagacc gtggagatgc tgcccagcaa ggccggcatc   3360
tggagggtgg agtgcctgat cggcgagcac ctgcacgccg gcatgagcac cctgttcctg   3420
gtgtacagca acaagtgcca gacccccctg ggcatggcca gcggccacat cagggacttc   3480
cagatcaccg cctctggcca gtacggccag tgggccccca gctggccag ctgcactac   3540 agcggcagca tcaacgcctg gagcaccaag gagcccttca gctggatcaa ggtggacctg   3600
ctggccccca tgatcatcca cggcatcaag acccagggcg ccaggcagaa gttcagcagc   3660
ctgtacatca gccagttcat catcatgtac agcctggacg caagaagtg gcagacctac   3720 aggggcaaca gcaccggcac cctgatggtg ttcttcggca acgtggacag cagcggcatc   3780
aagcacaaca tcttcaaccc ccccatcatc gccaggtaca tcaggctgca ccccacccac   3840
tacagcatca ggagcaccct gcggatggaa ctgatgggct gcgacctgaa cagctgcagc   3900
atgcccctgg gcatggagag caaggccatc tctgacgccc agatcaccgc cagcagctac   3960
ttcaccaaca tgttcgccac ctggagcccc agcaaggcca ggctgcacct gcagggcagg   4020
agcaacgcct ggaggcccca ggtgaacaac cccaaggagt ggctgcaggt ggacttccag   4080
aagaccatga aggtgaccgg cgtgaccacc caggcgtga agagcctgct gaccagcatg   4140
tacgtgaagg agttcctgat cagcagcagc caggacggcc accagtggac cctgttcttc   4200
cagaacggca aagtgaaggt gttccagggc aaccaggaca gcttcacccc cgtggtgaac   4260
agcctggacc ccccctgct gaccaggtat ctgaggatcc accccagag ctgggtgcac   4320 cagatcgccc tgagaatgga agtgctggga tgcgaggccc aggacctgta ctga         4374
```

<210> SEQ ID NO 21
<211> LENGTH: 1457
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 21

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg

-continued

```
            35                  40                  45
Phe Pro Pro Arg Val Pro Lys Ser Phe Pro Phe Asn Thr Ser Val Val
 50                  55                  60
Tyr Lys Lys Thr Leu Phe Val Glu Phe Thr Asp His Leu Phe Asn Ile
 65                  70                  75                  80
Ala Lys Pro Arg Pro Trp Met Gly Leu Leu Gly Pro Thr Ile Gln
                 85                  90                  95
Ala Glu Val Tyr Asp Thr Val Val Ile Thr Leu Lys Asn Met Ala Ser
                100                 105                 110
His Pro Val Ser Leu His Ala Val Gly Val Ser Tyr Trp Lys Ala Ser
                115                 120                 125
Glu Gly Ala Glu Tyr Asp Asp Gln Thr Ser Gln Arg Glu Lys Glu Asp
130                 135                 140
Asp Lys Val Phe Pro Gly Gly Ser His Thr Tyr Val Trp Gln Val Leu
145                 150                 155                 160
Lys Glu Asn Gly Pro Met Ala Ser Asp Pro Leu Cys Leu Thr Tyr Ser
                165                 170                 175
Tyr Leu Ser His Val Asp Leu Val Lys Asp Leu Asn Ser Gly Leu Ile
                180                 185                 190
Gly Ala Leu Leu Val Cys Arg Glu Gly Ser Leu Ala Lys Glu Lys Thr
                195                 200                 205
Gln Thr Leu His Lys Phe Ile Leu Leu Phe Ala Val Phe Asp Glu Gly
                210                 215                 220
Lys Ser Trp His Ser Glu Thr Lys Asn Ser Leu Met Gln Asp Arg Asp
225                 230                 235                 240
Ala Ala Ser Ala Arg Ala Trp Pro Lys Met His Thr Val Asn Gly Tyr
                245                 250                 255
Val Asn Arg Ser Leu Pro Gly Leu Ile Gly Cys His Arg Lys Ser Val
                260                 265                 270
Tyr Trp His Val Ile Gly Met Gly Thr Thr Pro Glu Val His Ser Ile
                275                 280                 285
Phe Leu Glu Gly His Thr Phe Leu Val Arg Asn His Arg Gln Ala Ser
290                 295                 300
Leu Glu Ile Ser Pro Ile Thr Phe Leu Thr Ala Gln Thr Leu Leu Met
305                 310                 315                 320
Asp Leu Gly Gln Phe Leu Leu Phe Cys His Ile Ser Ser His Gln His
                325                 330                 335
Asp Gly Met Glu Ala Tyr Val Lys Val Asp Ser Cys Pro Glu Glu Pro
                340                 345                 350
Gln Leu Arg Met Lys Asn Asn Glu Glu Ala Glu Asp Tyr Asp Asp Asp
                355                 360                 365
Leu Thr Asp Ser Glu Met Asp Val Val Arg Phe Asp Asp Asp Asn Ser
                370                 375                 380
Pro Ser Phe Ile Gln Ile Arg Ser Val Ala Lys Lys His Pro Lys Thr
385                 390                 395                 400
Trp Val His Tyr Ile Ala Ala Glu Glu Glu Asp Trp Asp Tyr Ala Pro
                405                 410                 415
Leu Val Leu Ala Pro Asp Asp Arg Ser Tyr Lys Ser Gln Tyr Leu Asn
                420                 425                 430
Asn Gly Pro Gln Arg Ile Gly Arg Lys Tyr Lys Lys Val Arg Phe Met
                435                 440                 445
Ala Tyr Thr Asp Glu Thr Phe Lys Thr Arg Glu Ala Ile Gln His Glu
450                 455                 460
```

```
Ser Gly Ile Leu Gly Pro Leu Leu Tyr Gly Val Gly Asp Thr Leu
465                 470                 475                 480

Leu Ile Ile Phe Lys Asn Gln Ala Ser Arg Pro Tyr Asn Ile Tyr Pro
            485                 490                 495

His Gly Ile Thr Asp Val Arg Pro Leu Tyr Ser Arg Arg Leu Pro Lys
        500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
                580                 585                 590

Ile Leu Phe Ser Val Phe Asp Glu Asn Arg Ser Trp Tyr Leu Thr Glu
            595                 600                 605

Asn Ile Gln Arg Phe Leu Pro Asn Pro Ala Gly Val Gln Leu Glu Asp
610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
                660                 665                 670

Ser Gly Tyr Thr Phe Lys His Lys Met Val Tyr Glu Asp Thr Leu Thr
                675                 680                 685

Leu Phe Pro Phe Ser Gly Glu Thr Val Phe Met Ser Met Glu Asn Pro
690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
                740                 745                 750

Asn Asn Ala Ile Glu Pro Arg Ser Phe Ser Gln Asn Pro Pro Val Leu
            755                 760                 765

Lys Arg His Gln Arg Glu Ile Thr Arg Thr Thr Leu Gln Ser Asp Gln
            770                 775                 780

Glu Glu Ile Asp Tyr Asp Asp Thr Ile Ser Val Glu Met Lys Lys Glu
785                 790                 795                 800

Asp Phe Asp Ile Tyr Asp Glu Asp Glu Asn Gln Ser Pro Arg Ser Phe
                805                 810                 815

Gln Lys Lys Thr Arg His Tyr Phe Ile Ala Ala Val Glu Arg Leu Trp
            820                 825                 830

Asp Tyr Gly Met Ser Ser Ser Pro His Val Leu Arg Asn Arg Ala Gln
            835                 840                 845

Ser Gly Ser Val Pro Gln Phe Lys Lys Val Val Phe Gln Glu Phe Thr
            850                 855                 860

Asp Gly Ser Phe Thr Gln Pro Leu Tyr Arg Gly Glu Leu Asn Glu His
865                 870                 875                 880
```

```
Leu Gly Leu Leu Gly Pro Tyr Ile Arg Ala Glu Val Glu Asp Asn Ile
                885                 890                 895

Met Val Thr Phe Arg Asn Gln Ala Ser Arg Pro Tyr Ser Phe Tyr Ser
                900                 905                 910

Ser Leu Ile Ser Tyr Glu Glu Asp Gln Arg Gln Gly Ala Glu Pro Arg
                915                 920                 925

Lys Asn Phe Val Lys Pro Asn Glu Thr Lys Thr Tyr Phe Trp Lys Val
                930                 935                 940

Gln His His Met Ala Pro Thr Lys Asp Glu Phe Asp Cys Lys Ala Trp
945                 950                 955                 960

Ala Tyr Phe Ser Asp Val Asp Leu Glu Lys Asp Val His Ser Gly Leu
                965                 970                 975

Ile Gly Pro Leu Leu Val Cys His Thr Asn Thr Leu Asn Pro Ala His
                980                 985                 990

Gly Arg Gln Val Thr Val Gln Glu Phe Ala Leu Phe Phe Thr Ile Phe
                995                 1000                1005

Asp Glu Thr Lys Ser Trp Tyr Phe Thr Glu Asn Met Glu Arg Asn
        1010                1015                1020

Cys Arg Ala Pro Cys Asn Ile Gln Met Glu Asp Pro Thr Phe Lys
        1025                1030                1035

Glu Asn Tyr Arg Phe His Ala Ile Asn Gly Tyr Ile Met Asp Thr
        1040                1045                1050

Leu Pro Gly Leu Val Met Ala Gln Asp Gln Arg Ile Arg Trp Tyr
        1055                1060                1065

Leu Leu Ser Met Gly Ser Asn Glu Asn Ile His Ser Ile His Phe
        1070                1075                1080

Ser Gly His Val Phe Thr Val Arg Lys Lys Glu Glu Tyr Lys Met
        1085                1090                1095

Ala Leu Tyr Asn Leu Tyr Pro Gly Val Phe Glu Thr Val Glu Met
        1100                1105                1110

Leu Pro Ser Lys Ala Gly Ile Trp Arg Val Glu Cys Leu Ile Gly
        1115                1120                1125

Glu His Leu His Ala Gly Met Ser Thr Leu Phe Leu Val Tyr Ser
        1130                1135                1140

Asn Lys Cys Gln Thr Pro Leu Gly Met Ala Ser Gly His Ile Arg
        1145                1150                1155

Asp Phe Gln Ile Thr Ala Ser Gly Gln Tyr Gly Gln Trp Ala Pro
        1160                1165                1170

Lys Leu Ala Arg Leu His Tyr Ser Gly Ser Ile Asn Ala Trp Ser
        1175                1180                1185

Thr Lys Glu Pro Phe Ser Trp Ile Lys Val Asp Leu Leu Ala Pro
        1190                1195                1200

Met Ile Ile His Gly Ile Lys Thr Gln Gly Ala Arg Gln Lys Phe
        1205                1210                1215

Ser Ser Leu Tyr Ile Ser Gln Phe Ile Ile Met Tyr Ser Leu Asp
        1220                1225                1230

Gly Lys Lys Trp Gln Thr Tyr Arg Gly Asn Ser Thr Gly Thr Leu
        1235                1240                1245

Met Val Phe Phe Gly Asn Val Asp Ser Ser Gly Ile Lys His Asn
        1250                1255                1260

Ile Phe Asn Pro Pro Ile Ile Ala Arg Tyr Ile Arg Leu His Pro
        1265                1270                1275

Thr His Tyr Ser Ile Arg Ser Thr Leu Arg Met Glu Leu Met Gly
```

| | | | | | | | | | |
|---|---|---|---|---|---|---|---|---|---|
| | | 1280 | | | 1285 | | | 1290 | |
| Cys | Asp | Leu | Asn | Ser | Cys | Ser | Met | Pro | Leu | Gly | Met | Glu | Ser | Lys |
| | | 1295 | | | 1300 | | | 1305 | |
| Ala | Ile | Ser | Asp | Ala | Gln | Ile | Thr | Ala | Ser | Ser | Tyr | Phe | Thr | Asn |
| | | 1310 | | | 1315 | | | 1320 | |
| Met | Phe | Ala | Thr | Trp | Ser | Pro | Ser | Lys | Ala | Arg | Leu | His | Leu | Gln |
| | | 1325 | | | 1330 | | | 1335 | |

Cys Asp Leu Asn Ser Cys Ser Met Pro Leu Gly Met Glu Ser Lys
            1295                1300                1305

Ala Ile Ser Asp Ala Gln Ile Thr Ala Ser Ser Tyr Phe Thr Asn
            1310                1315                1320

Met Phe Ala Thr Trp Ser Pro Ser Lys Ala Arg Leu His Leu Gln
            1325                1330                1335

Gly Arg Ser Asn Ala Trp Arg Pro Gln Val Asn Asn Pro Lys Glu
            1340                1345                1350

Trp Leu Gln Val Asp Phe Gln Lys Thr Met Lys Val Thr Gly Val
            1355                1360                1365

Thr Thr Gln Gly Val Lys Ser Leu Leu Thr Ser Met Tyr Val Lys
            1370                1375                1380

Glu Phe Leu Ile Ser Ser Ser Gln Asp Gly His Gln Trp Thr Leu
            1385                1390                1395

Phe Phe Gln Asn Gly Lys Val Lys Val Phe Gln Gly Asn Gln Asp
            1400                1405                1410

Ser Phe Thr Pro Val Val Asn Ser Leu Asp Pro Pro Leu Leu Thr
            1415                1420                1425

Arg Tyr Leu Arg Ile His Pro Gln Ser Trp Val His Gln Ile Ala
            1430                1435                1440

Leu Arg Met Glu Val Leu Gly Cys Glu Ala Gln Asp Leu Tyr
            1445                1450                1455

<210> SEQ ID NO 22
<211> LENGTH: 2220
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22

```
gccaccagga gatactacct gggcgccgtg gagctgagct gggactacat gcagtctgac      60
ctgggcgagc tgcctgtgga cgccaggttc ccccccagag tgcccaagag cttcccttc     120
aacacctcag tggtgtacaa gaagaccctg ttcgtggagt tcaccgacca cctgttcaac     180
atcgccaagc caggcccccc ctggatgggc ctgctgggcc caccatcca ggccgaggtg     240
tacgacaccg tggtgatcac cctgaagaac atggccagcc accccgtgag cctgcacgcc     300
gtgggcgtga gctactggaa ggcctctgag ggcgccgagt atgacgacca gaccagccag     360
agggagaagg aggacgacaa ggtgttcccc ggcggcagcc acacctacgt gtggcaggtg     420
ctgaaggaga acggccccat ggccagcgac cccctgtgcc tgacctacag ctacctgagc     480
cacgtggacc tggtgaagga cctgaactct ggcctgatcg gcgccctgct ggtgtgcagg     540
gagggcagcc tggccaagga gaagacccag accctgcaca gttcatcct gctgttcgcc     600
gtgttcgatg agggcaagag ctggcacagc gagaccaaga caagcctgat gcaggacagg     660
gatgccgcct ctgccagggc ctggcccaag atgcacaccg tgaacggcta cgtgaacagg     720
agcctgcccg gcctgatcgg ctgccacagg aagtctgtgt actggcacgt gatcggcatg     780
ggcaccaccc ccgaggtgca cagcatcttc ctggagggcc acaccttcct ggtgaggaac     840
cacaggcagg ccagcctgga gatcagcccc atcaccttcc tgaccgccca gaccctgctg     900
atggacctgg gccagttcct gctgttctgc cacatcagca gccaccagca cgacggcatg     960
gaggcctacg tgaaggtgga cagctgcccc gaggagcccc agctgaggat gaagaacaac    1020
```

```
gaggaggccg aggactatga tgatgacctg accgactctg agatggacgt ggtgaggttt    1080
gatgatgaca acagccccag cttcatccag atcaggtctg tggccaagaa gcaccccaag    1140
acctgggtgc actacatcgc cgccgaggag gaggactggg actacgcccc cctggtgctg    1200
gcccccgacg acaggagcta caagagccag tacctgaaca acggccccca gaggatcggc    1260
aggaagtaca agaaggtcag attcatggcc tacaccgacg agaccttcaa gaccagggag    1320
gccatccagc acgagtctgg catcctgggc cccctgctgt acggcgaggt gggcgacacc    1380
ctgctgatca tcttcaagaa ccaggccagc aggccctaca acatctaccc ccacggcatc    1440
accgatgtga ggcccctgta cagcaggagg ctgcccaagg gcgtgaagca cctgaaggac    1500
ttccccatcc tgcccggcga gatcttcaag tacaagtgga ccgtgaccgt ggaggatggc    1560
cccaccaagt ctgaccccag gtgcctgacc aggtactaca gcagcttcgt gaacatggag    1620
agggacctgg cctctggcct gatcggcccc ctgctgatct gctacaagga gagcgtggac    1680
cagaggggca accagatcat gtctgacaag aggaacgtga tcctgttctc tgtgttcgat    1740
gagaacagga gctggtatct gaccgagaac atccagaggt tcctgcccaa ccccgccggc    1800
gtgcagctgg aggaccccga gttccaggcc agcaacatca tgcacagcat caacggctac    1860
gtgttcgaca gcctgcagct gtctgtgtgc ctgcacgagg tggcctactg gtacatcctg    1920
agcatcggcg cccagaccga cttcctgtct gtgttcttct ctggctacac cttcaagcac    1980
aagatggtgt acgaggacac cctgaccctg ttccccttca gcggcgagac cgtgttcatg    2040
agcatggaga ccccggcct gtggatcctg ggctgccaca acagcgactt caggaacagg    2100
ggcatgaccg ccctgctgaa agtcagcagc tgcgacaaga acaccggcga ctactacgag    2160
gacagctacg aggacatcag cgcctacctg ctgagcaaga caacgccat cgagcccagg    2220
```

<210> SEQ ID NO 23
<211> LENGTH: 2052
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23

```
gagatcacca ggaccaccct gcagagcgac caggaggaga tcgactatga tgacaccatc      60
agcgtggaga tgaagaagga ggacttcgac atctacgacg aggacgagaa ccagagcccc     120
aggagcttcc agaagaagac caggcactac ttcatcgccg ccgtggagag ctgtgggac      180 tatggcatga gcagcagccc ccacgtgctg aggaacaggg cccagagcgg cagcgtgccc     240
cagttcaaga aggtggtgtt ccaggagttc accgacggca gcttcaccca gcccctgtac     300
agaggcgagc tgaacgagca cctgggcctg ctgggcccct acatcagggc cgaggtggag     360
gacaacatca tggtgacctt caggaaccag gccagcaggc cctacagctt ctacagcagc     420
ctgatcagct acgaggagga ccagaggcag ggcgccgagc caggaagaa cttcgtgaag     480 cccaacgaga ccaagaccta cttctggaag gtgcagcacc acatggcccc caccaaggac     540
gagttcgact gcaaggcctg gcctacttc tctgatgtgg acctggagaa ggacgtgcac     600
agcggcctga tcggcccct gctggtgtgc cacaccaaca ccctgaaccc cgcccacggc     660
aggcaggtga ccgtgcagga gttcgccctg ttcttcacca tcttcgacga gaccaagagc     720
tggtacttca ccgagaacat ggagaggaac tgcagggccc cctgcaacat ccagatggag     780
gaccccacct tcaaggagaa ctacaggttc cacgccatca acggctacat catggacacc     840
```

```
ctgcccggcc tggtgatggc ccaggaccag aggatcaggt ggtatctgct gagcatgggc    900
agcaacgaga acatccacag catccacttc agcggccacg tgttcaccgt gaggaagaag    960
gaggagtaca agatggccct gtacaacctg taccccggcg tgttcgagac cgtggagatg   1020
ctgcccagca aggccggcat ctggagggtg gagtgcctga tcggcgagca cctgcacgcc   1080
ggcatgagca ccctgttcct ggtgtacagc aacaagtgcc agaccccct gggcatggcc    1140 agcggccaca tcagggactt ccagatcacc gcctctggcc agtacggcca gtgggccccc   1200
aagctgggcc ggctgcacta cagcggcagc atcaacgcct ggagcaccaa ggagcccttc   1260
agctggatca aggtggacct gctggccccc atgatcatcc acggcatcaa gacccagggc   1320
gccaggcaga agttcagcag cctgtacatc agccagttca tcatcatgta cagcctggac   1380
ggcaagaagt ggcagaccta cagggcaac agcaccggca ccctgatggt gttcttcggc    1440
aacgtggaca gcagcggcat caagcacaac atcttcaacc cccccatcat cgccaggtac   1500
atcaggctgc accccaccca ctacagcatc aggagcaccc tgcggatgga actgatgggc   1560
tgcgacctga acagctgcag catgcccctg ggcatggaga gcaaggccat ctctgacgcc   1620
cagatcaccg ccagcagcta cttcaccaac atgttcgcca cctggagccc cagcaaggcc   1680
aggctgcacc tgcagggcag gagcaacgcc tggaggcccc aggtgaacaa ccccaaggag   1740
tggctgcagg tggacttcca gaagaccatg aaggtgaccg gcgtgaccac ccagggcgtg   1800
aagagcctgc tgaccagcat gtacgtgaag gagttcctga tcagcagcag ccaggacggc   1860
caccagtgga ccctgttctt ccagaacggc aaagtgaagg tgttccaggg caaccaggac   1920
agcttcaccc ccgtggtgaa cagcctggac ccccccctgc tgaccaggta tctgaggatc   1980
cacccccaga gctgggtgca ccagatcgcc ctgagaatgg aagtgctggg atgcgaggcc   2040
caggacctgt ac                                                        2052

<210> SEQ ID NO 24
<211> LENGTH: 2220
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24
gccaccagga gatactacct gggggctgtg aactttcttg ggactacatg cagtctgac     60 ctgggagagc tgcctgtgga tgccaggttc ccacccagag tgcccaagtc cttcccattc    120
aacacctctg tggtctacaa gaagacactc tttgtggaat tcactgacca cctgttcaac    180
attgcaaaac ccagaccacc ctggatggga ctcctgggac ccaccattca ggctgaggtg    240
tatgacactg tggtcatcac cctcaagaac atggcatccc accctgtgtc tctgcatgct    300
gtgggagtct catactggaa agcctctgaa ggggctgagt atgatgacca gacatcccag    360
agagagaaag aggatgacaa ggtgttccct gggggatctc acacctatgt gtggcaagtc    420
ctcaaggaga atggacccat ggcatctgac ccactctgcc tgacatactc ctacctttct    480
catgtggacc tggtcaagga cctcaactct ggactgattg ggcactgct ggtgtgcagg     540 gaaggatccc tggccaagga gaaacccag acactgcaca gttcattct cctgtttgct     600 gtctttgatg agggcaagtc ttggcactct gaaacaaaga actccctgat gcaagacagg    660
gatgctgcct tgccagggc atgggcccaag atgcacactg tgaatggcta tgtgaacaga    720
tcactgcctg gactcattgg ctgccacagg aaatctgtct actggcatgt gattggcatg    780
```

| | | |
|---|---|---|
| gggacaaccc ctgaagtgca ctccattttc ctggagggac acaccttcct ggtcaggaac | 840 | |
| cacagacaag cctctctgga gatctctccc atcaccttcc tcactgcaca gacactgctg | 900 | |
| atggaccttg acagttcct gctgttctgc cacatctctt cccaccagca tgatggcatg | 960 | |
| gaagcctatg tcaaggtgga ctcatgccct gaggaaccac agctcaggat gaagaacaat | 1020 | |
| gaggaggctg aggactatga tgatgacctg actgactctg agatggatgt ggtcagattt | 1080 | |
| gatgatgaca actctccatc cttcattcag atcaggtctg tggcaaagaa acaccccaag | 1140 | |
| acatgggtgc actacattgc tgctgaggaa gaggactggg actatgcacc actggtcctg | 1200 | |
| gcccctgatg acaggagcta caagtctcag tacctcaaca atggcccaca agaattgga | 1260 | |
| agaaagtaca gaaagtcag attcatggcc tacactgatg aaaccttcaa gacaagagaa | 1320 | |
| gccattcagc atgagtctgg cattctggga ccactcctgt atgggaagt gggagacacc | 1380 | |
| ctgctcatca tcttcaagaa ccaggcctcc aggccctaca acatctaccc acatggcatc | 1440 | |
| actgatgtca ggcccctgta cagcaggaga ctgccaaaag gggtgaaaca cctcaaggac | 1500 | |
| ttccccattc tgcctggaga gatcttcaag tacaagtgga ctgtcactgt ggaggatgga | 1560 | |
| ccaacaaagt ctgaccccag gtgcctcacc agatactact cctcttttgt gaacatggag | 1620 | |
| agagacctgg catctggact gattggacca ctgctcatct gctacaagga gtctgtggac | 1680 | |
| cagagaggca accagatcat gtctgacaag agaaatgtga ttctgttctc tgtctttgat | 1740 | |
| gagaacagat catggtacct gactgagaac attcagagat tcctgcccaa ccctgctggg | 1800 | |
| gtgcaactgg aagaccctga gttccaggca agcaacatca tgcactccat caatggctat | 1860 | |
| gtgtttgact ctctccagct ttctgtctgc ctgcatgagg tggcctactg gtacattctt | 1920 | |
| tctattgggg cacaaactga cttcctttct gtcttcttct ctggatacac cttcaagcac | 1980 | |
| aagatggtgt atgaggacac cctgacactc ttcccattct ctggggaaac tgtgttcatg | 2040 | |
| agcatggaga accctggact gtggattctg gatgccaca actctgactt cagaaacagg | 2100 | |
| ggaatgactg cactgctcaa agtctcctcc tgtgacaaga acactgggga ctactatgag | 2160 | |
| gactcttatg aggacatctc tgcctacctg ctcagcaaga caatgccat tgagcccaga | 2220 | |

<210> SEQ ID NO 25
<211> LENGTH: 2052
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25

| | | |
|---|---|---|
| gagatcacca ggacaaccct ccagtctgac caggaagaga ttgactatga tgacaccatt | 60 | |
| tctgtggaga tgaagaagga ggactttgac atctatgatg aggacgagaa ccagtctcca | 120 | |
| agatcattcc agaagaagac aagacactac ttcattgctg ctgtggaaag actgtgggac | 180 | |
| tatggcatgt cttcctctcc ccatgtcctc aggaacaggg cacagtctgg ctctgtgcca | 240 | |
| cagttcaaga aagtggtctt ccaggagttc actgatggct cattcaccca gccctgtac | 300 | |
| agagggaac tgaatgagca cctgggactc tgggaccat acatcagggc tgaggtggaa | 360 | |
| gacaacatca tggtgacatt cagaaaccag gcctccaggc cctacagctt ctactcttcc | 420 | |
| ctcatcagct atgaggaaga ccagagacaa ggggctgagc caagaaagaa ctttgtgaaa | 480 | |
| cccaatgaaa ccaagaccta cttctggaaa gtccagcacc atggcacc accaaggat | 540 | |
| gagtttgact gcaaggcctg gcatacttc tctgatgtgg acctggagaa agatgtgcac | 600 | |

```
tctggcctga ttggcccact cctggtctgc cacaccaaca ccctgaaccc tgcacatgga    660
aggcaagtga ctgtgcagga gtttgccctc ttcttcacca tctttgatga aaccaagtca    720
tggtacttca ctgagaacat ggagagaaac tgcagagcac catgcaacat tcagatggaa    780
gaccccacct tcaaggagaa ctacaggttc catgccatca atggctacat catggacacc    840
ctgcctgggc ttgtcatggc acaggaccag agaatcagat ggtacctgct ttctatggga    900
tccaatgaga acattcactc catccacttc tctgggcatg tcttcactgt gagaaagaag    960
gaggaataca agatggccct gtacaacctc taccctgggg tctttgagac tgtggagatg   1020
ctgccctcca agctggcat ctggagggtg gaatgcctca ttggggagca cctgcatgct   1080
ggcatgtcaa ccctgttcct ggtctacagc aacaagtgcc agacacccct gggaatggcc   1140
tctggccaca tcagggactt ccagatcact gcctctggcc agtatggcca gtgggcaccc   1200
aaactggcca ggctccacta ctctggctcc atcaatgcat ggtcaaccaa ggagccattc   1260
tcttggatca aggtggacct gctggcaccc atgatcattc atggcatcaa gacacagggg   1320
gcaagacaga aattctcctc tctgtacatc tcacagttca tcatcatgta ctctctggat   1380
ggcaagaagt ggcagacata cagaggcaac tccactggca ccctcatggt cttctttggc   1440
aatgtggaca gctctggcat caagcacaac atcttcaacc ctcccatcat tgccagatac   1500
atcaggctgc accccaccca ctactcaatc agatcaaccc tcaggatgga actgatggga   1560
tgtgacctga actcctgctc aatgccctg ggaatggaga gcaaggccat ttctgatgcc   1620
cagatcactg catcctctta cttcaccaac atgtttgcca cctggtcacc atcaaaagcc   1680
aggctgcacc tccagggaag aagcaatgcc tggagacccc aggtcaacaa cccaaaggaa   1740
tggctgcaag tggacttcca gaagacaatg aaagtcactg gggtgacaac ccaggggggtc   1800 aagtctctgc tcacctcaat gtatgtgaag gagttcctga tctcttcctc acaggatggc   1860
caccagtgga cactcttctt ccagaatggc aaagtcaagg tgttccaggg caaccaggac   1920
tctttcacac ctgtggtgaa ctcactggac cccccctcc tgacaagata cctgagaatt   1980
cacccccagt cttgggtcca ccagattgcc ctgagaatgg aagtcctggg atgtgaggca   2040
caagacctgt ac                                                      2052
```

<210> SEQ ID NO 26
<211> LENGTH: 4332
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 26

```
atgcagattg agctgtccac ctgcttcttt ctgtgcctgc tgagattctg cttctctgcc     60
accaggagat actacctggg ggctgtggaa ctttcttggg actacatgca gtctgacctg    120
ggagagctgc ctgtggatgc caggttccca cccagagtgc caagtccttt cccattcaac    180
acctctgtgg tctacaagaa gacactcttt gtggaattca ctgaccacct gttcaacatt    240
gcaaaaccca gaccacctg gatgggactc ctgggaccca ccattcaggc tgaggtgtat    300
gacactgtgg tcatcacccct caagaacatg gcatcccacc ctgtgtctct gcatgctgtg    360
ggagtctcat actggaaagc ctctgaaggg gctgagtatg atgaccagac atcccagaga    420
gagaaagagg atgacaaggt gttccctggg ggatctcaca cctatgtgtg gcaagtcctc    480
aaggagaatg gacccatggc atctgaccca ctctgcctga catactccta cctttctcat    540
```

```
gtggacctgg tcaaggacct caactctgga ctgattgggg cactgctggt gtgcagggaa    600
ggatccctgg ccaaggagaa acccagaca ctgcacaagt tcattctcct gtttgctgtc     660
tttgatgagg gcaagtcttg gcactctgaa acaaagaact ccctgatgca agacagggat    720
gctgcctctg ccagggcatg gcccaagatg cacactgtga atggctatgt gaacagatca    780
ctgcctggac tcattggctg ccacaggaaa tctgtctact ggcatgtgat tggcatgggg    840
acaacccctg aagtgcactc cattttcctg gagggacaca ccttcctggt caggaaccac    900
agacaagcct ctctggagat ctctcccatc accttcctca ctgcacagac actgctgatg    960
gaccttggac agttcctgct gttctgccac atctcttccc accagcatga tggcatggaa   1020
gcctatgtca aggtggactc atgccctgag gaaccacagc tcaggatgaa gaacaatgag   1080
gaggctgagg actatgatga tgacctgact gactctgaga tggatgtggt cagatttgat   1140
gatgacaact ctccatcctt cattcagatc aggtctgtgg caaagaaaca ccccaagaca   1200
tgggtgcact acattgctgc tgaggaagag gactgggact atgcaccact ggtcctggcc   1260
cctgatgaca ggagctacaa gtctcagtac ctcaacaatg gcccacaaag aattggaaga   1320
aagtacaaga aagtcagatt catggcctac actgatgaaa ccttcaagac aagagaagcc   1380
attcagcatg agtctggcat tctgggacca ctcctgtatg gggaagtggg agacaccctg   1440
ctcatcatct tcaagaacca ggcctccagg ccctacaaca tctacccaca tggcatcact   1500
gatgtcaggc ccctgtacag caggagactg ccaaaagggg tgaaacacct caaggacttc   1560
cccattctgc ctggagagat cttcaagtac aagtggactg tcactgtgga ggatggacca   1620
acaaagtctg accccaggtg cctcaccaga tactactcct cttttgtgaa catggagaga   1680
gacctggcat ctggactgat tggaccactg ctcatctgct acaaggagtc tgtggaccag   1740
agaggcaacc agatcatgtc tgacaagaga aatgtgattc tgttctctgt ctttgatgag   1800
aacagatcat ggtacctgac tgagaacatt cagagattcc tgcccaaccc tgctggggtg   1860
caactggaag accctgagtt ccaggcaagc aacatcatgc actccatcaa tggctatgtg   1920
tttgactctc tccagctttc tgtctgcctc catgaggtgg cctactggta cattctttct   1980 attgggcac aaactgactt cctttctgtc ttcttctctg atacaccttc aagcacaag   2040 atggtgtatg aggacaccct gacactcttc ccattctctg ggaaactgt gttcatgagc    2100 atggagaacc tggactgtg gattctggga tgccacaact ctgacttcag aaacagggga    2160
atgactgcac tgctcaaagt ctcctcctgt gacaagaaca ctggggacta ctatgaggac    2220
tcttatgagg acatctctgc ctacctgctc agcaagaaca atgccattga cccagagag    2280 atcaccagga caaccctcca gtctgaccag gaagagattg actatgatga caccatttct    2340
gtggagatga gaaggagga ctttgacatc tatgatgagg acgagaacca gtctccaaga    2400
tcattccaga agaagacaag acactacttc attgctgctg tggaaagact gtgggactat    2460
ggcatgtctt cctctcccca tgtcctcagg aacaggcac agtctggctc tgtgccacag    2520
ttcaagaaag tggtcttcca ggagttcact gatggctcat tcacccagcc cctgtacaga    2580
ggggaactga atgagcacct gggactcctg gaccataca tcaggctga ggtggaagac    2640 aacatcatgg tgacattcag aaaccaggcc tccaggccct acagcttcta ctcttccctc    2700
atcagctatg aggaagacca gagacaaggg gctgagccaa gaaagaactt tgtgaaaccc    2760
aatgaaacca agacctactt ctggaaagtc cagcaccaca tggcacccac caaggatgag    2820
tttgactgca aaggcctggg atacttctct gatgtggacc tggagaaaga tgtgcactct    2880
```

| | |
|---|---:|
| ggcctgattg gcccactcct ggtctgccac accaacaccc tgaaccctgc acatggaagg | 2940 |
| caagtgactg tgcaggagtt tgccctcttc ttcaccatct ttgatgaaac caagtcatgg | 3000 |
| tacttcactg agaacatgga gagaaactgc agagcaccat gcaacattca gatggaagac | 3060 |
| cccaccttca aggagaacta caggttccat gccatcaatg ctacatcat ggacaccctg | 3120 |
| cctgggcttg tcatggcaca ggaccagaga atcagatggt acctgctttc tatgggatcc | 3180 |
| aatgagaaca ttcactccat ccacttctct gggcatgtct tcactgtgag aagaaggag | 3240 |
| gaatacaaga tggccctgta caacctctac cctggggtct tgagactgt ggagatgctg | 3300 |
| ccctccaaag ctggcatctg gagggtggaa tgcctcattg gggagcacct gcatgctggc | 3360 |
| atgtcaaccc tgttcctggt ctacagcaac aagtgccaga caccctggg aatggcctct | 3420 |
| ggccacatca gggacttcca gatcactgcc tctggccagt atggccagtg ggcacccaaa | 3480 |
| ctggccaggc tccactactc tggctccatc aatgcatggt caaccaagga gccattctct | 3540 |
| tggatcaagg tggacctgct ggcacccatg atcattcatg gcatcaagac acagggggca | 3600 |
| agacagaaat tctcctctct gtacatctca cagttcatca tcatgtactc tctgatggc | 3660 |
| aagaagtggc agacatacag aggcaactcc actggcaccc tcatggtctt ctttggcaat | 3720 |
| gtggacagct ctggcatcaa gcacaacatc ttcaaccctc ccatcattgc cagatacatc | 3780 |
| aggctgcacc ccacccacta ctcaatcaga tcaaccctca ggatggaact gatgggatgt | 3840 |
| gacctgaact cctgctcaat gcccctggga atggagagca aggccatttc tgatgcccag | 3900 |
| atcactgcat cctcttactt caccaacatg tttgccacct ggtcaccatc aaaagccagg | 3960 |
| ctgcacctcc agggaagaag caatgcctgg agacccagg tcaacaaccc aaaggaatgg | 4020 |
| ctgcaagtgg acttccagaa gacaatgaaa gtcactgggg tgacaaccca gggggtcaag | 4080 |
| tctctgctca cctcaatgta tgtgaaggag ttcctgatct cttcctcaca ggatggccac | 4140 |
| cagtggacac tcttcttcca gaatggcaaa gtcaaggtgt tccagggcaa ccaggactct | 4200 |
| ttcacacctg tggtgaactc actggacccc cccctcctga caagatacct gagaattcac | 4260 |
| ccccagtctt gggtccacca gattgccctg agaatggaag tcctgggatg tgaggcacaa | 4320 |
| gacctgtact ga | 4332 |

<210> SEQ ID NO 27
<211> LENGTH: 4368
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27

| | |
|---|---:|
| atgcagattg agctgtccac ctgcttcttt ctgtgcctgc tgagattctg cttctctgcc | 60 |
| accaggagat actacctggg ggctgtggaa cttttcttggg actacatgca gtctgacctg | 120 |
| ggagagctgc ctgtggatgc caggttccca cccagagtgc ccaagtcctt cccattcaac | 180 |
| acctctgtgg tctacaagaa gacactcttt gtggaattca ctgaccacct gttcaacatt | 240 |
| gcaaaaccca gaccaccctg gatgggactc ctgggaccca ccattcaggc tgaggtgtat | 300 |
| gacactgtgt tcatcaccct caagaacatg catcccacc ctgtgtctct gcatgctgtg | 360 |
| ggagtctcat actggaaagc ctctgaaggg gctgagtatg atgaccagac atcccagaga | 420 |
| gagaaagagg atgacaaggt gttccctggg ggatctcaca cctatgtgtg caagtcctc | 480 |
| aaggagaatg gacccatggc atctgaccca ctctgcctga catactccta cctttctcat | 540 |

```
gtggacctgg tcaaggacct caactctgga ctgattgggg cactgctggt gtgcagggaa    600
ggatccctgg ccaaggagaa aacccagaca ctgcacaagt tcattctcct gtttgctgtc    660
tttgatgagg gcaagtcttg gcactctgaa acaaagaact ccctgatgca agacagggat    720
gctgcctctg ccagggcatg gcccaagatg cacactgtga atggctatgt gaacagatca    780
ctgcctggac tcattggctg ccacaggaaa tctgtctact ggcatgtgat tggcatgggg    840
acaacccctg aagtgcactc cattttcctg gagggacaca ccttcctggt caggaaccac    900
agacaagcct ctctggagat ctctcccatc accttcctca ctgcacagac actgctgatg    960
gaccttggac agttcctgct gttctgccac atctcttccc accagcatga tggcatggaa   1020
gcctatgtca aggtggactc atgccctgag gaaccacagc tcaggatgaa gaacaatgag   1080
gaggctgagg actatgatga tgacctgact gactctgaga tggatgtggt cagatttgat   1140
gatgacaact ctccatcctt cattcagatc aggtctgtgg caaagaaaca ccccaagaca   1200
tgggtgcact acattgctgc tgaggaagag gactgggact atgcaccact ggtcctggcc   1260
cctgatgaca ggagctacaa gtctcagtac ctcaacaatg gcccacaaag aattggaaga   1320
aagtacaaga aagtcagatt catggcctac actgatgaaa ccttcaagac aagagaagcc   1380
attcagcatg agtctggcat tctgggacca ctcctgtatg gggaagtggg agacaccctg   1440
ctcatcatct tcaagaacca ggcctccagg ccctacaaca tctacccaca tggcatcact   1500
gatgtcaggc ccctgtacag caggagactg ccaaaagggg tgaaacacct caaggacttc   1560
cccattctgc tggagagat cttcaagtac aagtggactg tcactgtgga ggatggacca   1620
acaaagtctg accccaggtg cctcaccaga tactactcct cttttgtgaa catggagaga   1680
gacctggcat ctggactgat tggaccactg ctcatctgct acaaggagtc tgtggaccag   1740
agaggcaacc agatcatgtc tgacaagaga atgtgattc tgttctctgt ctttgatgag   1800
aacagatcat ggtacctgac tgagaacatt cagagattcc tgcccaaccc tgctggggtg   1860
caactggaag accctgagtt ccaggcaagc aacatcatgc actccatcaa tggctatgtg   1920
tttgactctc tccagctttc tgtctgcctg catgaggtgg cctactggta cattctttct   1980
attggggcac aaactgactt cctttctgtc ttcttctctg atacacctt caagcacaag   2040
atggtgtatg aggacaccct gacactcttc ccattctctg ggaaactgt gttcatgagc   2100
atggagaacc ctggactgtg gattctggga tgccacaact ctgacttcag aaacagggga   2160
atgactgcac tgctcaaagt ctcctcctgt gacaagaaca ctggggacta ctatgaggac   2220
tcttatgagg acatctctgc ctacctgctc agcaagaaca atgccattga gcccagaagc   2280
ttctctcaga attccagaca ccccagcacc agggagatca ccaggacaac cctccagtct   2340
gaccaggaag agattgacta tgatgacacc atttctgtgg agatgaagaa ggaggacttt   2400
gacatctatg atgaggacga gaaccagtct ccaagatcat tccagaagaa gacaagacac   2460
tacttcattg ctgctgtgga aagactgtgg gactatggca tgtcttcctc tcccatgtc    2520
ctcaggaaca gggcacagtc tggctctgtg ccacagttca gaaaagtggt cttccaggag   2580
ttcactgatg gctcattcac ccagcccctg tacagagggg aactgaatga gcacctggga   2640
ctcctgggac catacatcag ggctgaggtg gaagacaaca tcatggtgac attcagaaac   2700
caggcctcca ggcctacag cttctactct tccctcatca gctatgagga agaccagaga   2760
caaggggctg agccaagaaa gaactttgtg aaacccaatg aaaccaagac ctacttctgg   2820
aaagtccagc accacatggc acccaccaag gatgagtttg actgcaaggc ctgggcatac   2880
ttctctgatg tggacctgga gaaagatgtg cactctggcc tgattggccc actcctggtc   2940
```

```
tgccacacca acaccctgaa ccctgcacat ggaaggcaag tgactgtgca ggagtttgcc    3000
ctcttcttca ccatctttga tgaaaccaag tcatggtact tcactgagaa catggagaga    3060
aactgcagag caccatgcaa cattcagatg gaagacccca ccttcaagga gaactacagg    3120
ttccatgcca tcaatggcta catcatggac accctgcctg gcttgtcat ggcacaggac     3180 cagagaatca gatggtacct gctttctatg ggatccaatg agaacattca ctccatccac    3240
ttctctgggc atgtcttcac tgtgagaaag aaggaggaat acaagatggc cctgtacaac    3300
ctctaccctg ggtctttga dactgtggag atgctgccct ccaaagctgg catctggagg    3360
gtggaatgcc tcattgggga gcacctgcat gctggcatgt caaccctgtt cctggtctac    3420
agcaacaagt gccagacacc cctgggaatg gcctctggcc acatcaggga cttccagatc    3480
actgcctctg ccagtatgg ccagtgggca cccaaactgg ccaggctcca ctactctggc     3540
tccatcaatg catggtcaac caaggagcca ttctcttgga tcaaggtgga cctgctggca    3600
cccatgatca ttcatggcat caagacacag ggggcaagac agaaattctc ctctctgtac    3660
atctcacagt tcatcatcat gtactctctg gatggcaaga agtggcagac atacagaggc    3720
aactccactg gcaccctcat ggtcttcttt ggcaatgtgg acagctctgg catcaagcac    3780
aacatcttca ccctcccat cattgccaga tacatcaggc tgcaccccac ccactactca    3840
atcagatcaa ccctcaggat ggaactgatg ggatgtgacc tgaactcctg ctcaatgccc    3900
ctgggaatgg agagcaaggc catttctgat gcccagatca ctgcatcctc ttacttcacc    3960
aacatgtttg ccacctggtc accatcaaaa gccaggctgc acctccaggg aagaagcaat    4020
gcctggagac cccaggtcaa caacccaaag gaatggctgc aagtggactt ccagaagaca    4080
atgaaagtca ctggggtgac aacccagggg gtcaagtctc tgctcacctc aatgtatgtg    4140
aaggagttcc tgatctcttc ctcacaggat ggccaccagt ggacactctt cttccagaat    4200
ggcaaagtca aggtgttcca gggcaaccag gactcttca cacctgtggt gaactcactg    4260 gaccccccc tcctgacaag atacctgaga attcaccccc agtcttgggt ccaccagatt    4320
gccctgagaa tggaagtcct gggatgtgag gcacaagacc tgtactga                 4368
```

<210> SEQ ID NO 28
<211> LENGTH: 4332
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 28

```
atgcagattg agctgagcac ctgcttcttc ctgtgcctgc tgaggttctg cttctctgcc     60
accaggagat actacctggg cgccgtggag ctgagctggg actacatgca gtctgacctg    120
ggcgagctgc ctgtggacgc caggttcccc cccagagtgc caagagctt ccccttcaac     180 acctcagtgg tgtacaagaa gacccctgttc gtggagttca ccgaccacct gttcaacatc    240
gccaagccca ggccccctg gatgggcctg ctgggcccca ccatccaggc cgaggtgtac    300
gacaccgtgg tgatcaccct gaagaacatg gccagccacc ccgtgagcct gcacgccgtg    360
ggcgtgagct actggaaggc ctctgagggc gccgagtatg acgaccagac cagccagagg    420
gagaaggagg acgacaaggt gttccccggc ggcagccaca cctacgtgtg gcaggtgctg    480
aaggagaacg gccccatggc cagcgacccc ctgtgcctga cctacagcta cctgagccac    540
gtggacctgg tgaaggacct gaactctggc ctgatcggcg ccctgctggt gtgcagggag    600
```

```
ggcagcctgg ccaaggagaa gacccagacc ctgcacaagt tcatcctgct gttcgccgtg    660
ttcgatgagg gcaagagctg gcacagcgag accaagaaca gcctgatgca ggacagggat    720
gccgcctctg ccagggcctg gcccaagatg cacaccgtga acggctacgt gaacaggagc    780
ctgcccggcc tgatcggctg ccacaggaag tctgtgtact ggcacgtgat cggcatgggc    840
accacccccg aggtgcacag catcttcctg agggccacag ccttcctggt gaggaaccac    900
aggcaggcca gcctggagat cagccccatc accttcctga ccgcccagac cctgctgatg    960
gacctgggcc agttcctgct gttctgccac atcagcagcc accagcacga cggcatggag   1020
gcctacgtga aggtggacag ctgccccgag gagccccagc tgaggatgaa gaacaacgag   1080
gaggccgagg actatgatga tgacctgacc gactctgaga tggacgtggt gaggtttgat   1140
gatgacaaca gccccagctt catccagatc aggtctgtgg ccaagaagca ccccaagacc   1200
tgggtgcact acatcgccgc cgaggaggag gactgggact acgcccccct ggtgctggcc   1260
cccgacgaca ggagctacaa gagccagtac ctgaacaacg cccccagag gatcggcagg   1320 aagtacaaga aggtcagatt catggcctac accgacgaga ccttcaagac cagggaggcc   1380
atccagcacg agtctggcat cctgggcccc ctgctgtacg gcgaggtggg cgacaccctg   1440
ctgatcatct tcaagaacca ggccagcagg ccctacaaca tctaccccca cggcatcacc   1500
gatgtgaggc ccctgtacag caggaggctg cccaagggcg tgaagcacct gaaggacttc   1560
cccatcctgc ccggcgagat cttcaagtac aagtggaccg tgaccgtgga ggatggcccc   1620
accaagtctg accccaggtg cctgaccagg tactacagca gcttcgtgaa catggagagg   1680
gacctggcct ctggcctgat cggccccctg ctgatctgct acaaggagag cgtggaccag   1740
aggggcaacc agatcatgtc tgacaagagg aacgtgatcc tgttctctgt gttcgatgag   1800
aacaggagct ggtatctgac cgagaacatc cagaggttcc tgcccaaccc cgccggcgtg   1860
cagctggagg accccgagtt ccaggccagc aacatcatgc acagcatcaa cggctacgtg   1920
ttcgacagcc tgcagctgtc tgtgtgcctg cacgaggtgg cctactggta catcctgagc   1980
atcggcgccc agaccgactt cctgtctgtg ttcttctctg gctacacctt caagcacaag   2040
atggtgtacg aggacaccct gaccctgttc cccttcagcg cgagaccgt gttcatgagc   2100 atggagaacc ccggcctgtg gatcctgggc tgccacaaca gcgacttcag gaacaggggc   2160
atgaccgccc tgctgaaagt cagcagctgc gacaagaaca ccggcgacta ctacgaggac   2220
agctacgagg acatcagcgc ctacctgctg agcaagaaca acgccatcga gcccagggag   2280
atcaccagga ccaccctgca gagcgaccag gaggagatcg actatgatga caccatcagc   2340
gtggagatga agaaggagga cttcgacatc tacgacgagg acgagaacca gagccccagg   2400
agcttccaga agaagaccag gcactacttc atcgccgccg tggagaggct gtgggactat   2460
ggcatgagca gcagccccca cgtgctgagg aacagggccc agagcggcag cgtgccccag   2520
ttcaagaagt ggtgttcca ggagttcacc gacggcagct tcacccagcc cctgtacaga   2580
ggcgagctga acgagcacct gggcctgctg ggccccetaca tcagggccga ggtggaggac   2640
aacatcatgg tgaccttcag gaaccaggcc agcaggccct acagcttcta cagcagcctg   2700
atcagctacg aggaggacca gaggcagggc gccgagccca gaagaacttc gtgaagccc    2760 aacgagacca agacctactt ctggaaggtg cagcaccaca tggccccac caaggacgag   2820 ttcgactgca aggcctgggc ctacttctct gatgtggacc tggagaagga cgtgcacagc   2880
ggcctgatcg gccccctgct ggtgtgccac accaacaccc tgaaccccgc ccacggcagg   2940
```

-continued

```
caggtgaccg tgcaggagtt cgccctgttc ttcaccatct tcgacgagac caagagctgg    3000
tacttcaccg agaacatgga gaggaactgc agggcccccct gcaacatcca gatggaggac    3060
cccaccttca aggagaacta caggttccac gccatcaacg gctacatcat ggacaccctg    3120
cccggcctgg tgatggccca ggaccagagg atcaggtggt atctgctgag catgggcagc    3180
aacgagaaca tccacagcat ccacttcagc ggccacgtgt tcaccgtgag gaagaaggag    3240
gagtacaaga tggccctgta caacctgtac cccggcgtgt tcgagaccgt ggagatgctg    3300
cccagcaagg ccggcatctg gagggtggag tgcctgatcg gcgagcacct gcacgccggc    3360
atgagcaccc tgttcctggt gtacagcaac aagtgccaga cccccctggg catggccagc    3420
ggccacatca gggacttcca gatcaccgcc tctggccagt acggccagtg ggcccccaag    3480
ctggccaggc tgcactacag cggcagcatc aacgcctgga gcaccaagga gcccttcagc    3540
tggatcaagg tggacctgct ggcccccatg atcatccacg gcatcaagac caggcgcc      3600 aggcagaagt tcagcagcct gtacatcagc cagttcatca tcatgtacag cctggacggc    3660
aagaagtggc agacctacag gggcaacagc accggcaccc tgatggtgtt cttcggcaac    3720
gtggacagca gcggcatcaa gcacaacatc ttcaacccccc ccatcatcgc caggtacatc    3780
aggctgcacc ccaccccacta cagcatcagg agcaccctgc ggatggaact gatgggctgc    3840
gacctgaaca gctgcagcat gcccctgggc atggagagca aggccatctc tgacgcccag    3900
atcaccgcca gcagctactt caccaacatg ttcgccacct ggagccccag caaggccagg    3960
ctgcacctgc agggcaggag caacgcctgg aggcccccagg tgaacaaccc caaggagtgg    4020
ctgcaggtgg acttccagaa gaccatgaag gtgaccggcg tgaccaccca gggcgtgaag    4080
agcctgctga ccagcatgta cgtgaaggag ttcctgatca gcagcagcca ggacggccac    4140
cagtggaccc tgttcttcca gaacggcaaa gtgaaggtgt tccagggcaa ccaggacagc    4200
ttcacccccg tggtgaacag cctggacccc cccctgctga ccaggtatct gaggatccac    4260
ccccagagct gggtgcacca gatcgccctg agaatggaag tgctgggatg cgaggcccag    4320
gacctgtact ga                                                         4332
```

<210> SEQ ID NO 29
<211> LENGTH: 4368
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29

```
atgcagattg agctgagcac ctgcttcttc ctgtgcctgc tgaggttctg cttctctgcc      60
accaggagat actacctggg cgccgtggag ctgagctggg actacatgca gtctgacctg     120
ggcgagctgc ctgtggacgc caggttcccc cccagagtgc ccaagagctt ccccttcaac     180
acctcagtgg tgtacaagaa gaccctgttc gtggagttca ccgaccacct gttcaacatc     240
gccaagccca ggccccccctg gatgggcctg ctggccccca ccatccaggc cgaggtgtac     300
gacaccgtgg tgatcaccct gaagaacatg gccagccacc ccgtgagcct gcacgccgtg     360
ggcgtgagct actggaaggc ctctgagggc gccgagtatg acgaccagac cagccagagg     420
gagaaggagg acgacaaggt gttccccggc ggcagccaca cctacgtgtg gcaggtgctg     480
aaggagaacg gccccatggc cagcgacccc tgtgcctga cctacagcta cctgagccac     540
gtggacctgg tgaaggacct gaactctggc ctgatcggcg ccctgctggt gtgcagggag     600
```

```
ggcagcctgg ccaaggagaa gacccagacc ctgcacaagt tcatcctgct gttcgccgtg    660
ttcgatgagg gcaagagctg gcacagcgag accaagaaca gcctgatgca ggacagggat    720
gccgcctctg ccagggcctg gcccaagatg cacaccgtga acggctacgt gaacaggagc    780
ctgcccggcc tgatcggctg ccacaggaag tctgtgtact ggcacgtgat cggcatgggc    840 accaccccg aggtgcacag catcttcctg gagggccaca ccttcctggt gaggaaccac    900
aggcaggcca gcctggagat cagccccatc accttcctga ccgcccagac cctgctgatg    960
gacctgggcc agttcctgct gttctgccac atcagcagcc accagcacga cggcatggag   1020
gcctacgtga aggtggacag ctgccccgag gagccccagc tgaggatgaa gaacaacgag   1080
gaggccgagg actatgatga tgacctgacc gactctgaga tggacgtggt gaggtttgat   1140
gatgacaaca gccccagctt catccagatc aggtctgtgg ccaagaagca ccccaagacc   1200
tgggtgcact acatcgccgc cgaggaggag gactgggact acgccccct ggtgctggcc   1260 cccgacgaca ggagctacaa gagccagtac ctgaacaacg gccccagag gatcggcagg   1320 aagtacaaga aggtcagatt catggcctac accgacgaga ccttcaagac cagggaggcc   1380
atccagcacg agtctggcat cctgggcccc ctgctgtacg gcgaggtggg cgacaccctg   1440
ctgatcatct tcaagaacca ggccagcagg ccctacaaca tctaccccca cggcatcacc   1500
gatgtgaggc ccctgtacag caggaggctg cccaagggcg tgaagcacct gaaggacttc   1560
cccatcctgc ccggcgagat cttcaagtac aagtggaccg tgaccgtgga ggatggcccc   1620
accaagtctg accccaggtg cctgaccagg tactacagca gcttcgtgaa catggagagg   1680
gacctggcct ctggcctgat cggccccctg ctgatctgct acaaggagag cgtggaccag   1740
aggggcaacc agatcatgtc tgacaagagg aacgtgatcc tgttctctgt gttcgatgag   1800
aacaggagct ggtatctgac cgagaacatc cagaggttcc tgcccaaccc cgccggcgtg   1860
cagctggagg accccgagtt ccaggccagc aacatcatgc acagcatcaa cggctacgtg   1920
ttcgacagcc tgcagctgtc tgtgtgcctg cacgaggtgg cctactgtta catcctgagc   1980
atcggcgccc agaccgactt cctgtctgtg ttcttctctg gctacacctt caagcacaag   2040
atggtgtacg aggacaccct gacccctgttc cccttcagcg cgagaccgt gttcatgagc   2100 atggagaacc ccggcctgtg gatcctgggc tgccacaaca gcgacttcag gaacaggggc   2160
atgaccgccc tgctgaaagt cagcagctgc gacaagaaca ccggcgacta ctacgaggac   2220
agctacgagg acatcagcgc ctacctgctg agcaagaaca acgccatcga gcccaggagc   2280
ttcagccaga actccagaca ccccagcacc agggagatca ccaggaccac cctgcagagc   2340
gaccaggagg agatcgacta tgatgacacc atcagcgtgg agatgaagaa ggaggacttc   2400
gacatctacg acgaggacga gaaccagagc cccaggagct tccagaagaa gaccaggcac   2460
tacttcatcg ccgccgtgga gaggctgtgg gactatggca tgagcagcag cccccacgtg   2520
ctgaggaaca gggcccagag cggcagcgtg ccccagttca gaaggtggt gttccaggag   2580 ttcaccgacg gcagcttcac ccagcccctg tacagaggcg agctgaacga gcacctgggc   2640
ctgctgggcc cctacatcag ggccgaggtg gaggacaaca tcatggtgac cttcaggaac   2700
caggccagca ggcccctacag cttctacagc agcctgatca gctacgagga ggaccagagg   2760
cagggcgccg agcccaggaa gaacttcgtg aagcccaacg agaccaagac ctacttctgg   2820
aaggtgcagc accacatggc ccccaccaag gacgagttcg actgcaaggc ctgggcctac   2880
ttctctgatg tggacctgga aaggacgtg cacagcggcc tgatcggccc cctgctggtg   2940
tgccacacca acaccctgaa ccccgcccac ggcaggcagg tgaccgtgca ggagttcgcc   3000
```

```
ctgttcttca ccatcttcga cgagaccaag agctggtact tcaccgagaa catggagagg    3060
aactgcaggg cccctgcaa catccagatg gaggacccca ccttcaagga gaactacagg     3120
ttccacgcca tcaacggcta catcatggac accctgcccg gcctggtgat ggcccaggac    3180
cagaggatca ggtggtatct gctgagcatg ggcagcaacg agaacatcca cagcatccac    3240
ttcagcggcc acgtgttcac cgtgaggaag aaggaggagt acaagatggc cctgtacaac    3300
ctgtaccccg cgtgttcga gaccgtggag atgctgccca gcaaggccgg catctggagg     3360
gtggagtgcc tgatcggcga gcacctgcac gccggcatga gcaccctgtt cctggtgtac    3420
agcaacaagt gccagacccc cctgggcatg ccagcggcc acatcaggga cttccagatc     3480
accgcctctg gccagtacgg ccagtgggcc cccaagctgg ccaggctgca ctacagcggc    3540
agcatcaacg cctggagcac caaggagccc ttcagctgga tcaaggtgga cctgctggcc    3600
cccatgatca tccacggcat caagacccag ggcgccaggc agaagttcag cagcctgtac    3660
atcagccagt tcatcatcat gtacagcctg gacggcaaga gtggcagac ctacagggg      3720 aacagcaccg gcaccctgat ggtgttcttc ggcaacgtgg acagcagcgg catcaagcac    3780
aacatcttca ccccccccat catcgccagg tacatcaggc tgcaccccac ccactacagc    3840
atcaggagca ccctgcggat ggaactgatg ggctgcgacc tgaacagctg cagcatgccc    3900
ctgggcatgg agagcaaggc catctctgac gcccagatca ccgccagcag ctacttcacc    3960
aacatgttcg ccacctggag ccccagcaag gccaggctgc acctgcaggg caggagcaac    4020
gcctggaggc cccaggtgaa caacccccaag gagtggctgc aggtggactt ccagaagacc    4080
atgaaggtga ccggcgtgac cacccagggc gtgaagagcc tgctgaccag catgtacgtg    4140
aaggagttcc tgatcagcag cagccaggac ggccaccagt ggaccctgtt cttccagaac    4200
ggcaaagtga aggtgttcca gggcaaccag gacagcttca ccccgtggt gaacagcctg      4260 gacccccccc tgctgaccag gtatctgagg atccacccc agagctgggt gcaccagatc     4320
gccctgagaa tggaagtgct gggatgcgag gcccaggacc tgtactga               4368
```

<210> SEQ ID NO 30
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ser Phe Ser Gln Asn Pro Pro Val Leu Lys Arg His Gln Arg
1               5                   10

<210> SEQ ID NO 31
<211> LENGTH: 24
<212> TYPE: PRT
<213> ORGANISM: Sus sp.

<400> SEQUENCE: 31

Ser Phe Ala Gln Asn Ser Arg Pro Pro Ser Ala Ser Ala Pro Lys Pro
1               5                   10                  15

Pro Val Leu Arg Arg His Gln Arg
            20

<210> SEQ ID NO 32
<211> LENGTH: 16
<212> TYPE: PRT

```
<213> ORGANISM: Sus sp.

<400> SEQUENCE: 32

Ser Phe Ser Gln Asn Ser Arg His Gln Ala Tyr Arg Tyr Arg Arg Gly
1               5                   10                  15
```